(12) United States Patent
Ginhoux et al.

(10) Patent No.: US 11,249,081 B2
(45) Date of Patent: Feb. 15, 2022

(54) METHODS FOR THE IDENTIFICATION, TARGETING AND ISOLATION OF HUMAN DENDRITIC CELL (DC) PRECURSORS "PRE-DC" AND THEIR USES THEREOF

(71) Applicant: AGENCY FOR SCIENCE, TECHNOLOGY AND RESEARCH, Singapore (SG)

(72) Inventors: Florent Ginhoux, Singapore (SG); Chi Ee Peter See, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 36 days.

(21) Appl. No.: 16/329,751

(22) PCT Filed: Aug. 31, 2017

(86) PCT No.: PCT/SG2017/050435
§ 371 (c)(1),
(2) Date: Feb. 28, 2019

(87) PCT Pub. No.: WO2018/044238
PCT Pub. Date: Mar. 8, 2018

(65) Prior Publication Data
US 2019/0324038 A1 Oct. 24, 2019

(30) Foreign Application Priority Data

Aug. 31, 2016 (SG) .............................. 10201607246S
May 3, 2017 (SG) .............................. 10201703621Q

(51) Int. Cl.
*G01N 33/569* (2006.01)
*A61K 35/15* (2015.01)
*C07K 16/28* (2006.01)

(52) U.S. Cl.
CPC ....... *G01N 33/56972* (2013.01); *A61K 35/15* (2013.01); *C07K 16/2803* (2013.01); *C07K 16/2851* (2013.01); *C07K 16/2863* (2013.01); *C07K 16/2878* (2013.01); *C07K 16/2896* (2013.01); *G01N 2333/70503* (2013.01); *G01N 2333/70578* (2013.01); *G01N 2333/70596* (2013.01); *G01N 2333/71* (2013.01)

(58) Field of Classification Search
None
See application file for complete search history.

(56) References Cited

U.S. PATENT DOCUMENTS

2005/0013810 A1  1/2005  Waller et al.
2013/0058947 A1  3/2013  Stull et al.

FOREIGN PATENT DOCUMENTS

| CN | 101035807 | A | 9/2007 | |
|---|---|---|---|---|
| CN | 103080136 | A | 5/2013 | |
| CN | 103476429 | A | 12/2013 | |
| CN | 104168903 | B | 11/2014 | |
| EP | 2606897 | A1 | 6/2013 | |
| EP | 2950095 | A1 | 12/2015 | |
| WO | 2005/124358 | A2 | 12/2005 | |
| WO | 2011/159980 | A1 | 12/2011 | |
| WO | 2012123570 | A1 | 9/2012 | |
| WO | 2016005593 | A1 | 1/2016 | |
| WO | 2016/049641 | A1 | 3/2016 | |
| WO | WO-2018035364 | A1 * | 2/2018 | ......... G01N 33/5047 |

OTHER PUBLICATIONS

Nguyen et al., 2006, Exp. Hem. vol. 34: 728-735.*
Xiong et al., 2014, Rheum. vol. 53: 250-259.*
Crocker et al., 2007, Nat. Immunol. vol. 7: 255-266.*
Donovan et al. "CD45 and the immune response" Journal of the American Society of Nephrology, vol. 4 Issue 4, Oct. 1993, pp. 976-985.
Haniffa et al. "Human mononuclear phagocyte system reunited" Seminars in Cell & Developmental Biology, vol. 41, May 15, 2015, pp. 59-69.
Mass et al. "Specification of tissue—resident macrophages during organogenesis" Science, vol. 353, Issue 6304, Sep. 9, 2016, pp. 1-32.
Matcovitch-Natan et al. "Microglia development follows a stepwise program to regulate brain homeostasis" Science, vol. 353, Issue 6301, Aug. 19, 2016, pp. aad8670-1-12.
Milush et al. "Functionally distinct subsets of human NK cells and monocyte/DC-like cells identified by coexpression of CD56, CD7, and CD4" Blood, vol. 114, Issue 23, Octobers, 2009, pp. 4823-4831.
Nakayama et al. "CD15 expression in mature granulocytes is determined by alpha 1,3-fucosyltransferase IX, but in promyelocytes and monocytes by alpha 1,3-fucosyltransferase IV" Journal of Biological Chemistry, vol. 276, No. 19, Feb. 23, 2001, pp. 16100-16106.
O'Doherty et al., "Human blood contains two subsets of dendritic cells, one immunologically mature and the other immature" Immunology, vol. 82, Issue 3, Jul. 1994, pp. 487-493.

(Continued)

*Primary Examiner* — Amy E Juedes
(74) *Attorney, Agent, or Firm* — Womble Bond Dickinson (US) LLP

(57) ABSTRACT

Biomarkers for the detection and identification of a precursor of conventional dendritic cell (cDC) (pre-DC) and its cell subsets (pre-cDC1 or pre-cDC2), are defined, which include CD169, CD327, AXL, CD271, CD324 and combinations thereof for detecting pre-DCs. Methods for detecting a disease or condition, prognosis of an existing disease or condition comprising determining the number of pre-DC cells in sample from a subject as compared to control, as well as methods of treating a patient comprising administration of antibodies against CD169, CD327, AXL, CD271, CD324 and combinations thereof are also disclosed. In addition, an immunogenic composition comprising one or more binding molecules specific for one or more biomarkers or antigen of a target disease and/or one or more cells selected from the group consisting of early pre-DC, pre-cDC1 and pre-cDC2 are also disclosed for eliciting an immune response against an infectious disease or cancer.

5 Claims, 85 Drawing Sheets

(56) References Cited

OTHER PUBLICATIONS

Paul et al., "Transcriptional heterogeneity and lineage commitment in myeloid progenitors" Cell, vol. 163, Issue 7, Dec. 17, 2015, pp. 1663-1677.
Poulin et al., "Characterization of human DNGR-1 + BDCA3+ leukocytes as putative equivalents of mouse CD8 alpha+ dendritic cells" Journal of Experimental Medicine, vol. 207, No. 6, Jun. 7, 2010, pp. 1261-1271.
Schutz et al. "Identification of novel dendritic cell subset markers in human blood" Biochemical and Biophysical Research Communications, vol. 443, No. 2, Jan. 10, 2014, pp. 453-457.
Watchmaker et al., "Comparative transcriptional and functional profiling defines conserved programs of intestinal DC differentiation in humans and mice" Nature Immunology, vol. 15, No. 1, Dec. 1, 2013, pp. 98-108.
Weber et al. "Differential chemokine receptor expression and function in human monocyte subpopulations" Journal of Leukocyte Biology, vol. 67, Issue 5, May 1, 2000, pp. 699-704.
Zheng et al. "Massively parallel digital transcriptional profiling of single cells" Nature Communications, vol. 8, No. 14049, Jan. 16, 2017, pp. 1-12.
Ziegler-Heitbrock et al. "Nomenclature of monocytes and dendritic cells in blood" Blood, vol. 116, No. 16, Oct. 21, 2010, pp. e74-80.
The Extended European Search Report for European Application No. SS15783PCEP dated Jul. 3, 2020, 12 pages.
Amir et al., "viSNE enables visualization of high dimensional single-cell data and reveals phenotypic heterogeneity of leukemia", Nature Biotechnology, vol. 31, No. 6, Jun. 2013, 25 pages.
Becher et al., "High-dimensional analysis of the murine myeloid cell system", Nature Immunology, vol. 15, No. 12, Dec. 2014, pp. 1181-1189.
Bendall et al., "Single-Cell Trajectory Detection Uncovers Progression and Regulatory Coordination in Human B Cell Development", Cell, vol. 157, Issue 3, Apr. 24, 2014, pp. 714-725.
Benjamini et al., "Controlling the False Discovery Rate: A Practical and Powerful Approach to Multiple Testing", Journal of the Royal Statistical Society. Series B (Methodological), vol. 57, No. 1, 1995, pp. 289-300.
Breton et al., "Circulating precursors of human CD1c+ and CD141+ dendritic cells", J. Exp. Med., vol. 212, No. 3, 2015, pp. 401-413.
Cella et al., "Plasmacytoid dendritic cells activated by influenza virus and CD40L drive a potent TH1 polarization", Nature Immunology, vol. 1, No. 4, Oct. 2000, pp. 305-310.
Cella et al., "Plasmacytoid monocytes migrate to inflamed lymph nodes and produce large amounts of type I interferon", Nature Medicine, vol. 5, No. 8, Aug. 1999, pp. 919-923.
Chen et al., "Cytotkit: A Bioconductor Package for an Integrated Mass Cytometry Data Analysis Pipeline", PLoS Computational Biology, vol. 12, e1005112, 2016, 17 pages.
Chen et al., "Mpath maps multi-branching single-cell trajectories revealing progenitor cell progression during development", Nature Communications, vol. 7, No. 11988, 2016, 15 pages.
Cheng et al., "Characterization of species-specific genes regulated by E2-2 in human plasmacytoid dendritic cells", Scientific Reports, vol. 5, No. 10752, 2015, 11 pages.
Cisse et al., "Transcription factor E2-2 is an essential and specific regulator of plasmacytoid dendritic cell development", Cell., vol. 135, No. 1, Oct. 3, 2008, pp. 37-48.
Coifman et al., "Geometric diffusions as a tool for harmonic analysis and structure definition of data: multiscale methods", Proceedings of the National Academy of Sciences, vol. 102, No. 21, May 24, 2005, pp. 7432-7437.
Diao et al., "Recruitment and Differentiation of Conventional Dendritic Cell Precursors in Tumors", Journal of Immunology, vol. 184, 2010, pp. 1261-1267.
Doulatov et al., "Revised map of the human progenitor hierarchy shows the origin of macrophages and dendritic cells in early lymphoid development", Nature Immunology, vol. 11, No. 7, Jul. 2010, pp. 585-593.
Dzionek et al., "BDCA-2, BDCA-3, and BDCA-4: Three Markers for Distinct Subsets of Dendritic Cells in Human Peripheral Blood", Journal of Immunology, vol. 165, 2000, pp. 6037-6046.
Dzionek et al., "Plasmacytoid Dendritic Cells: From Specific Surface Markers to Specific Cellular Functions", Human Immunology, vol. 63, No. 12, Dec. 2002, pp. 1133-1148.
Finck et al., "Normalization of mass cytometry data with bead standards", Cytometry Part A., vol. 83, No. 5, May 2013, pp. 483-494.
Fonteneau et al., "Activation of influenza virus—specific CD4 and CD8 T cells: a new role for piasmacytoid dendritic cells in adaptive immunity", Blood, vol. 101, No. 9, May 1, 2003, pp. 3520-3526.
Galibert et al., "Nectin-like protein 2 defines a subset of T-cell zone dendritic cells and is a ligand for class-I-restricted T-cell-associated molecule", The Journal of Biological Chemistry, vol. 280, No. 23, 2005, pp. 21955-21964.
Ginhoux et al., "The origin and development of nonlymphoid tissue CD103+ DCs", The Journal of Experimental Medicine, vol. 206, No. 13, 2009, pp. 3115-3130.
Grajales-Reyes et al., "Batf3 maintains Irf8 autoactivation for commitment of a CD8a+ eDC clonogenic progenitor", Nat. Immunol., vol. 16, No. 7, Jul. 2015, pp. 708-717.
Griffin et al., "Differential Expression of HLA-DR Antigens in Subsets of Human CFU-GM" Blood, vol. 66, No. 4, Oct. 1985, pp. 788-795.
Grouard et al., "The Enigmatic Plasmacytoid T Cells Develop into Dendritic Cells with Interleukin (IL)-3 and CD40-Ligand", J. Exp. Med., vol. 185, No. 6, Mar. 17, 1997, pp. 1101-1111.
Grün et al., "Single-cell messenger RNA sequencing reveals rare intestinal cell types", Nature, vol. 525, No. 7568, 2015, pp. 251-255.
Guilliams et al., "Dendritic cells, monocytes and macrophages: a unified nomenclature based on ontogeny", Nat. Rev. Immunol., vol. 14, No. 8, Aug. 2014, pp. 571-578.
Hahsler et al., "dbscan: Density Based Clustering of Applications with Noise (DBSCAN) and Related Algorithms", R package version 1.0-0, 2017, 1 page.
Haniffa et al., "Human Tissues Contain CD141hi Cross-Presenting Dendritic Cells with Functional Homology to Mouse CD103+ Nonlymphoid Dendritic Cells", Immunity, vol. 37, Jul. 27, 2012, pp. 60-73.
Harrow et al., "GENCODE: The reference human genome annotation for The ENCODE Project", Genome Research, vol. 22, 2012, pp. 1760-1774.
Hoeffel et al., "Antigen Crosspresentation by Human Plasmacytoid Dendritic Cells", Immunity, vol. 27, Sep. 2007, pp. 481-492.
International Preliminary Report on Patentability received for PCT Patent Application No. PCT/SG2017/050435, dated Nov. 30, 2018, 40 pages.
International Search Report and Written Opinion received for PCT Patent Application No. PCT/SG2017/050435, dated Nov. 28, 2017, 15 pages.
Ito et al., "Plasmacytoid dendritic cells prime IL-10-producing T regulatory cells by inducible costimulator ligand", The Journal of Experimental Medicine, vol. 204, No. 1, Jan. 22, 2007, pp. 105-115.
Jaitin et al., "Massively Parallel Single-Cell RNA-Seq for Marker-Free Decomposition of Tissues into Cell Types", Science, vol. 343, No. 6172, Feb. 14, 2014, pp. 776-779.
Jongbloed et al., "Human CD141+ (BDCA-3)+ dendritic cells (DCs) represent a unique myeloid DC subset that cross-presents necrotic cell antigens", The Journal of Experimental Medicine, vol. 207, No. 6, 2010, 14 pages.
Kriegel et al., "A density-based algorithm for discovering clusters in large spatial databases with noise", KDD'96 Proceedings of the Second International Conference on Knowledge Discovery and Data Mining, 1996, pp. 226-231.
Krug et al., "Toll-like receptor expression reveals CpG DNA as a unique microbial stimulus for plasmacytoid dendritic cells which synergizes with CD40 ligand to induce high amounts of IL-12", Eur. J. Immunol., vol. 31, 2001, pp. 3026-3037.
Lamb et al., "The Connectivity Map: Using Gene-Expression Signatures to Connect Small Molecules, Genes, and Disease", Science, vol. 313, Sep. 29, 2006, pp. 1929-1935.

(56) References Cited

OTHER PUBLICATIONS

Langmead et al., "Ultrafast and memory-efficient alignment of short DNA sequences to the human genome", Genome Biol., vol. 10, No. 3, 2009, 10 pages.
Lee et al., "Clonal analysis of human dendritic cell progenitor using a stromal cell culture", J. Immunol. Methods., vol. 425, Oct. 2015, pp. 21-26.
Lee et al., "Restricted dendritic cell and monocyte progenitors in human cord blood and bone marrow", The Journal of Experimental Medicine, vol. 212, No. 3, 2015, pp. 385-399.
Levine et al., "Data-Driven Phenotypic Dissection of AML Reveals Progenitor-like Cells that Correlate with Prognosis", Cell, vol. 162, Issue 1, Jul. 2, 2015, pp. 184-197.
Li et al., "RSEM: accurate transcript quantification from RNA-Seq data with or without a reference genome", BMC Bioinformatics, vol. 12, No. 323, 2011, 16 pages.
Liu et al., "In vivo analysis of dendritic cell development and homeostasis", Science, vol. 324, No. 5925, Apr. 17, 2009, pp. 392-397.
Liu, Yong-Jun, "IPC: Professional Type 1 Interferon-Producing Cells and Plasmacytoid Dendritic Cell Precursors", Annual Review of Immunology, vol. 23, 2005, pp. 275-306.
Maaten et al., "Visualizing Data using t-SNE", Journal of Machine Learning Research, vol. 9, 2008, pp. 2579-2605.
MacDonald et al., "Characterization of human blood dendritic cell subsets", Blood, vol. 100, No. 13, Dec. 15, 2002, pp. 4512-4520.
Matsui et al., "CD2 distinguishes two subsets of human plasmacytoid dendritic cells with distinct phenotype and functions", J. Immunol., vol. 182, No. 11, Jun. 1, 2009, pp. 6815-6823.
Merad et al., "The Dendritic Cell Lineage: Ontogeny and Function of Dendritic Cells and Their Subsets in the Steady State and the Inflamed Setting", Annu. Rev. Immunol., vol. 31, 2013, 48 pages.
Morandi et al., "Distinctive Lack of CD48 Expression in Subsets of Human Dendritic Cells Tunes NK Cell Activation", The Journal of Immunology, vol. 175, No. 6, Sep. 15, 2005, pp. 3690-3697.
Newell et al., "Cytometry by Time-of-Flight Shows Combinatorial Cytokine Expression and Virus-Specific Cell Niches within a Continuum of CD8+ T Cell Phenotypes", Immunity, vol. 36, Issue 1, Jan. 27, 2012, pp. 142-152.
Naik, et al., "Intrasplenic steady-state dendritic cell precursors that are distinct from monocytes," Nature Immunology, Jun. 2006, pp. 663-671, vol. 7, No. 6, Nature Publishing Group.
Pino, et al., "HIV-1 immune activation induces Siglec-1 expression and enhances viral trans-infection in blood and tissue myeloid cells," Retrovirology, 2015, 15 pgs., vol. 12, No. 37, BioMed Central.
The Partial Supplementary European Search Report for European Application No. 17847100.9 dated Apr. 1, 2020, 15 pages.
Oksanen et al., "vegan: Community Ecology Package", R package version 2.4-2, 2017, 1 page.
Onai et al., "A Clonogenic Progenitor with Prominent Plasmacytoid Dendritic Cell Developmental Potential", Immunity, vol. 38, May 23, 2013, pp. 943-957.
Parks et al., "A new "Logicle" display method avoids deceptive effects of logarithmic scaling for low signals and compensated data", Cytometry Part A., vol. 69, 2006, pp. 541-551.
Peter, See Chi Ee, "Identification and characterisation of novel human dendritic cell progenitors", School of Biological Sciences, Doctor of Philosophy, 2016, 120 pages.
Reizis et al., "Plasmacytoid Dendritic Cells: Recent Progress and Open Questions", Annu. Rev. Immunol., vol. 29, 2011, pp. 163-183.
Sadaka et al., "Developmental regulation of MHC II expression and transport in human plasmacytoid-derived dendritic cells", Blood, vol. 113, No. 10, Mar. 5, 2009, pp. 2127-2135.
Satija et al., "Spatial reconstruction of single-cell gene expression data", Nature Biotechnology, vol. 33, No. 5, May 2015, pp. 495-502.
Schlitzer et al., "Dendritic cells and monocyte-derived cells: Two complementary and integrated functional systems", Seminars in Cell & Developmental Biology, vol. 41, 2015, pp. 9-22.
Schlitzer et al., "Identification of CCR9—murine plasmacytoid DC precursors with plasticity to differentiate into conventional DCs", Blood, vol. 117, No. 24, Jun. 16, 2011, pp. 6562-6570.
Schlitzer et al., "Identification of cDC1- and cDC2—committed DC progenitors reveals early lineage priming at the common DC progenitor stage in the bone marrow", Nature Immunology, vol. 16, No. 7, Jul. 2015, pp. 718-728.
See et al., "Mapping the human DC lineage through the integration of high-dimensional techniques", Science, vol. 356, Jun. 9, 2017, 15 pages.
Setty et al., "Wishbone identifies bifurcating developmental trajectories from single-cell data", Nature Biotechnology, vol. 34, No. 6, Jun. 2016, pp. 637-645.
Siegal et al., "The Nature of the Principal Type 1 Interferon-Producing Cells in Human Blood", Science, vol. 284, Jun. 11, 1999, pp. 1835-1837.
Smyth, Gordon K., "Linear Models and Empirical Bayes Methods for Assessing Differential Expression in Microarray Experiments", Statistical Applications in Genetics and Molecular Biology, vol. 3, No. 1, 2004, 26 pages.
Strobl et al., "Identification of CD68+lin—peripheral blood cells with dendritic precursor characteristics", The Journal of Immunology, vol. 161, No. 2, Jul. 15, 1998, pp. 740-748.
Swiecki et al., "The multifaceted biology of plasmacytoid dendritic cells", Nat. Rev. Immunol., vol. 15, No. 8, Aug. 2015, pp. 471-485.
Tenenbaum et al., "A Global Geometric Framework for Nonlinear Dimensionality Reduction", Science, vol. 290, Issue 5500, Dec. 22, 2000, pp. 2319-2323.
Trapnell et al., "The dynamics and regulators of cell fate decisions are revealed by pseudotemporal ordering of single cells", Nature Biotechnology, vol. 32, No. 4. Apr. 2014, pp. 381-386.
Winter et al., "Phenotype and natural history in 101 individuals with PittHopkins syndrome through an internet questionnaire system", Orphanet Journal of Rare Diseases, vol. 11, No. 37, 2016, 12 pages.
Yates et al., "Ensembl 2016", Nucleic Acids Research, vol. 44, 2015, pp. D710-D716.
The Second Office Action for European Application No. 17847100.9 dated Jun. 16, 2021, 5 pages.
The First Office Action for Chinese Application No. 201780066143.4 dated Nov. 24, 2021, 19 pages, [English Translation].

\* cited by examiner

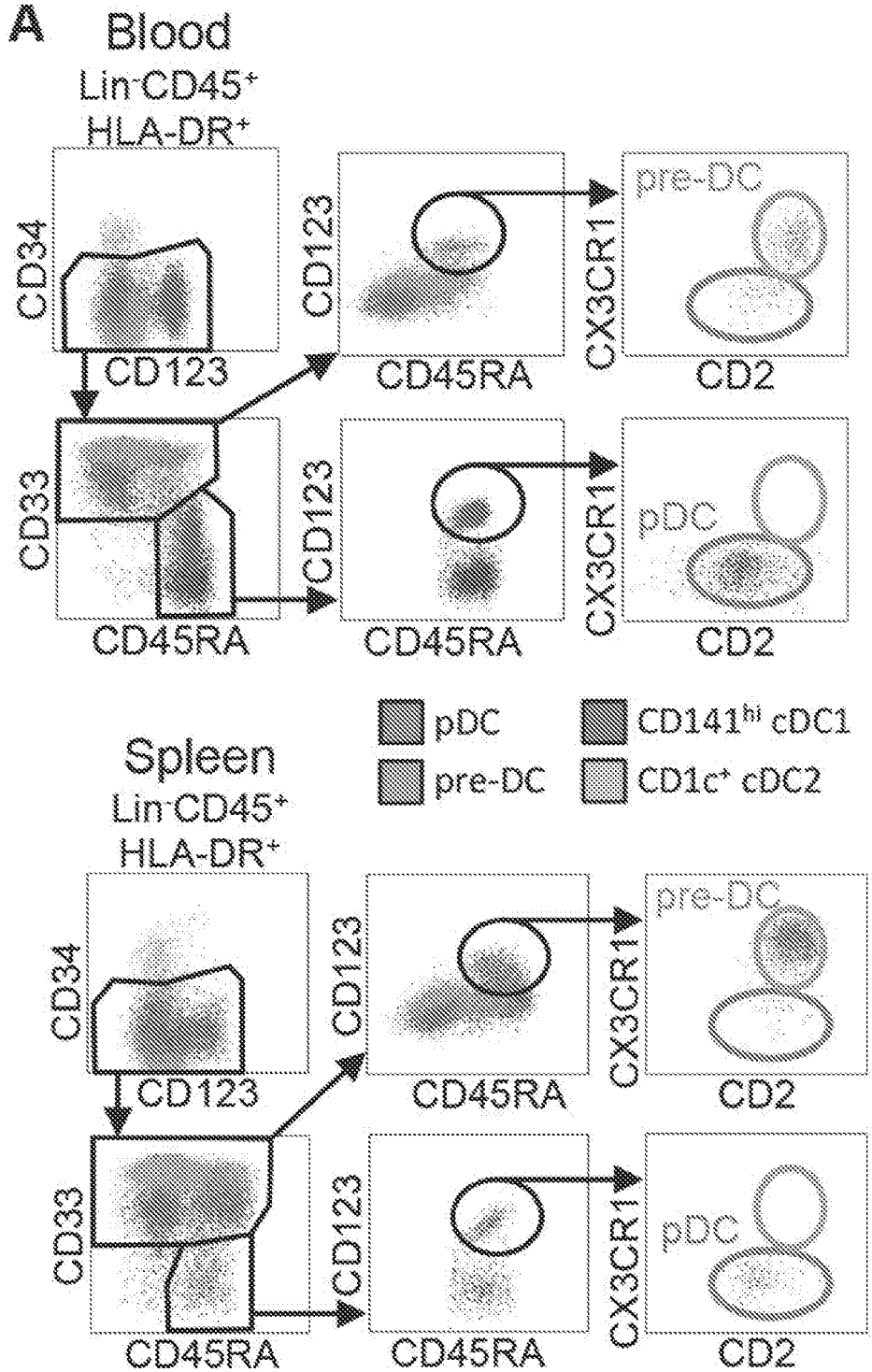

FIG. 2 (CONTINUED)
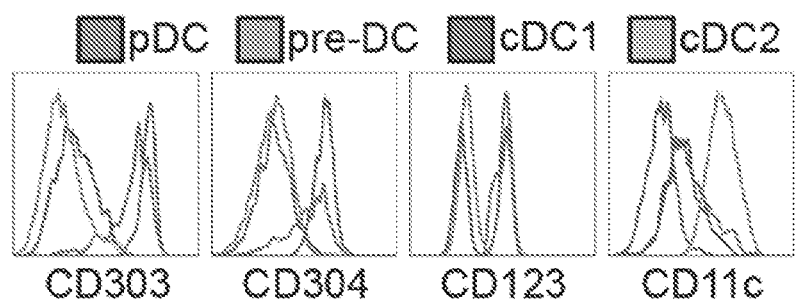
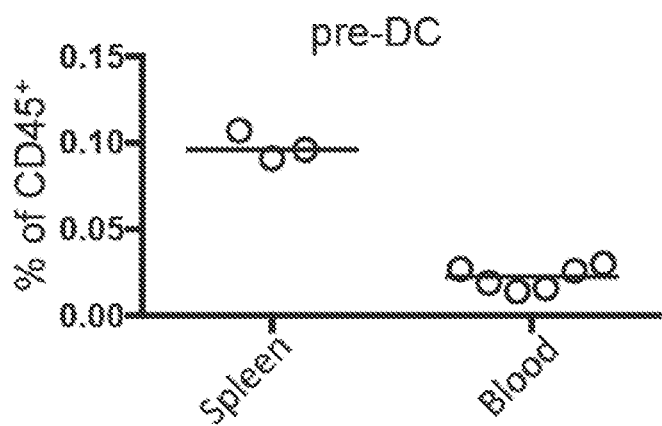
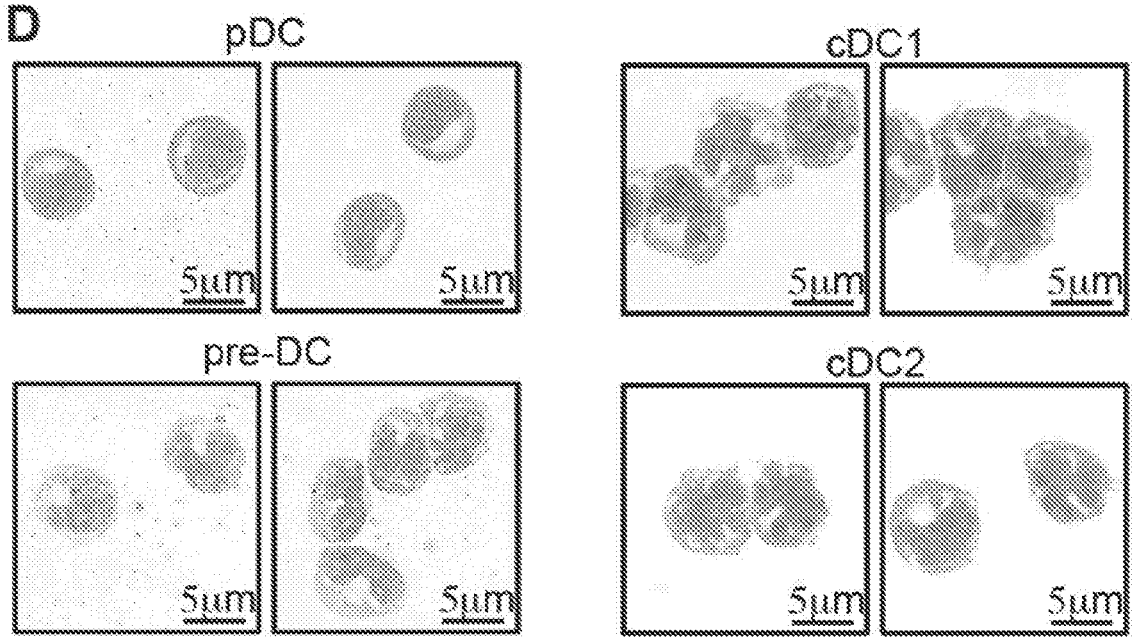

FIG. 2 (CONTINUED)
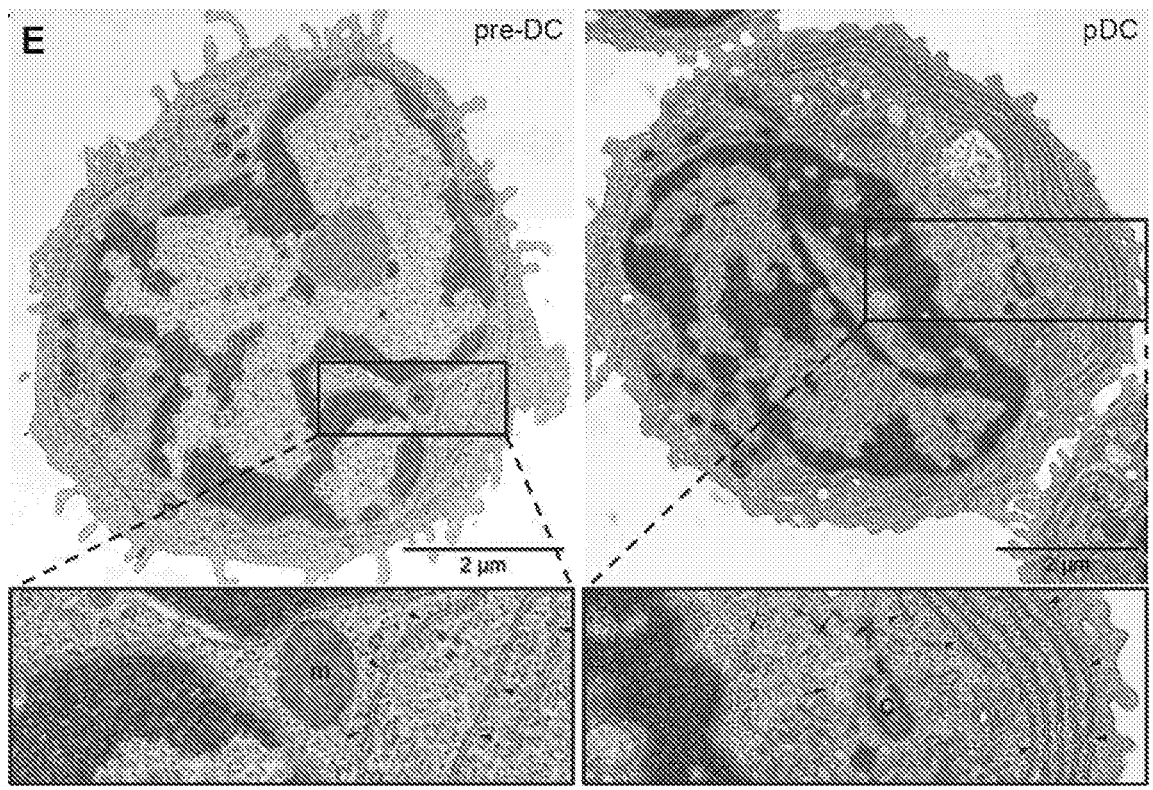
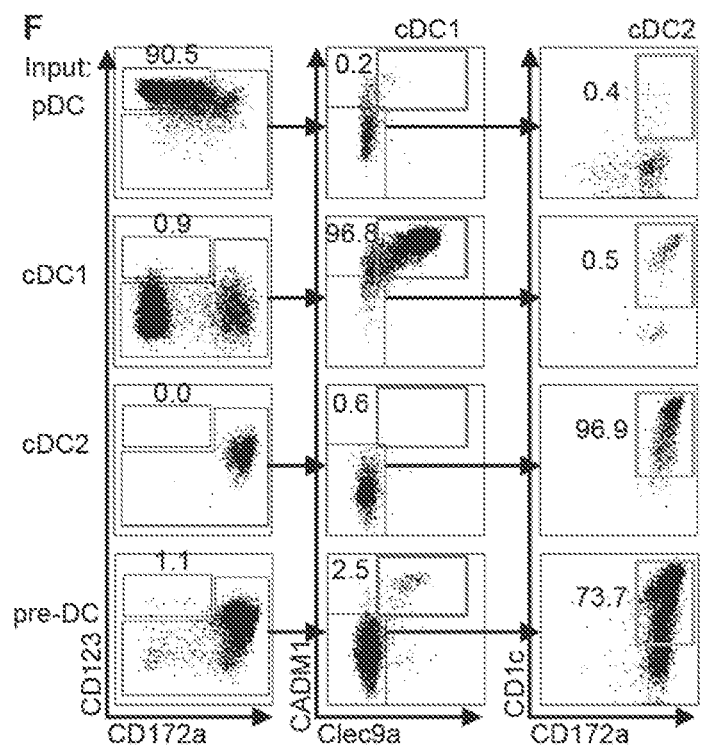

FIG. 4 (CONTINUED)
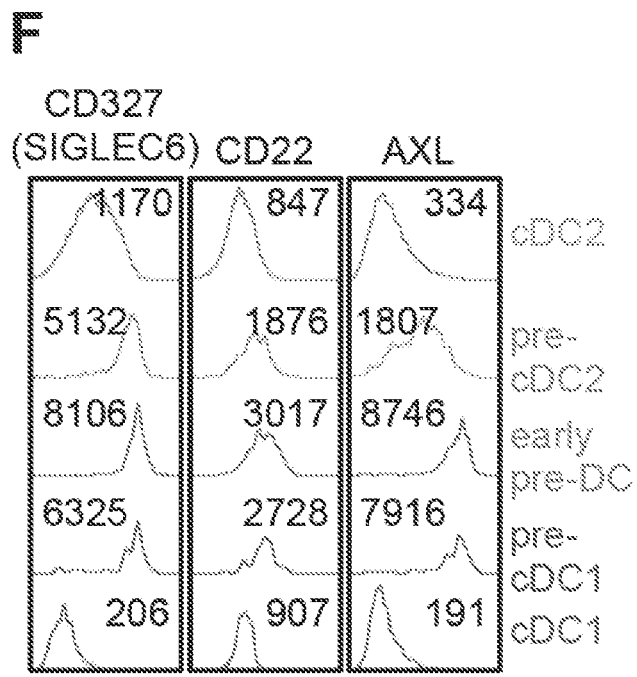
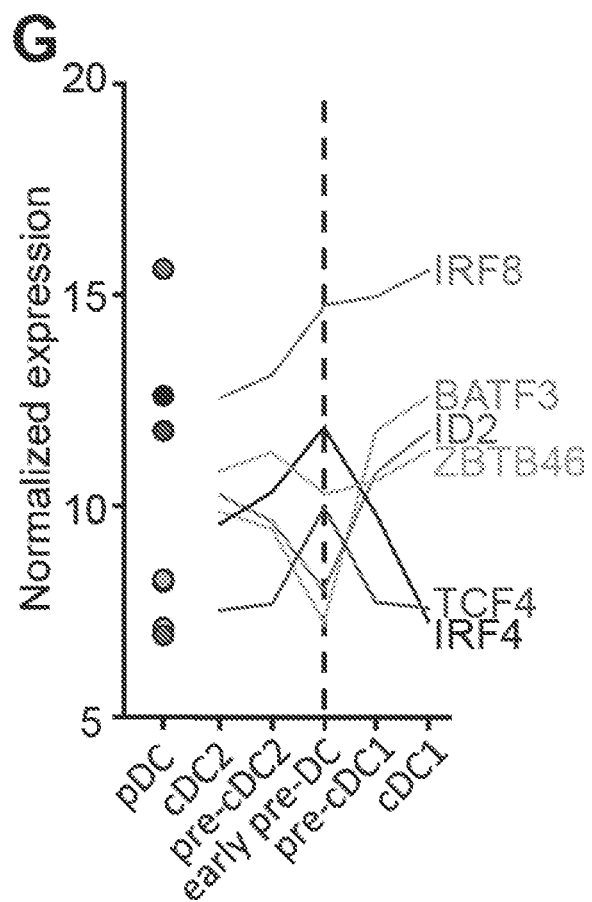

FIG. 6 (CONTINUED)
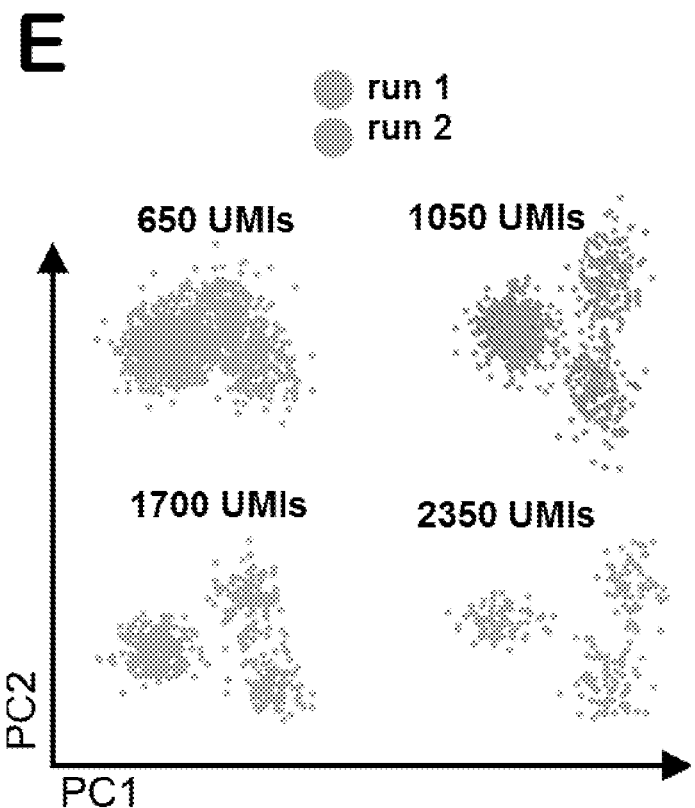
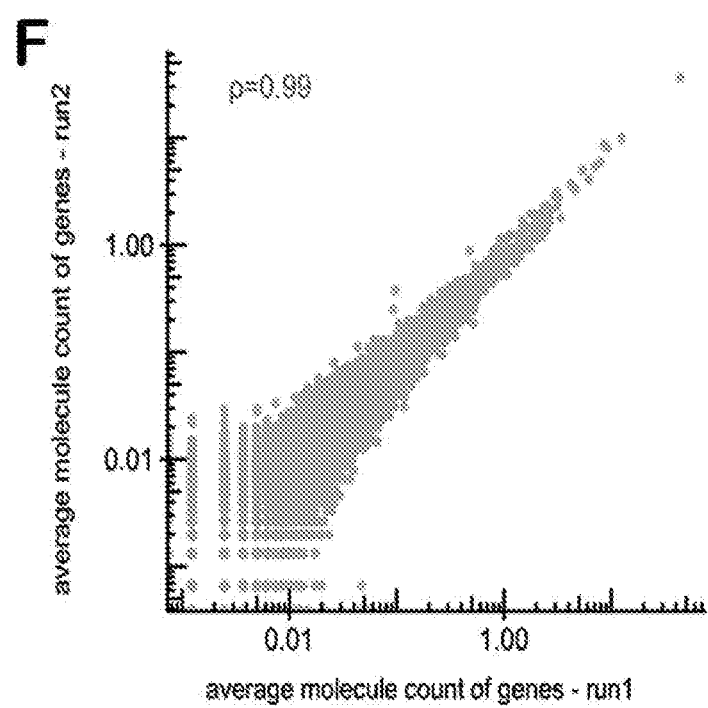

B *MARS-seq Mpath*

FIG. 7 (C) CONTINUED
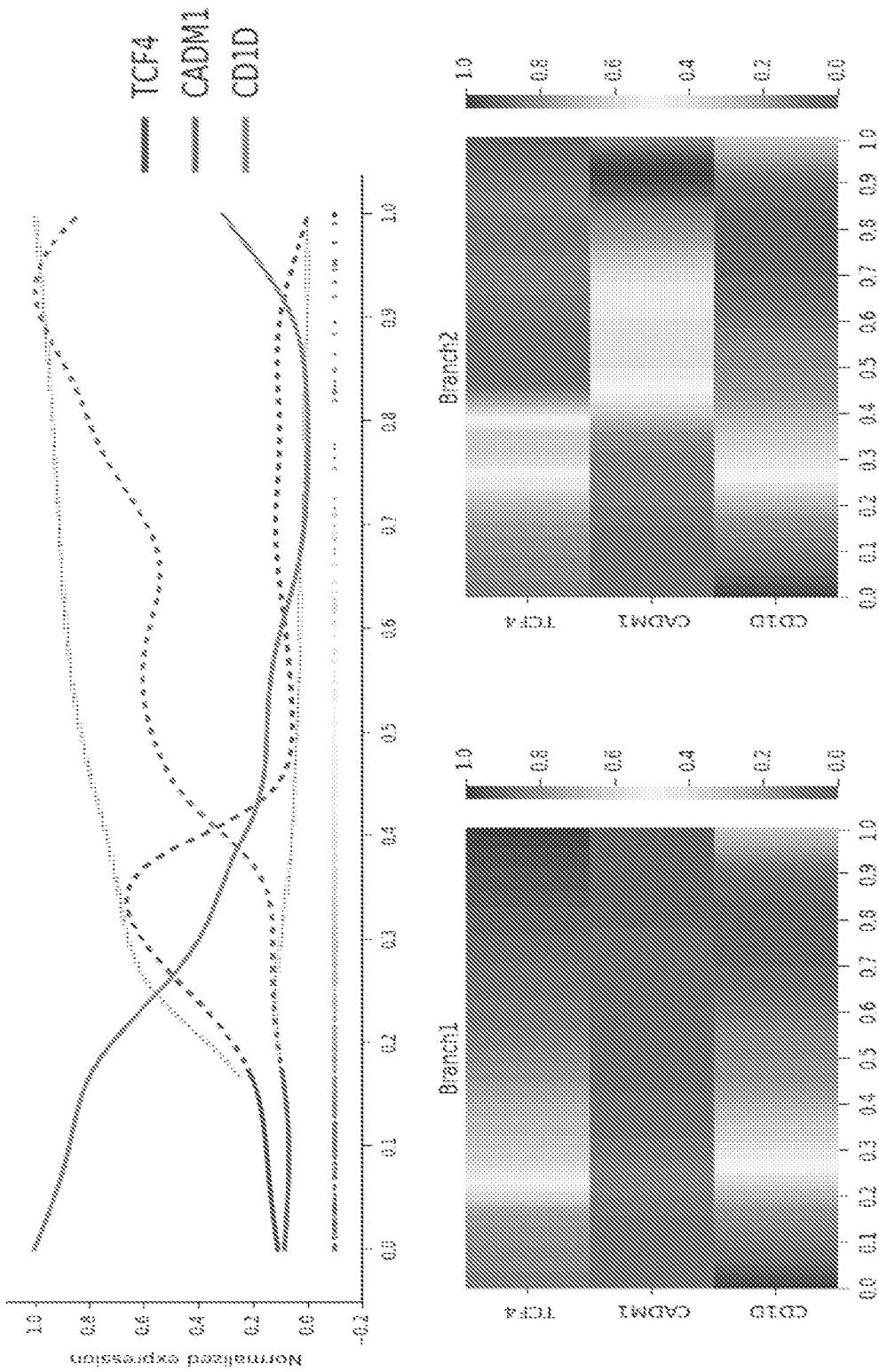

C Phenograph unsupervised clustering

FIG. 9
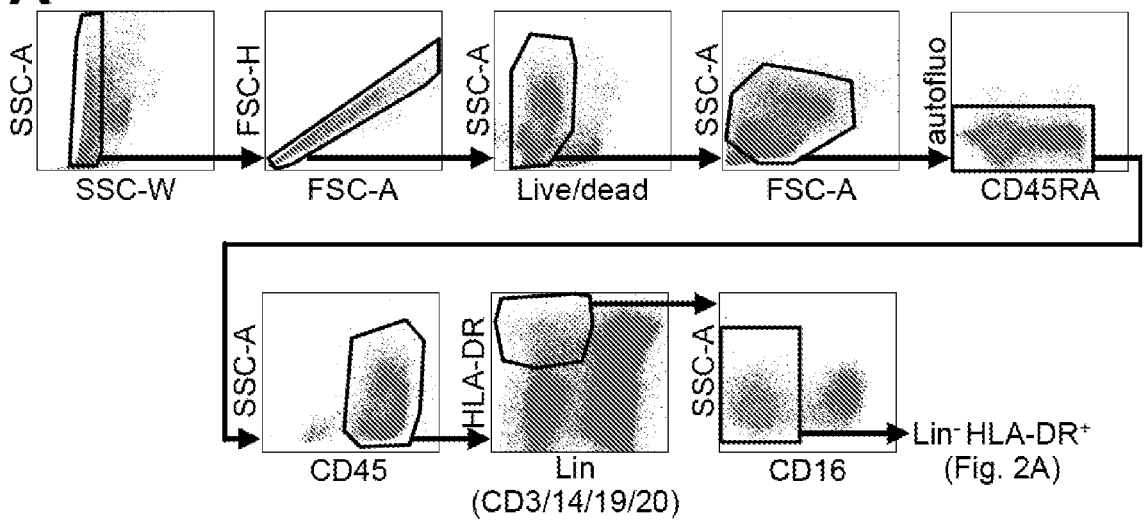
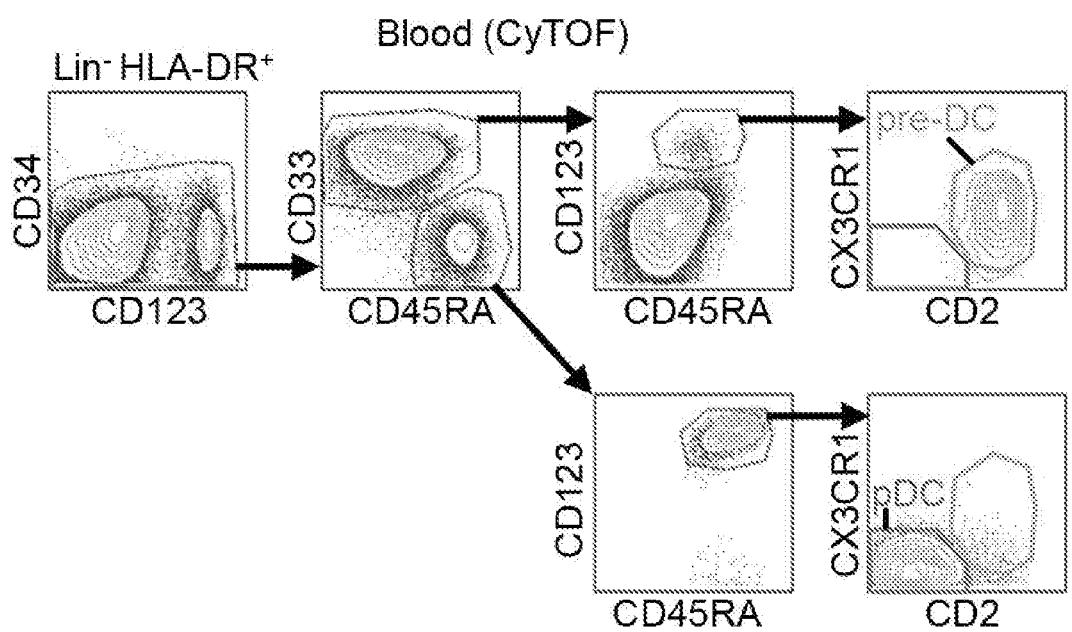

FIG. 9 (CONTINUED)
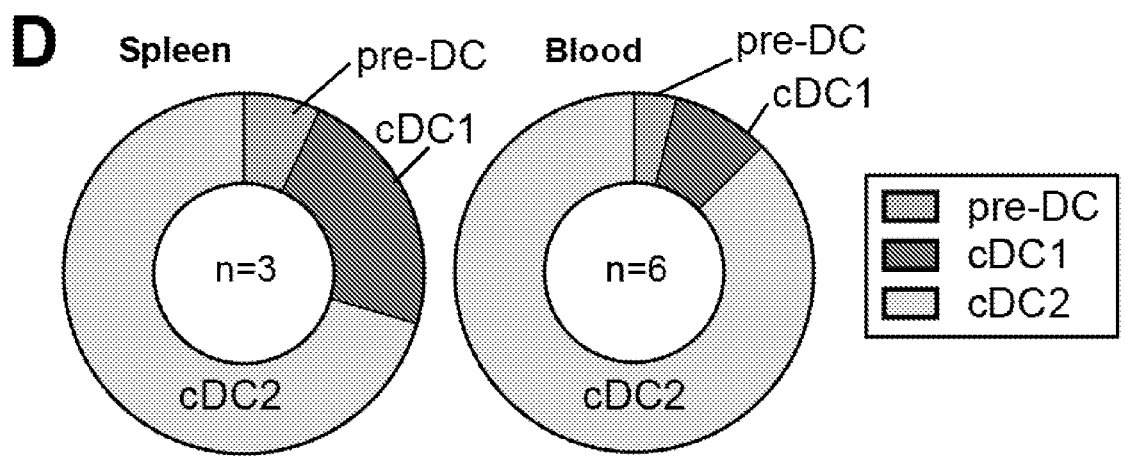
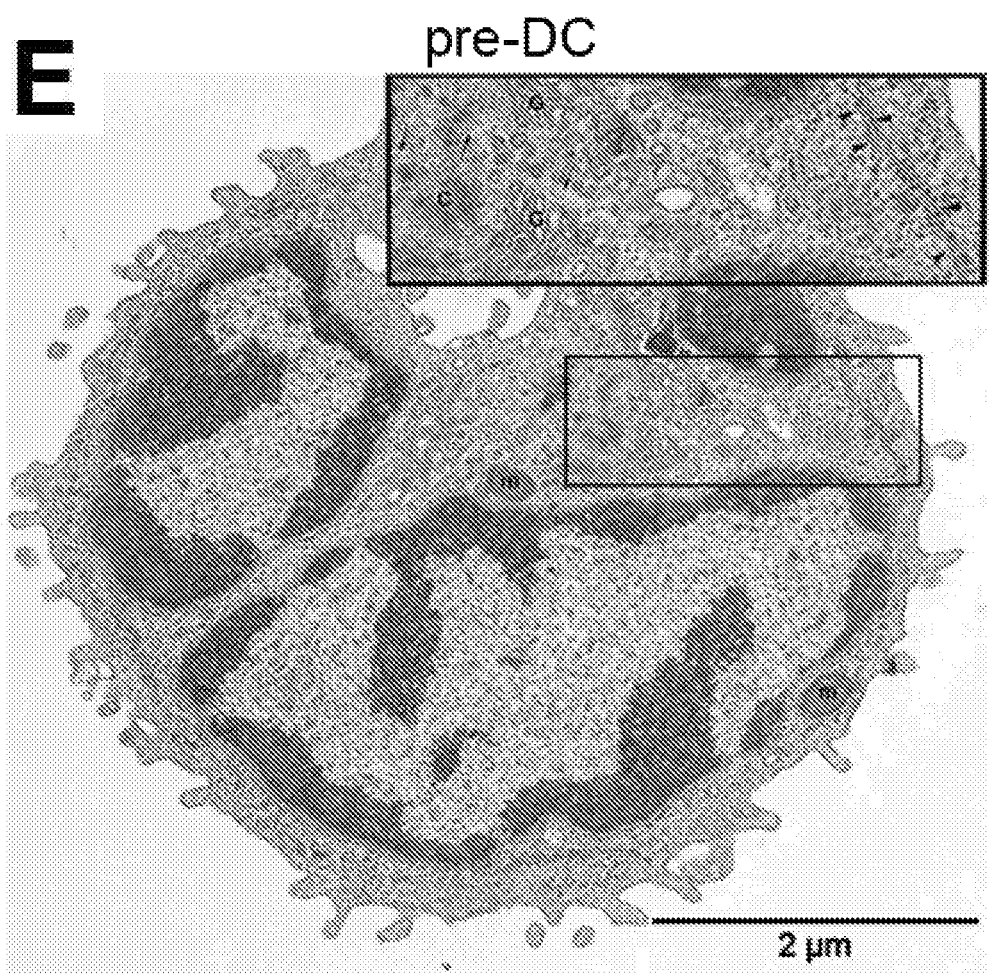

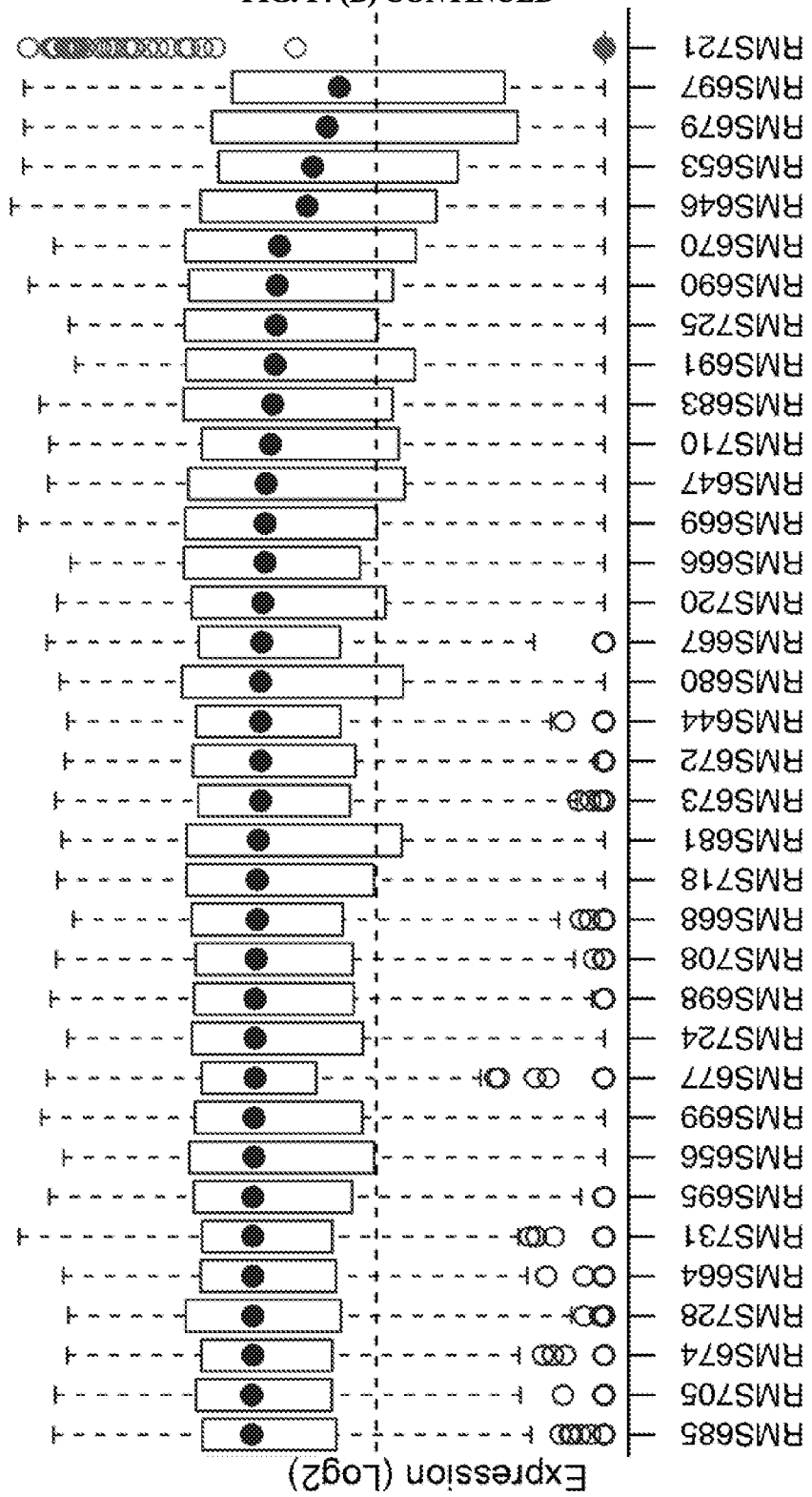
FIG. 14 (B) CONTINUED

FIG. 16 (CONTINUED)
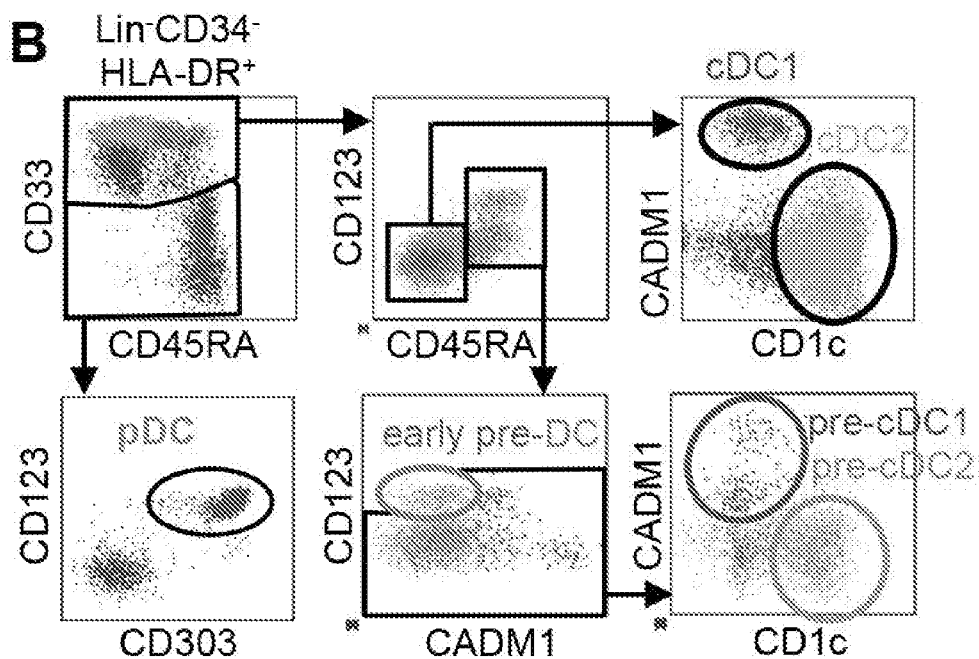
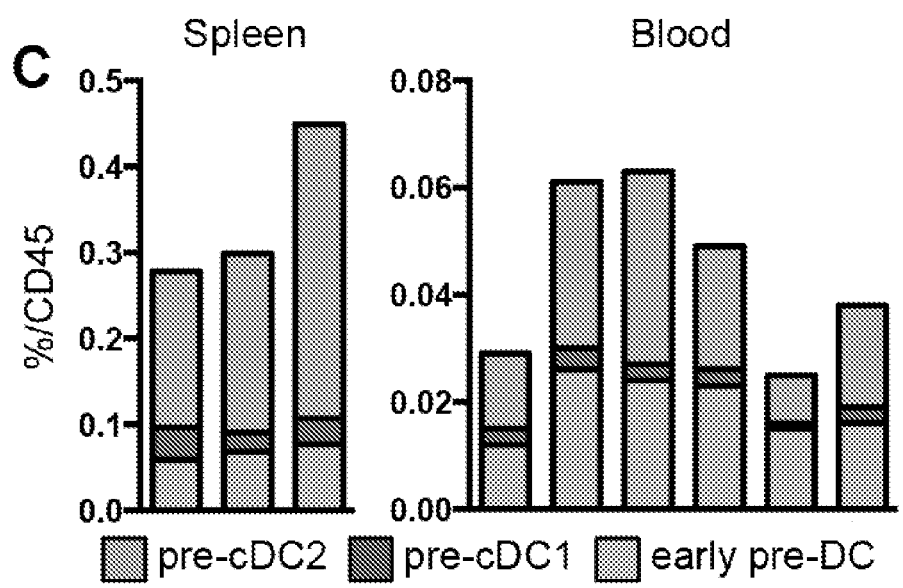

METHODS FOR THE IDENTIFICATION, TARGETING AND ISOLATION OF HUMAN DENDRITIC CELL (DC) PRECURSORS "PRE-DC" AND THEIR USES THEREOF

CROSS-REFERENCE TO RELATED APPLICATIONS

This patent application is a U.S. National Phase Application Under 35 U.S.C § 371 of International Application No. PCT/SG2017/050435, filed on Aug. 31, 2017, entitled "METHODS FOR THE IDENTIFICATION, TARGETING AND ISOLATION OF HUMAN DENDRITIC CELL (DC) PRECURSORS "PRE-DC" AND THEIR USES THEREOF," which claims the benefit of priority of Singapore Patent Application No. 10201607246S, filed on Aug. 31, 2016, and Singapore Patent Application No. 10201703621Q, filed on May 3, 2017.

TECHNICAL FIELD

The present disclosure generally relates to methods for the identification, targeting and isolation of human dendritic cell (DC) precursors "pre-DC" and their uses thereof in detecting and treatment of diseases. The disclosure provides specific markers and combinations of the markers for the identification of the pre-DC and various pre-DC subsets. The present disclosure also relates to immunogenic compositions of binding molecules specific to these markers or of the pre-DC and subsets thereof, and their uses in eliciting an immune response against diseases and cancer.

BACKGROUND

Dendritic cells (DC) are professional pathogen-sensing and antigen-presenting cells that are central to the initiation and regulation of immune responses (1). The DC cells are heterogeneous, and are capable of processing and presenting antigens to naïve T cells to initiate specific immune response. The DC population is classified into two lineages: plasmacytoid DC (pDC), and conventional DC (cDC), the latter comprising cDC1 and cDC2 sub-populations (2, 3). The DC subsets arise in a stepwise progression from DC-restricted progenitors that reside in the bone marrow. The common dendritic cell progenitors commit towards either the pDC lineage or the cDC lineage. The latter occurs through an intermediate precursor called the precursor of cDC (pre-DC).

Murine DC arise from unique DC-restricted bone-marrow (BM) progenitors known as common DC progenitors (CDP), which differentiate into pDC and DC precursors (pre-DC) and migrate out of the BM into peripheral tissues (4-6). It has been shown that: (a) pDC cultures possess cDC potential and acquire cDC-like morphology (10, 11), as recently observed in murine BM pDC (36); (b) pDC mediate Th1 immunity through production of IFNα and IL-12 (10, 37-41); (c) pDC exhibit naïve T-cell allostimulatory capacity (30, 39); and (d) pDC express co-stimulatory molecules and exhibit antigen-presentation/cross-presentation capabilities at the expense of IFNα secretion (37, 42).

Human equivalents of murine CDP and pre-DC have recently been described (8, 9). The human pre-DC comprise 0.001% of peripheral blood mononuclear cells (PBMC) and were identified by their expression of cytokine receptors that mark and drive DC differentiation in mice, including CD117 (c-Kit or Mast/stem cell growth factor receptor (SCF)), CD116 (Granulocyte-macrophage colony-stimulating factor receptor (GMCSF)), CD135 (FMS-like tyrosine kinase 3 (FLT3)) and CD123 (IL3-Ra) (9). Previous studies have observed similar receptor expression patterns within human pDC populations, which can differentiate into cDC-like cells when stimulated with IL-3 and CD40L (10, 11). Therefore, either pDC are precursors of cDC due to the detected expression of the cytokine receptors (11), or the conventionally-defined pDC population is heterogeneous, incorporating an independent pre-DC sub-population.

Dissecting the origins and differentiation pathways giving rise to DC sub-populations or subsets is necessary to understand their homeostasis and role in immune responses, and for the development of DC subset-specific therapeutic interventions.

Human pDC and pre-DC express various common markers such as CD123, CD303, CD304 and CD45RA. These markers are commonly used to identify pDC. Therefore, these markers cannot be used to also identify pre-DC or distinguish pre-DC from pDC. Conventional gating strategies used for identification of pDC are not sufficient to discriminate human pre-DC from a cell population. Moreover, DC subsets, including pre-DC, have distinct functional specializations, hence some subsets could also serve as a potential biomarker to monitor progression of disease (e.g. changes in the number of cells in a certain subset could indicate a predisposition to specific inflammation and/or infection).

Therefore there is a need to provide means for detecting, identifying and isolating the early pre-DC, pre-cDC1 and/or pre-cDC2 subsets in human to overcome or at least ameliorate, one or more of the disadvantages described above.

There is a need to provide specific biomarkers or combinations of biomarkers for detecting, identifying and isolating the early pre-DC, pre-cDC1 and/or pre-cDC2 subsets in human which can clearly distinguish the subsets from other subsets of DC, or from each other, for further subset-specific studies or uses thereof.

There is also a need to provide means for modulating diseases or improving vaccination by targeting therapeutic compounds to the early pre-DC, pre-cDC1 and/or pre-cDC2 subsets to modulate, expand or deplete the subsets.

SUMMARY

According to a first aspect, there is provided a method of detecting a precursor of conventional dendritic cell (cDC) (pre-DC), comprising determining the presence of a biomarker selected from a group consisting of CD169, CD327, AXL, CD271, CD324 and combinations thereof.

Advantageously, the method enables detection, identification and sorting of early pre-DC, pre-cDC1 and pre-cDC2, which were not possible prior to the present disclosure, allowing for a wide range of potential applications which are subset-specific. For example, it enables determination of the correlation between a specific subset (such as cell population size of a subset) with a specific disease.

According to a second aspect, there is provided a method of detecting a disease/condition, prognosis of an existing disease/condition, and/or determining the likelihood of an individual developing a disease/condition, comprising determining the number of pre-DC cells in a sample from a subject using the method as disclosed herein, and comparing the determined number of cells to the number of pre-DC cells in a control sample, wherein a higher number of pre-DC cells in the sample from the subject compared to the number of pre-DC cells in the control sample indicates the presence of, or the likelihood of developing the disease/ condition in the individual, wherein pre-DC comprises a cell selected from early pre-DC, pre-cDC1, pre-cDC2 and combinations thereof, and wherein the control sample is a sample selected from a group consisting of a sample obtained from the same patient prior to developing the disease/conditions, and a sample from a healthy individual.

According to a third aspect, there is provided a method of treating a patient determined to have a disease/condition according to the method as disclosed herein, comprising administering to said patient an antibody selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

Advantageously, the method allows for target-specific therapeutic applications.

According to a fourth aspect, there is provided a use of an antibody or an antigen-binding fragment thereof in the manufacture of a medicament for treating a patient determined to have a disease/condition according to the method as disclosed herein, wherein the antibody is selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

According to a fifth aspect, there is provided an antibody or an antigen-binding fragment thereof for use in treating a patient determined to have a disease/condition according to the method as disclosed herein, wherein the antibody is selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

According to a sixth aspect, there is provided a kit for use in the method as disclosed herein, wherein the kit comprises reagents for determining the presence of one or more biomarkers selected from the biomarkers as disclosed herein, and wherein the kit further optionally comprises instructions for use.

According to a seventh aspect, there is provided an immunogenic composition comprising: (a) one or more binding molecules specific for one or more of the biomarkers as defined herein, (b) an antigen of a target disease and/or (c) one or more cells selected from the group consisting of pre-DC, pre-cDC1, and pre-cDC2.

According to an eighth aspect, there is provided a method of eliciting an immune response against an infectious disease or cancer in a subject comprising administering the immunogenic composition as disclosed herein.

According to a ninth aspect, there is provided a method of detecting a precursor of conventional dendritic cell (cDC) (pre-DC) in a sample, wherein:
(I) the pre-DC comprises early pre-DC cells, and the method comprises the following steps in the following order:
  (i) removing dead cells from the sample;
  (ii) optionally isolating cells having a particular size, optionally 7-10 μm in diameter;
  (iii) determining the presence of a CD45 biomarker and the absence of a CD34 biomarker;
  (iv) determining the absence of CD3/19/20/14 and CD16 biomarkers;
  (v) determining the presence of HLA-DR and CD123 biomarkers;
  (vi) determining the presence of CD45RA and CD123 biomarkers; and
  (vii) determining the presence of CD169, CD327, CD271 and/or CD324;
(II) the pre-DC comprises early pre-DC cells, and the method comprises the following steps in the following order:
  (i) determining the presence of a CD45 biomarker and the absence of a CD34 biomarker;
  (ii) determining the absence of CD3/19/20/14 and CD16 biomarkers;
  (iii) determining the presence of HLA-DR and CD123 biomarkers;
  (iv) determining the presence of CD45RA and CD33 biomarkers; and
  (v) determining the presence of CD169, CD327, CD271 and/or CD324;
(III) the pre-DC comprises early pre-DC cells, and the method comprises the following steps in the following order:
  (i) determining the presence of a CD45 biomarker and the absence of a CD34 biomarker;
  (ii) determining the absence of CD3/19/20/14 and CD16 biomarkers;
  (iii) determining the presence of HLA-DR and CD123 biomarkers;
  (iv) determining the presence of CD45RA and CD33 biomarkers;
  (v) determining the presence of CD45RA biomarker;
  (vi) determining the absence of CADM1 biomarker; and
  (vii) determining the presence of CD123 biomarker and the absence of CD biomarker;
(IV) the pre-DC comprises pre-cDC1 cells, and the method comprises the following steps in the following order:
  (i) determining the presence of a CD45 biomarker and the absence of a CD34 biomarker;
  (ii) determining the absence of CD3/19/20/14 and CD16 biomarkers;
  (iii) determining the presence of HLA-DR and CD123 biomarkers;
  (iv) determining the presence of CD45RA and CD33 biomarkers; and
  (v) determining the presence of CADM1 and CD45RA biomarkers; and
(V) the pre-DC comprises pre-cDC2 cells, and the method comprises the following steps in the following order:
  (i) determining the presence of a CD45 biomarker and the absence of a CD34 biomarker;
  (ii) determining the absence of CD3/19/20/14 and CD16 biomarkers;
  (iii) determining the presence of HLA-DR and CD123 biomarkers;
  (iv) determining the presence of CD45RA and CD33 biomarkers;
  (v) determining the absence of CADM1 biomarker; and
  (vi) determining the presence of CD1c and CD45RA biomarkers.

Definition of Terms

The following words and terms used herein shall have the meaning indicated:

The term "detect", and all grammatical variations thereof such as "detecting", can refer to the determination of the presence or absence of one or more biomarkers, or quantification of one or more biomarkers, or quantification of the gene or protein expression of one or more biomarkers. Detecting a biomarker also enables identification of one or more cell types on which the biomarker(s) is present.

In the context of detecting a cell, such as a pre-DC, the term "absence" (or grammatical variants thereof) can refer to when a cell cannot be detected using a particular detection methodology. For example, pre-DC may be considered to be absent in a sample if the sample is free of pre-DC, such as, 95% free, 96% free, 97% free, 98% free, 99% free, 99.9% free, or 100% free of the pre-DC, or is undetectable as measured by the detection methodology used. Alternatively, if the level of pre-DC (such as pre-DC number, or gene or protein expression of one or more of its biomarkers) is below a previously determined cut-off level, the pre-DC may also be considered to be "absent" from the sample.

In the context of detecting a cell, such as a pre-DC, the term "presence" can refer to when a cell can be detected using a particular detection methodology. For example, if the level of pre-DC (such as pre-DC number, or gene or protein expression of one or more of its biomarkers) is above a previously determined threshold level, the pre-DC may be considered to be "present" in the sample.

The term "biomarker" refers to any biological compound, such as a protein and a fragment thereof, a peptide, a polypeptide, or other biological material whose presence, absence, level or activity is correlative of or predictive of a characteristic such as a cell type. Such specific biomarkers detectable by the methods of the present disclosure include cell surface proteins. A biomarker may be recognized, for example, by an antibody (or an antigen-binding fragment thereof) or other specific binding protein(s). Reference to a biomarker may also include its isoforms, preforms, mature forms, variants, degraded forms thereof, and metabolites thereof.

The terms "label" refers to a detectable compound or composition that is conjugated directly or indirectly to another molecule to facilitate detection of that molecule. Specific, non-limiting examples of labels include fluorescent labels (such as fluorescent tags), radioactive labels (such as radioisotopes), chemical labels (such as chemiluminescent tags), enzymatic labels, protein labels, a magnetic label and a heavy metal.

The term "treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment.

The term "patient" refers to patients of human or other mammal and includes any individual it is desired to examine or treat using the methods of the disclosure. However, it will be understood that "patient" does not imply that symptoms are present. Suitable non-human mammals that fall within the scope of the disclosure include, but are not restricted to, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes).

The term "administering" and variations of that term including "administer" and "administration", includes contacting, applying, delivering or providing a compound or composition of the disclosure to an organism, or a surface by any appropriate means.

The term "target-specific" when used in relation to therapy such as in "target-specific therapy," it is meant the administration of a compound, for example a drug (such as an antibody identified in the present disclosure), to a patient in need of therapy, that is capable of binding to a particular biological target (such as a specific subset of cell as disclosed herein) to cause a desired biological or therapeutic effect on the patient in order to treat the patient.

The word "substantially" does not exclude "completely" e.g. a composition which is "substantially free" from Y may be completely free from Y. Where necessary, the word "substantially" may be omitted from the definition of the disclosure.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF THE EMBODIMENT

In a first aspect, the present disclosure refers to a method of detecting a precursor of conventional dendritic cell (cDC) (pre-DC), comprising (i) determining the presence of a biomarker selected from a group consisting of CD169, CD327, AXL, CD271, CD324 and combinations thereof. Advantageously, the biomarkers and the combinations disclosed herein allow for clear separation of pre-DC, pDC and the cDC subsets, and thus subsequent isolation of the desired cell subsets for the desired application or uses. In one example, CD271 (NGF-R) and CD324 (E-cadherin) were found to be highly expressed in blood pre-DC, while the pDC subset expresses less of these two surface markers (see FIG. 31). This enables the detection and identification of the pre-DC cells from other subsets (such as pDC which express CD271 and CD324 at a lower level than pre-DC).

The biomarker(s) may be CD169; CD327; AXL; CD271; CD324; a combination of CD169, and CD327; a combination of CD169, and AXL; a combination of CD169, and CD271; a combination of CD169, and CD324; a combination of CD327, and AXL; a combination of CD327, and CD271; a combination of CD327, and CD324; a combination of AXL, and CD271; a combination of AXL, and CD324; a combination of CD271, and CD324; a combination of CD169, CD327, and AXL; a combination of CD169, CD327, and CD271; a combination of CD169, CD327, and CD324; a combination of CD169, AXL, and CD271; a combination of CD169, AXL, and CD324; a combination of CD169, CD271, and CD324; a combination of CD327, AXL, and CD271; a combination of CD327, AXL, and CD324; a combination of CD327, CD271, and CD324; a combination of AXL, CD271, and CD324; a combination of CD169, CD327, AXL, and CD271; a combination of CD169, CD327, AXL, and CD324; a combination of CD169, CD327, CD271, and CD324; a combination of CD169, AXL, CD271, and CD324; a combination of CD327, AXL, CD271, and CD324; or a combination of CD169, CD327, AXL, CD271, and CD324.

In one embodiment, the step (i) of the method comprises determining the presence of CD169 and AXL to detect the early pre-DC cell population within the pre-DC cell population. The method may further comprise (ii) determining for the presence of one or more biomarkers selected from a group consisting of: HLA-DR, CD123, CD45RA, CD45, CD303, CD304, CD33, CD5, CX3CR1, CD2 and combinations thereof; and (iii) determining the absence of one or more biomarkers selected from a group consisting of: CD34, CD3, CD19/CD20, CD14, CD16, and combinations thereof, prior to the detection of CD169 and AXL to detect the early pre-DC cell population. Various gating steps used in arriving at the desired early pre-DC cell population are described in the examples below.

In another embodiment, step (i) comprises determining the presence of CD169, and further comprises determining the presence of cell adhesion molecule 1 (CADM1) to detect pre-cDC1. The method may further comprise (ii) determining for the presence of one or more biomarkers selected from a group consisting of: HLA-DR, CD123, CD45RA, CD45, CD303, CD304, CD33, CX3CR1, CD2, CD5, and combinations thereof; and (iii) determining for the absence of one or more biomarkers selected from a group consisting of: CD34, CD3, CD19/CD20, CD14, CD16, CD1c, and combinations thereof, prior to the detection of CD169 and CADM1 to detect pre-cDC1. Various gating steps used in arriving at the desired early pre-cDC1 cell population are described in the examples below, for example in FIG. 28.

In another embodiment, step (i) comprises determining the presence of CD327, and further comprises determining the presence of a CD1c to detect pre-cDC2. The method may further comprise (ii) determining for the presence of one or more biomarkers selected from a group consisting of: HLA-DR, CD123, CD45RA, CD45, CD33, CX3CR1, CD2, CD5, and combinations thereof; and (iii) determining for the absence of one or more biomarkers selected from a group consisting of: CD34, CD3, CD19/CD20, CD14, CD16, CADM1, and combinations thereof, prior to the detection of CD327 and CD1c to detect pre-cDC2. Various gating steps used in arriving at the desired early pre-cDC2 cell population are described in the examples below, for example in FIG. 28.

In another embodiment, the method disclosed herein further comprises determining the level of expression of any one or more of the biomarkers that have been detected with the method described herein, wherein;

(I) (a) an increased expression level of any one or more biomarkers selected from a group consisting of CD169, CD327, AXL, CD271, CD324 and combinations thereof, or selected from a group consisting of HLA-DR, CD123, CD45RA, CD45, CD303, CD304, CD33, CD5, CX3CR1, CD2, and combinations thereof, relative to a control indicates that the cell is an early pre-DC; and/or (b) a decreased (for example non-expression or reduced expression) expression level of any one or more biomarkers selected from a group consisting of: CD34, CD3, CD19/CD20, CD14, CD16, and combinations thereof, relative to a control indicates that the cell is an early pre-DC;

or (II) (a) an increased expression level of any one or more biomarkers selected from a group consisting of CD169, CD327, AXL, CD271, CD324 and combinations thereof, or selected from a group consisting of: HLA-DR, CD123, CD45RA, CD45, CD303, CD304, CD33, CX3CR1, CD2, CD5, and combinations thereof, relative to a control indicates that the cell is a pre-cDC1; and/or (b) a decreased (for example non-expression or reduced expression) expression level of any one or more selected from a group consisting of: CD34, CD3, CD19/CD20, CD14, CD16, CD1c, and combinations thereof, relative to a control indicates that the cell is a pre-cDC1;

or (III) (a) an increased expression level of any one or more biomarkers selected from a group consisting of CD169, CD327, AXL, CD271, CD324 and combinations thereof, or selected from a group consisting of: HLA-DR, CD123, CD45RA, CD45, CD33, CX3CR1, CD2, CD5, and combinations thereof, relative to a control indicates that the cell is a pre-cDC2; and/or (b) a decreased (for example non-expression or reduced expression) expression level of any one or more biomarkers selected from a group consisting of: CD34, CD3, CD19/CD20, CD14, CD16, CADM1, and combinations thereof, relative to a control indicates that the cell is a pre-cDC2;

wherein the control comprises other cellular populations present or a pDC population that does not express CD169, CD327, AXL, CD271 and/or CD324. The other cellular populations may be cell types such as cDC1 and cDC2 and may be suitably determined by a person skilled in the art. Expression of the biomarkers may be determined based on the gene expression or protein expression levels using methods known in the art, such as but are not limited to, flow cytometry, fluorescent microscopy, immunoblotting, RNA sequencing, gene arrays, mass spectrometry, mass cytometry (Cy TOF) and PCR methods.

In one embodiment, the method further comprises determining the change in the level of expression of any one or more of the biomarkers, wherein; (a) a change in the level of expression of any one or more of the biomarkers compared to the level of expression of any one or more of the biomarkers in a control indicates that the cell is a pre-DC, pre-cDC1 or pre-cDC2; and (b) no change in the level of expression of any one or more of the biomarkers compared to the level of expression of any one or more of the biomarkers in a control indicates that the cell is not a pre-DC, pre-cDC1 or pre-cDC2, wherein the control comprises other cellular populations present or a pDC population that does not express CD169, CD327, AXL, CD271 and/or CD234. For example, a change can be a significant increase or a significant decrease in the level of expression, while no change can be a non-significant increase or non-significant decrease in the level of expression, or no detectable increase or decrease in the level of expression.

In one embodiment, the detecting in the methods disclosed herein comprises contacting a sample suspected of containing pre-DC, comprising early pre-DC, pre-cDC1 and/or pre-cDC2 cells, with one or more binding molecules specific for the biomarkers as defined herein. Non-limiting examples of the binding molecules include, but are not limited to, an antibody, an antigen-binding fragment of an antibody, an aptamer and a ligand. The term "contacting" refers to any types of contacting which a person skilled in the art would consider to be suitable for the present disclosure. With regards to the present disclosure, the contacting may refer to bringing a sample into physical association with the biomarker. Contacting can occur in vitro, in vivo or ex vivo. For example, where the sample is a fluid sample (such as a blood sample), the "contacting" may comprise mixing a solution of the binding molecule with the blood sample. For example, where the sample is a tissue sample, then the tissue may be digested using enzymatic solutions and single cell suspensions will be mixed with a solution of binding molecule.

In one embodiment, the method further comprises the step of isolating the pre-DC cells detected using the method as disclosed herein. Non-limiting examples of cell isolation techniques known in art are cell sorters, fluorescent nanodiamonds, magnetic beads and microfluidics. Any of these techniques may be used in the methods disclosed herein to isolate the subset of cells of interest.

The binding molecule may be coupled to a detectable label, such as, but not limited to a fluorescent label, a radioactive label, a chemical label, an enzymatic label, a protein label, a magnetic label and a heavy metal.

The detection of the biomarkers may be achieved using various methods used in the art, such as flow cytometry. Other non-limiting examples for detection of biomarkers are fluorescent microscopy, RNA sequencing, gene arrays, mass spectrometry and mass cytometry (Cy TOF).

Exemplary samples to which the method as disclosed herein may be applied include, but are not limited to, blood samples, tissue samples, cell samples, and bodily fluid.

The tissue samples may include bone marrow, lung, spleen, liver, heart, bone, skin, adipose tissue, dermis, intestine, urinary bladder, tendon, ligament, muscle, fascia, neurologic tissue, vessel, kidney, cartilage, sections of tissues such as biopsy and autopsy samples, frozen sections taken for histologic purposes, archival samples, explants and primary and/or transformed cell cultures derived from patient tissues and/or any other suitable tissue.

Cell samples to which the method described above may be applied include peripheral blood mononuclear cells.

The bodily fluids may be lymph fluids, cystic fluids, sputum, stool, tears, mucus, ascitic fluid, cystic fluid, urine, nipple exudates or nipple aspirates. The method as disclosed herein may also be applied to other bodily fluids.

In one embodiment, the sample is from a human subject. The human can be a healthy individual when the sample is a control sample. The human can also be a patient in need of a diagnosis or treatment, for example, a human suspected of having, or having, a disease/condition that may be detected or treated using the methods disclosed herein.

In a second aspect, there is provided a method of detecting a disease/condition, prognosis of an existing disease/condition, and/or determining the likelihood of an individual developing a disease/condition, comprising determining the number of pre-DC cells in a sample from a subject using the method as disclosed herein, and comparing the determined number of cells to the number of pre-DC cells in a control sample, wherein a higher number of pre-DC cells in the sample from the subject compared to the number of pre-DC cells in the control sample indicates the presence of, or the likelihood of developing the disease/condition in the individual, wherein pre-DC comprises a cell selected from early pre-DC, pre-cDC1, pre-cDC2 and combinations thereof. Where the method aims to detect a disease/condition, or to determine the likelihood of an individual developing a disease/condition, the control sample may be a sample obtained from a healthy individual. Where the method is for prognosis of an existing disease/condition, the control sample may be a sample obtained from the same patient (whose sample is being tested using the method) at an earlier time point, for example prior to initiation of treatment. In one example described below, in the case of Pitt-Hopkins Syndrome (PHS), the blood pDC of the patient showed marked reduction in their blood. However, pre-DC were not reduced (FIG. 2H and FIG. 13). The analysis above shows that genetic defect underlying PHS (which is TCF4 mutations) only affect pDC and not pre-DC. Thus, the different effects show that pDC and pre-DC are independent entities.

Exemplary diseases/condition in which the method as disclosed herein may be useful include, but are not limited to, an inflammatory disease, obesity (related to both inflammatory and metabolic diseases), cancer, an autoimmune disease, an infectious disease, and a metabolic disease/condition. For example, as discussed below, the progression of systemic lupus erythematosus (SLE, an autoimmune disease) was correlated to increasing pre-DC in patient blood. Increased presence of pre-DC in the lesion of SLE patients compared to the non-lesional skin sample was also observed. Since pre-DC can be inflammatory cells, the higher number of pre-DC could be a contributory factor to the severity of the disease. Therefore, pre-DC can be used as a marker for detecting autoimmune disease progression or severity.

The inflammatory disease may be selected from a group consisting of lichen planus, atopic dermatitis and psoriasis, and the autoimmune disease may be systemic lupus erythematosus. As discussed below, FIG. 38 shows the increase of pre-DC subsets in obese patients (2.8 fold higher), and patients suffering from lichen planus (1.3 fold higher), atopic dermatitis (1.4 fold higher) and psoriasis (2 fold higher) compared to healthy individuals.

The infectious disease may be selected from a group consisting of HIV and Zika, or the like. The pre-DC subset has been found to be able to enhance proliferation of naïve $CD4^+$ T cells. Therefore the pre-DC subset may be used as targets for vaccine delivery. For example, adjuvants which activate pre-DC subsets may be used to augment immune response to a vaccine for infectious diseases (comprising antigens from infectious agents) or cancer vaccine.

In a third aspect, there is provided a method for treating a patient determined to have a disease/condition according to the method disclosed herein, comprising administering to said patient an antibody selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

Exemplary diseases in which the method as disclosed herein may be useful include, but are not limited to, diseases whereby pathogenesis is caused by or is driven by pre-DC, early pre-DC, pre-cDC1, pre-cDC2, or a combination thereof, or the like. In one embodiment, the administration of said antibody causes depletion of a particular subset of cells. In one embodiment, the early pre-DC is depleted. In yet another embodiment, the pre-cDC1 is depleted. In a further embodiment, the pre-cDC2 is depleted. In yet another embodiment, two or more, or all of the pre-DC, early-pre-DC, pre-cDC1 and pre-cDC2, are depleted. As shown in FIG. 34, pre-DC cells are susceptible to HIV-1 infection. Therefore, as an example, a target-specific therapy to specifically decrease the infected subset (in this case, the pre-DC subset) can be achieved using the pre-DC biomarkers identified in the present disclosure. As another example, a target-specific therapy can also be delivery of specific therapeutic compounds or drugs to a specific subset of cell population for example, pretreatment with anti-CD169 was shown to induce a decrease of HIV-1 infection of pre-DC, especially for X4 virus (see FIG. 36). For vaccination, an antigen may be (i) specifically targeted to a subset of cell population which is a target for an infectious disease or (ii) to deliver the vaccine antigen to the relevant antigen presenting cells (i.e. pre-DC) to more effectively induce an immune response. The general aim of the target-specific therapy is to deplete, mobilize and/or modulate the specific cell populations.

In a fourth aspect, there is provided use of an antibody or an antigen-binding fragment thereof in the manufacture of a medicament for treating a patient determined to have a disease/condition according to the method as disclosed herein, wherein the antibody or an antigen-binding fragment thereof is selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

In a fifth aspect, there is provided an antibody or an antigen-binding fragment thereof for use in treating a patient determined to have a disease/condition according to the method as disclosed herein, wherein the antibody or an antigen-binding fragment thereof is selected from a group consisting of an anti-CD169 antibody or an antigen-binding fragment thereof, an anti-CD327 antibody or an antigen-binding fragment thereof, an anti-AXL antibody or an antigen-binding fragment thereof, an anti-CD271 antibody or an antigen-binding fragment thereof, an anti-CD324 antibody or an antigen-binding fragment thereof, and combinations thereof.

In a sixth aspect, there is provided a kit for use in the method as disclosed herein, wherein the kit comprises reagents for determining the presence of one or more biomarkers selected from the biomarkers as disclosed herein, and wherein the kit further optionally comprises instructions for use. Other components of a kit may include, but are not limited to, one or more of the biomarkers described above in the form of an antibody or an antigen-binding fragment thereof, one or more buffers, and one or more diluents.

In a seventh aspect, there is provided an immunogenic composition comprising: (a) one or more binding molecules specific for one or more of the biomarkers disclosed herein, (b) an antigen of a target disease and/or (c) one or more cells selected from the group consisting of early pre-DC, pre0cDC1, and pre-cDC2 detected using the methods disclosed herein. Examples of target disease include, but are not limited to, infectious diseases, and cancer. In one embodiment, the one or more binding molecules are selected from a group consisting of an antibody, an antigen binding fragment of an antibody and a ligand. In another embodiment, the immunogenic composition further comprises an adjuvant, a preservative, a stabilizer, an encapsulating agent and/or a pharmaceutically acceptable carrier. Exemplary adjuvants which may be useful include, but are not limited to (a) aluminum hydroxide, (b) aluminum phosphate, (c) gamma inulin, (d) algammulin (a combination of aluminum hydroxide and gamma inulin), (e) cholecalciferol in oil, (0 an oil in water emulsion OWEM1, containing squalene, tween-80, Span-85 in 10 mM phosphate-citrate buffer, (0 oil in water emulsion OWEM2 containing squalene, tween-80, Span-85, alpha tocopherol in phosphate-citrate buffer, and (g) an oil in water emulsion OWEM3 containing squalene, tween-80, Span-85, cholecalciferol in phosphate-citrate buffer, or the like.

In one embodiment, the immunogenic composition comprises: (a) binding molecules (e.g. mAb, scFv, aptamers) directed against pre-DC markers for targeting of preDCs, pre-cDC1, and/or pre-cDC2, (b) a specific antigen derived from an infectious agent or cancer for generation of immune response for the purpose of vaccination against the disease, (c) an adjuvant, and/or (d) an encapsulating agent to prevent the dispersal or degradation of antigen prior to delivery to pre-DC (e.g. lipid membranes, chitosan particles, biocompatible polymers).

In an eighth aspect, there is provided a method of eliciting an immune response against an infectious disease or cancer in a subject comprising administering the immunogenic composition as described above. Exemplary infectious diseases which may be targeted include, but are not limited to HIV, Zika, Chikungunya, hepatitis A, hepatitis B, hepatitis C, viral hemorrhagic fevers, pox virus infections and mosquito-borne encephalitis viruses, or the like. Examples of viral hemorrhagic fevers may be, but are not limited to, dengue and Ebola, or the like. In one embodiment, the immunogenic composition is to be administered by a route selected from a group consisting of intramuscular, intradermal, subcutaneous, intravenous, oral, and intranasal administration. Exemplary cancers may be acute and chronic leukaemia (such as acute lymphatic leukaemia, acute lymphocytic leukaemia, acute myeloid leukaemia, chronic lymphatic leukaemia, chronic lymphocytic leukaemia, and chronic myeloid leukaemia), bone tumors (such as osteosarcoma), all types of glioma (such as oligodendroglioma and glioblastoma), breast cancer, colon cancer, lung cancer, prostate cancer, and stomach cancer.

In a ninth aspect, there is provided a method of detecting a precursor of conventional dendritic cell (cDC) (pre-DC) in a sample, wherein:

(I) the pre-DC comprises early pre-DC cells, and the method comprises the following steps in the following order:
(i) removing dead cells from the sample;
(ii) optionally isolating cells having a particular size, optionally 7-10 μm in diameter;
(iii) determining the presence of a CD45 biomarker and the absence of a CD34 biomarker;
(iv) determining the absence of CD3/19/20/14 and CD16 biomarkers;
(v) determining the presence of HLA-DR and CD123 biomarkers;
(vi) determining the presence of CD45RA and CD123 biomarkers; and
(vii) determining the presence of CD169, CD327, CD271 and/or CD324;

(II) the pre-DC comprises early pre-DC cells, and the method comprises the following steps in the following order:
(i) determining the presence of a CD45 biomarker and the absence of a CD34 biomarker;
(ii) determining the absence of CD3/19/20/14 and CD16 biomarkers;
(iii) determining the presence of HLA-DR and CD123 biomarkers;
(iv) determining the presence of CD45RA and CD33 biomarkers; and
(v) determining the presence of CD169, CD327, CD271 and/or CD324;

(III) the pre-DC comprises early pre-DC cells, and the method comprises the following steps in the following order:
(i) determining the presence of a CD45 biomarker and the absence of a CD34 biomarker;
(ii) determining the absence of CD3/19/20/14 and CD16 biomarkers;
(iii) determining the presence of HLA-DR and CD123 biomarkers;
(iv) determining the presence of CD45RA and CD33 biomarkers;
(v) determining the presence of CD45RA biomarker;
(vi) determining the absence of CADM1 biomarker; and
(vii) determining the presence of CD123 biomarker and the absence of CD1c biomarker;

(IV) the pre-DC comprises pre-cDC1 cells, and the method comprises the following steps in the following order:
(i) determining the presence of a CD45 biomarker and the absence of a CD34 biomarker;
(ii) determining the absence of CD3/19/20/14 and CD16 biomarkers;
(iii) determining the presence of HLA-DR and CD123 biomarkers;
(iv) determining the presence of CD45RA and CD33 biomarkers; and
(v) determining the presence of CADM1 and CD45RA biomarkers;
and (V) the pre-DC comprises pre-cDC2 cells, and the method comprises the following steps in the following order:
(i) determining the presence of a CD45 biomarker and the absence of a CD34 biomarker;
(ii) determining the absence of CD3/19/20/14 and CD16 biomarkers;
(iii) determining the presence of HLA-DR and CD123 biomarkers;
(iv) determining the presence of CD45RA and CD33 biomarkers;
(v) determining the absence of CADM1 biomarker; and
(vi) determining the presence of CD1c and CD45RA biomarkers.

The removal of dead cells which tend to bind non-specifically to many reagents, in the initial step of the method described above may advantageously increase accuracy of detection. The step of specifically isolating cells of a particular size may also increase the specificity of the method described above for targeting the desired population.

BRIEF DESCRIPTION OF THE DRAWINGS

The disclosure will be better understood with reference to the detailed description when considered in conjunction with the non-limiting examples and the accompanying drawings, in which.

2A in the blood (upper panels) and spleen (lower panels). (D) Ring graphical representation of the proportion of pre-DC, cDC1 and cDC2 among total Lin$^-$ CD34$^-$HLA-DR$^+$CD33$^+$cDC defined in FIG. 2A in the spleen (left) and blood (right). (E) Representative electron micrographs showing morphological characteristics of a pre-DC. (F) Histograms of the mean relative numbers of CD123$^+$CD172α$^-$ cells, Clec9A$^+$CADM1$^+$cDC1 or CD172α$^+$CD1c$^+$cDC2 from the in vitro differentiation assays as described in FIG. 2F (n=4). Error bars represent mean±SEM.

Figure 10:
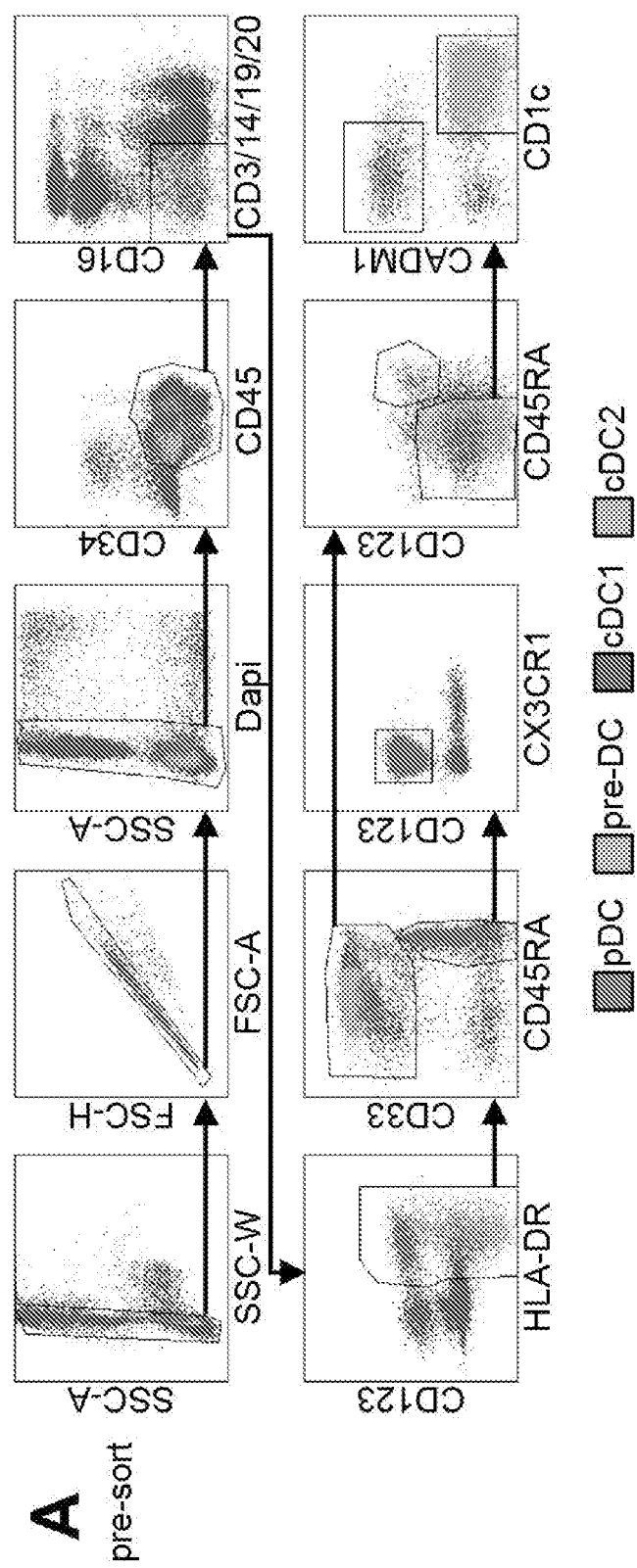
Figure 10:
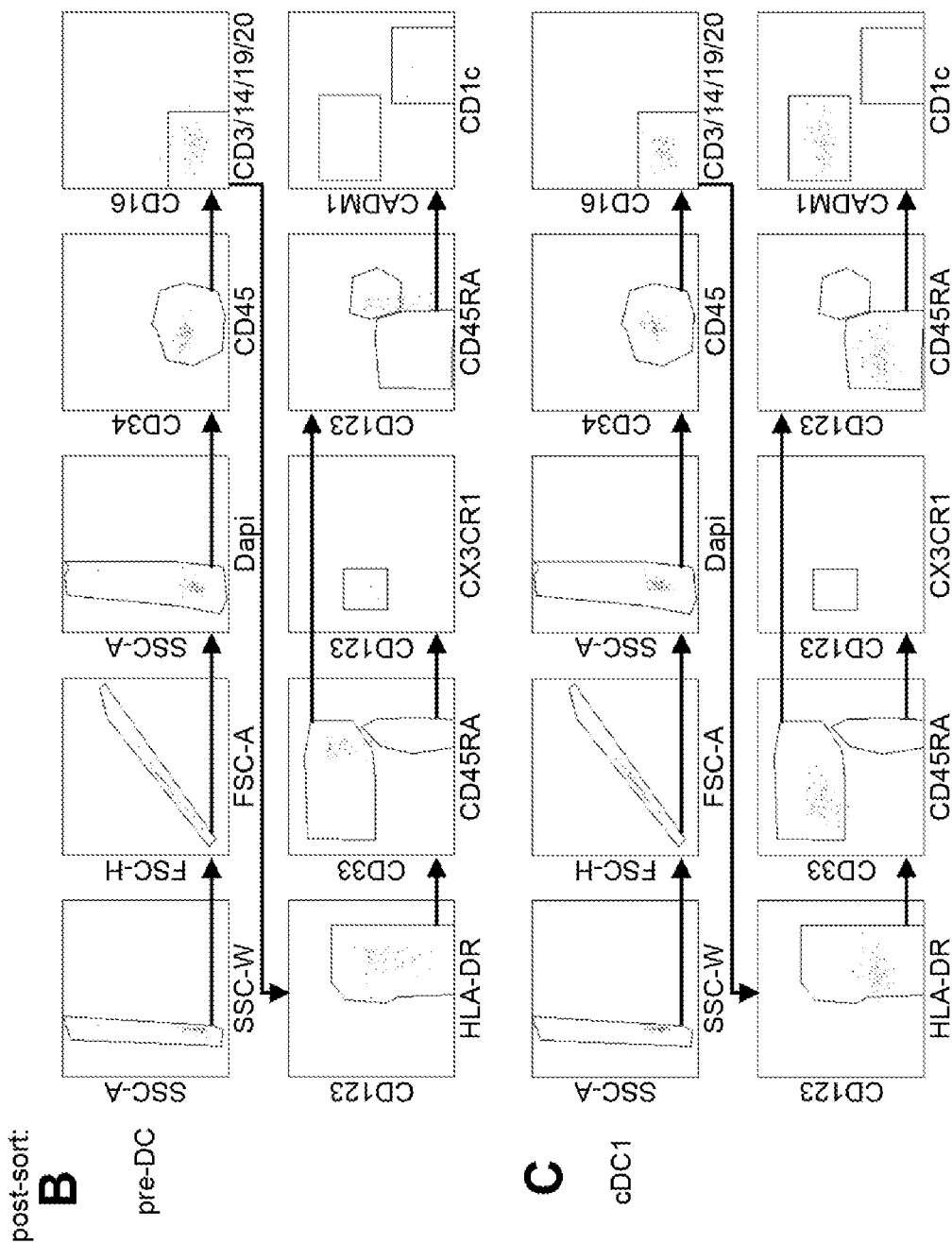
Figure 10:
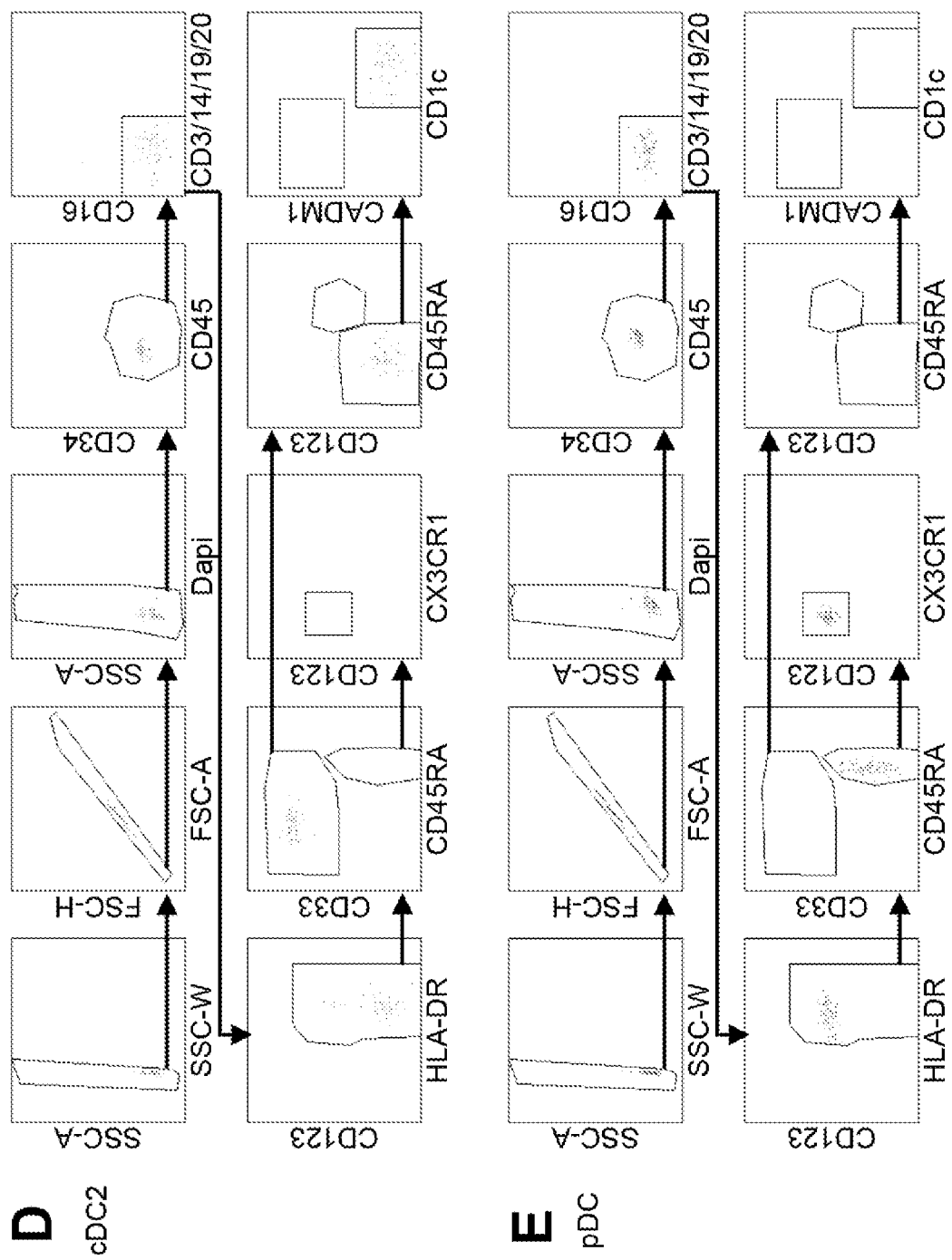

FIG. 10. Gating strategy for the fluorescence-activated cell sorting of DC subsets and pre-DC used in the in vitro differentiation assays (FIG. 2F). (A) Pre-sorted data and B-D. post-sorted re-analysis of (B) pre-DC, (C) cDC1, (D) cDC2, and (E) pDC.

Figure 11:
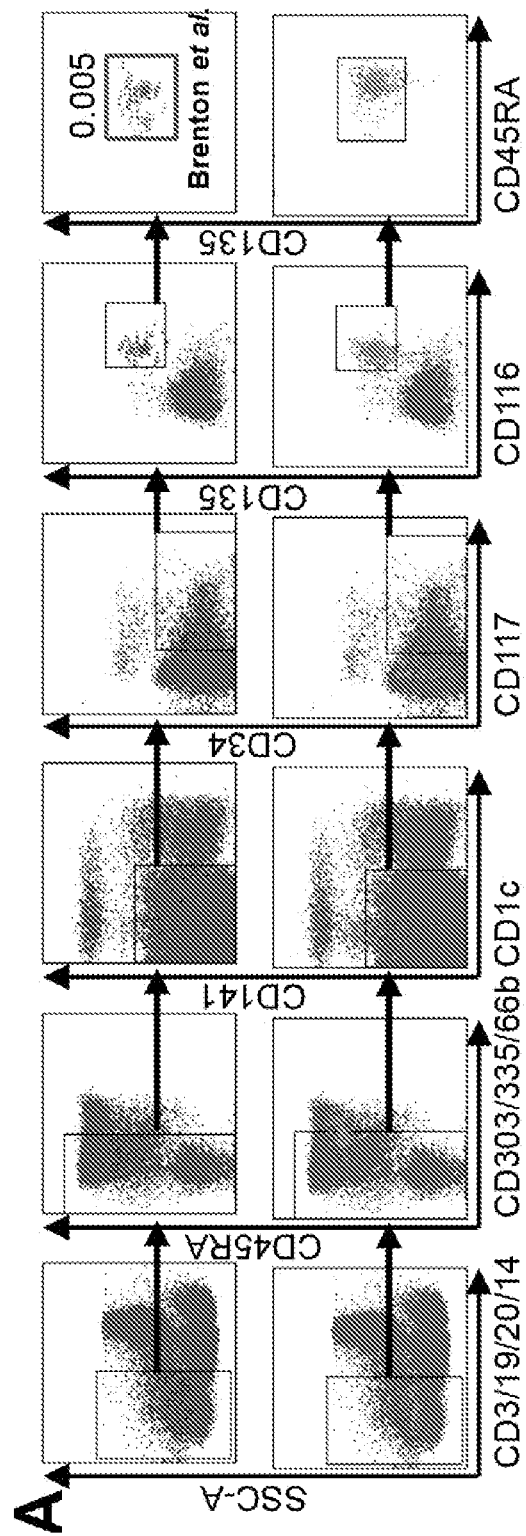
Figure 11:
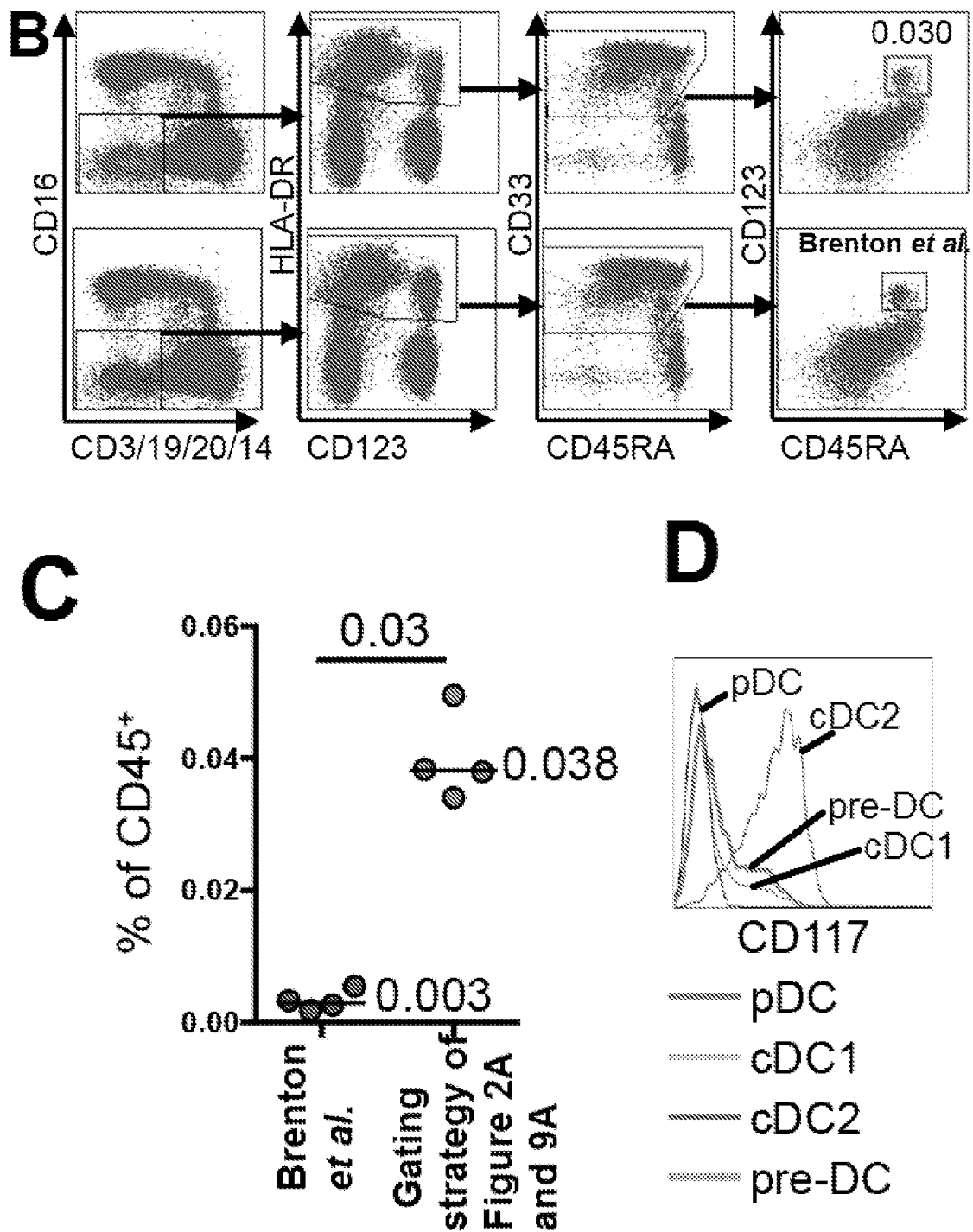
Figure 11:
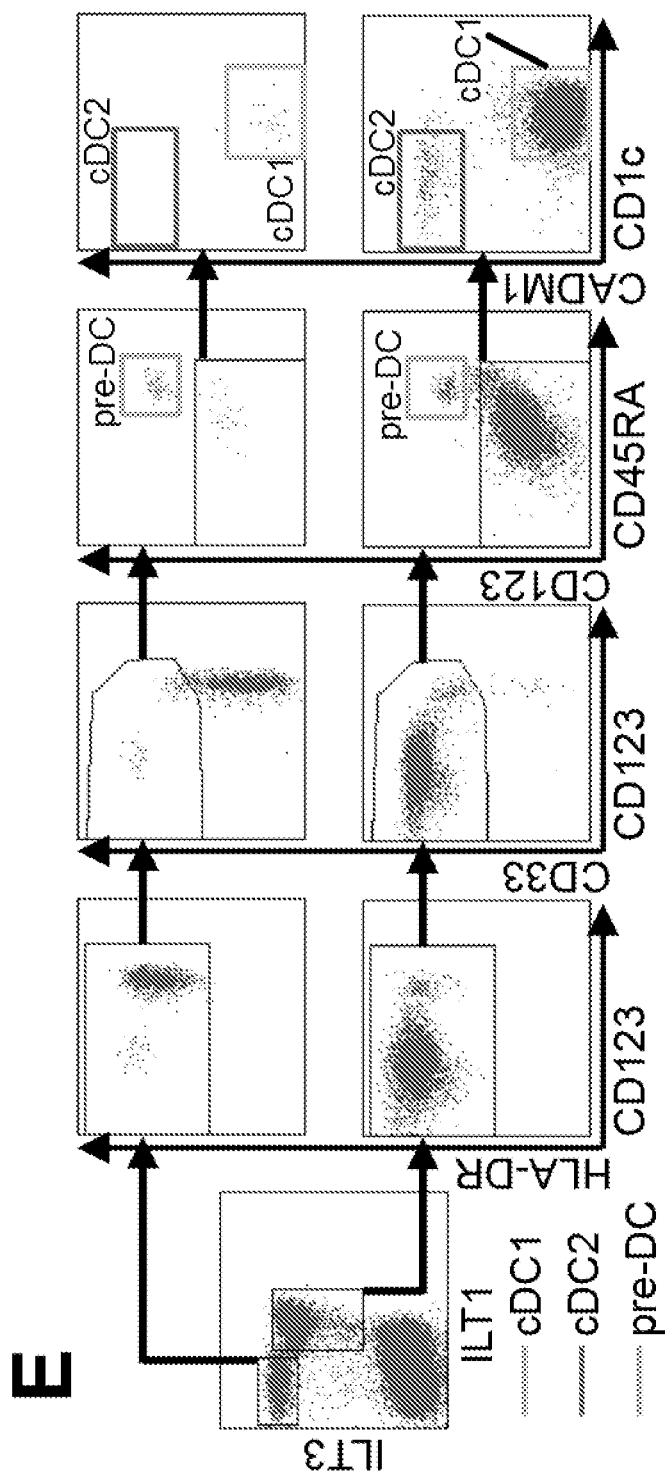
Figure 11:
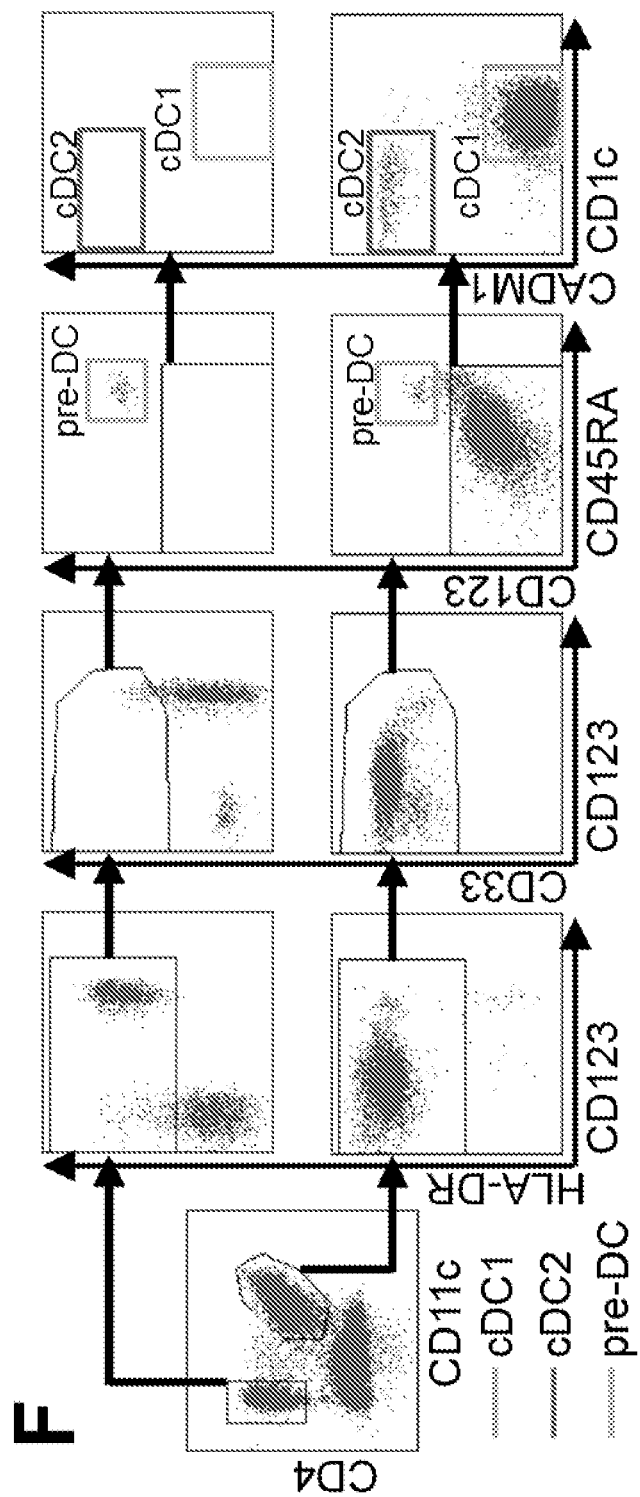

FIG. 11. (A)-(C) Comparison of (A) the gating strategy from Breton et al. (9) pre-DC are shown in green) and (B) the gating strategy used in FIG. 2A and FIG. 9A (pre-DC displayed in purple) to define pre-DC. The relative numbers of pre-DC defined using the two gating strategies among live CD45$^+$ peripheral blood mononuclear cells are indicated in the dot plots. (C) Graphical representation of the median relative numbers of pre-DC defined using the two gating strategies among live CD45$^+$ blood mononuclear cells (n=4). The median percentages of CD45$^+$ values are indicated. P-values were calculated using the Mann-Whitney test. (D) Histogram showing the expression of CD117 by DC subsets and pre-DC determined by flow cytometry. (E)-(F) Identification of pre-DC (purple gate), cDC1 (red gate) and cDC2 (beige gate) among Lin$^-$HLA-DR$^+$ (E) ILT3$^+$ ILT1$^-$ cells (10) or ILT3$^+$ ILT1$^+$ (cDC), and (F) CD4$^+$CD11c$^-$ cells (11) or CD4$^{int}$ CD11c$^+$cDC.

Figure 12:
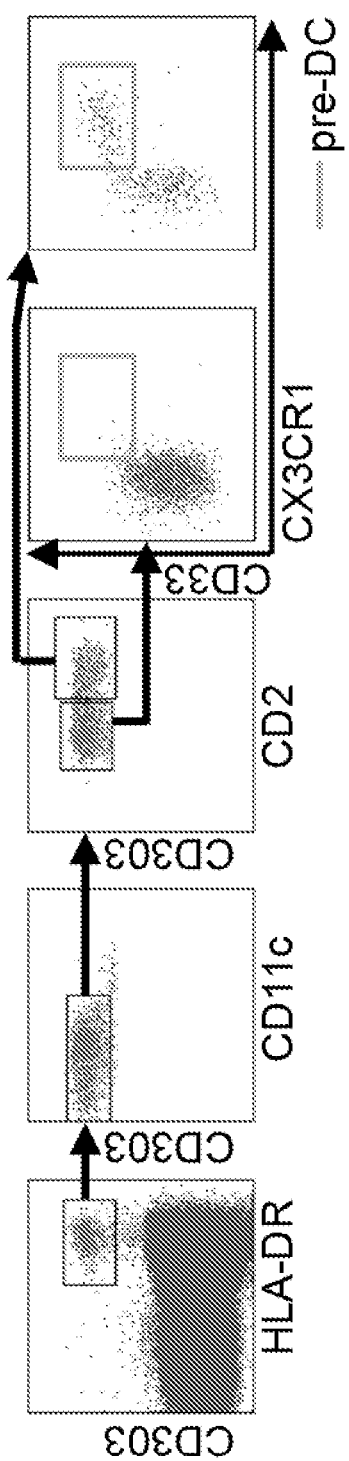

FIG. 12. Identification of CD33$^+$CX3CR1$^+$ pre-DC among Lin$^-$HLA-DR$^+$CD303$^+$CD2$^+$ cells (33).

Figure 13:
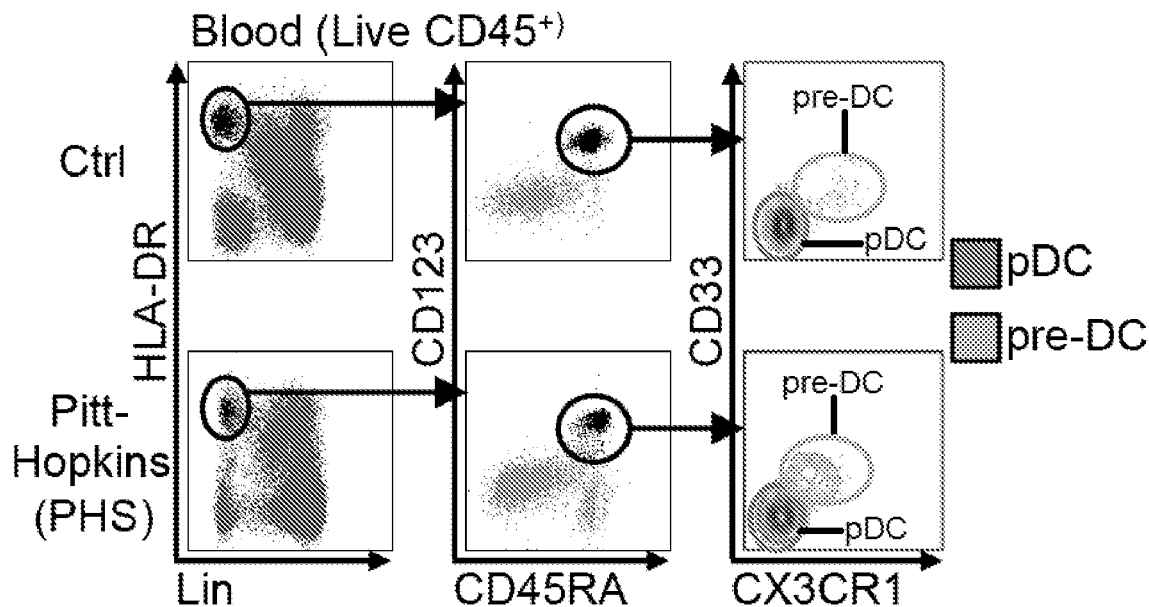

FIG. 13. Gating strategy for the fluorescence-activated cell sorting analysis of peripheral blood mononuclear cells from control subjects (Ctrl, n=11) and patients with Pitt-Hopkins Syndrome (PHS; n=4). pDC (circled in blue) and pre-DC (circled in purple) were defined among Lin-HLA-DR+CD45RA+CD123+ cells.

Figure 3:
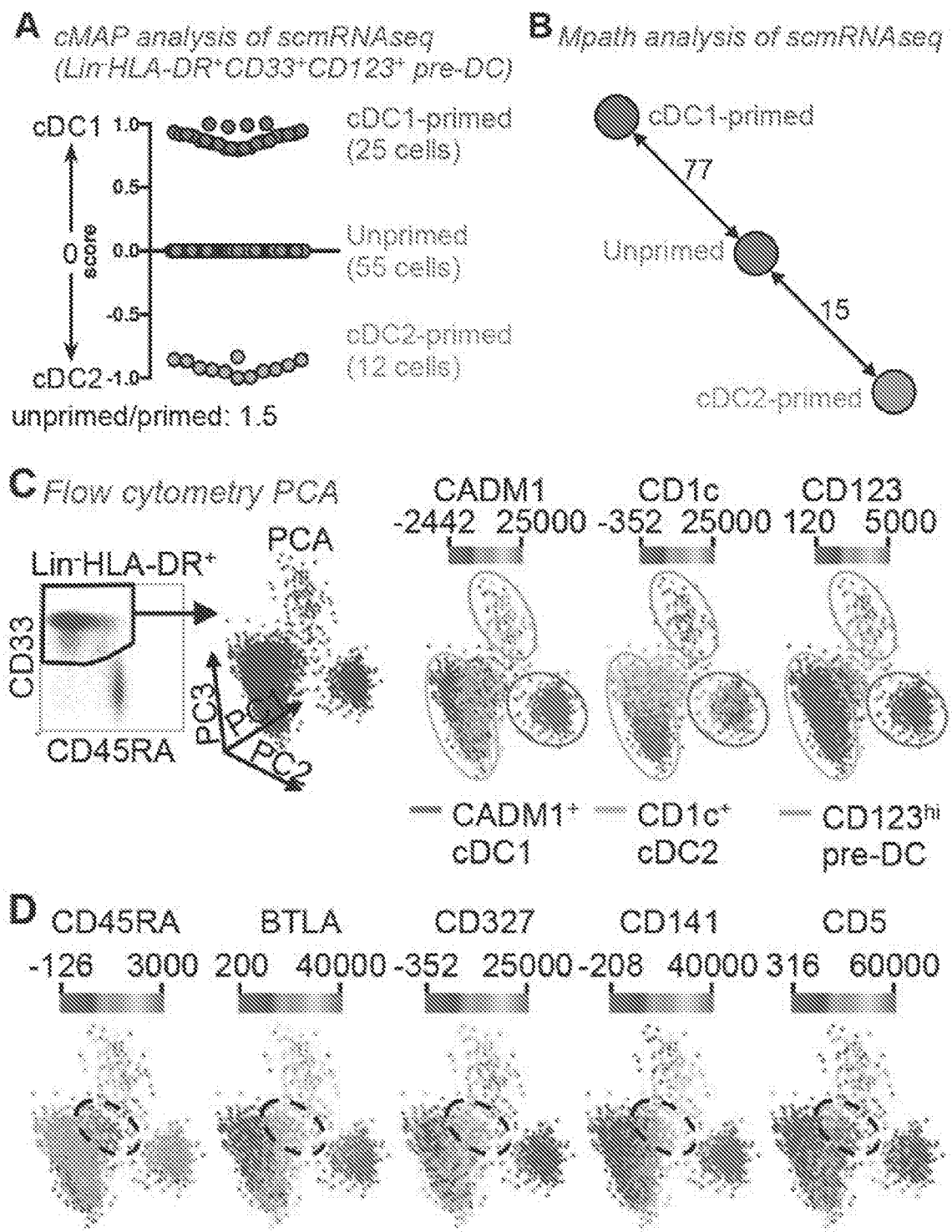
FIG. 3. Identification of committed human pre-DC subsets. (A-B) Single-cell mRNA sequencing (scmRNAseq) of 92 Lin(CD3/14/16/19/20)$^-$HLA-DR$^+$CD33$^+$CD123$^+$ cells (sort gating strategy in FIG. 12A). (A) Connectivity MAP (cMAP) enrichment score of cells (cDC1- vs cDC2-specific signatures). (B) Mpath analysis showing the developmental relationship between "unprimed", cDC1-primed or cDC2-primed cells defined in (A). (C) Lin⁻HLA-DR⁺CD33⁺ PBMC analyzed by flow cytometry and visualized as 3D-PCA of three cell clusters (pre-DC, cDC1 and cDC2) and the relative expression of CADM1, CD1c and CD123. (D) Relative expression of CD45RA, BTLA, CD327, CD141 and CD5 in the same 3D-PCA plot. The dashed black circles indicate the intermediate CD45RA⁺ population. (E) CD45RA/CD123 dot plots showing overlaid cell subsets defined in the 3D-PCA plot (left panel) with the relative expression of BTLA, CD327, CD141 and CD5. (F) Overlay of the Wanderlust dimension (progression from early (dark) to late (clear) events is shown) onto the 3D-PCA and CD45RA/CD123 dot plots. (G) Gating strategy starting from live CD45⁺Lin(CD3/14/16/19/20)⁻CD34⁻HLA-DR⁺ PBMC to define pre-DC subsets among CD33⁺CD45RA⁺ cDC. (H) Pre-DC subsets were co-cultured for 5 days with MS-5 feeder-cells, FLT3L, GM-CSF and SCF (n=3). Their capacity to differentiate into Clec9A⁺CADM1⁺cDC1 (red), or CD1c⁺CD11c⁺cDC2 (beige) was analyzed by flow cytometry. (I) Scanning electron microscopy of pre-DC and DC subsets (scale bar: 1 μm).
Figure 3:
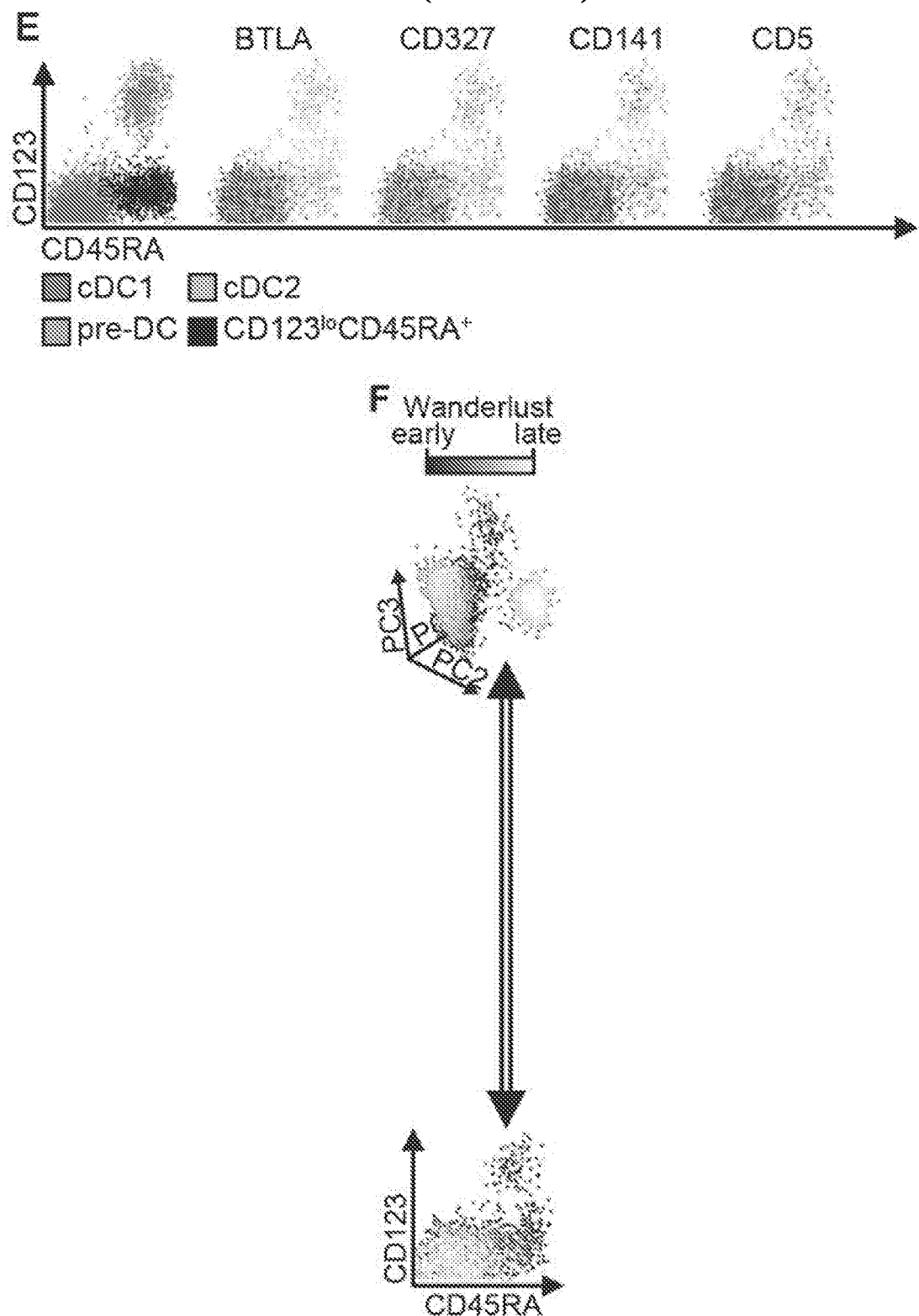
Figure 3:
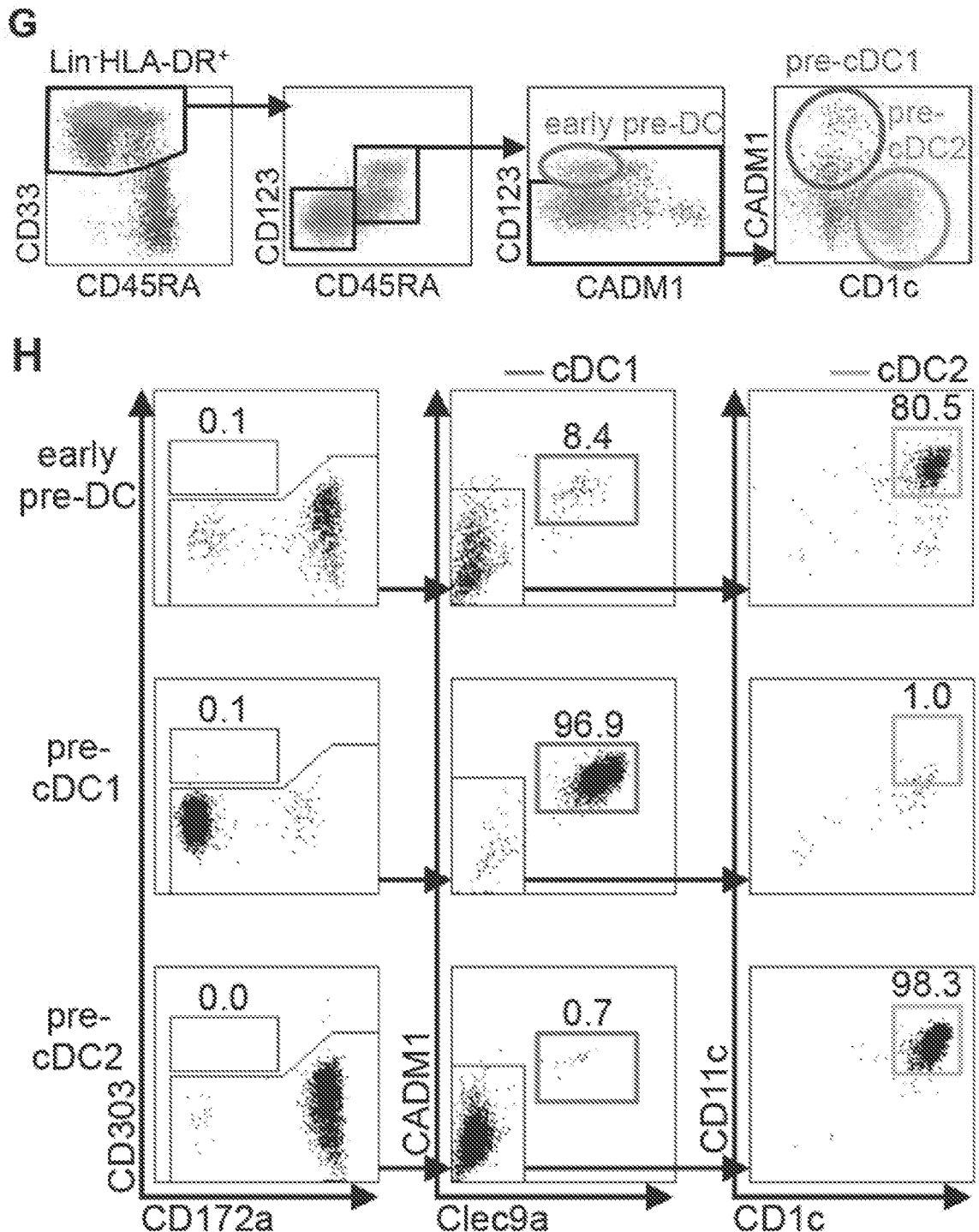
Figure 3:
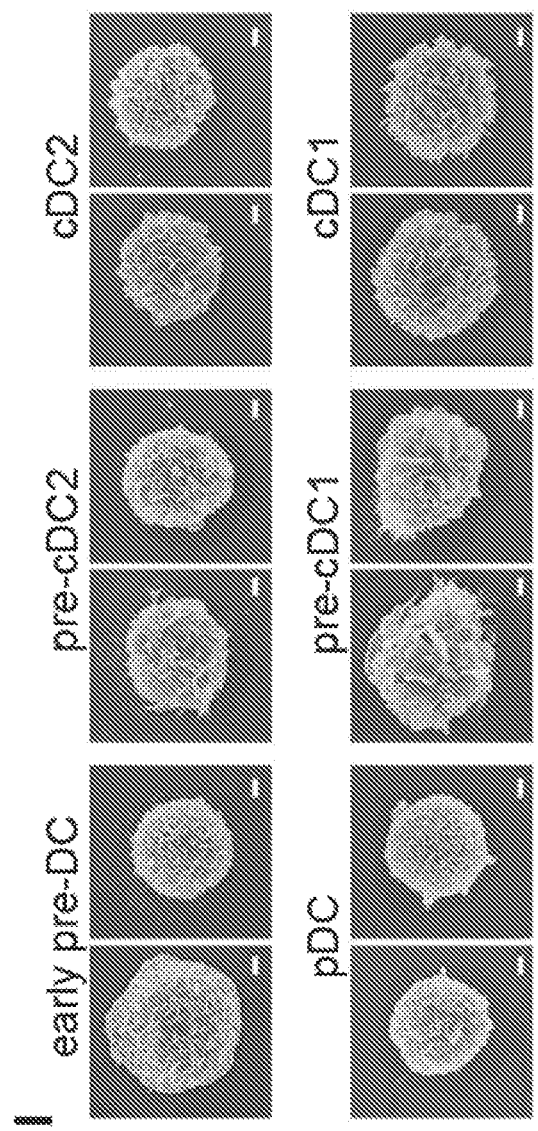
Figure 14:
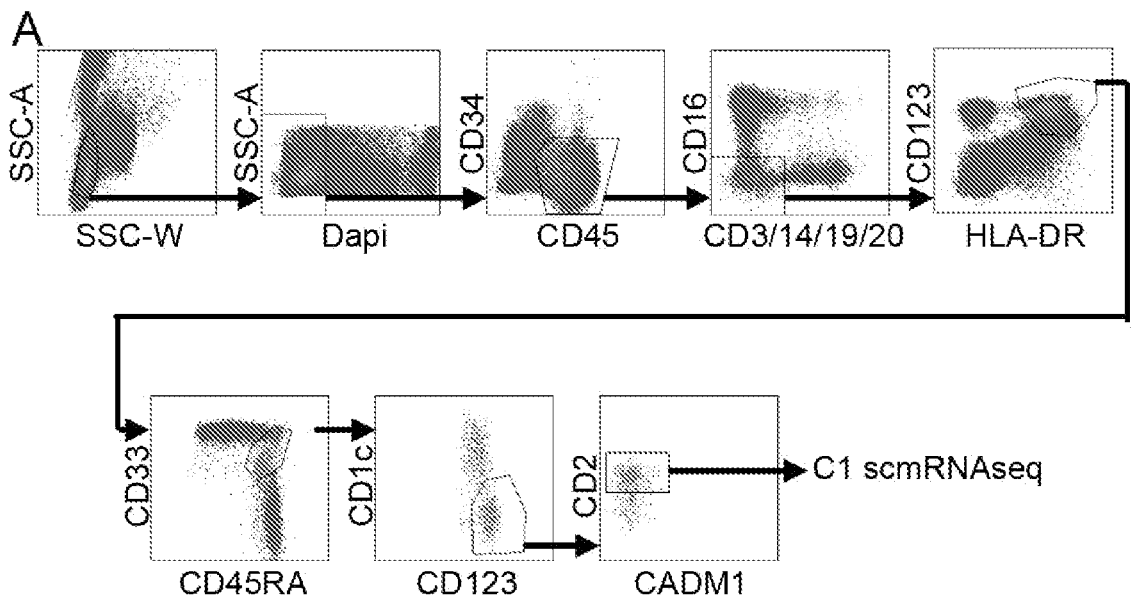
Figure 14:
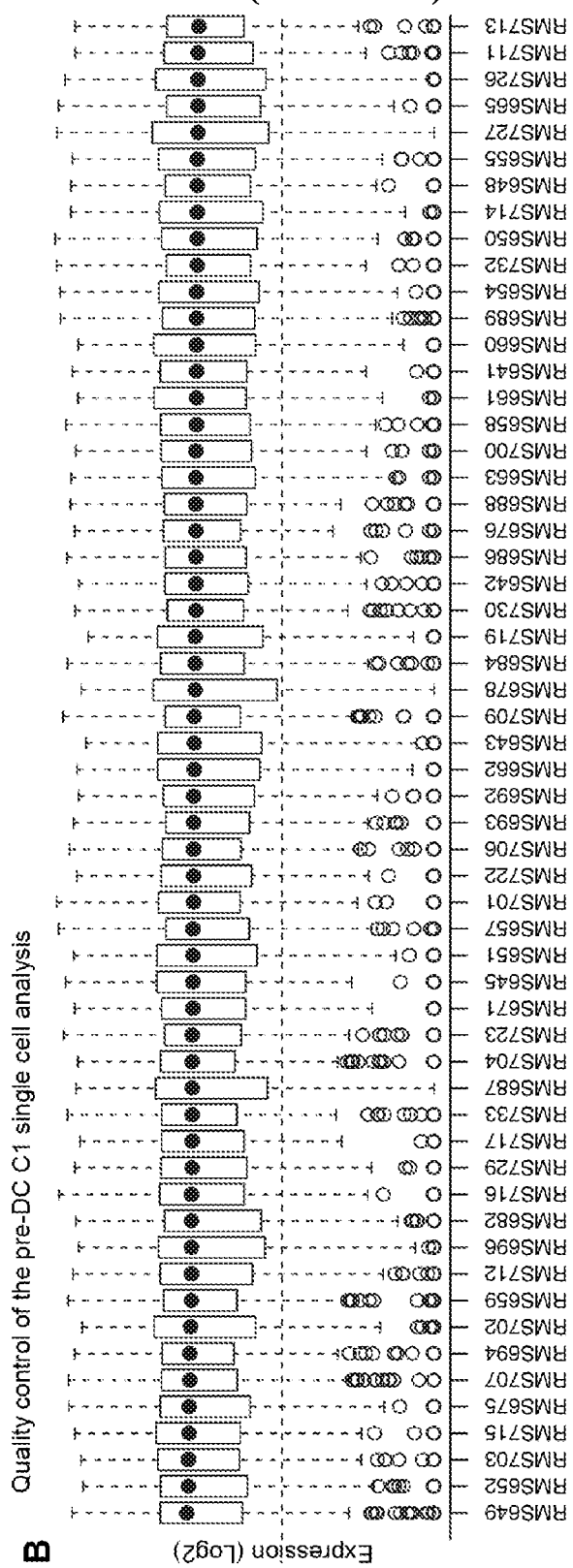
Figure 14:
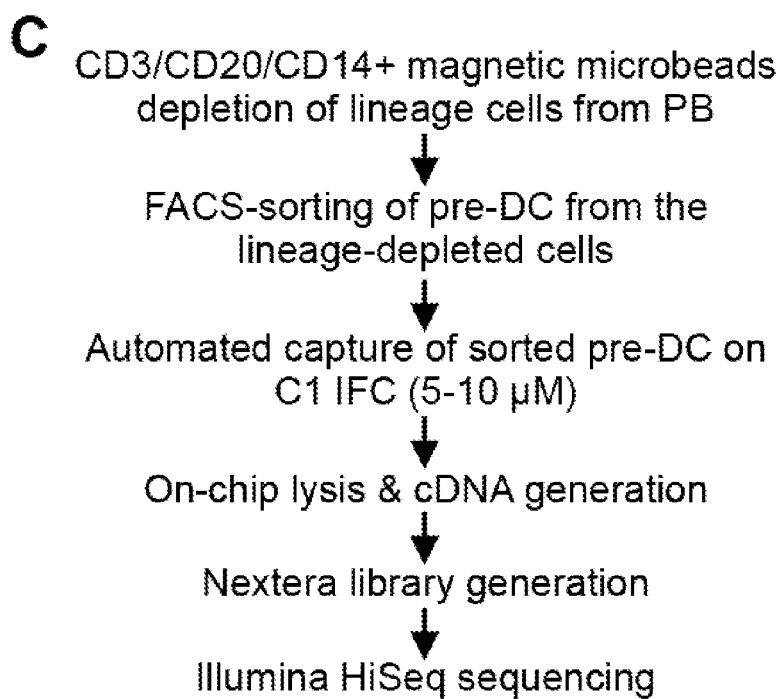

FIG. 14. (A) Gating strategy for FACS of Lin$^-$HLA-DR$^+$CD33$^+$CD45RA$^+$CD1c$^{lo/-}$CD2$^+$CADM1$^{lo/-}$CD123$^+$ pre-DC analyzed by C1 single cell mRNA sequencing (scmR-NAseq). (B) Quality control (removing low-quality cells and minimally-expressed genes below the limits of accurate detection; low-quality cells that were identified using SIN-GuLAR toolbox; minimally-expressed genes with transcripts per million (TPM) values≥1 in <95% of the cells) and (C) work flow of the C1 scmRNAseq analyses shown in FIG. 3A-B. Error bars represent the maximum, third quartile, median, first quartile and minimum.

Figure 15:
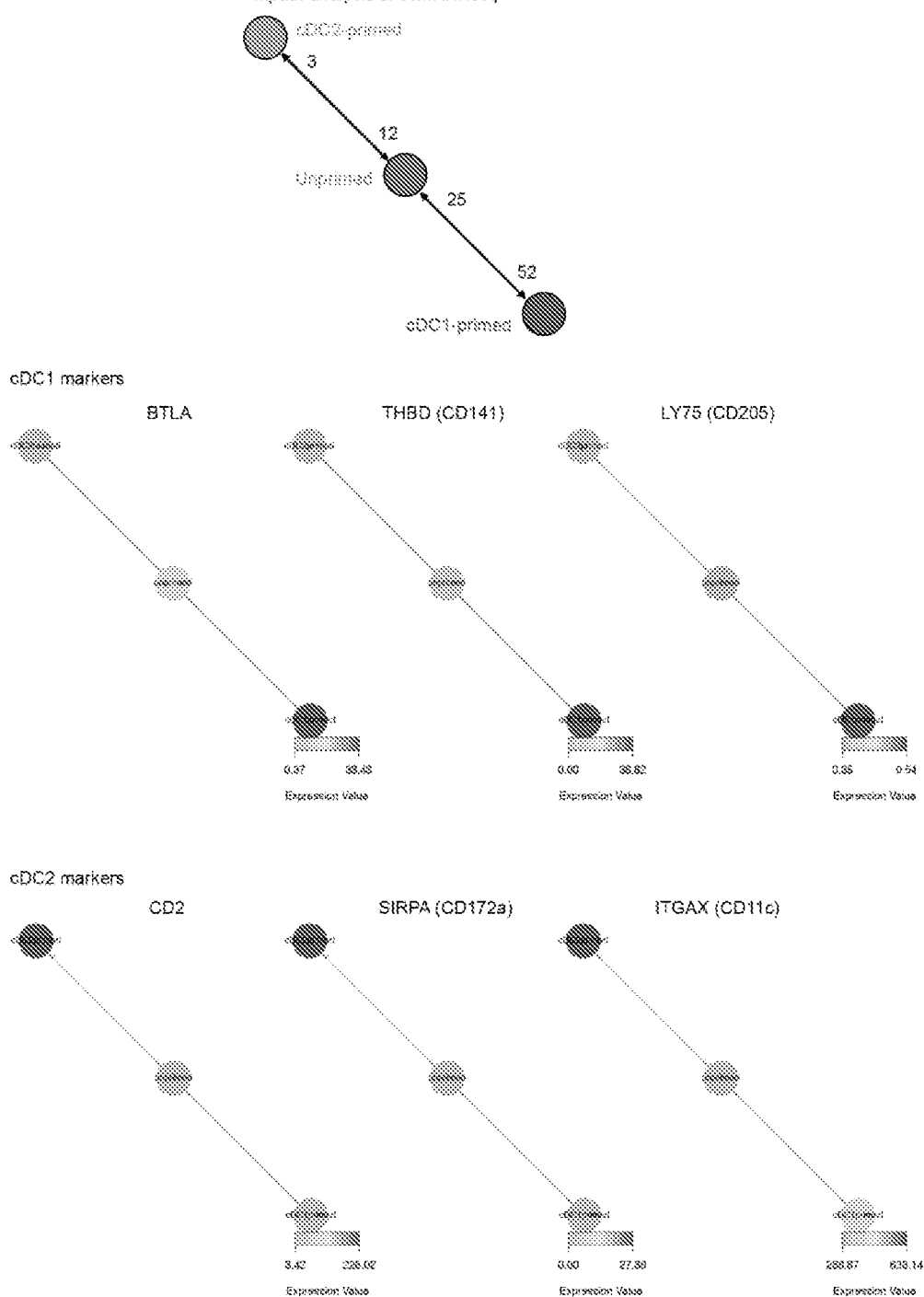

FIG. 15. Relative expression levels of signature genes of cDC1 (BTLA, THBD and, LY75) and cDC2 (CD2, SIRPA and ITGAX) in Mpath clusters defined in FIG. 3B.

Figure 16:
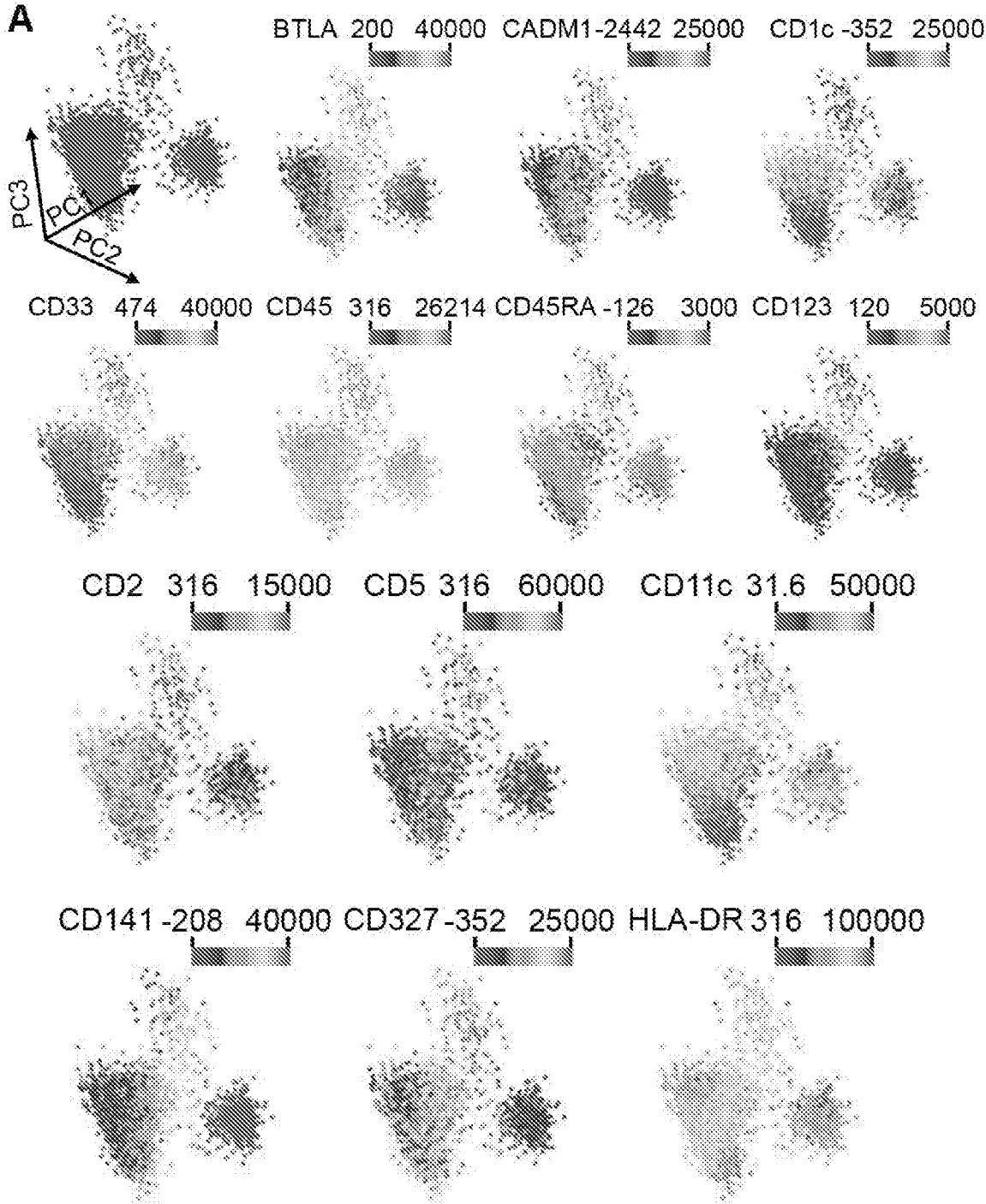
Figure 16:
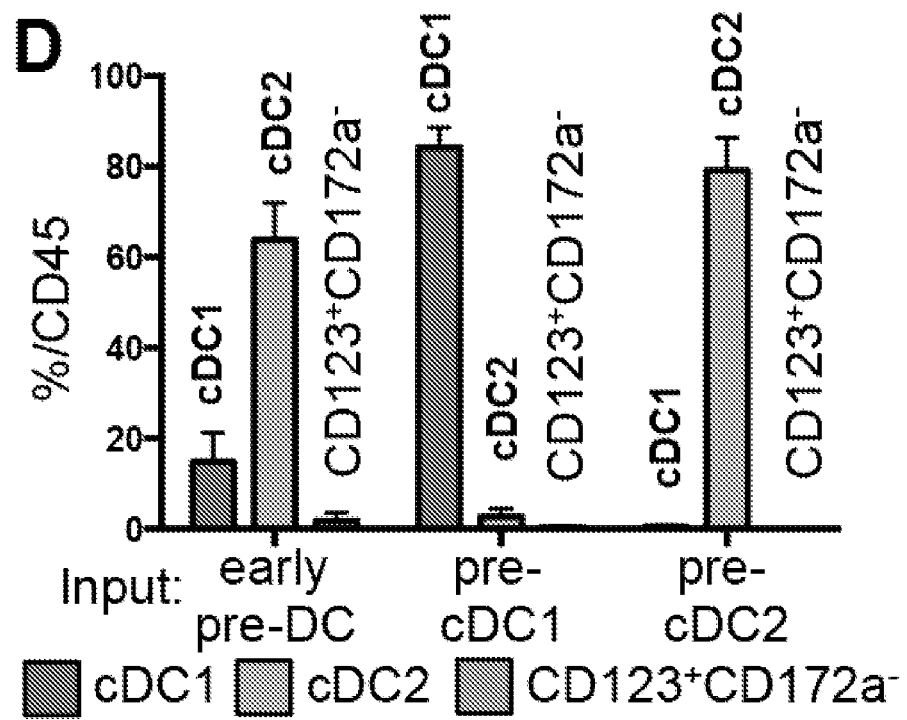

FIG. 16. (A) Expression level of markers in the 3D-Principal Component Analysis (PCA) plots from FIGS. 3, C and D are shown. (B) Sequential gating strategy of flow cytometry data starting from Live CD45$^+$Lin(CD3/14/16/19/20)$^-$CD34$^-$HLA-DR$^+$ peripheral blood mononuclear cells defining CD33$^-$CD123$^+$CD303$^+$ pDC, CD33$^+$CD45RA$^-$ differentiated cDC (CADM1$^+$cDC1, CD1c$^+$cDC2), and CD33$^+$CD45RA$^+$ cells (comprising CD123$^+$CD45RA$^+$ pre-DC and CD123$^{lo}$CD45RA$^+$ intermediate cells). (C) Proportion of CD45$^+$ mononuclear cells in spleen (n=3) (left) and peripheral blood (n=6) (right) of the above-mentioned pre-DC subsets. (D) Histograms of the mean proportion of CD303$^+$CD172α$^-$ cells, Clec9A$^+$CADM1$^+$cDC1 or CD1c$^+$CD11c$^+$cDC2 obtained in the in vitro differentiation assays as described in FIG. 3H (n=3). Error bars represent mean±SEM.

Figure 17:
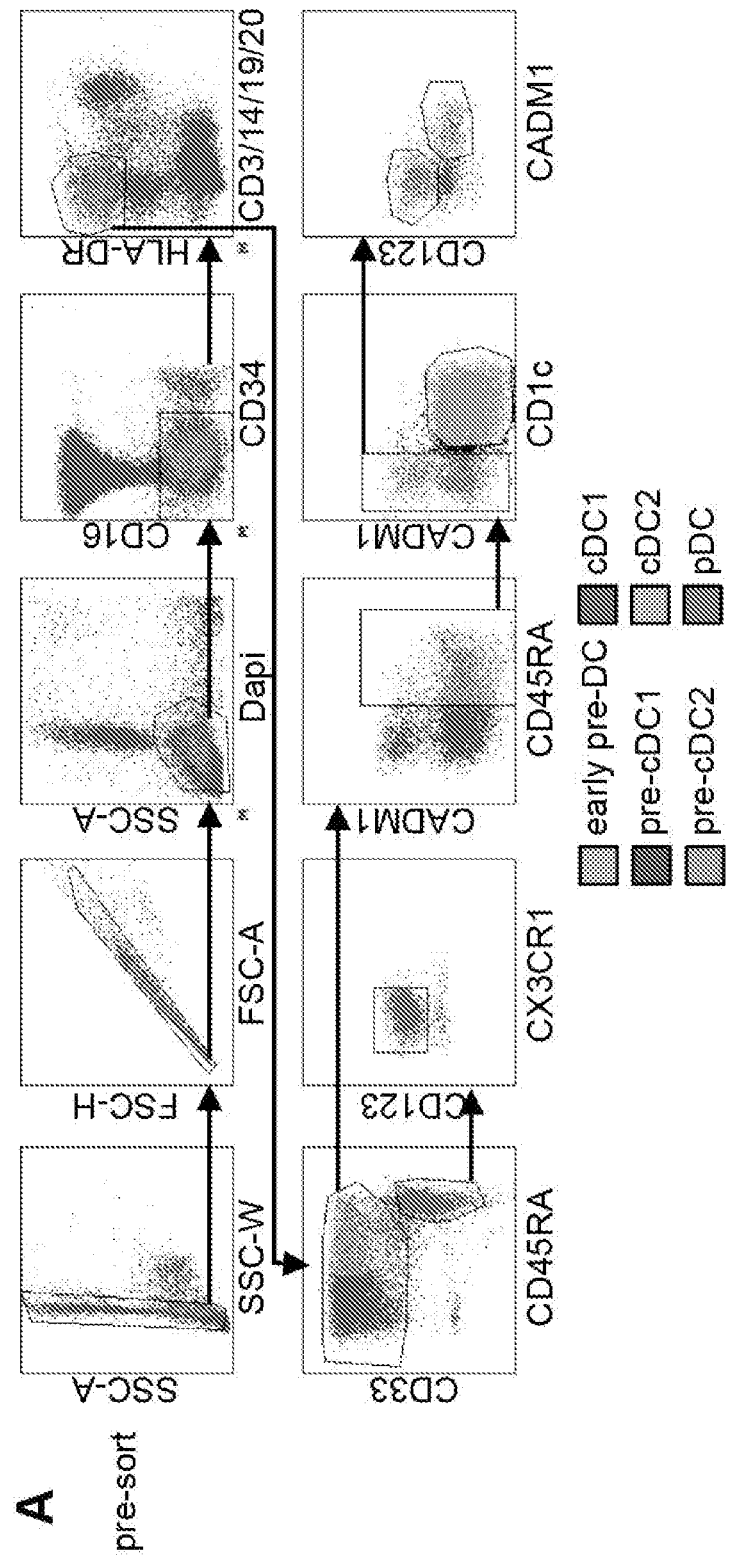
Figure 17:
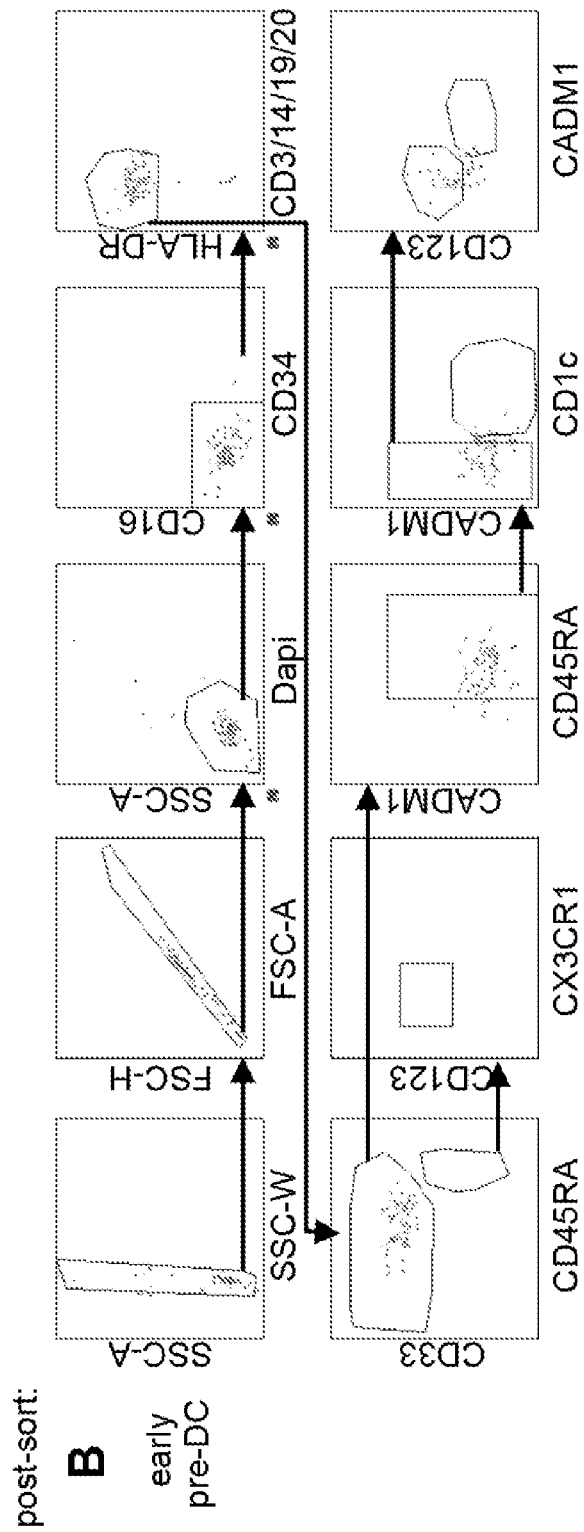
Figure 17:
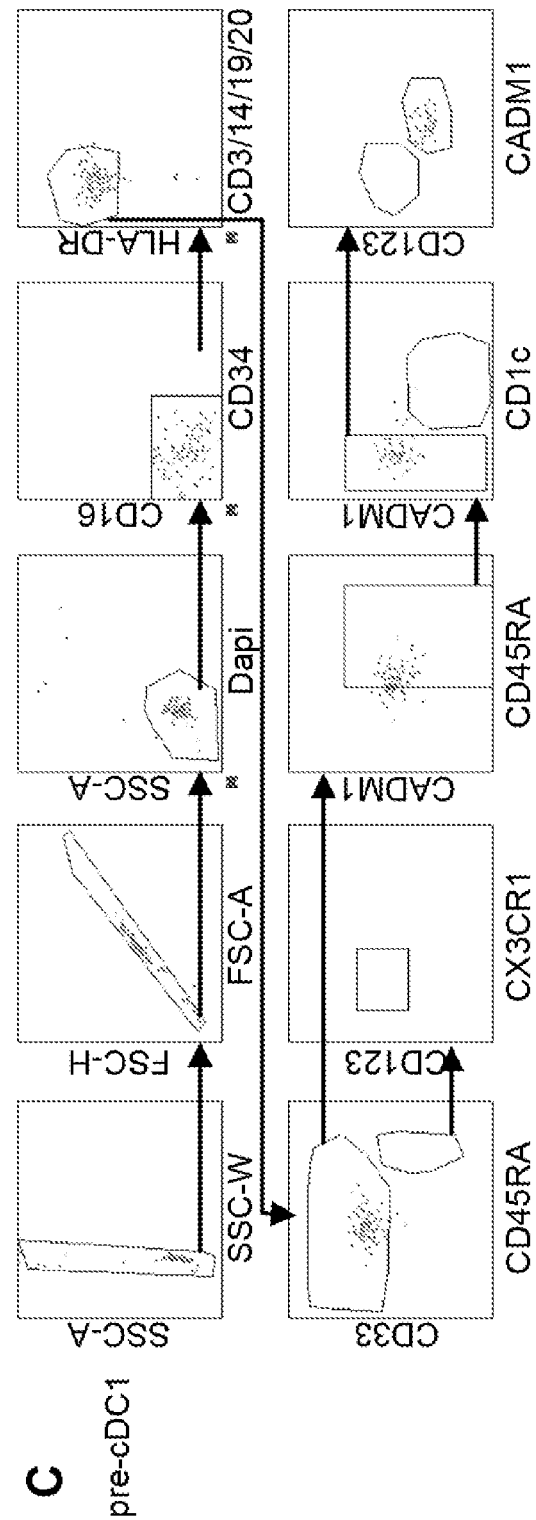
Figure 17:
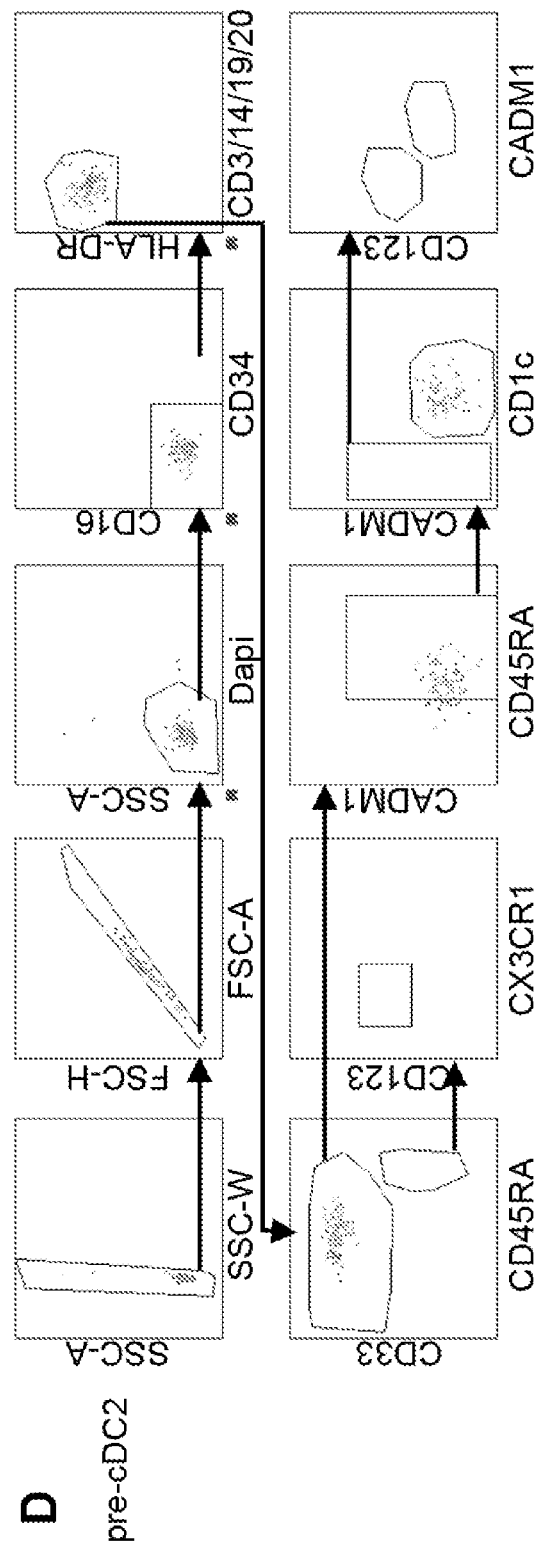

FIG. 17. Gating strategy for sorting of pre-DC subsets used in the in vitro differentiation assays (FIG. 3G). (A) Pre-sorted data and B-D. post-sorted re-analysis of (B) early pre-DC, (C) pre-cDC1, and (D) pre-cDC2 are shown.

Figure 18:
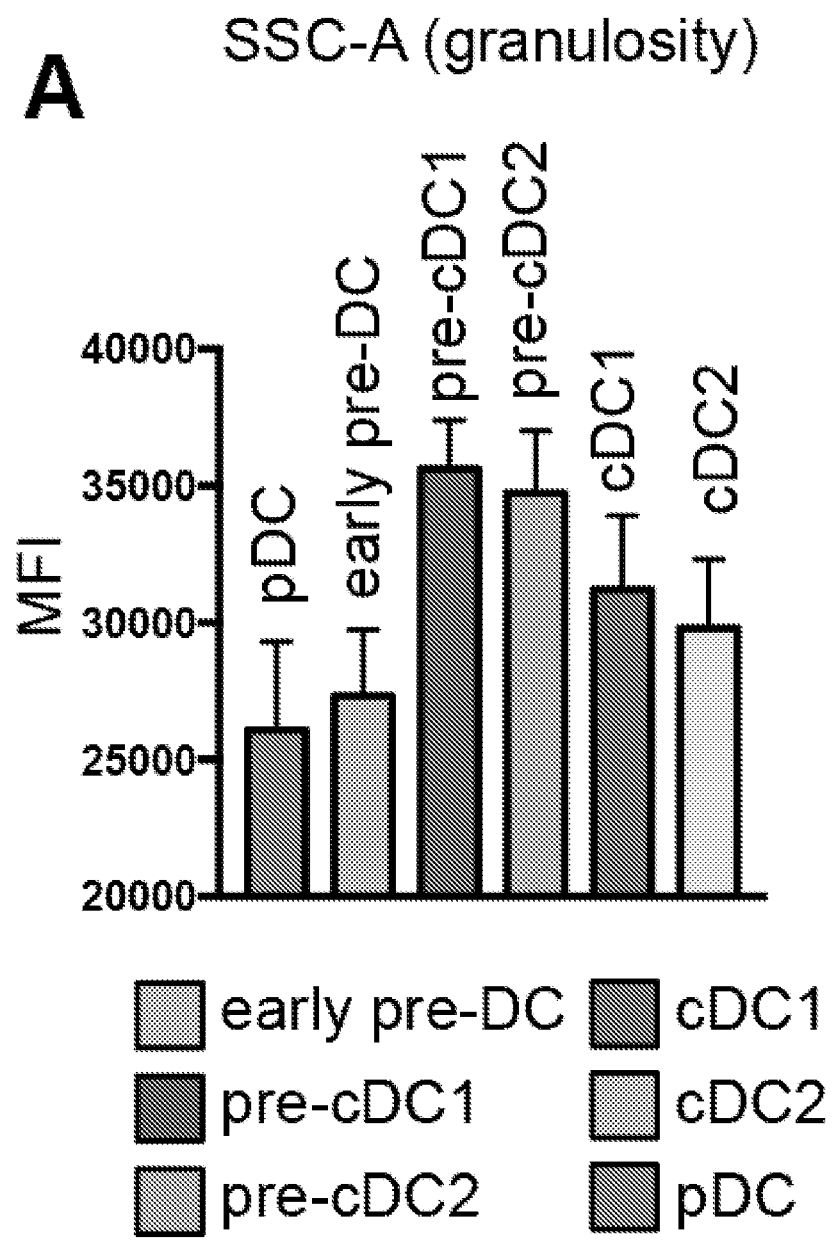
Figure 18:
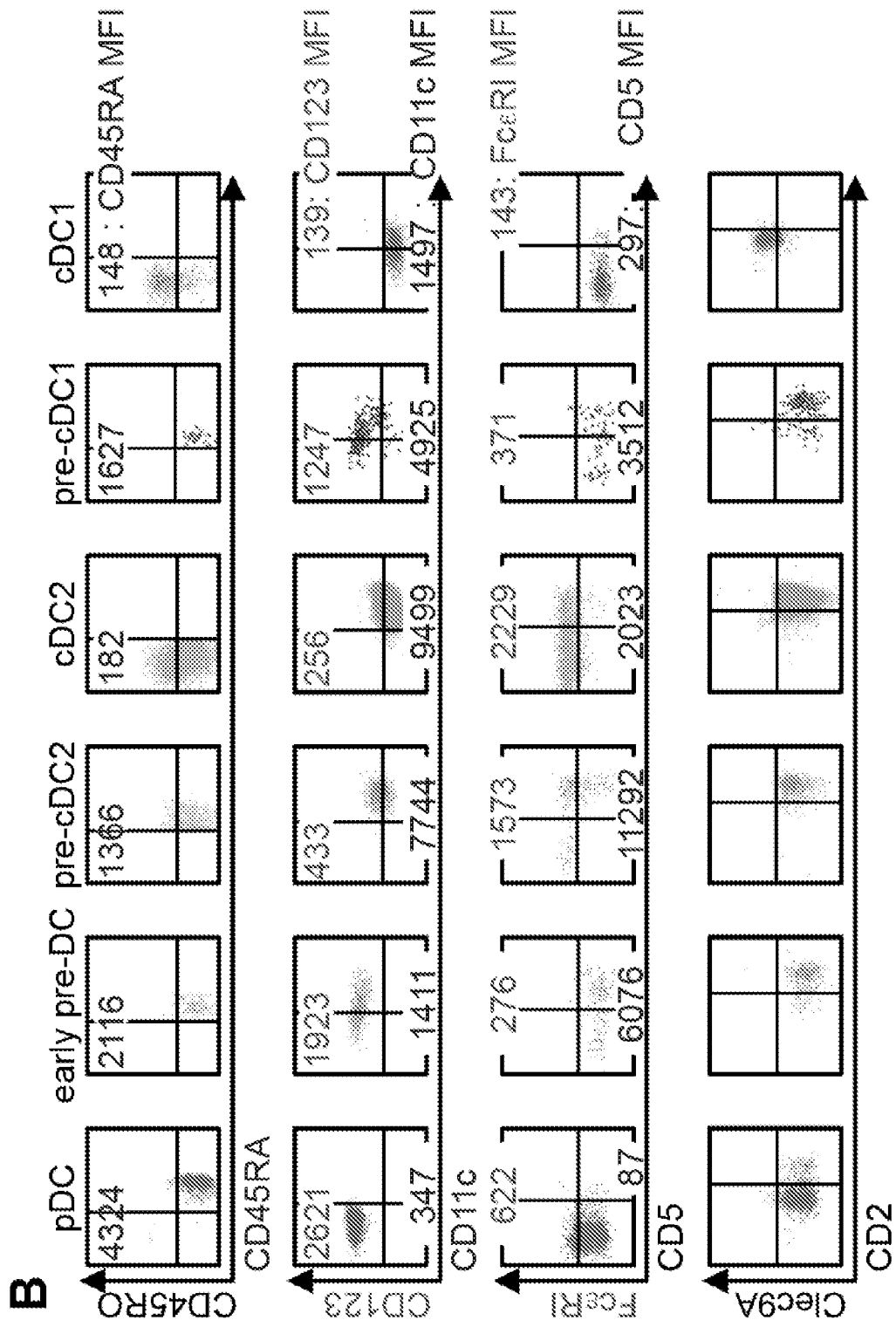
Figure 18:
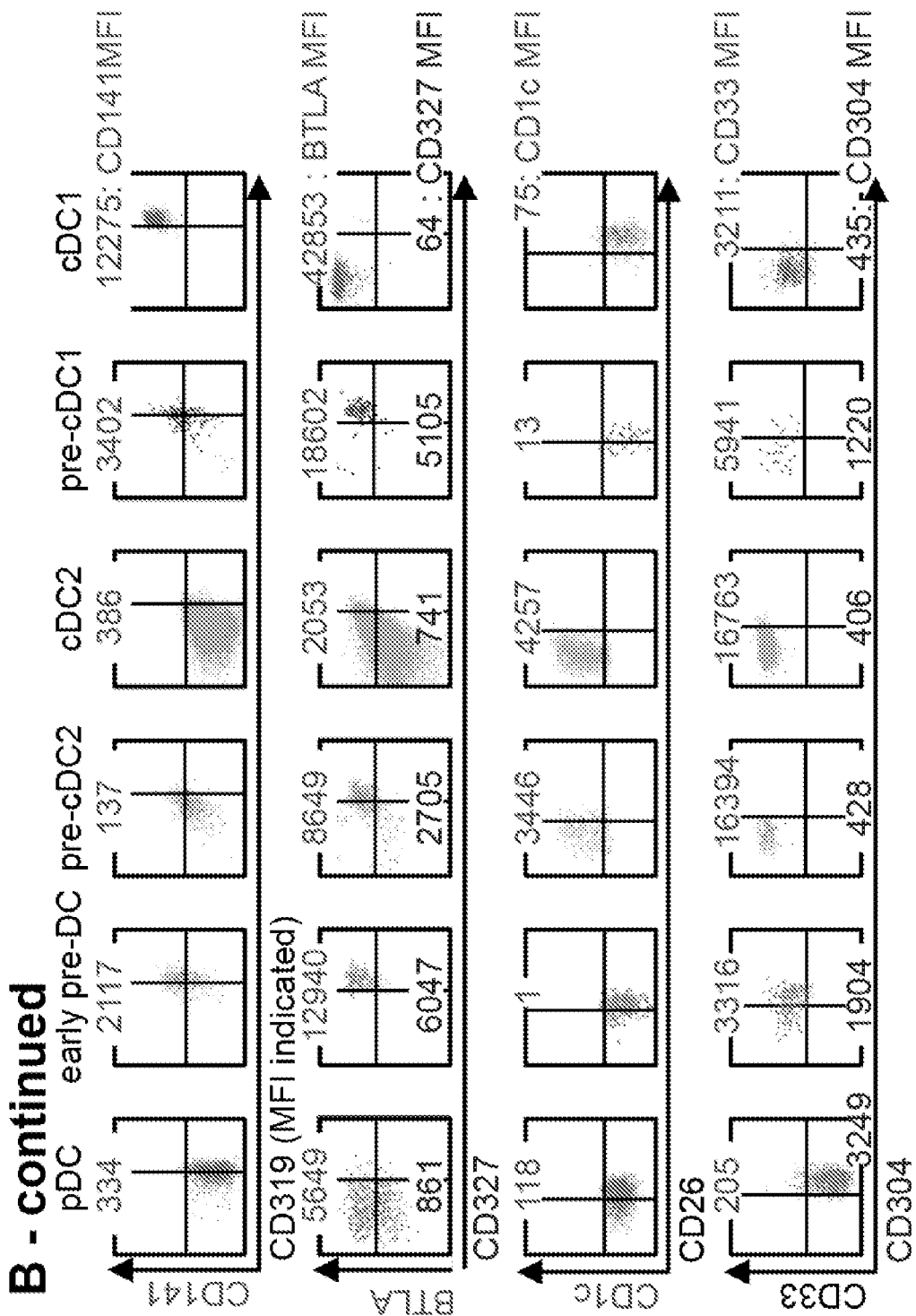
Figure 18:
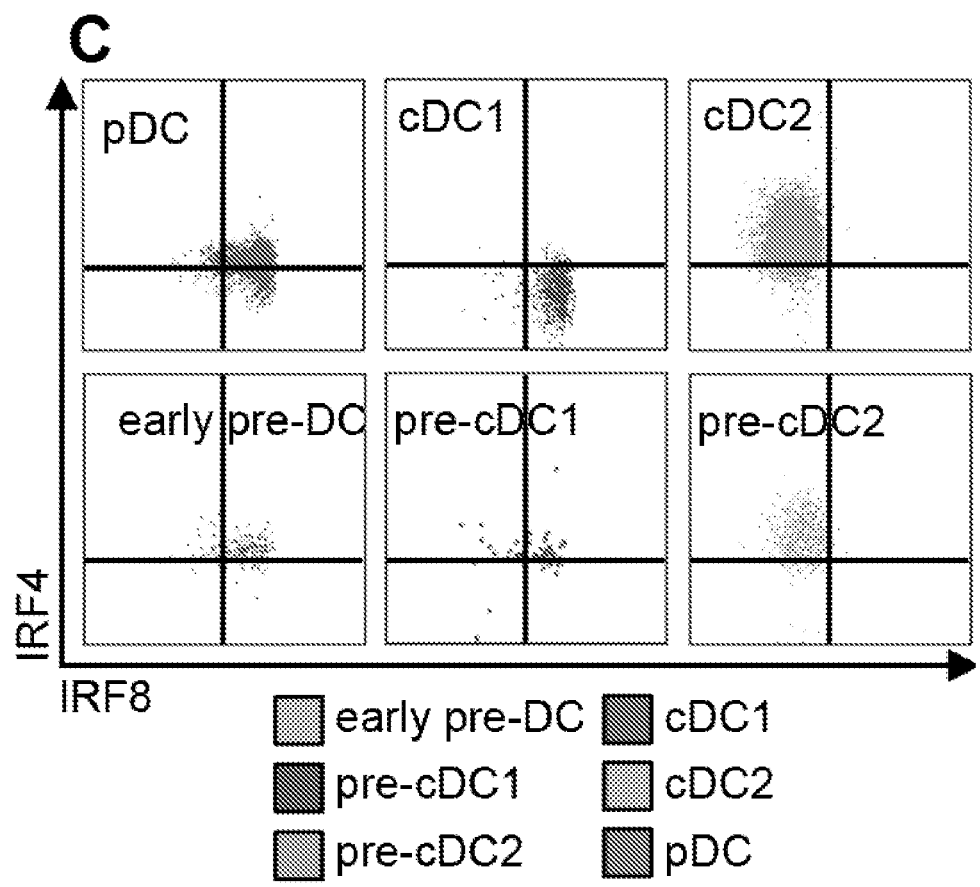

FIG. 18. (A) Expression level in terms of mean fluorescence intensity (MFI) of the side scatter area (SSC-A) indicating cellular granularity of blood pre-DC and DC subsets from five individual human donors (n=5) Error bars represent mean±SEM. B-C. Flow cytometry data showing the relative expression of (B) CD45RA, CD169, CD11c, CD123, CD33, FcεRI, CD2, Clec9A, CD319, CD141, BTLA, CD327, CD26, CD1c, CD304 or of (C) IRF4 and IRF8 by pDC, early pre-DC, pre-cDC2, cDC2, pre-cDC1 and cDC1 defined in FIG. 3G and in FIG. 16B.

Figure 4:
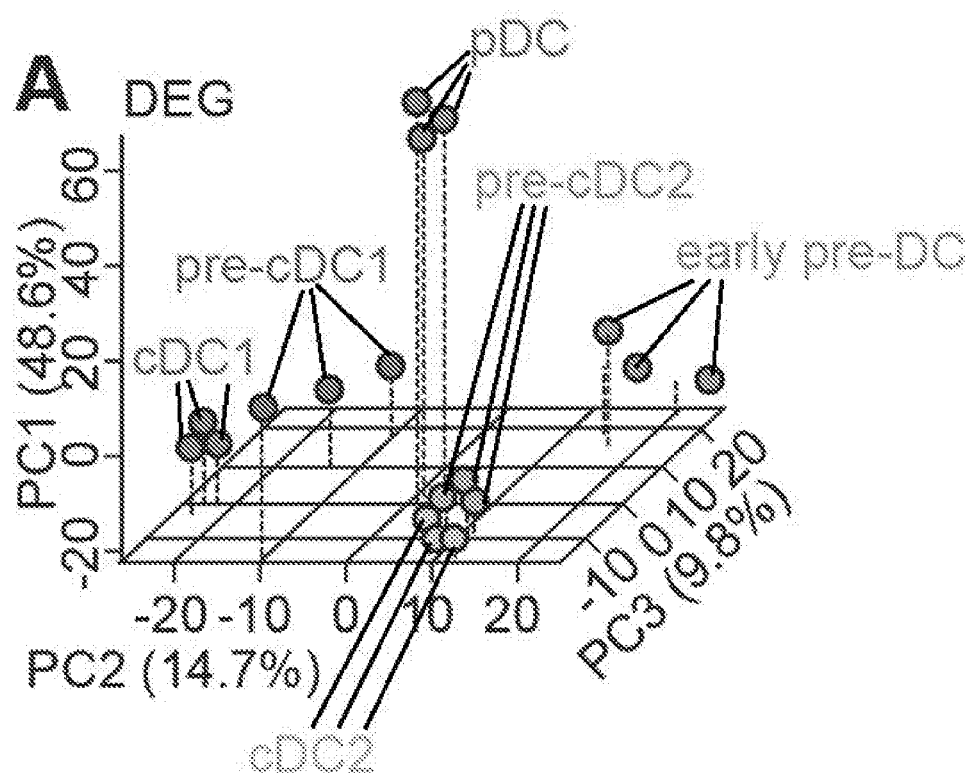
FIG. 4. DC and pre-DC subset gene expression analysis. (A) Microarray data from sorted DC and pre-DC subsets (shown in FIG. 3) were analyzed by 3D PCA using differentially-expressed genes (DEG). For each PCA dimension (principal component, PC), the variance explained by each component is indicated. (B-D) Heat maps of DEG between (B) early pre-DC/pDC, (C) early pre-DC/pre-cDC1/cDC1 and (D) early pre-DC/pre-cDC2/cDC2. (E) Expression profiles of 62 common genes identified from DEG analysis comparisons along the lineage progression from early pre-DC to mature cDC, for cDC1 and cDC2 respectively. The profiles were plotted with the log 2 fold-change values (versus early pre-DC). (F) Expression level of CD327 (SI-GLEC6), CD22 and AXL proteins by DC and pre-DC subsets evaluated by flow cytometry. The mean fluorescence intensities are indicated. (G) Expression profile of selected transcription factors.
Figure 4:
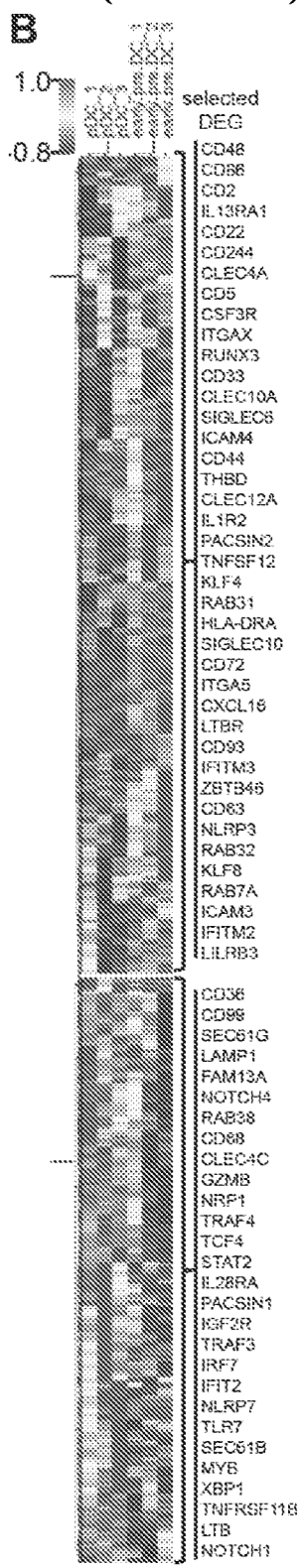
Figure 4:
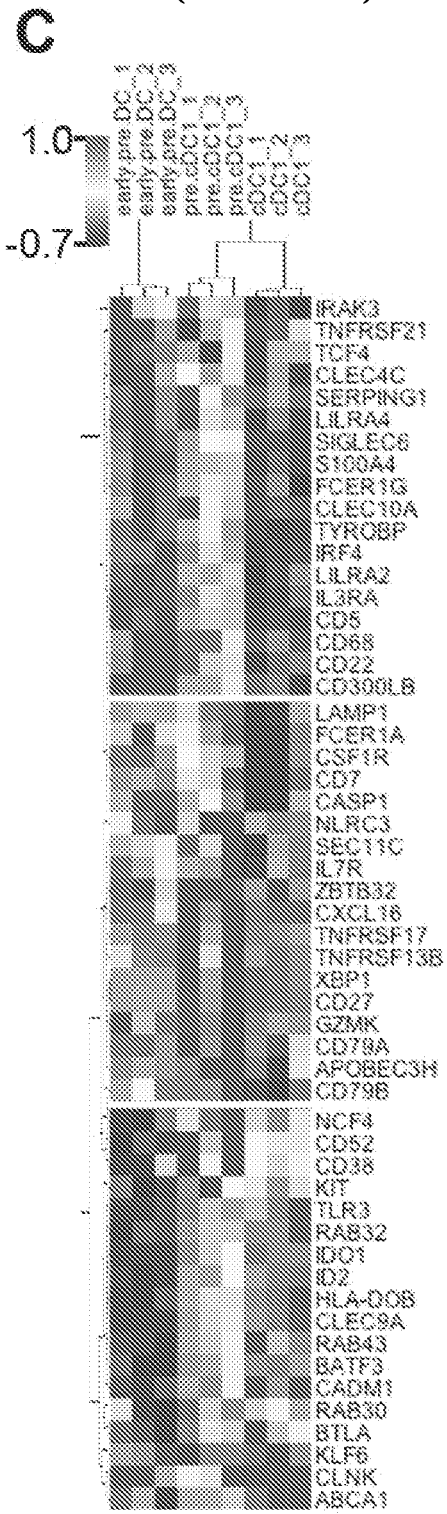
Figure 4:
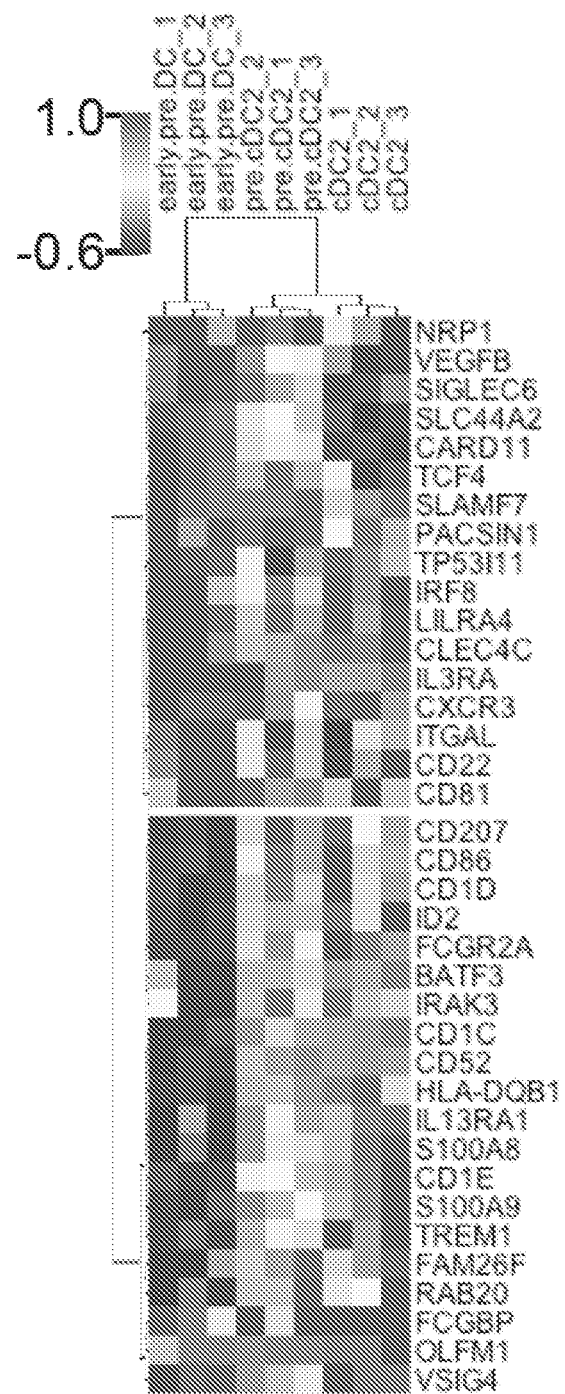
Figure 4:
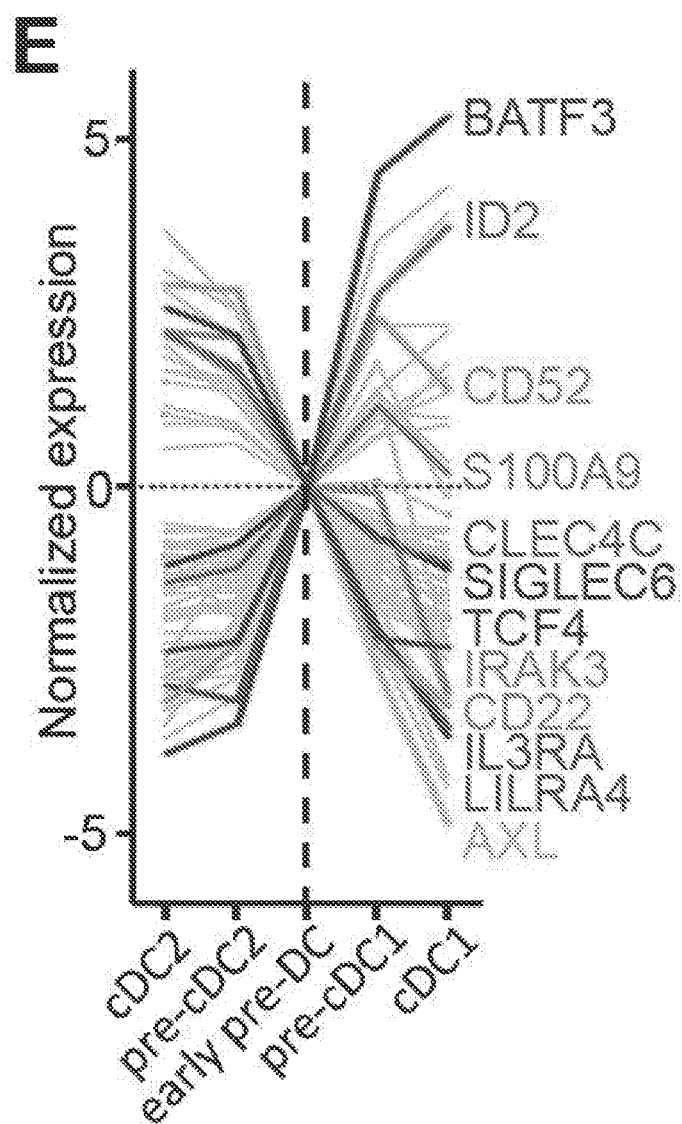
Figure 19:
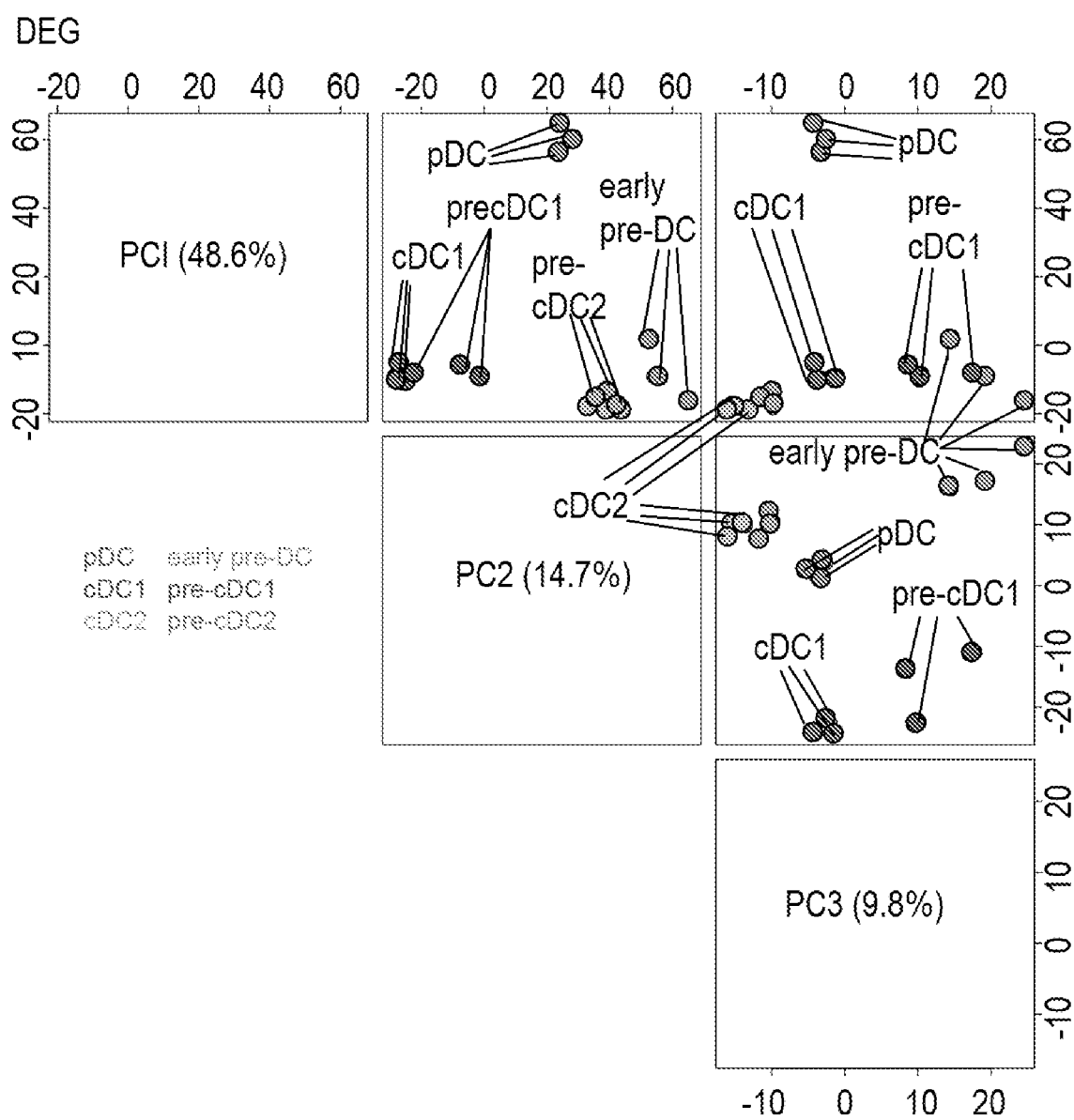

FIG. 19. 2D-plots showing combinations of Principal Component Analysis components 1, 2 or 3 (PC1-3) using differentially-expressed genes from the microarray analysis of FIG. 4.

Figure 20:
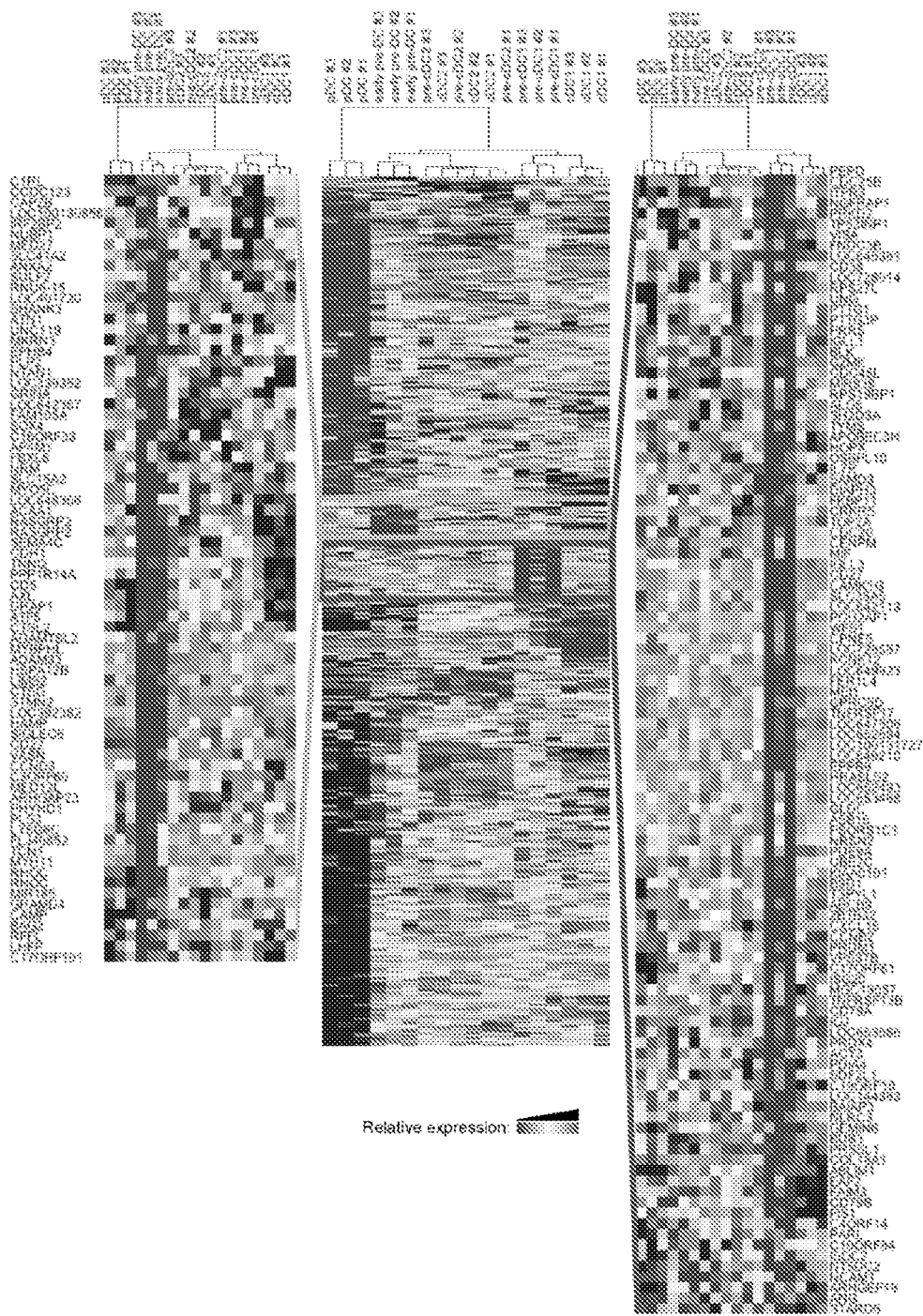

FIG. 20. Heat maps of relative expression levels of all differentially-expressed genes, with magnifications of the specific genes in early pre-DC (boxed yellow region) and pre-cDC1 (boxed green region) from the microarray analysis of FIG. 4.

Figure 21:
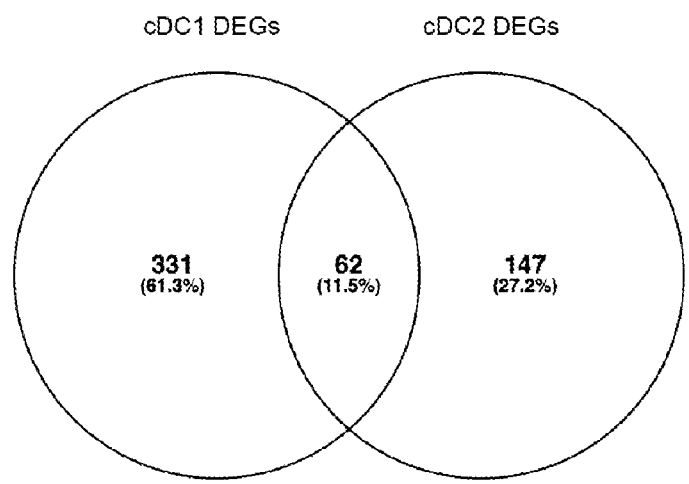

FIG. 21. Venn diagram showing genes common between the lists of cDC1 DEGs (the union of DEGs from comparing pre-cDC1 vs early pre-DC and cDC1 vs pre-cDC1) and cDC2 DEGs (the union of DEGs from comparing pre-cDC2 vs early pre-DC and cDC2 vs pre-cDC2). These 62 genes were then plotted in FIG. 4E with the log 2 fold-change values (versus early pre-DC).

Figure 22:
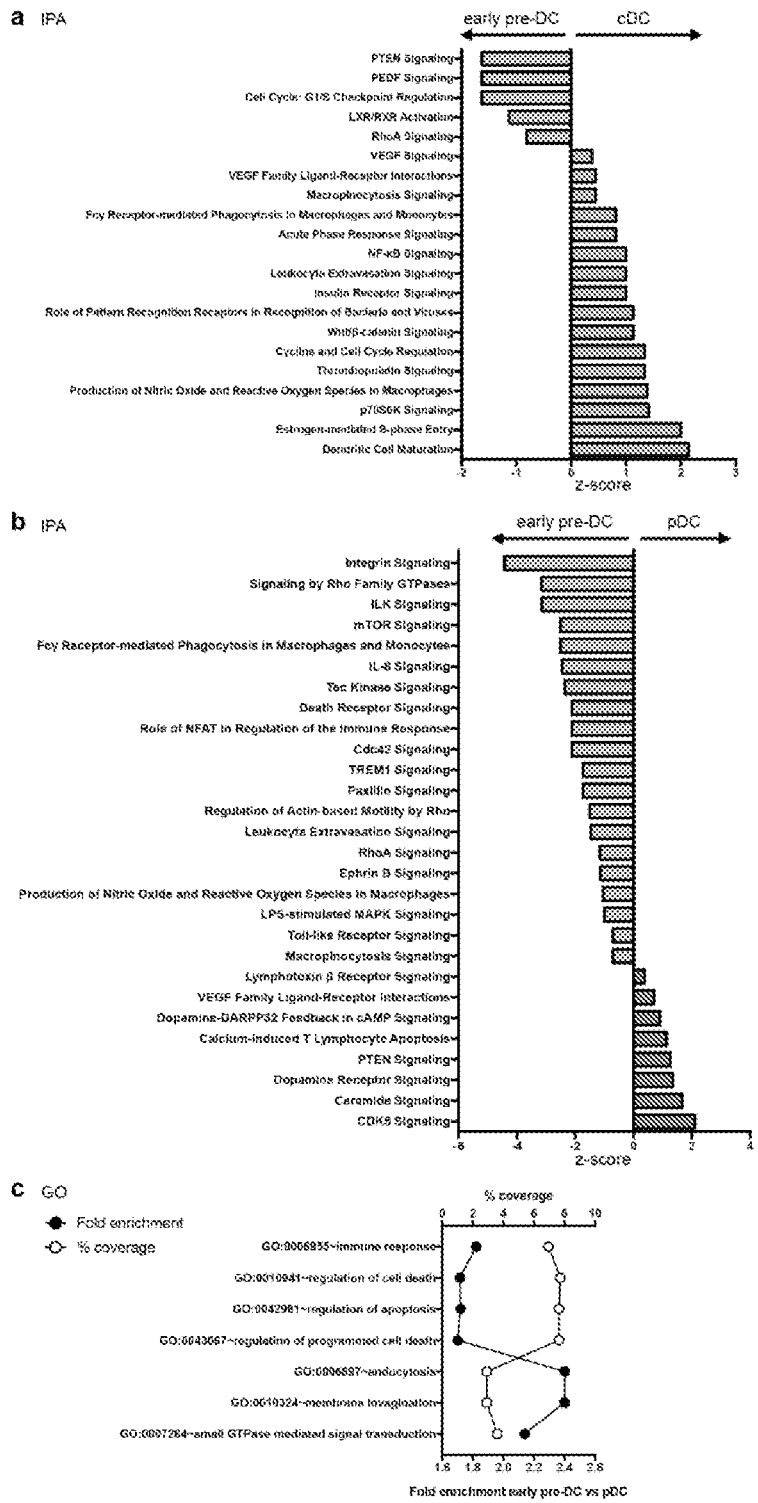

FIG. 22. a-c. Ingenuity Pathway analysis (IPA) based on genes that were differentially-expressed between (a) cDC and early pre-DC or (b) pDC and early pre-DC. Only the DC biology-related pathways were shown, and all displayed pathways were significantly enriched (P<0.05, right-tailed Fischer's Exact Test). The heights of the bars correspond to the activation z-scores of the pathways. Enriched pathways predicted to be more activated in early pre-DC pathways are shown in pink and enriched pathways predicted to be more activated in cDC or pDC are shown in orange and blue, respectively. IPA predicts pathway activation/inhibition based on the correlation between what is known about the pathways in the literature (the Ingenuity Knowledge Base) and the directional expression observed in the user's data. Please refer to IPA Upstream Regulator Analysis Whitepaper and IPA Downstream Effectors Analysis Whitepaper for full description of the activation z-score calculation. (c) Gene Ontology (GO) enrichment analysis of differentially-expressed genes (DEGs) in early pre-DC and pDC indicating biological processes that were significantly enriched (Benjamini-Hochberg adjusted p value<0.05) with genes expressed more abundantly in early pre-DC as compared to pDC. Note that no biological process was significantly enriched with genes expressed more abundantly in pDC as compared to early pre-DC.

Figure 23:
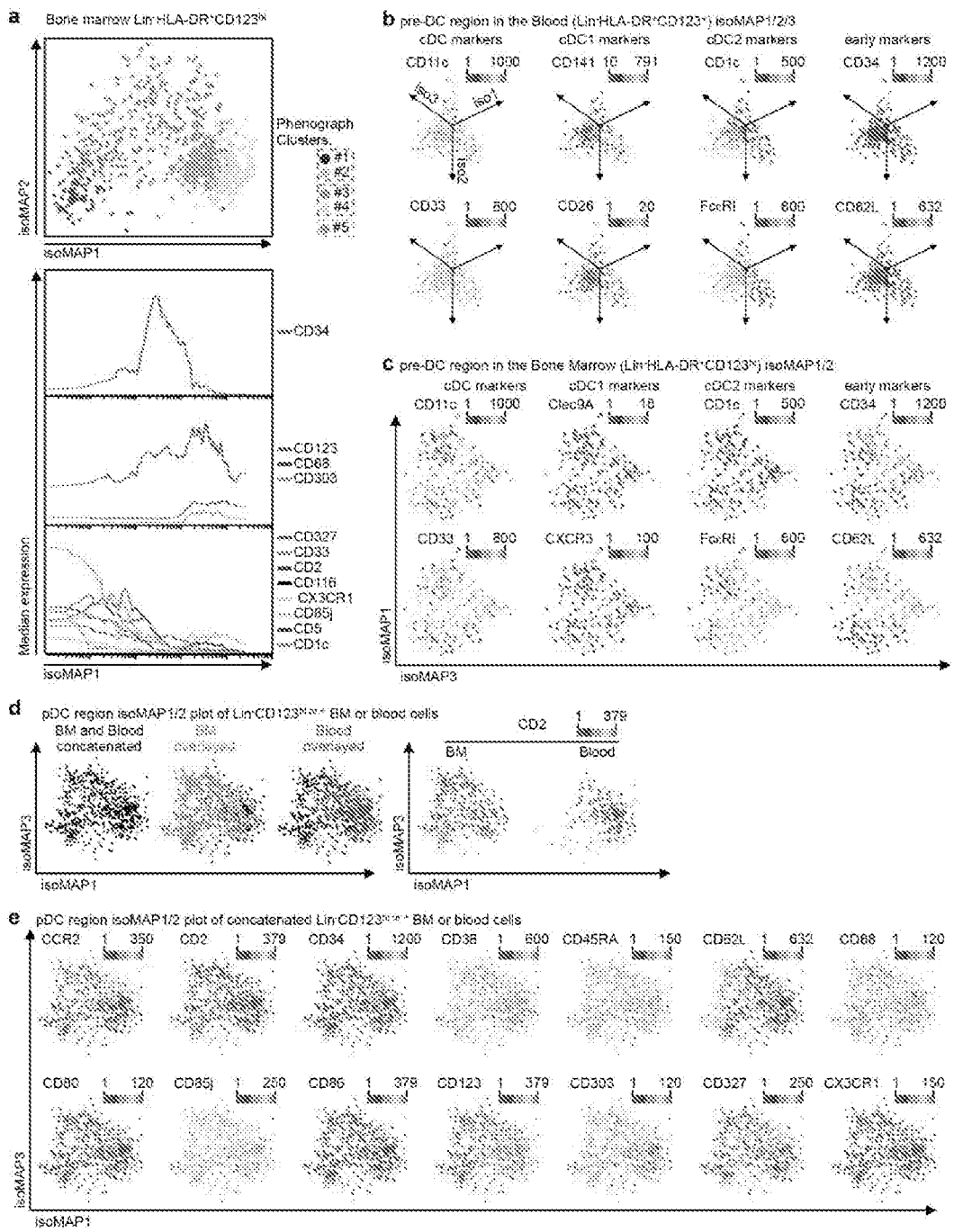

FIG. 23. (a) isoMAP1-2 plot of bone marrow (BM) Lin(CD3/CD7/CD14/CD15/CD19/CD34)$^-$CD123$^{hi}$ cells (upper panel) and graphics of the binned median expression of defining markers along the phenotypic progression of cells defined by the isoMAP1 dimension (lower panels) are shown. (b) Expression level of selected markers in the isoMAP1-2-3 3D-plots (FIG. 5C, lower left panel) corresponding to cells within the pre-DC phenograph clusters (#1 and #2) of the blood Lin⁻CD123⁺ cells isoMAP analysis. (c) Expression level of selected markers in the isoMAP1-2 plots (FIG. 5C, upper left panel) corresponding to cells within the pre-DC phenograph clusters (#3 and #4) of the BM Lin⁻CD123$^{hi}$ cells isoMAP analysis. (d) pDC defined in BM Lin⁻CD123$^{hi}$ (green: phenograph clusters #3 and #4) or blood Lin⁻CD123⁺ (red: phenograph cluster #7) cells of FIGS. 5A and 5B, respectively, were exported and analyzed using the isoMAP method and subdivided into clusters using the phenograph algorithm. BM and blood concatenated (black) and overlaid BM (green) and blood (red) isoMAP1/3 plots are shown (left panels). Expression level of CD2 in BM (left) and blood (right) pDC in the isoMAP1/3 plot. (e) Expression level of selected markers in the BM and blood concatenated isoMAP1/3 plot of FIG. 5C (right panels).

Figure 24:
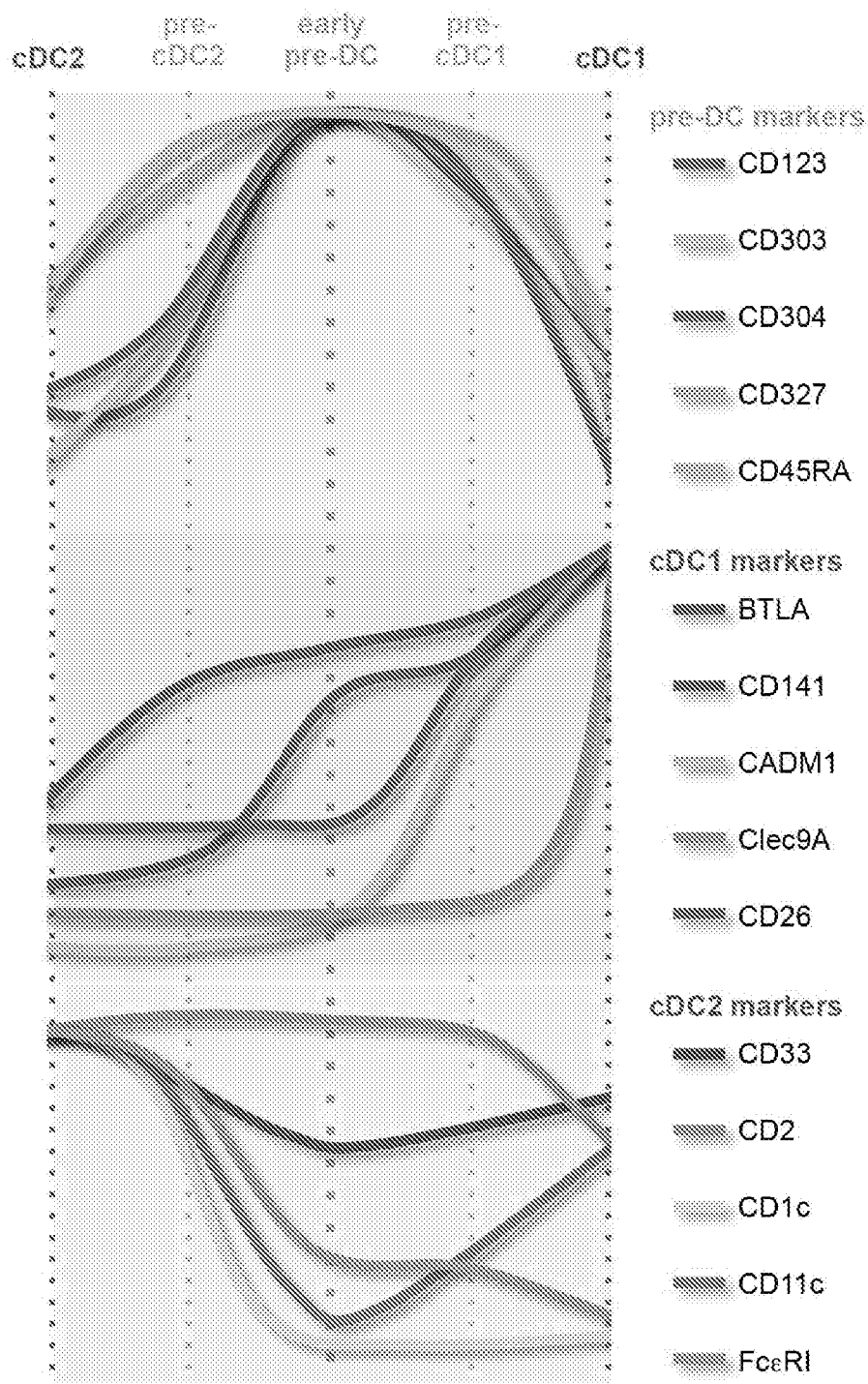

FIG. 24 Schematic representation of the expression of major pre-DC, cDC1 and cDC2 markers as pre-DC differentiate towards cDC.

Figure 25:
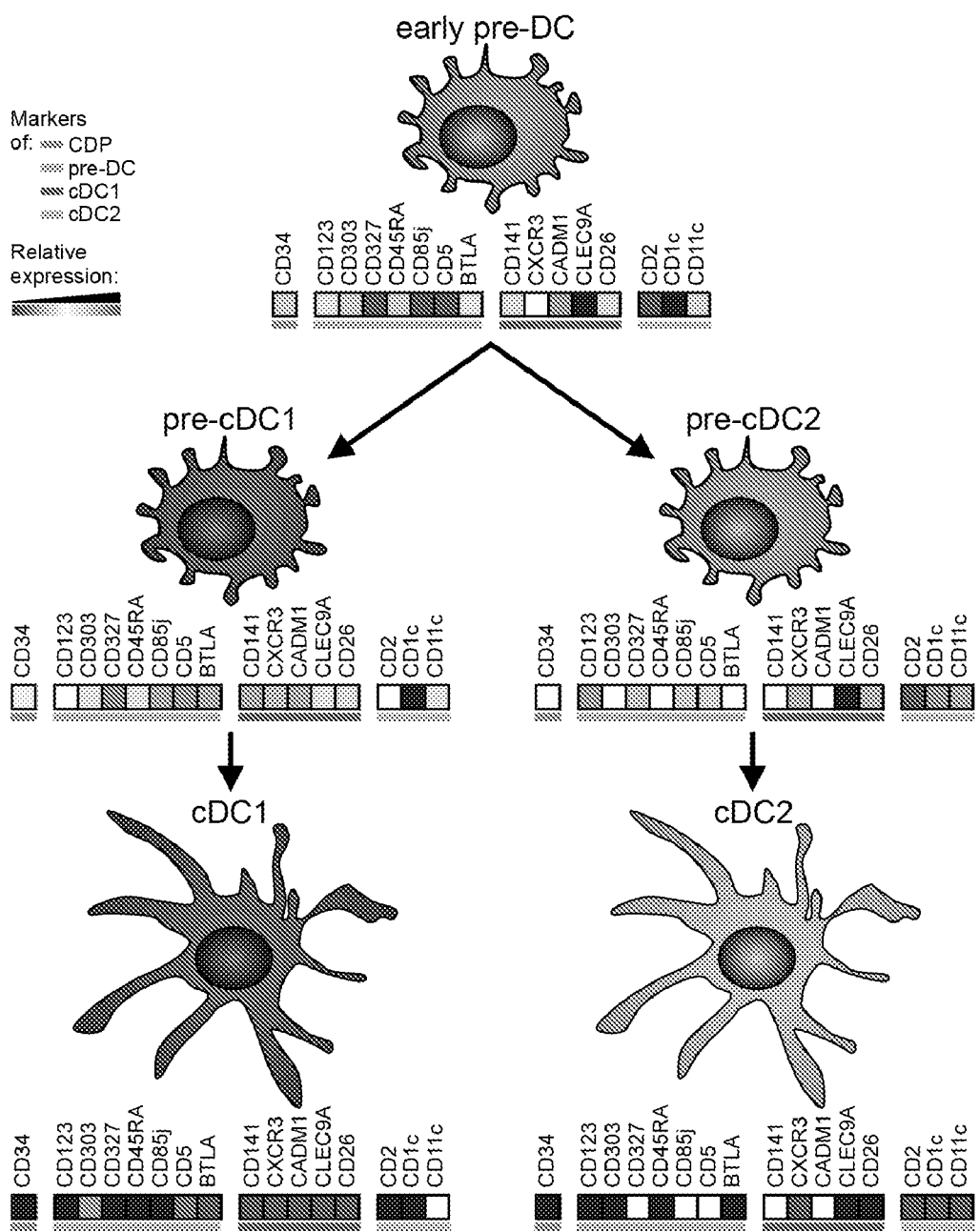

FIG. 25. Schematic representation of the expression of major pre-DC, cDC1 and cDC2 markers as pre-DC differentiate towards cDC.

Figure 26:
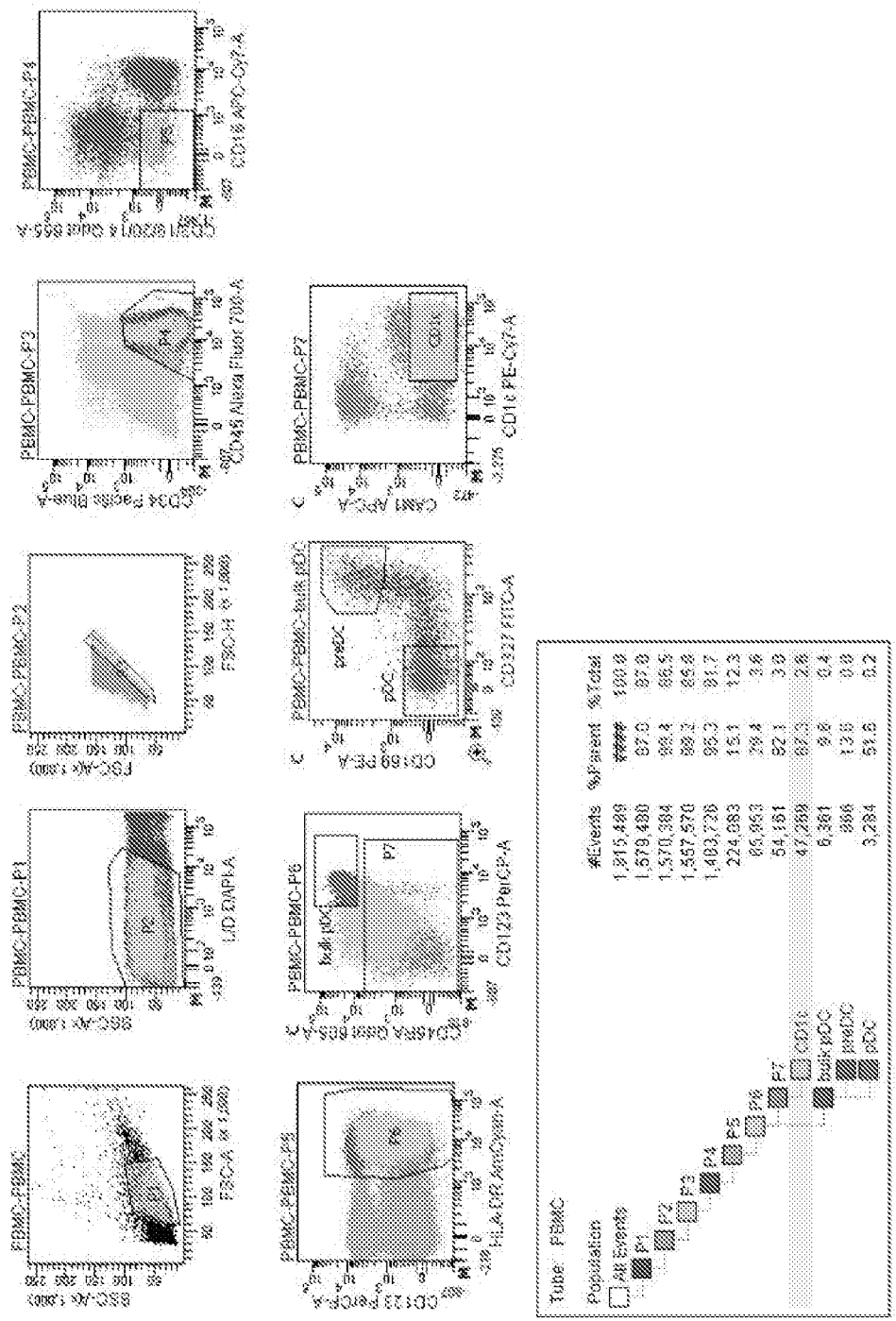

FIG. 26. Markers and gating strategy for the identification of human pre-DC and pDC and cDC subsets.

Figure 27:
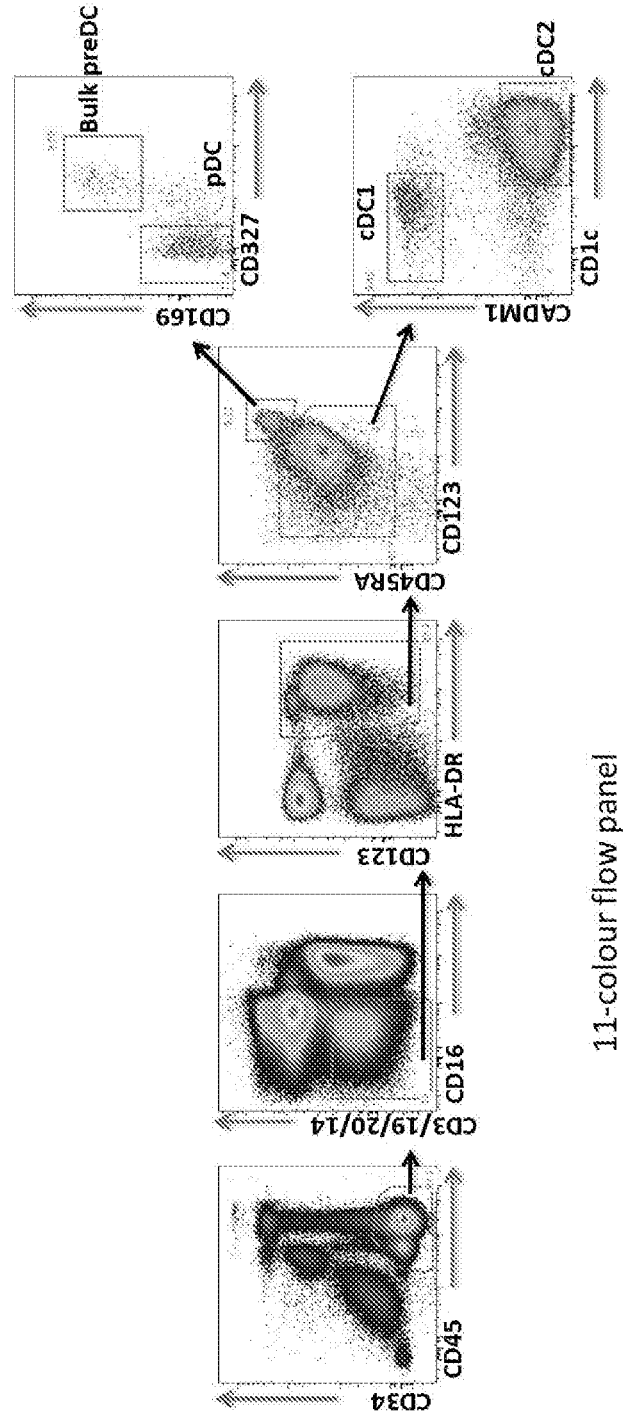

FIG. 27. Identification of bulk pre-DC by 11-color flow panel.

Figure 28:
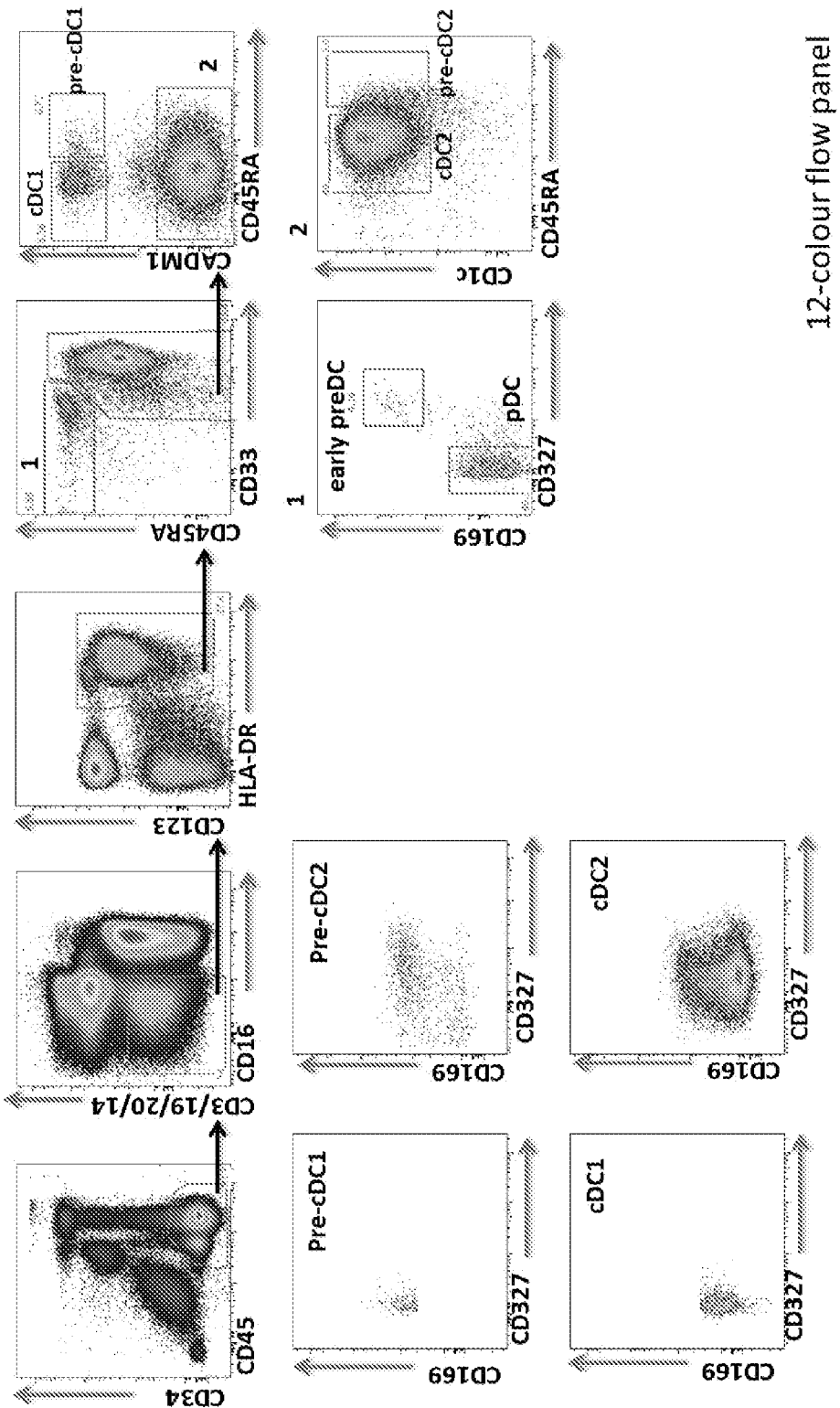

FIG. 28. Identification of bulk pre-DC by 12-color if including dead cell exclusion dye.

Figure 29:
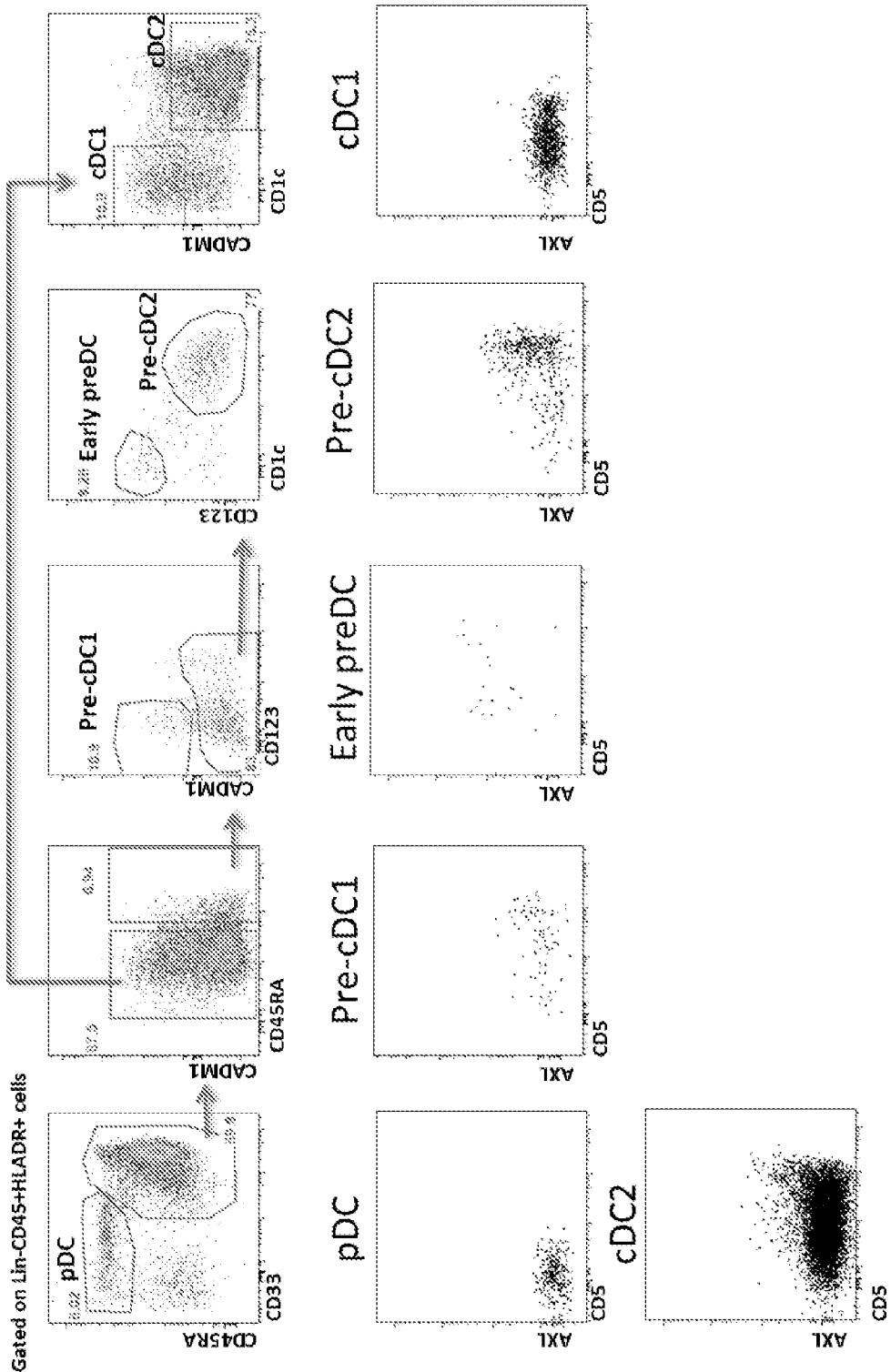

FIG. 29. AXL and CD5 expression on pre-DC and DC subsets.

Figure 30:
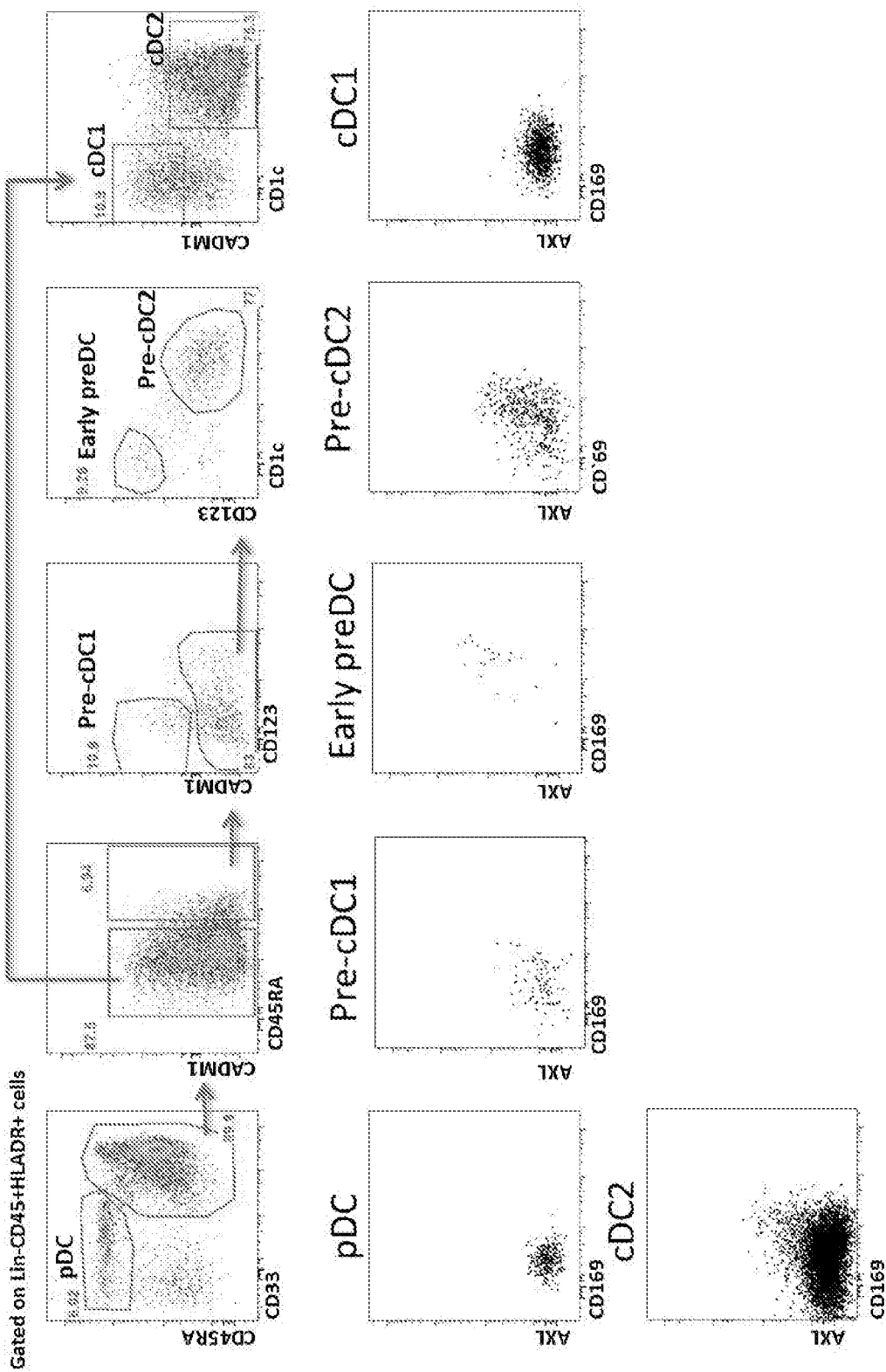

FIG. 30. AXL and CD169 expression on pre-DC and DC subsets.

Figure 31:
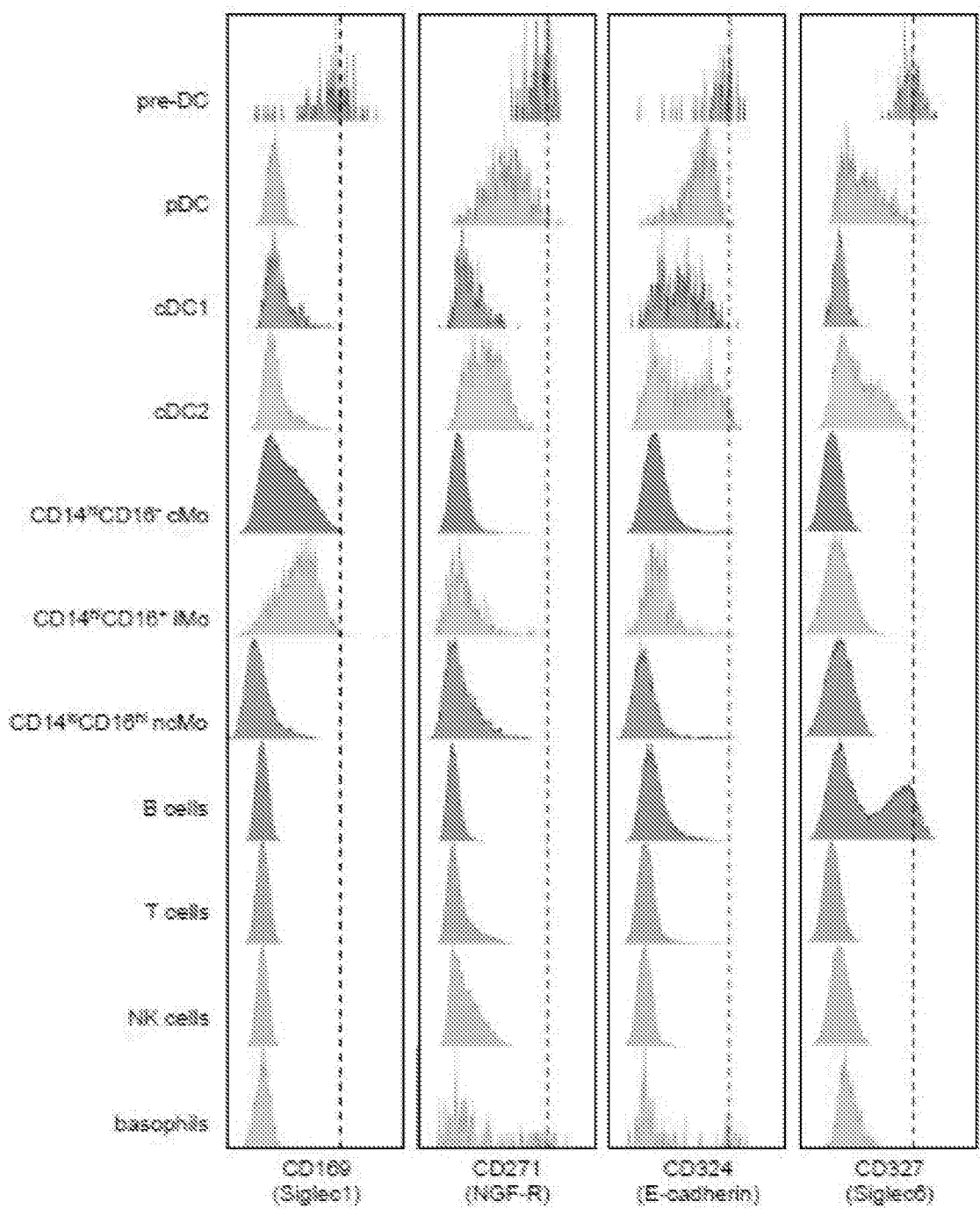

FIG. 31. Expression of markers CD169, CD271, CD324 and CD327 in different cell types.

Figure 32:
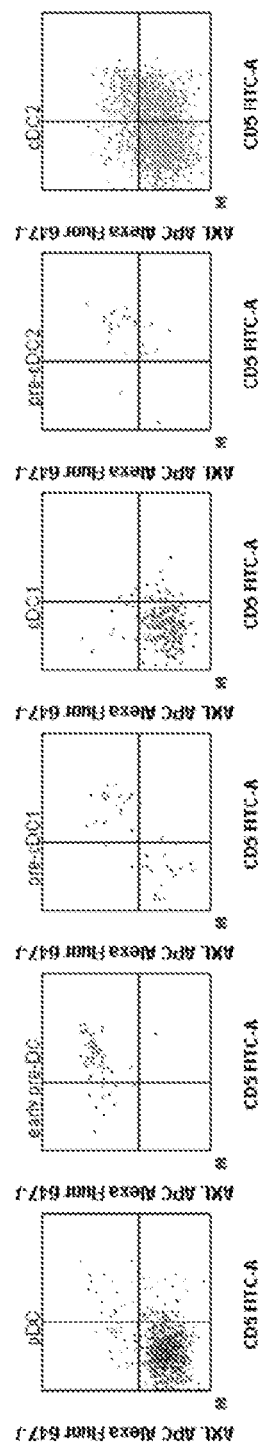

FIG. 32. AXL (Zika Virus Receptor) staining on human blood DC and pre-DC subsets.

Figure 33:
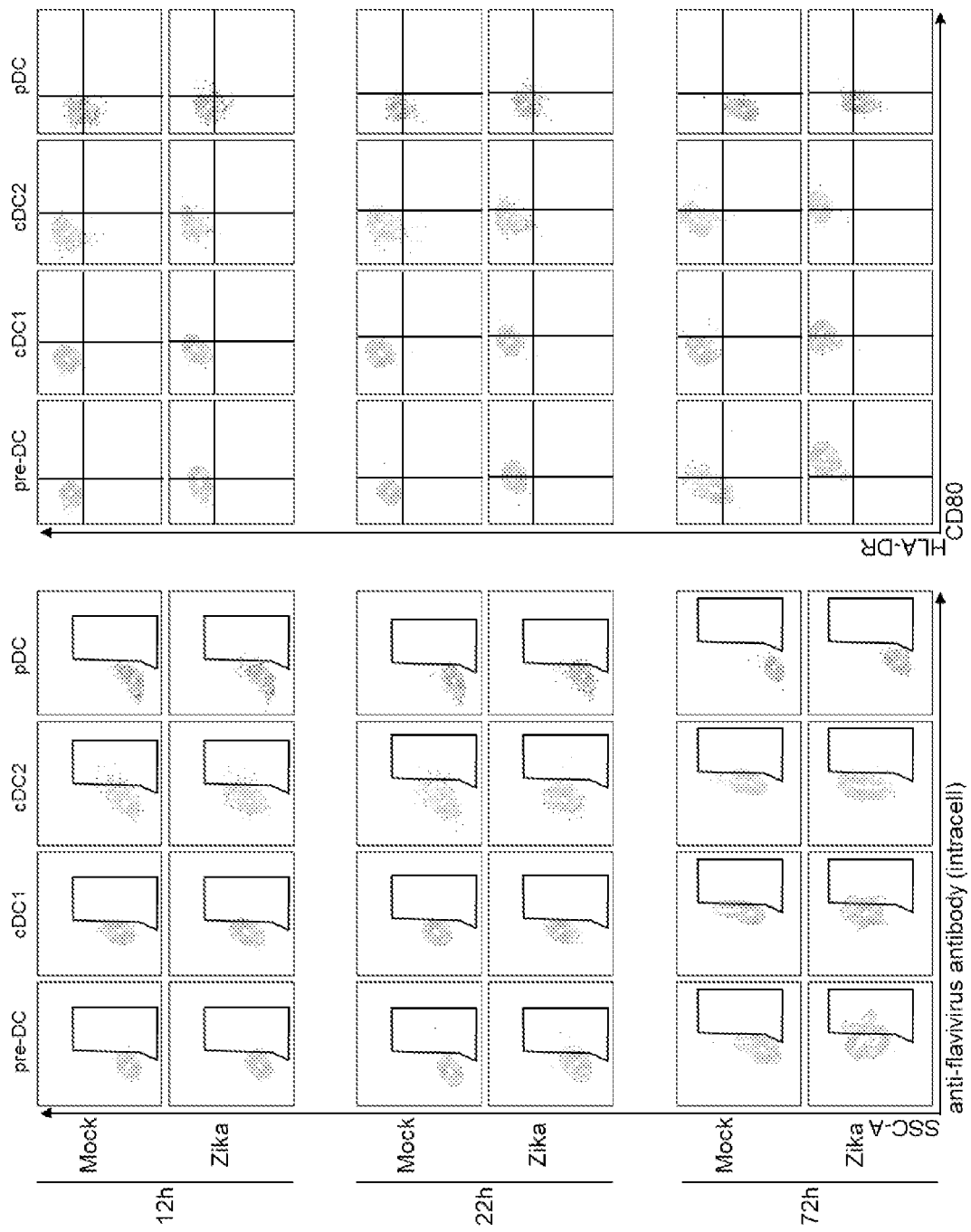

FIG. 33. In vitro infection of PBMC and intracellular detection of the Zika virus in DC and pre-DC.

Figure 34:
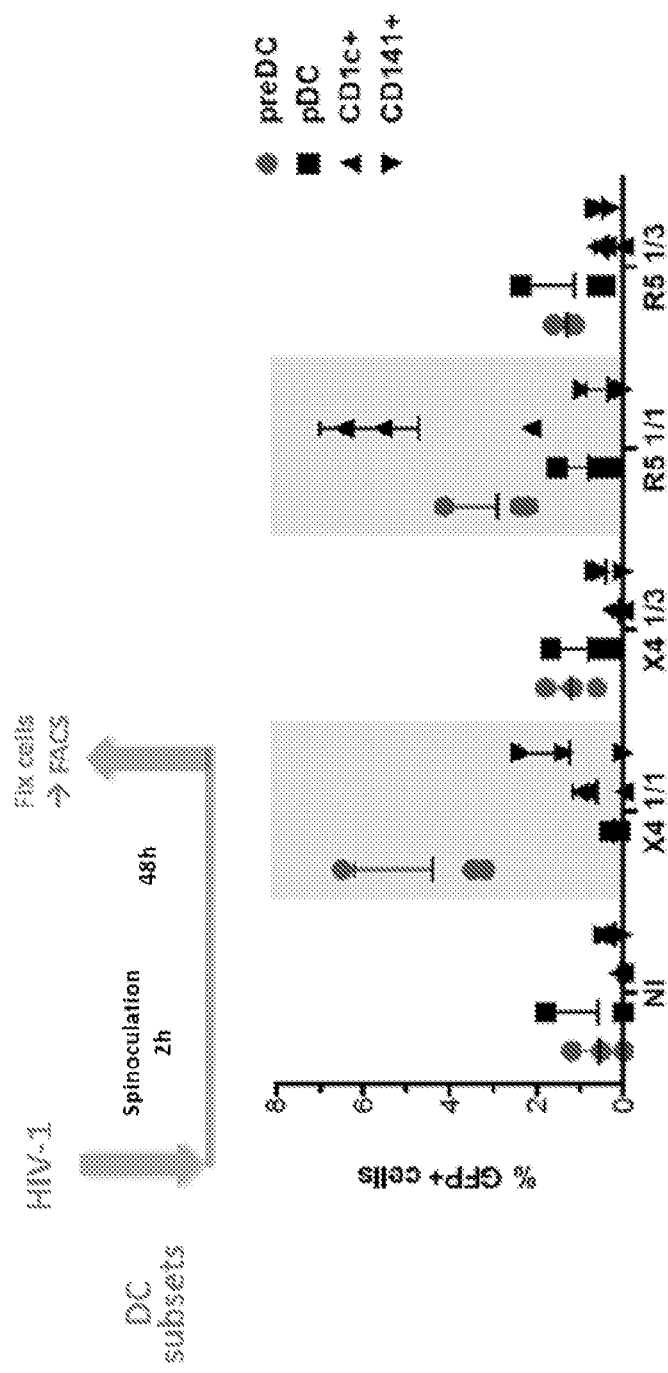

FIG. 34. Pre-DC are susceptible to HIV-1 infection with both R5 and X4 tropic viruses.

Figure 35:
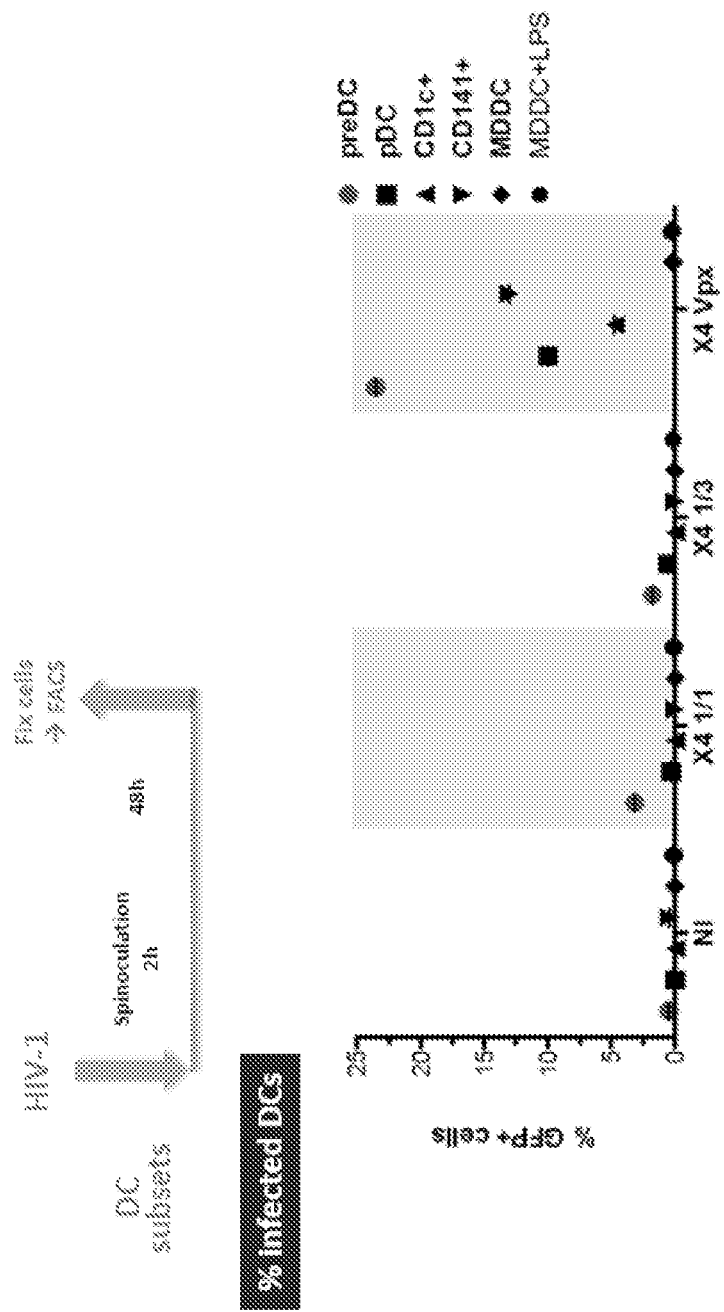

FIG. 35. HIV-1 infection of pre-DC and DC.

Figure 36:
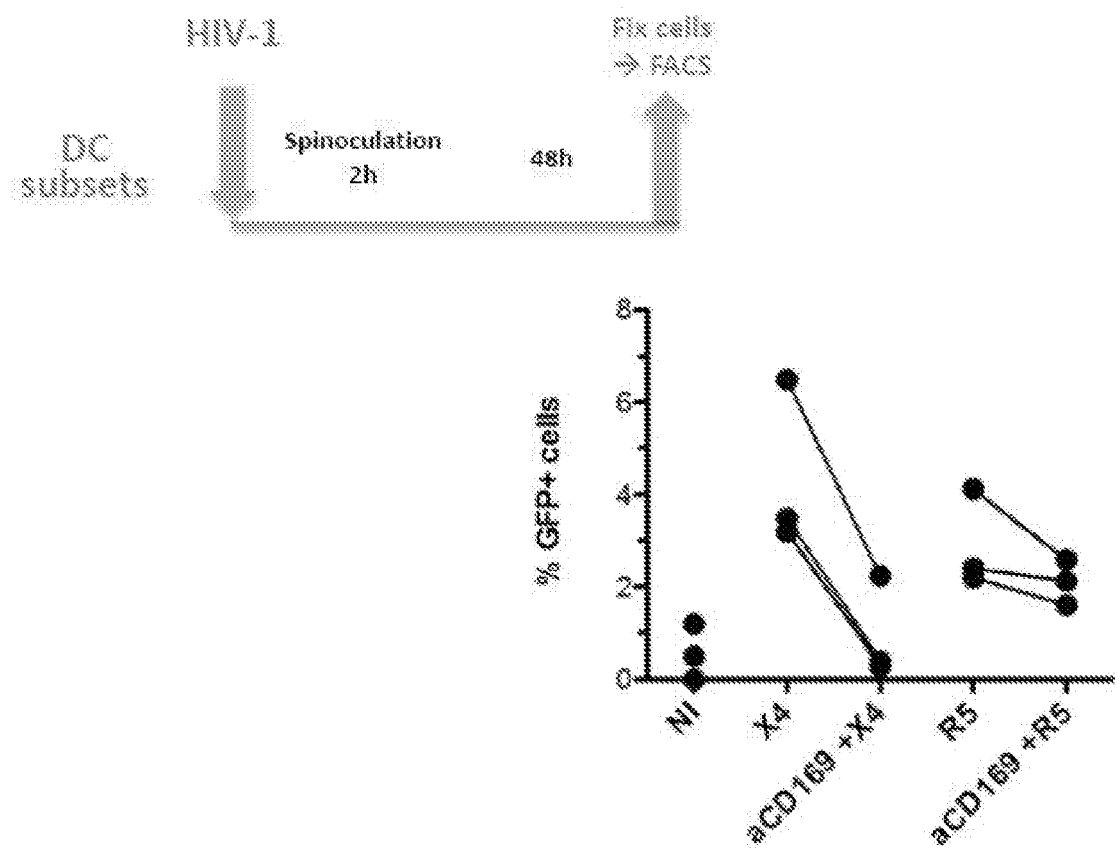

FIG. 36. Anti-CD169 pretreatment induces a decrease of HIV-1 infection of pre-DC, especially for X4 virus.

Figure 37:
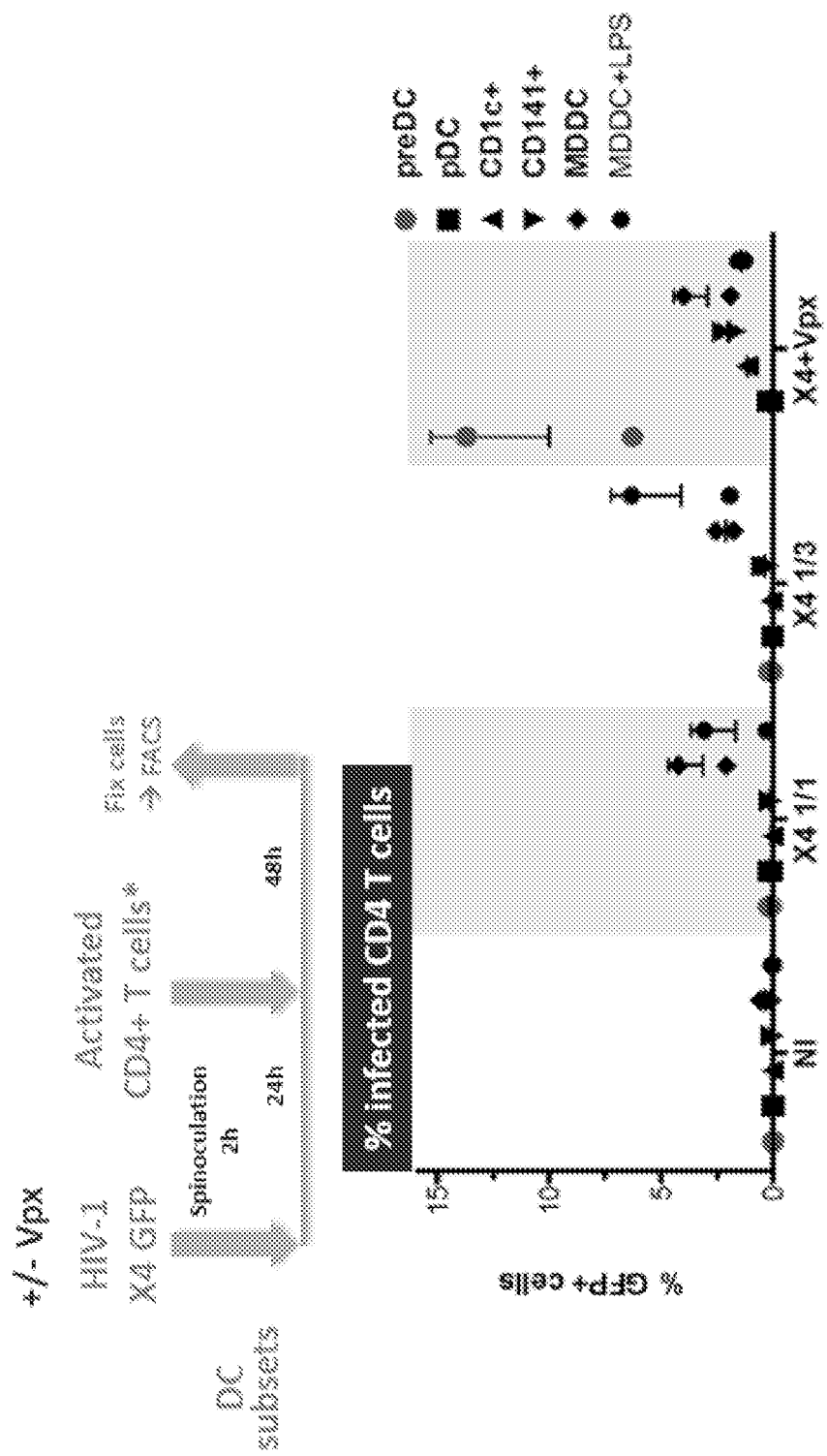

FIG. 37. HIV-1 transmission from infected pre-DC.

Figure 38:
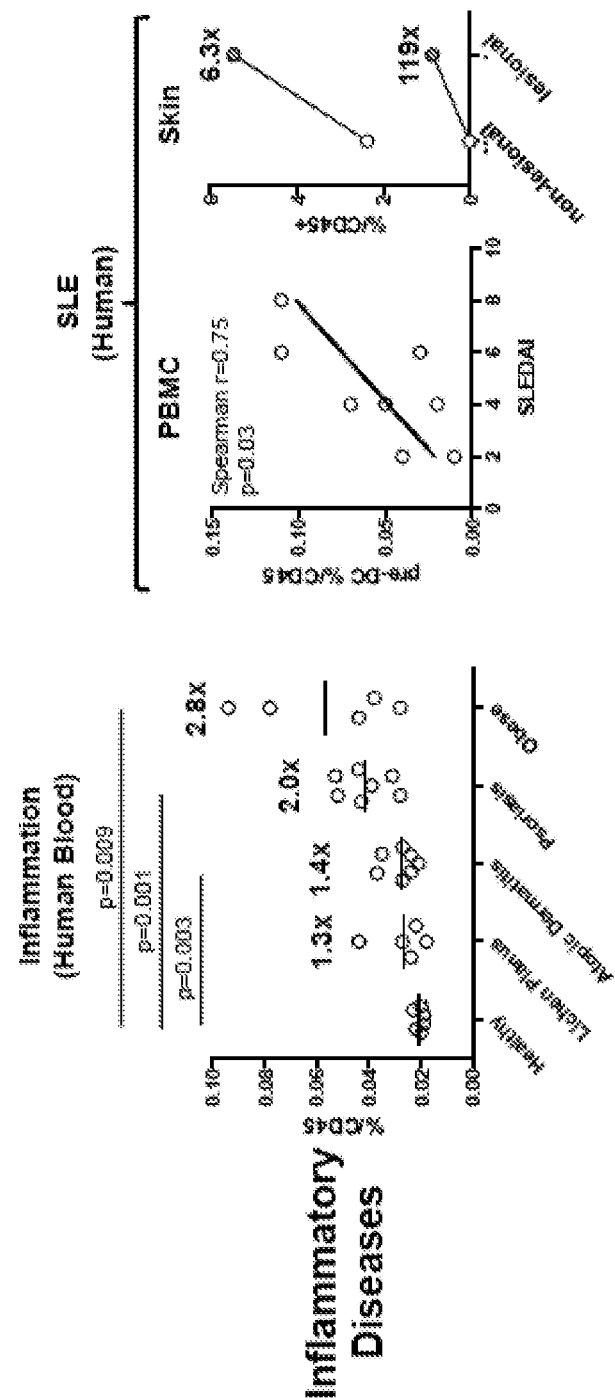

FIG. 38. The proportion of circulating pre-DC is increased in inflammatory conditions, including autoimmune diseases, cancer and infectious diseases.

Figure 39:
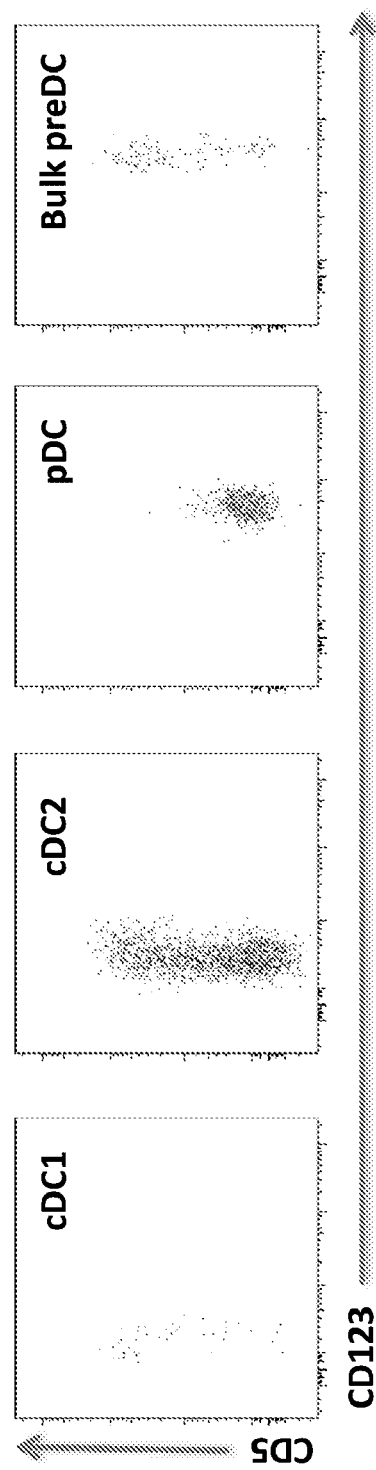

FIG. 39. Pre-DC also express CD5.

Figure 40:
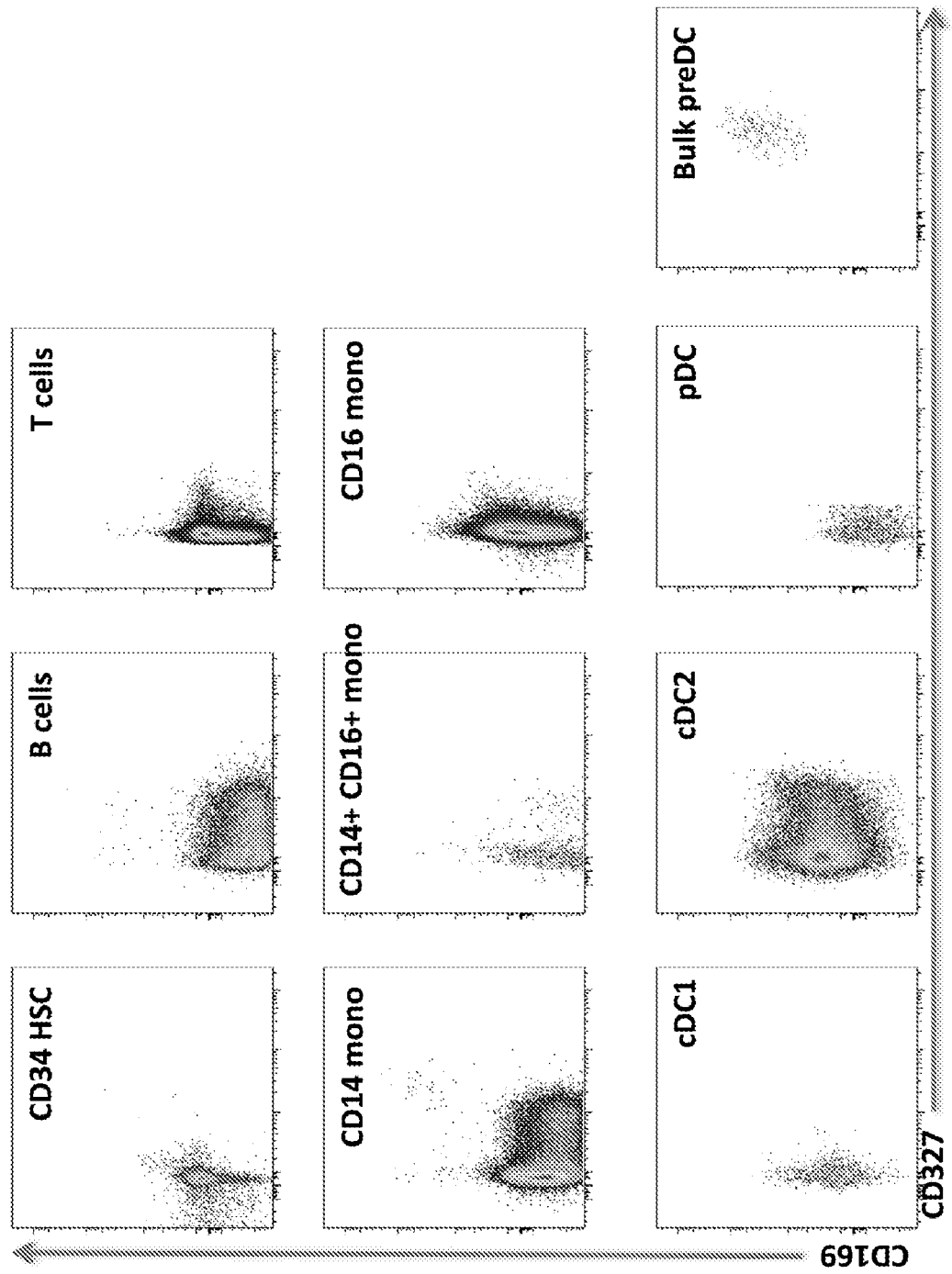

FIG. 40. Blood pre-DC show the highest expression of CD169 and CD327 compared to other cell types.

TABLES

TABLE 1

Number of detected genes per cell in the total DC MARS-seq experiment.

| Cell | Count |
| --- | --- |
| SCB_105 | 787 |
| SCB_106 | 785 |
| SCB_107 | 744 |
| SCB_108 | 774 |
| SCB_109 | 779 |
| SCB_110 | 755 |
| SCB_111 | 770 |
| SCB_112 | 740 |
| SCB_113 | 766 |
| SCB_114 | 751 |
| SCB_115 | 749 |
| SCB_116 | 780 |
| SCB_117 | 764 |
| SCB_118 | 734 |
| SCB_119 | 742 |
| SCB_120 | 787 |
| SCB_121 | 766 |
| SCB_122 | 766 |
| SCB_123 | 755 |
| SCB_124 | 758 |
| SCB_125 | 762 |
| SCB_126 | 767 |
| SCB_127 | 758 |
| SCB_128 | 756 |
| SCB_129 | 783 |
| SCB_130 | 744 |
| SCB_131 | 766 |
| SCB_132 | 729 |
| SCB_133 | 717 |
| SCB_134 | 781 |
| SCB_135 | 794 |
| SCB_136 | 775 |
| SCB_137 | 745 |
| SCB_138 | 784 |
| SCB_139 | 745 |
| SCB_140 | 748 |
| SCB_141 | 771 |
| SCB_142 | 767 |
| SCB_143 | 768 |
| SCB_144 | 670 |
| SCB_145 | 701 |
| SCB_146 | 752 |
| SCB_147 | 746 |
| SCB_148 | 726 |
| SCB_149 | 750 |
| SCB_150 | 781 |
| SCB_151 | 738 |
| SCB_152 | 775 |
| SCB_153 | 750 |
| SCB_154 | 788 |
| SCB_155 | 781 |
| SCB_156 | 773 |
| SCB_157 | 770 |
| SCB_158 | 762 |
| SCB_159 | 766 |
| SCB_160 | 768 |
| SCB_161 | 752 |
| SCB_162 | 767 |
| SCB_163 | 719 |
| SCB_164 | 748 |
| SCB_165 | 774 |
| SCB_166 | 769 |
| SCB_167 | 792 |
| SCB_168 | 772 |
| SCB_169 | 721 |
| SCB_170 | 752 |
| SCB_171 | 745 |
| SCB_172 | 749 |
| SCB_173 | 774 |
| SCB_174 | 745 |
| SCB_175 | 780 |
| SCB_176 | 763 |
| SCB_177 | 770 |
| SCB_178 | 777 |
| SCB_179 | 755 |
| SCB_180 | 719 |
| SCB_181 | 756 |
| SCB_182 | 759 |
| SCB_183 | 720 |
| SCB_184 | 730 |
| SCB_185 | 741 |
| SCB_186 | 741 |
| SCB_187 | 760 |
| SCB_188 | 783 |

TABLE 1-continued

Number of detected genes per cell in the total DC MARS-seq experiment.

| Cell | Count |
| --- | --- |
| SCB_189 | 760 |
| SCB_190 | 757 |
| SCB_191 | 786 |
| SCB_192 | 753 |
| SCB_193 | 786 |
| SCB_194 | 761 |
| SCB_195 | 749 |
| SCB_196 | 737 |
| SCB_197 | 720 |
| SCB_198 | 781 |
| SCB_199 | 749 |
| SCB_200 | 780 |
| SCB_201 | 793 |
| SCB_202 | 747 |
| SCB_203 | 771 |
| SCB_204 | 719 |
| SCB_205 | 754 |
| SCB_206 | 779 |
| SCB_207 | 742 |
| SCB_208 | 750 |
| SCB_209 | 751 |
| SCB_210 | 756 |
| SCB_211 | 732 |
| SCB_212 | 760 |
| SCB_213 | 734 |
| SCB_214 | 740 |
| SCB_215 | 714 |
| SCB_216 | 727 |
| SCB_217 | 748 |
| SCB_218 | 772 |
| SCB_219 | 772 |
| SCB_220 | 743 |
| SCB_221 | 686 |
| SCB_222 | 758 |
| SCB_223 | 771 |
| SCB_224 | 766 |
| SCB_225 | 755 |
| SCB_226 | 709 |
| SCB_227 | 733 |
| SCB_228 | 758 |
| SCB_229 | 756 |
| SCB_230 | 709 |
| SCB_231 | 756 |
| SCB_232 | 748 |
| SCB_233 | 782 |
| SCB_234 | 688 |
| SCB_235 | 626 |
| SCB_236 | 730 |
| SCB_237 | 757 |
| SCB_238 | 726 |
| SCB_239 | 734 |
| SCB_240 | 757 |
| SCB_241 | 773 |
| SCB_242 | 745 |
| SCB_243 | 750 |
| SCB_244 | 725 |
| SCB_245 | 725 |
| SCB_246 | 711 |
| SCB_247 | 729 |
| SCB_248 | 722 |
| SCB_249 | 734 |
| SCB_250 | 722 |
| SCB_251 | 729 |
| SCB_252 | 725 |
| SCB_253 | 763 |
| SCB_254 | 778 |
| SCB_255 | 768 |
| SCB_256 | 748 |
| SCB_257 | 787 |
| SCB_258 | 736 |
| SCB_259 | 730 |
| SCB_260 | 782 |
| SCB_261 | 753 |
| SCB_262 | 758 |
| SCB_263 | 690 |
| SCB_264 | 735 |
| SCB_265 | 735 |
| SCB_266 | 739 |
| SCB_267 | 682 |
| SCB_268 | 788 |
| SCB_269 | 729 |
| SCB_270 | 729 |
| SCB_271 | 764 |
| SCB_272 | 746 |
| SCB_273 | 774 |
| SCB_274 | 759 |
| SCB_275 | 749 |
| SCB_276 | 773 |
| SCB_277 | 777 |
| SCB_278 | 755 |
| SCB_279 | 748 |
| SCB_280 | 755 |
| SCB_281 | 752 |
| SCB_282 | 762 |
| SCB_283 | 723 |
| SCB_284 | 742 |
| SCB_285 | 776 |
| SCB_286 | 726 |
| SCB_287 | 786 |
| SCB_1 | 721 |
| SCB_2 | 768 |
| SCB_3 | 746 |
| SCB_4 | 791 |
| SCB_5 | 734 |
| SCB_6 | 754 |
| SCB_7 | 760 |
| SCB_8 | 757 |
| SCB_9 | 763 |
| SCB_10 | 706 |
| SCB_11 | 713 |
| SCB_12 | 776 |
| SCB_13 | 749 |
| SCB_14 | 765 |
| SCB_15 | 762 |
| SCB_16 | 772 |
| SCB_17 | 767 |
| SCB_18 | 705 |
| SCB_19 | 721 |
| SCB_20 | 740 |
| SCB_21 | 765 |
| SCB_22 | 774 |
| SCB_23 | 766 |
| SCB_24 | 765 |
| SCB_25 | 682 |
| SCB_26 | 772 |
| SCB_27 | 730 |
| SCB_28 | 763 |
| SCB_29 | 735 |
| SCB_30 | 754 |
| SCB_31 | 737 |
| SCB_32 | 787 |
| SCB_33 | 758 |
| SCB_34 | 768 |
| SCB_35 | 713 |
| SCB_36 | 722 |
| SCB_37 | 765 |
| SCB_38 | 741 |
| SCB_39 | 757 |
| SCB_40 | 759 |
| SCB_41 | 750 |
| SCB_42 | 776 |
| SCB_43 | 713 |
| SCB_44 | 675 |
| SCB_45 | 775 |
| SCB_46 | 757 |
| SCB_47 | 760 |
| SCB_48 | 764 |
| SCB_49 | 730 |
| SCB_50 | 755 |
| SCB_51 | 751 |

TABLE 1-continued

Number of detected genes per cell in the total DC MARS-seq experiment.

| Cell | Count |
|---|---|
| SCB_52 | 774 |
| SCB_53 | 743 |
| SCB_54 | 714 |
| SCB_55 | 739 |
| SCB_56 | 750 |
| SCB_57 | 758 |
| SCB_58 | 755 |
| SCB_59 | 776 |
| SCB_60 | 759 |
| SCB_61 | 697 |
| SCB_62 | 721 |
| SCB_63 | 741 |
| SCB_64 | 682 |
| SCB_65 | 756 |
| SCB_66 | 766 |
| SCB_67 | 725 |
| SCB_68 | 774 |
| SCB_69 | 733 |
| SCB_70 | 710 |
| SCB_71 | 758 |
| SCB_72 | 743 |
| SCB_73 | 758 |
| SCB_74 | 740 |
| SCB_75 | 725 |
| SCB_76 | 713 |
| SCB_77 | 735 |
| SCB_78 | 768 |
| SCB_79 | 715 |
| SCB_80 | 713 |
| SCB_81 | 751 |
| SCB_82 | 745 |
| SCB_83 | 742 |
| SCB_84 | 782 |
| SCB_85 | 783 |
| SCB_86 | 753 |
| SCB_87 | 744 |
| SCB_88 | 743 |
| SCB_89 | 741 |
| SCB_90 | 736 |
| SCB_91 | 691 |
| SCB_92 | 772 |
| SCB_93 | 764 |
| SCB_94 | 748 |
| SCB_95 | 770 |
| SCB_96 | 744 |
| SCB_97 | 732 |
| SCB_98 | 749 |
| SCB_99 | 763 |
| SCB_100 | 718 |
| SCB_101 | 781 |
| SCB_102 | 711 |
| SCB_103 | 753 |
| SCB_104 | 781 |
| SCB_360 | 761 |
| SCB_361 | 754 |
| SCB_362 | 775 |
| SCB_363 | 762 |
| SCB_364 | 779 |
| SCB_365 | 782 |
| SCB_366 | 763 |
| SCB_367 | 779 |
| SCB_368 | 786 |
| SCB_369 | 748 |
| SCB_370 | 779 |
| SCB_371 | 764 |
| SCB_372 | 745 |
| SCB_373 | 754 |
| SCB_374 | 778 |
| SCB_375 | 802 |
| SCB_376 | 788 |
| SCB_377 | 732 |
| SCB_378 | 718 |
| SCB_379 | 698 |
| SCB_380 | 761 |
| SCB_381 | 747 |
| SCB_382 | 812 |
| SCB_383 | 784 |
| SCB_384 | 781 |
| SCB_385 | 715 |
| SCB_386 | 717 |
| SCB_387 | 773 |
| SCB_388 | 699 |
| SCB_389 | 703 |
| SCB_390 | 768 |
| SCB_391 | 712 |
| SCB_392 | 759 |
| SCB_393 | 747 |
| SCB_394 | 747 |
| SCB_395 | 776 |
| SCB_396 | 794 |
| SCB_397 | 788 |
| SCB_398 | 770 |
| SCB_399 | 734 |
| SCB_400 | 719 |
| SCB_401 | 752 |
| SCB_402 | 774 |
| SCB_403 | 768 |
| SCB_404 | 754 |
| SCB_405 | 764 |
| SCB_406 | 729 |
| SCB_407 | 750 |
| SCB_408 | 731 |
| SCB_409 | 784 |
| SCB_410 | 785 |
| SCB_411 | 738 |
| SCB_412 | 775 |
| SCB_413 | 722 |
| SCB_414 | 803 |
| SCB_415 | 782 |
| SCB_416 | 778 |
| SCB_417 | 768 |
| SCB_418 | 749 |
| SCB_419 | 770 |
| SCB_420 | 731 |
| SCB_421 | 785 |
| SCB_422 | 747 |
| SCB_423 | 733 |
| SCB_424 | 732 |
| SCB_425 | 732 |
| SCB_426 | 759 |
| SCB_427 | 740 |
| SCB_428 | 741 |
| SCB_429 | 769 |
| SCB_430 | 713 |
| SCB_431 | 720 |
| SCB_432 | 773 |
| SCB_433 | 753 |
| SCB_434 | 742 |
| SCB_435 | 721 |
| SCB_436 | 798 |
| SCB_437 | 756 |
| SCB_438 | 767 |
| SCB_439 | 790 |
| SCB_440 | 768 |
| SCB_441 | 771 |
| SCB_442 | 738 |
| SCB_443 | 760 |
| SCB_444 | 765 |
| SCB_445 | 770 |
| SCB_446 | 752 |
| SCB_447 | 799 |
| SCB_448 | 749 |
| SCB_449 | 712 |
| SCB_450 | 777 |
| SCB_451 | 700 |
| SCB_452 | 748 |
| SCB_453 | 795 |
| SCB_454 | 738 |
| SCB_455 | 782 |
| SCB_456 | 742 |

TABLE 1-continued

Number of detected genes per cell in the total DC MARS-seq experiment.

| Cell | Count |
|---|---|
| SCB_457 | 763 |
| SCB_458 | 762 |
| SCB_459 | 665 |
| SCB_460 | 707 |
| SCB_511 | 787 |
| SCB_512 | 779 |
| SCB_513 | 753 |
| SCB_514 | 766 |
| SCB_515 | 775 |
| SCB_516 | 771 |
| SCB_517 | 777 |
| SCB_518 | 774 |
| SCB_519 | 757 |
| SCB_520 | 756 |
| SCB_521 | 750 |
| SCB_522 | 758 |
| SCB_523 | 719 |
| SCB_524 | 731 |
| SCB_525 | 736 |
| SCB_526 | 744 |
| SCB_527 | 765 |
| SCB_528 | 755 |
| SCB_529 | 737 |
| SCB_530 | 768 |
| SCB_531 | 769 |
| SCB_532 | 796 |
| SCB_533 | 757 |
| SCB_534 | 726 |
| SCB_535 | 741 |
| SCB_536 | 731 |
| SCB_537 | 802 |
| SCB_538 | 731 |
| SCB_539 | 715 |
| SCB_540 | 785 |
| SCB_541 | 758 |
| SCB_542 | 779 |
| SCB_543 | 800 |
| SCB_544 | 741 |
| SCB_545 | 779 |
| SCB_546 | 729 |
| SCB_547 | 737 |
| SCB_548 | 773 |
| SCB_549 | 787 |
| SCB_550 | 771 |
| SCB_551 | 750 |
| SCB_552 | 746 |
| SCB_553 | 742 |
| SCB_554 | 767 |
| SCB_555 | 743 |
| SCB_556 | 750 |
| SCB_557 | 744 |
| SCB_558 | 756 |
| SCB_559 | 765 |
| SCB_560 | 759 |
| SCB_561 | 741 |
| SCB_562 | 730 |
| SCB_563 | 762 |
| SCB_564 | 737 |
| SCB_565 | 770 |
| SCB_566 | 774 |
| SCB_567 | 720 |
| SCB_568 | 763 |
| SCB_569 | 725 |
| SCB_570 | 735 |
| SCB_571 | 713 |
| SCB_572 | 747 |
| SCB_573 | 750 |
| SCB_574 | 763 |
| SCB_575 | 768 |
| SCB_576 | 800 |
| SCB_577 | 788 |
| SCB_578 | 726 |
| SCB_579 | 761 |
| SCB_580 | 764 |
| SCB_581 | 735 |
| SCB_582 | 729 |
| SCB_583 | 812 |
| SCB_584 | 718 |
| SCB_585 | 745 |
| SCB_586 | 742 |
| SCB_587 | 728 |
| SCB_588 | 752 |
| SCB_589 | 758 |
| SCB_590 | 769 |
| SCB_591 | 742 |
| SCB_592 | 752 |
| SCB_593 | 777 |
| SCB_594 | 718 |
| SCB_595 | 777 |
| SCB_596 | 776 |
| SCB_597 | 706 |
| SCB_598 | 750 |
| SCB_599 | 777 |
| SCB_600 | 761 |
| SCB_601 | 731 |
| SCB_602 | 729 |
| SCB_603 | 776 |
| SCB_604 | 717 |
| SCB_605 | 747 |
| SCB_606 | 757 |
| SCB_607 | 737 |
| SCB_608 | 760 |
| SCB_609 | 804 |
| SCB_610 | 758 |
| SCB_611 | 771 |
| SCB_612 | 767 |
| SCB_613 | 762 |
| SCB_614 | 747 |
| SCB_615 | 764 |
| SCB_616 | 761 |
| SCB_617 | 746 |
| SCB_618 | 782 |
| SCB_619 | 777 |
| SCB_620 | 700 |
| SCB_621 | 757 |
| SCB_622 | 747 |
| SCB_623 | 770 |
| SCB_624 | 772 |
| SCB_625 | 792 |
| SCB_626 | 733 |
| SCB_627 | 776 |
| SCB_699 | 769 |
| SCB_700 | 805 |
| SCB_701 | 799 |
| SCB_702 | 712 |
| SCB_703 | 672 |
| SCB_704 | 788 |
| SCB_705 | 672 |
| SCB_706 | 755 |
| SCB_707 | 708 |
| SCB_708 | 709 |
| SCB_709 | 752 |
| SCB_710 | 718 |
| SCB_288 | 716 |
| SCB_289 | 767 |
| SCB_290 | 770 |
| SCB_291 | 720 |
| SCB_292 | 704 |
| SCB_293 | 787 |
| SCB_294 | 732 |
| SCB_295 | 728 |
| SCB_296 | 746 |
| SCB_297 | 782 |
| SCB_298 | 682 |
| SCB_299 | 760 |
| SCB_300 | 687 |
| SCB_301 | 745 |
| SCB_302 | 777 |
| SCB_303 | 701 |
| SCB_304 | 773 |

TABLE 1-continued

Number of detected genes per cell in the total DC MARS-seq experiment.

| Cell | Count |
|---|---|
| SCB_305 | 748 |
| SCB_306 | 772 |
| SCB_307 | 795 |
| SCB_308 | 753 |
| SCB_309 | 753 |
| SCB_310 | 714 |
| SCB_311 | 758 |
| SCB_312 | 695 |
| SCB_313 | 748 |
| SCB_314 | 747 |
| SCB_315 | 750 |
| SCB_316 | 746 |
| SCB_317 | 774 |
| SCB_318 | 723 |
| SCB_319 | 753 |
| SCB_320 | 741 |
| SCB_321 | 718 |
| SCB_322 | 744 |
| SCB_323 | 750 |
| SCB_324 | 711 |
| SCB_325 | 731 |
| SCB_326 | 764 |
| SCB_327 | 699 |
| SCB_328 | 755 |
| SCB_329 | 716 |
| SCB_330 | 783 |
| SCB_331 | 739 |
| SCB_332 | 747 |
| SCB_333 | 752 |
| SCB_334 | 766 |
| SCB_335 | 715 |
| SCB_336 | 765 |
| SCB_337 | 745 |
| SCB_338 | 698 |
| SCB_339 | 770 |
| SCB_340 | 730 |
| SCB_341 | 767 |
| SCB_342 | 786 |
| SCB_343 | 709 |
| SCB_344 | 767 |
| SCB_345 | 778 |
| SCB_346 | 745 |
| SCB_347 | 778 |
| SCB_348 | 759 |
| SCB_349 | 755 |
| SCB_350 | 733 |
| SCB_351 | 759 |
| SCB_352 | 708 |
| SCB_353 | 721 |
| SCB_354 | 792 |
| SCB_355 | 761 |
| SCB_356 | 686 |
| SCB_357 | 733 |
| SCB_358 | 765 |
| SCB_359 | 756 |
| SCB_628 | 763 |
| SCB_629 | 715 |
| SCB_630 | 719 |
| SCB_631 | 774 |
| SCB_632 | 691 |
| SCB_633 | 691 |
| SCB_634 | 687 |
| SCB_635 | 706 |
| SCB_636 | 708 |
| SCB_637 | 702 |
| SCB_638 | 743 |
| SCB_639 | 752 |
| SCB_640 | 772 |
| SCB_641 | 739 |
| SCB_642 | 733 |
| SCB_643 | 767 |
| SCB_644 | 735 |
| SCB_645 | 756 |
| SCB_646 | 775 |
| SCB_647 | 728 |
| SCB_648 | 750 |
| SCB_649 | 768 |
| SCB_461 | 723 |
| SCB_462 | 804 |
| SCB_463 | 713 |
| SCB_464 | 699 |
| SCB_465 | 766 |
| SCB_466 | 768 |
| SCB_467 | 759 |
| SCB_468 | 765 |
| SCB_469 | 784 |
| SCB_470 | 702 |
| SCB_471 | 703 |
| SCB_472 | 775 |
| SCB_473 | 753 |
| SCB_474 | 764 |
| SCB_475 | 680 |
| SCB_476 | 768 |
| SCB_477 | 709 |
| SCB_478 | 761 |
| SCB_479 | 777 |
| SCB_480 | 719 |
| SCB_481 | 761 |
| SCB_482 | 784 |
| SCB_483 | 718 |
| SCB_484 | 771 |
| SCB_485 | 766 |
| SCB_486 | 733 |
| SCB_487 | 767 |
| SCB_488 | 793 |
| SCB_489 | 758 |
| SCB_490 | 768 |
| SCB_491 | 764 |
| SCB_492 | 811 |
| SCB_493 | 779 |
| SCB_494 | 691 |
| SCB_495 | 694 |
| SCB_496 | 766 |
| SCB_497 | 756 |
| SCB_498 | 780 |
| SCB_499 | 770 |
| SCB_500 | 757 |
| SCB_501 | 776 |
| SCB_502 | 806 |
| SCB_503 | 737 |
| SCB_504 | 769 |
| SCB_505 | 754 |
| SCB_506 | 736 |
| SCB_507 | 773 |
| SCB_508 | 726 |
| SCB_509 | 773 |
| SCB_510 | 756 |
| SCB_677 | 690 |
| SCB_678 | 728 |
| SCB_679 | 725 |
| SCB_680 | 749 |
| SCB_681 | 759 |
| SCB_682 | 746 |
| SCB_683 | 740 |
| SCB_684 | 689 |
| SCB_685 | 698 |
| SCB_686 | 737 |
| SCB_687 | 741 |
| SCB_688 | 729 |
| SCB_689 | 808 |
| SCB_690 | 701 |
| SCB_691 | 789 |
| SCB_692 | 775 |
| SCB_693 | 811 |
| SCB_694 | 727 |
| SCB_695 | 778 |
| SCB_696 | 718 |
| SCB_697 | 724 |
| SCB_698 | 690 |
| SCB_650 | 797 |

TABLE 1-continued

Number of detected genes per cell in the total DC MARS-seq experiment.

| Cell | Count |
| --- | --- |
| SCB_651 | 736 |
| SCB_652 | 773 |
| SCB_653 | 703 |
| SCB_654 | 772 |
| SCB_655 | 769 |
| SCB_656 | 797 |
| SCB_657 | 765 |
| SCB_658 | 764 |
| SCB_659 | 741 |
| SCB_660 | 732 |
| SCB_661 | 768 |
| SCB_662 | 758 |
| SCB_663 | 773 |
| SCB_664 | 753 |
| SCB_665 | 745 |
| SCB_666 | 709 |
| SCB_667 | 705 |
| SCB_668 | 662 |
| SCB_669 | 729 |
| SCB_670 | 784 |
| SCB_671 | 726 |
| SCB_672 | 691 |
| SCB_673 | 782 |
| SCB_674 | 651 |
| SCB_675 | 760 |
| SCB_676 | 705 |

TABLE 2

DC subsets signature genes derived from Gene Expression Omnibus data series GSE35457 and used for MARS-seq and C1 data analyses.

| pDC signature genes | | cDC1 signature genes | | cDC2 signature genes |
| --- | --- | --- | --- | --- |
| ABCA7 | MTMR2 | ABCB4 | STX11 | ABCG1 |
| ABCB6 | MUPCDH | ABI3 | STX6 | ACP5 |
| ABHD15 | MX1 | ABR | SVIL | ACP6 |
| ABTB2 | MYB | ACER3 | SWAP70 | ACSL1 |
| ACACB | MYBPH | ACOT11 | SYN1 | ACSL5 |
| ACN9 | MYH3 | ACPP | SYT11 | ACSS2 |
| ACSBG1 | MYL6B | ACTA2 | SYTL3 | ACTB |
| ACSM3 | N4BP2L1 | ACVRL1 | TBL1X | ACTR3 |
| ADA | N6AMT1 | ADAM15 | TBXAS1 | ADAD2 |
| ADAM19 | NADK | ADAM8 | TESC | ADAM28 |
| ADARB1 | NAT8L | ADAMTSL4 | TICAM2 | ADORA2B |
| ADAT3 | NCF1C | ADAP1 | TIMP1 | ADORA3 |
| ADC | NCLN | AGTPBP1 | TIPARP | AGPAT1 |
| ADI1 | NCRNA00153 | ALDH3B1 | TKT | AGPS |
| AEBP1 | NDST2 | ALOX5 | TLE4 | AIG1 |
| AHI1 | NEK8 | AMICA1 | TLR2 | AIM2 |
| AJAP1 | NFATC2IP | AMOT | TLR5 | ALDH1A1 |
| AKR1C3 | NFX1 | ANG | TLR8 | ALDH3A2 |
| ALDH5A1 | NGLY1 | ANXA1 | TM6SF1 | AMY1A |
| ALOX5AP | NHEDC1 | ANXA2 | TMC6 | ANPEP |
| ANKRD33 | NIN | ANXA2P1 | TMEM154 | ANXA6 |
| APOBEC3D | NIPA1 | ANXA5 | TMEM173 | AP3M2 |
| APP | NLRP2 | AOAH | TMEM2 | APOL1 |
| ARHGAP25 | NLRP7 | APAF1 | TMEM71 | APOL2 |
| ARHGAP27 | NOP56 | APLP2 | TNFAIP2 | APOL3 |
| ARHGAP9 | NOTCH3 | ARAP3 | TNFRSF10D | ASAP1 |
| ARHGEF10 | NOTCH4 | ARHGAP10 | TNFRSF1A | ASB2 |
| ARHGEF4 | NPAL3 | ARL4A | TNFRSF1B | ATG3 |
| ARID3A | NPC1 | ARRDC2 | TNFSF10 | ATL1 |
| ARMC5 | NPC2 | ASCL2 | TNFSF12 | ATP1A1 |
| ARMET | NR5A1 | ASGR1 | TNFSF13B | AZI1 |
| ARRDC5 | NRP1 | ASGR2 | TOB1 | B4GALT5 |
| ASIP | NTAN1 | ATP1B1 | TPPP3 | BAG3 |
| ATP10A | NUCB2 | ATP6V1B2 | TREM1 | BATF3 |
| ATP13A2 | NUMA1 | BACH2 | TRIB1 | BCAR3 |
| ATP2A3 | OAS1 | BATF | TRIB2 | BCL6 |
| ATP8B2 | ODC1 | BLVRA | TSC22D3 | BEND5 |
| AUTS2 | OFD1 | BTBD11 | TSPAN32 | BIK |
| AVEN | OGT | C10orf11 | TSPAN4 | BIVM |
| B4GALT1 | OPN3 | C10orf54 | TSPO | BTLA |
| BAIAP2L1 | OPTN | C15orf39 | TTYH3 | C10orf105 |
| BCAS4 | OR3A3 | C16orf7 | UBAC1 | C10orf64 |
| BCL11A | P2RX1 | C17orf44 | UPP1 | C13orf15 |
| BEND6 | P4HB | C2CD2 | USP3 | C13orf11 |
| BLK | PACAP | C3orf59 | VCAN | C15orf18 |
| BLNK | PACSIN1 | C4orf18 | VENTX | C17orf58 |
| BSPRY | PAFAH2 | C9orf72 | VIPR1 | C1orf115 |
| BTAF1 | PAG1 | CA2 | VPS37C | C1orf162 |
| BTG1 | PANX2 | CACNA2D3 | VSIG4 | C1orf165 |
| C10orf141 | PAPLN | CALHM2 | XAF1 | C1orf186 |
| C10orf47 | PARP10 | CAPN2 | XYLT1 | C1orf21 |

TABLE 2-continued

DC subsets signature genes derived from Gene Expression Omnibus
data series GSE35457 and used for MARS-seq and C1 data analyses.

| pDC signature genes | | cDC1 signature genes | | cDC2 signature genes |
|---|---|---|---|---|
| C10orf58 | PARVB | CARD16 | YIF1B | C1orf24 |
| C11orf24 | PBX3 | CARD9 | ZAK | C1orf51 |
| C11orf67 | PCNT | CASP1 | ZBP1 | C1orf54 |
| C11orf80 | PCNX | CASP4 | ZEB2 | C20orf27 |
| C12orf23 | PCSK4 | CAST | ZFAND5 | C21orf63 |
| C12orf44 | PDCD4 | CCL5 | ZFP36 | C5orf30 |
| C12orf57 | PDIA4 | CCND2 | ZNF562 | C8orf47 |
| C13orf18 | PDXP | CCR6 | ZYG11B | CADM1 |
| C14orf4 | PFKFB2 | CD14 | | CAMK2D |
| C14orf45 | PFKP | CD151 | | CAMP |
| C16orf33 | PGD | CD163 | | CBL |
| C16orf58 | PGM2L1 | CD1A | | CCDC6 |
| C16orf93 | PHACTR1 | CD1B | | CCDC62 |
| C18orf25 | PHEX | CD1C | | CCDC90A |
| C18orf8 | PHF16 | CD1D | | CCND1 |
| C1orf109 | PI4KAP2 | CD1E | | CCR9 |
| C20orf100 | PIK3AP1 | CD2 | | CD226 |
| C20orf103 | PIK3CD | CD209 | | CD38 |
| C20orf132 | PIK4CA | CD244 | | CD48 |
| C21orf2 | PLAC8 | CD300A | | CD59 |
| C2orf55 | PLAU | CD300C | | CDCA7 |
| C3orf21 | PLD6 | CD300LF | | CDH2 |
| C4BPB | PLEKHG4 | CD33 | | CDK2AP1 |
| C5orf62 | PLP2 | CD5 | | CDK6 |
| C6orf170 | PLS3 | CD52 | | CHD7 |
| C7orf41 | PMEPA1 | CD69 | | CHST2 |
| C7orf54 | PNOC | CDC42EP4 | | CLEC1A |
| C8orf13 | POLB | CDCP1 | | CLEC9A |
| C9orf127 | POLE | CDH23 | | CLNK |
| C9orf128 | POMGNT1 | CDS1 | | CLSTN2 |
| C9orf142 | POU4F1 | CEBPA | | CNTLN |
| C9orf37 | PPM1J | CEBPB | | CPNE3 |
| C9orf45 | PPP1R14A | CEBPD | | CREG1 |
| C9orf91 | PPP1R14B | CENPN | | CSRP1 |
| C9orf95 | PPP1R16B | CENTA1 | | CST3 |
| CA8 | PPP2R1B | CENTG3 | | CTPS2 |
| CADM4 | PPP2R5C | CES1 | | CXCL16 |
| CARD11 | PRAGMIN | CFD | | CXCL9 |
| CASZ1 | PRIM1 | CFP | | CYB5R3 |
| CBLB | PRKCB | CHD1 | | CYP2E1 |
| CBX4 | PRKCB1 | CHST13 | | DBN1 |
| CBX6 | PRKD1 | CIDEB | | DCLRE1A |
| CCDC102A | PROC | CLEC10A | | DCTPP1 |
| CCDC50 | PSCD4 | CLEC12A | | DFNA5 |
| CCDC69 | PSD4 | CLEC4A | | DHCR24 |
| CCR2 | PTCRA | CLEC4F | | DHRS3 |
| CCR3 | PTGDS | CMTM1 | | DLG3 |
| CCR7 | PTGR1 | COL9A2 | | DOCK7 |
| CCS | PTK7 | COQ10A | | DPP4 |
| CD164 | PTPRCAP | CPNE8 | | DSE |
| CD247 | PTPRM | CPPED1 | | DYSF |
| CD2AP | PVRL1 | CREB5 | | EGLN3 |
| CD320 | QDPR | CRTAP | | EHD4 |
| CD36 | RAB15 | CRYL1 | | ELOVL5 |
| CD4 | RAB38 | CRYZL1 | | ENOX1 |
| CD68 | RAB40B | CSF1R | | ENPP1 |
| CD7 | RAB9P1 | CSF3R | | ENPP3 |
| CD99 | RABGAP1L | CST7 | | ENPP4 |
| CDC14A | RALGPS1 | CSTA | | ERAP2 |
| CDCA7L | RASD1 | CTSH | | ERMP1 |
| CDH1 | RBM38 | CX3CR1 | | ERO1L |
| CDK2 | RECQL5 | CXCR7 | | EVI2A |
| CDK5R1 | RELN | CYBRD1 | | EVL |
| CDKN2D | REXO2 | CYFIP1 | | FAH |
| CDR2 | RGS1 | DAGLB | | FAM102A |
| CDYL | RGS7 | DDX60L | | FAM125B |
| CENPV | RHBDF2 | DEM1 | | FAM129A |
| CETP | RIMS3 | DENND3 | | FAM149A |
| CHST12 | RLTPR | DEPDC6 | | FAM160A2 |
| CHST15 | RNASE6 | DHRS9 | | FAM20C |
| CIB2 | RNASEL | DOK2 | | FAM57A |
| CIRBP | RNF11 | DPEP2 | | FAR2 |
| CLDN23 | RNF121 | DPYD | | FARS2 |
| CLEC4C | RNF165 | DTD1 | | FBXL20 |
| CLIC3 | RPA1 | DTNA | | FKBP1B |

TABLE 2-continued

DC subsets signature genes derived from Gene Expression Omnibus
data series GSE35457 and used for MARS-seq and C1 data analyses.

| pDC signature genes | | cDC1 signature genes | cDC2 signature genes |
|---|---|---|---|
| CLN8 | RPP25 | ECGF1 | FLJ10916 |
| CMTM3 | RPPH1 | EFNB1 | FLJ22795 |
| CNTNAP1 | RPS6KA2 | EMP1 | FLT3 |
| COBL | RPS6KA4 | EMR2 | FMNL2 |
| COBLL1 | RRBP1 | EMR3 | FNBP1 |
| COL24A1 | RSPH1 | ENHO | FNIP2 |
| CORO1C | RTKN | ENTPD1 | FUCA1 |
| CPLX1 | RUNX2 | EPB41L2 | FUT8 |
| CREB3L2 | RWDD2A | EPB41L3 | GCET2 |
| CRTC3 | SAP130 | EPSTI1 | GFOD1 |
| CRYM | SBDS | ERMAP | GINS2 |
| CTNS | SBF1 | ETS2 | GLTP |
| CTSB | SCAMP5 | F13A1 | GNAZ |
| CTSC | SCARA5 | FAM102B | GPER |
| CTSL2 | SCARB1 | FAM104B | GPR126 |
| CUEDC1 | SCARB2 | FAM109A | GPRIN3 |
| CUTL1 | SCN9A | FAM110A | GPSM1 |
| CUX2 | SCYL3 | FAM111A | GPT2 |
| CXCR3 | SDC1 | FAM129B | GSTP1 |
| CXorfl2 | SDK2 | FAM38A | GYPC |
| CXorf57 | SEC11C | FAM46A | H2AFY2 |
| CXXC5 | SEC61A1 | FBLN2 | HCP5 |
| CYBASC3 | SEC61A2 | FBN2 | HLA-DOB |
| CYBB | SEC61B | FCGBP | HLA-DPA1 |
| CYFIP2 | SEL1L3 | FCGR2A | HLA-DPB1 |
| CYP2J2 | SELL | FCGR2B | HLA-DQB1 |
| CYP46A1 | SELS | FCN1 | HLA-DRB1 |
| CYSLTR1 | SEMA4D | FCRLB | HLA-DRB3 |
| CYTH4 | SEMA5A | FGD4 | HLA-DRB4 |
| CYYR1 | SEPHS1 | FILIP1L | HMOX1 |
| DAAM1 | SERPINF1 | FLVCR2 | HN1 |
| DAB2 | SERPING1 | FOSB | HOXA9 |
| DACH1 | SETBP1 | FOXO1 | HPS5 |
| DAPK2 | SH2D3C | FPR1 | HSD17B8 |
| DBNDD1 | SH3D19 | FPR3 | HSDL2 |
| DCK | SH3PXD2A | FRAT2 | HYAL3 |
| DCPS | SHD | FXYD5 | ICA1 |
| DDB1 | SIDT1 | FYB | ICAM3 |
| DDIT4 | SIK1 | GABBR1 | ID2 |
| DEDD2 | SIRPB1 | GADD45B | IDO1 |
| DERL3 | SIVA | GALM | IDO2 |
| DEXI | SIVA1 | GAPDH | IFNGR2 |
| DHRS7 | SLA2 | GBP1 | IFT20 |
| DHTKD1 | SLAMF6 | GBP2 | IL15 |
| DIP2A | SLC15A4 | GBP3 | INADL |
| DKFZP586I1420 | SLC20A1 | GBP4 | INDO |
| DKFZp761P0423 | SLC23A1 | GBP5 | IRAK2 |
| DNASE2 | SLC25A4 | GHRL | ITGB7 |
| DPPA4 | SLC29A1 | GIMAP1 | ITPR3 |
| DRD4 | SLC2A1 | GIMAP2 | KATNA1 |
| DSG2 | SLC2A6 | GIMAP4 | KIAA1598 |
| DSN1 | SLC2A8 | GIMAP6 | KIAA1688 |
| DTX2 | SLC35A3 | GIMAP7 | KIF16B |
| DUSP28 | SLC35C2 | GIMAP8 | KIF20B |
| DUSP5 | SLC35F3 | GK | KIT |
| DYRK4 | SLC37A1 | GLIPR2 | KLHL22 |
| E2F2 | SLC39A6 | GPBAR1 | KLHL5 |
| E2F5 | SLC3A2 | GPR162 | KLRG1 |
| EBI2 | SLC43A3 | GPR44 | LAT |
| EIF4A3 | SLC44A2 | GRK5 | LFNG |
| EIF4ENIF1 | SLC47A1 | HBEGF | LIMA1 |
| ELMO2 | SLC7A5 | HDAC4 | LMNA |
| EMID2 | SLC7A6 | HK1 | LOC100133583 |
| ENOSF1 | SLC9A3R1 | HK2 | LOC100133866 |
| ENPP2 | SLFN11 | HK3 | LOC150223 |
| EPDR1 | SLITRK5 | HNMT | LOC25845 |
| EPHB1 | SMARCAL1 | HSPA1A | LOC439949 |
| ERCC1 | SMC6 | HSPA6 | LOC642073 |
| ERN1 | SMPD3 | HSPA7 | LOC642590 |
| ESR2 | SNAP91 | ICAM2 | LOC645638 |
| ETS1 | SNCA | IER5 | LOC649143 |
| FAM107B | SNRNP25 | IFI30 | LOC653344 |
| FAM108C1 | SNRPN | IFI6 | LOC730101 |
| FAM113B | SORL1 | IFIH1 | LONRF1 |
| FAM129C | SPCS1 | IFIT1 | LPAR5 |

TABLE 2-continued

DC subsets signature genes derived from Gene Expression Omnibus
data series GSE35457 and used for MARS-seq and C1 data analyses.

| pDC signature genes | | cDC1 signature genes | | cDC2 signature genes |
|---|---|---|---|---|
| FAM167A | SPHK1 | IFIT3 | | LPCAT2 |
| FAM43A | SPIB | IFITM1 | | LRBA |
| FAM65A | SPNS3 | IFITM2 | | LRRC1 |
| FAM81A | SPOCK2 | IFITM3 | | LRRCC1 |
| FAM82A2 | SRPR | IFT57 | | LRRK2 |
| FANCD2 | SRPX | IGLL1 | | LYRM4 |
| FBXO18 | SSR4 | IGSF6 | | MARCKSL1 |
| FCHSD2 | ST3GAL2 | IL13RA1 | | MATK |
| FCRLA | ST3GAL4 | IL17RA | | MCM4 |
| FEZ2 | ST6GALNAC4 | IL1B | | MESP1 |
| FGFR3 | ST6GALNAC6 | IL1R1 | | MFNG |
| FHL1 | STAG3L2 | IL1R2 | | MGC4677 |
| FLJ21986 | STAG3L3 | IL1RN | | MIST |
| FLJ42627 | STAMBPL1 | INPP1 | | MMP25 |
| FMNL3 | STAT4 | IRAK3 | | MND1 |
| FYCO1 | STK11IP | IRF1 | | MPP3 |
| FZD3 | STK32B | ISG15 | | MYC |
| GAL3ST4 | STMN1 | ITGA5 | | MYLK |
| GARNL4 | STOX1 | ITGAM | | MYO1D |
| GAS6 | STT3A | ITSN1 | | NAAA |
| GFI1 | SUGT1 | JDP2 | | NAALADL1 |
| GGA2 | SUPT3H | JHDM1D | | NAP1L1 |
| GGH | SUPT5H | JUN | | NAV1 |
| GINS3 | SUSD1 | JUP | | NBEAL2 |
| GLCE | SYCP2L | KCNK13 | | NCALD |
| GLDN | SYS1 | KCNQ1 | | NCKAP5 |
| GLS | SYTL2 | KIAA0922 | | NET1 |
| GLT25D1 | TACC1 | KIAA1683 | | NETO2 |
| GLT8D1 | TARBP1 | KLF11 | | NLRX1 |
| GNG7 | TATDN3 | KLF2 | | NMNAT3 |
| GPM6B | TAX1BP3 | KLF4 | | OSBPL3 |
| GPR114 | TBC1D14 | KLF9 | | OSBPL9 |
| GPR183 | TBC1D16 | LACTB | | P2RY10 |
| GPRC5C | TBC1D4 | LAMP3 | | PAM |
| GPX7 | TBX19 | LAYN | | PAPSS1 |
| GRAMD1B | TCF3 | LDLR | | PARM1 |
| GRB14 | TCF4 | LGALS1 | | PARP3 |
| GRIN1 | TCL1A | LILRA2 | | PDE8B |
| GSDMB | TCL1B | LILRA3 | | PDLIM7 |
| GZMB | TEX2 | LILRA6 | | PFKFB3 |
| GZMH | TFIP11 | LILRB3 | | PIGZ |
| HCST | TGFBR2 | LIMCH1 | | PIK3CB |
| HERC5 | TLCD1 | LIMS1 | | PITPNC1 |
| HERPUD1 | TLR7 | LMO2 | | PITPNM1 |
| HHAT | TLR9 | LOC129550 | | PKP2 |
| HIGD1A | TM7SF2 | | LOC100130520 | PKP4 |
| HIST1H2BD | TM9SF2 | LOC100170939 | | PLCD1 |
| HIST1H2BK | TMEM109 | LOC143941 | | PLEKHA5 |
| HOXB2 | TMEM141 | LOC153561 | | PLEKHA6 |
| HPS4 | TMEM149 | LOC338758 | | PLEKHO2 |
| HRASLS3 | TMEM170B | LOC391075 | | PLXNA1 |
| HSP90B1 | TMEM175 | LOC644237 | | PLXNB1 |
| HVCN1 | TMEM187 | LOC645626 | | PMM1 |
| IDH3A | TMEM194A | LOC648984 | | PNLDC1 |
| IFI44 | TMEM194B | LOC653778 | | PNMA1 |
| IFI44L | TMEM44 | LOC654103 | | POLA2 |
| IFIT2 | TMEM53 | LOC728093 | | PPA1 |
| IFNAR1 | TMEM63A | LOC728519 | | PPAP2A |
| IFNAR2 | TMEM91 | LOC728666 | | PPM1H |
| IGF2R | TMEM98 | LOC728855 | | PPM1M |
| IGFBP3 | TNFRSF17 | LOC729708 | | PPT1 |
| IGJ | TNFRSF21 | LOC730994 | | PPY |
| IL18RAP | TNNI2 | LOC731486 | | PRKCZ |
| IL28RA | TOM1 | LOC88523 | | PSEN2 |
| IL3RA | TOX2 | LRRC25 | | PSMB9 |
| INSM1 | TP53I13 | LRRC33 | | PTGER2 |
| INTS12 | TPM2 | LST1 | | PTK2 |
| IRF4 | TPRG1L | LYL1 | | PTPLB |
| IRF7 | TPST2 | LYST | | QPRT |
| ISCU | TRAF3 | MAFB | | RAB11FIP4 |
| ITCH | TRO | MAP3K6 | | RAB30 |
| ITGAE | TRPM2 | MARCO | | RAB32 |
| ITM2C | TSEN54 | MBOAT7 | | RAB33A |
| KANK1 | TSPAN13 | MEFV | | RAB3IP |
| KATNAL1 | TSPAN3 | MEGF9 | | RAB7B |

TABLE 2-continued

DC subsets signature genes derived from Gene Expression Omnibus data series GSE35457 and used for MARS-seq and C1 data analyses.

| pDC signature genes | | cDC1 signature genes | cDC2 signature genes |
|---|---|---|---|
| KCNA5 | TSPYL2 | MLKL | RAB7L1 |
| KCNH8 | TUBB6 | MMD | RAB8B |
| KCNK1 | TUBG1 | MOV10 | RALB |
| KCNK10 | TUBG2 | MPZL2 | RASGRP3 |
| KCNK17 | TULP4 | MS4A14 | RGS10 |
| KCTD5 | TXN | MS4A7 | RGS12 |
| KIAA0226 | TXNDC3 | MSLN | RUSC1 |
| KIAA0513 | TXNDC5 | MSN | RYK |
| KIAA1147 | UBE2E3 | MT1A | S100A10 |
| KIAA1274 | UBE2J1 | MTMR11 | Septin 3 |
| KIAA1370 | UBQLNL | MYBPC3 | SERPINB6 |
| KIAA1545 | UGCG | MYO1A | SERPINF2 |
| KIAA1641 | ULK1 | MYO1F | SH3RF2 |
| KIAA1984 | UNC93B1 | MYO5C | SHE |
| KIF13B | USF2 | MYPOP | SIGLEC10 |
| KIF26B | USP11 | NACC2 | SIGLECP3 |
| KLHL13 | USP24 | NCF2 | SLA |
| KLHL3 | USP36 | NFE2 | SLAMF7 |
| KMO | VASH2 | NINJ2 | SLAMF8 |
| KRT5 | VEGFB | NLRP12 | SLC1A3 |
| L3MBTL3 | VEZF1 | NLRP3 | SLC24A4 |
| LAIR1 | VIPR2 | NOD2 | SLC25A25 |
| LAMC1 | WDR19 | NR1H3 | SLC39A8 |
| LAMP1 | WDR51A | NR4A2 | SLC44A1 |
| LAMP2 | WNT10A | OAF | SLC46A3 |
| LAPTM4B | XBP1 | OAS3 | SLC9A9 |
| LASS6 | YPEL1 | OLFM1 | SLCO3A1 |
| LBH | ZC3H5 | OSCAR | SMO |
| LDOC1 | ZCCHC11 | P2RY13 | SNORA57 |
| LEPREL1 | ZCWPW1 | P2RY2 | SNX22 |
| LGMN | ZDHHC14 | P2RY5 | SNX3 |
| LHFPL2 | ZDHHC17 | PAPSS2 | SNX30 |
| LILRA4 | ZDHHC23 | PARP14 | SP140 |
| LILRB4 | ZDHHC4 | PARP9 | SPATS2L |
| LIME1 | ZDHHC8 | PCCA | SPI1 |
| LMNB2 | ZDHHC9 | PCK2 | SPIN3 |
| LOC100128410 | ZFYVE26 | PCSK5 | SPNS1 |
| LOC100129466 | ZHX2 | PEA15 | SPRY2 |
| LOC100129673 | ZKSCAN4 | PFKFB4 | ST3GAL5 |
| LOC100130633 | ZMYM6 | PHCA | ST5 |
| LOC100131289 | ZMYND11 | PID1 | ST6GALNAC2 |
| LOCI00132299 | ZNF175 | PILRA | ST7 |
| LOC100132740 | ZNF185 | PION | STK39 |
| LOC100134134 | ZNF219 | PIP3-E | STOM |
| LOC100190939 | ZNF521 | PIP4K2A | STX3 |
| LOC132241 | ZNF556 | PKIB | SUOX |
| LOC201175 | ZNF589 | PLA2G7 | SUSD3 |
| LOC221442 | ZNF706 | PLSCR3 | TACSTD2 |
| LOC283874 | ZNF767 | PLXDC2 | TANC2 |
| LOC285296 | ZNF789 | PNPLA6 | TAP1 |
| LOC285359 | ZSCAN16 | PPEF1 | TAP2 |
| LOC347544 | | PPFIA4 | TCEA3 |
| LOC387841 | | PPFIBP2 | TCEAL3 |
| LOC387882 | | PPM1F | TGM2 |
| LOC389442 | | PQLC3 | THBD |
| LOC389816 | | PRAM1 | THEM4 |
| LOC399804 | | PRDM1 | TJP2 |
| LOC400027 | | PRIC285 | TLR10 |
| LOC400657 | | PRKCD | TLR3 |
| LOC442535 | | PSRC1 | TMEM106C |
| LOC550112 | | PSTPIP2 | TMEM14A |
| LOC641298 | | PTAFR | TMEM97 |
| LOC642031 | | PTGER4 | TOX |
| LOC642299 | | PTGS1 | TPMT |
| LOC642755 | | PTGS2 | TRAF3IP2 |
| LOC643384 | | PTK6 | TRAF5 |
| LOC644879 | | PTPN12 | TRIB3 |
| LOC646576 | | PYGL | TSHZ3 |
| LOC647000 | | RAB24 | TSPAN2 |
| LOC647886 | | RAB27A | TSPAN33 |
| LOC650114 | | RARA | TSPYL3 |
| LOC651957 | | RARRES3 | TTF2 |
| LOC652128 | | RASSF4 | TUBA4A |
| LOC653158 | | RCBTB2 | VAC14 |
| LOC728308 | | RGL1 | VAV3 |

TABLE 2-continued

DC subsets signature genes derived from Gene Expression Omnibus
data series GSE35457 and used for MARS-seq and C1 data analyses.

| pDC signature genes | cDC1 signature genes | cDC2 signature genes |
|---|---|---|
| LOC728661 | RHOU | VCAMI |
| LOC728715 | RIN2 | VPS37D |
| LOC728743 | RIPK5 | WARS |
| LOC729148 | RNASE2 | WDFY4 |
| LOC729406 | RPGRIP1 | WDR41 |
| LOC729764 | RTN1 | WDR91 |
| LOC91431 | RXRA | YEATS2 |
| LOXL4 | S100A12 | ZBTB46 |
| LPXN | S100A4 | ZDHHC18 |
| LRP5 | S100A8 | ZFP36L1 |
| LRP8 | S100A9 | ZMYND15 |
| LRRC26 | SAMD9L | ZNF232 |
| LRRC36 | SAP30 | ZNF366 |
| LSS | SCO2 | ZNF532 |
| LTB | SCPEP1 | ZNF627 |
| LTK | SDHALP1 | ZNF662 |
| LY9 | SERPINA1 | ZNF788 |
| MAG | SGK | |
| MAGED1 | SGK1 | |
| MAP1A | SGSH | |
| MAP4K4 | SIDT2 | |
| MAPKAPK2 | SIGIRR | |
| MAST3 | SIGLEC14 | |
| MCM6 | SIGLEC16 | |
| MCOLN2 | SIGLEC9 | |
| MDC1 | SIPA1L2 | |
| MEF2D | SIRPA | |
| MEX3B | SLC11A1 | |
| MGAT4A | SLC16A5 | |
| MGC29506 | SLC22A16 | |
| MGC33556 | SLC26A11 | |
| MGC39900 | SLC27A3 | |
| MGC42367 | SLC2A3 | |
| MIB2 | SLC31A2 | |
| MIR155HG | SLC40A1 | |
| MKNK1 | SLC46A2 | |
| MLL4 | SLC7A7 | |
| MME | SLITRK4 | |
| MMP11 | SMAGP | |
| MMP23B | SMAP2 | |
| MMRN1 | SMARCD3 | |
| MNAT1 | SNRK | |
| MOXD1 | SNTB1 | |
| MPEG1 | SRBD1 | |
| MRPL36 | SRGAP3 | |
| MS4A4A | ST3GAL6 | |
| MSRB3 | STEAP3 | |

TABLE 3

List of anti-human antibodies used for mass cytometry (CyTOF).

| Metal | Name | Clone | Company | Cell expression |
|---|---|---|---|---|
| 89 | CD45 | HI30 | Fluidigm | all leukocytes |
| 112/114 | CD14 | TUK4 | Invitrogen | monocytes |
| 115 | CD15 | HI98 | Biolegend | PMN, monocytes |
| 141 | CD7 | 6B7 | Biolegend | T cells, NK cells |
| 142 | CD26 | BA26 | Biolegentd | cDC1 |
| 143 | CD62L | DREG-56 | Biolegend | Lymphocytes, monocytes, granulocytes |
| 144 | CD48 | BL40 | Biolegend | Lymphocytes, DCs |
| 145 | CD68 | KP1 | eBioscience | pDC, mono/macro |
| 146 | CD5 | UCHT2 | Biolegend | cDC2 |
| 147 | CD86 | IT2.2 | BD Biosciences | DC |
| 148 | CD85j | 292319 | R&D | B cells, DCs, monocytes, NK and T cells |
| 149 | HLA-DR | L243 | Biolegend | APC |
| 150 | CD80 | L307.4 | BD Biosciences | DC |
| 151 | CADM1 | 3E1 | MBL | cDC1 |
| 152 | CD1c | L161 | Biolegend | cDC2 |

TABLE 3-continued

List of anti-human antibodies used for mass cytometry (CyTOF).

| Metal | Name | Clone | Company | Cell expression |
|---|---|---|---|---|
| 153 | FceR1 | AER-37 | eBioscience | cDC2 |
| 154 | CD327 | 767329 | R&D | pDC |
| 155 | CD123 | 6H6 | BD Biosciences | pDC |
| 156 | CD163 | GHI | Biolegend | cDC2, mono |
| 157 | CXCR3 | 1C6 | BD Biosciences | cDC1 |
| 158 | CD56 | NCAM16.2 | BD Biosciences | NK cells, DC subsets |
| 159 | CD33 | WM53 | BD Biosciences | myeloid cells |
| 160 | Clec9a | 683409 | R&D Systems | cDC1 |
| 161 | CD38 | HIT2 | Biolegend | HSCs, plasma cells, NK cells, T and B cells |
| 162 | CD10 | HI10a | Biolegend | B cell precursors, T cell precursors, PMN |
| 163 | BTLA | MIH26 | Fluidigm | cDC1, cDC2 subset |
| 164 | CD141 | 1A4 | BD Biosciences | cDC1 |
| 165 | CD303 | 201A | Biolegend | pDC |
| 166 | CD16 | 3G8 | Biolegend | mono, NK cells |
| 167 | CX3CR1 | KO124E1 | Biolegend | cDC2, mono |
| 168 | CCR2 | KO36C2 | Biolegend | eDC, mono |
| 169 | CD116 | 4H11 | Biolegend | DC |
| 170 | CD19 | HIB19 | Biolegend | B cells |
| 171 | CD34 | 581 | Biolegend | HSC |
| 172 | CD2 | RPA-2.10 | Biolegend | cDC2 |
| 173 | CD13 | WM15 | Biolegend | cDC1 |
| 174 | CD45RA | HI100 | Biolegend | pDC |
| 175 | CD11c | B-Ly6 | BD Biosciences | eDC |
| 176 | CD11b | ICRF44 | Biolegend | cDC2 subset, mono |

TABLE 4

Number of expressed genes detected per cell in the pre-DC C1 scmRNAseq experiment.

| Cell ID | Number of detected genes |
|---|---|
| RMS641 | 4997 |
| RMS642 | 5935 |
| RMS643 | 4873 |
| RMS644 | 5000 |
| RMS645 | 3193 |
| RMS646 | 3255 |
| RMS647 | 2653 |
| RMS648 | 5217 |
| RMS649 | 5191 |
| RMS650 | 5235 |
| RMS651 | 4836 |
| RMS652 | 5715 |
| RMS653 | 5224 |
| RMS654 | 4681 |
| RMS655 | 4014 |
| RMS656 | 4134 |
| RMS657 | 4895 |
| RMS658 | 5094 |
| RMS659 | 5405 |
| RMS660 | 3701 |
| RMS661 | 4432 |
| RMS662 | 3298 |
| RMS663 | 3843 |
| RMS664 | 4417 |
| RMS665 | 5162 |
| RMS666 | 4042 |
| RMS667 | 5172 |
| RMS668 | 5129 |
| RMS669 | 3613 |
| RMS670 | 3571 |
| RMS671 | 5016 |
| RMS672 | 5170 |
| RMS673 | 4996 |
| RMS674 | 5462 |
| RMS675 | 4190 |
| RMS676 | 5206 |
| RMS677 | 5590 |
| RMS678 | 3177 |
| RMS679 | 3938 |
| RMS680 | 1802 |
| RMS681 | 3377 |
| RMS682 | 4166 |
| RMS683 | 3863 |
| RMS684 | 4279 |
| RMS685 | 5128 |
| RMS686 | 4884 |
| RMS687 | 4667 |
| RMS688 | 5199 |
| RMS689 | 5320 |
| RMS690 | 3683 |
| RMS691 | 3816 |
| RMS692 | 4366 |
| RMS693 | 5400 |
| RMS694 | 5018 |
| RMS695 | 3457 |
| RMS696 | 3660 |
| RMS697 | 4845 |
| RMS698 | 3945 |
| RMS699 | 3801 |
| RMS700 | 5533 |
| RMS701 | 5089 |
| RMS702 | 4365 |
| RMS703 | 4462 |
| RMS704 | 3770 |
| RMS705 | 4897 |
| RMS706 | 5048 |
| RMS707 | 5435 |
| RMS708 | 4930 |
| RMS709 | 5308 |
| RMS710 | 5067 |
| RMS711 | 5536 |
| RMS712 | 3275 |
| RMS713 | 4810 |
| RMS714 | 4878 |
| RMS715 | 5270 |
| RMS716 | 4324 |
| RMS717 | 4130 |
| RMS718 | 3840 |

TABLE 4-continued

Number of expressed genes detected per cell in the pre-DC C1 scmRNAseq experiment.

| Cell ID | Number of detected genes |
| --- | --- |
| RMS719 | 4134 |
| RMS720 | 3592 |
| RMS722 | 4461 |
| RMS723 | 4804 |
| RMS724 | 3950 |
| RMS725 | 4062 |
| RMS726 | 2551 |
| RMS727 | 3749 |
| RMS728 | 3574 |
| RMS729 | 4247 |
| RMS730 | 5363 |
| RMS731 | 5072 |
| RMS732 | 4992 |
| RMS733 | 5301 |

TABLE 5

Lists of genes identified from the microarray DEG analysis comparisons along the lineage progression from early pre-DC to mature eDC, for cDC1 and cDC2 respectively, and the list of the 62 common genes.

| Profile Genes cDC1 | Profile Genes cDC2 | 62 common elements |
| --- | --- | --- |
| ABCA1 | ABHD8 | ACTN1 |
| ABCB9 | ACAD8 | ADAM33 |
| ABLIM1 | ACTN1 | ADAMTSL2 |
| ACAA1 | ADAM19 | ARHGAP22 |
| ACP5 | ADAM33 | AXL |
| ACP6 | ADAMTSL2 | BATF3 |
| ACSS1 | AGPAT9 | CARD11 |
| ACTN1 | AIF1 | CCDC50 |
| ACY3 | ANXA2P1 | CCND3 |
| ADAM33 | AOAH | CD22 |
| ADAMTSL2 | AP4M1 | CD52 |
| ADAP1 | APLP2 | CLEC4C |
| AIM1 | ARHGAP1 | CTSG |
| ALG5 | ARHGAP22 | CYP2S1 |
| ALOX5 | ARHGAP23 | DAB2 |
| ALOX5AP | AXL | EXT1 |
| AMICA1 | BACH2 | FCN1 |
| ANG | BATF3 | GPRC5C |
| ANPEP | BTBD11 | GPX7 |
| ANXA2 | C10ORF11 | GRINA |
| APOBEC3H | C10ORF84 | HAMP |
| APOL2 | C15ORF48 | HRASLS3 |
| APOL3 | C16ORF33 | HSPA12B |
| ARHGAP22 | C20ORF27 | ID2 |
| ARMET | C2ORF89 | IL3RA |
| ASB16 | C3ORF60 | IRAK3 |
| ASCL2 | CARD11 | KCNK10 |
| ATN1 | CCDC50 | LGALS3 |
| ATP2A1 | CCL3L1 | LILRA4 |
| AXL | CCND3 | LIME1 |
| B9D1 | CD1C | LIMS2 |
| BAIAP3 | CD1D | LOC387841 |
| BATF3 | CD1E | LOC387882 |
| BLK | CD207 | LOC392382 |
| BTLA | CD22 | LOC401720 |
| BUB3 | CD52 | LTK |
| C10ORF105 | CD81 | MARCKS |
| C11ORF80 | CD86 | MUPCDH |
| C15ORF39 | CEBPB | MYBPHL |
| C17ORF61 | CHST7 | NCLN |
| C19ORF10 | CLEC4C | OSBPL3 |
| C1ORF21 | CLIC3 | PLAC8 |
| C1ORF54 | COQ10A | PLP2 |
| C1RL | CREB5 | PPP1R14A |
| C20ORF100 | CSTA | RARRES3 |
| C9ORF91 | CTSG | RHOC |
| CACNA2D3 | CXCR3 | RPP21 |
| CADM1 | CYBASC3 | RTN1 |

TABLE 5-continued

Lists of genes identified from the microarray DEG analysis comparisons along the lineage progression from early pre-DC to mature eDC, for cDC1 and cDC2 respectively, and the list of the 62 common genes.

| Profile Genes cDC1 | Profile Genes cDC2 | 62 common elements |
| --- | --- | --- |
| CALR | CYP2S1 | S100A9 |
| CAMK1G | DAB2 | SERPING1 |
| CAPN12 | DEF8 | SHD |
| CAPZB | DEK | SIGLEC6 |
| CARD11 | DEPDC6 | SLC15A2 |
| CASP1 | DFFB | SLC20A1 |
| CCDC123 | E2F7 | SLC44A2 |
| CCDC50 | ECE1 | STARD7 |
| CCNB2 | ELMO1 | STMN2 |
| CCND1 | ELOVL1 | TBC1D19 |
| CCND3 | EML4 | TCF4 |
| CD22 | EXT1 | TP53I11 |
| CD27 | FAM105A | ZBP1 |
| CD300LB | FAM129B | ZFP36L1 |
| CD300LF | FAM179A | |
| CD38 | FAM26F | |
| CD5 | FBXL6 | |
| CD52 | FCGBP | |
| CD68 | FCGR2A | |
| CD7 | FCN1 | |
| CD79A | FCRLA | |
| CD79B | FLJ22662 | |
| CDC20 | GADD45B | |
| CDC25B | GBP1 | |
| CDC45L | GPRC5C | |
| CDH1 | GPX7 | |
| CDH2 | GRINA | |
| CDKN1A | HAMP | |
| CDS1 | HAPLN3 | |
| CECR1 | HK2 | |
| CENPM | HLA-DPB1 | |
| CLEC10A | HLA-DQB1 | |
| CLEC4C | HRASLS3 | |
| CLEC9A | HSPA12B | |
| CLNK | HSPA7 | |
| CMTM3 | HTR3A | |
| COL18A1 | ID2 | |
| COMMD4 | IL13RA1 | |
| CPNE3 | IL3RA | |
| CPNE5 | IRAK3 | |
| CPVL | IRF8 | |
| CRKRS | ITGAL | |
| CSF1R | JDP2 | |
| CSRP1 | KCNK10 | |
| CTSG | LAT2 | |
| CXCL16 | LCNL1 | |
| CYP2E1 | LGALS3 | |
| CYP2S1 | LHFPL2 | |
| DAB2 | LILRA4 | |
| DAPK1 | LIME1 | |
| DBN1 | LIMS2 | |
| DEXI | LIPT1 | |
| DIAPH3 | LOC100134361 | |
| DUS3L | LOC339352 | |
| DUSP3 | LOC387841 | |
| DYSF | LOC387882 | |
| EAF2 | LOC389816 | |
| EEF1A2 | LOC392382 | |
| ENO1 | LOC401720 | |
| ENPP1 | LOC440280 | |
| EPPB9 | LOC642299 | |
| EXT1 | LOC642367 | |
| FAIM3 | LOC644879 | |
| FAM160A2 | LOC728069 | |
| FAM30A | LOC729406 | |
| FAR2 | LOXL3 | |
| FBLN2 | LRP1 | |
| FCER1A | LRP5 | |
| FCER1G | LRRC26 | |
| FCN1 | LTK | |
| FER1L4 | MADD | |
| FERMT3 | MARCKS | |
| FIS1 | MBNL1 | |

TABLE 5-continued

Lists of genes identified from the microarray DEG
analysis comparisons along the lineage progression
from early pre-DC to mature eDC, for cDC1 and cDC2
respectively, and the list of the 62 common genes.

| Profile Genes cDC1 | Profile Genes cDC2 | 62 common elements |
|---|---|---|
| FKBP11 | MEFV | |
| FKBP1B | MIIP | |
| FLJ40504 | MUPCDH | |
| FNDC3B | MYB | |
| GANC | MYBPHL | |
| GAS6 | MYL6B | |
| GDPD5 | NCKAP1L | |
| GEMIN6 | NCLN | |
| GGTL3 | NOXA1 | |
| GLDC | NRP1 | |
| GMPPB | NTAN1 | |
| GPER | OGFRL1 | |
| GPR162 | OLFM1 | |
| GPRC5C | OSBPL3 | |
| GPRC5D | PACSIN1 | |
| GPS2 | PAK1 | |
| GPX7 | PARP10 | |
| GRINA | PCBP1 | |
| GZMK | PCP4L1 | |
| H2AFY2 | PCSK4 | |
| HAMP | PHYHD1 | |
| HCST | PILRA | |
| HEXIM1 | PLAC8 | |
| HK3 | PLOD3 | |
| HLA-DOB | PLP2 | |
| HN1 | POLR2I | |
| HOPX | PPM1J | |
| HRASLS2 | PPP1R14A | |
| HRASLS3 | PPP1R14B | |
| HSH2D | PROC | |
| HSPA12B | PTGDS | |
| HSPA8 | PTGS2 | |
| HVCN1 | RAB20 | |
| ID2 | RAB7L1 | |
| IDH2 | RARRES3 | |
| IDO1 | RASSF4 | |
| IGJ | RHOC | |
| IGLL1 | RILPL2 | |
| IGLL3 | RPP21 | |
| IL3RA | RS1 | |
| IL7R | RTN1 | |
| INDO | S100A8 | |
| IRAK2 | S100A9 | |
| IRAK3 | SCMH1 | |
| IRF2BP2 | SCN9A | |
| IRF4 | SERPINA1 | |
| ISCU | SERPINF1 | |
| ISG20 | SERPING1 | |
| ITM2C | SGK | |
| ITPR3 | SGK1 | |
| JARID2 | SHANK3 | |
| KCNK10 | SHD | |
| KCNK12 | SIGLEC6 | |
| KIAA0101 | SLAMF7 | |
| KIAA0114 | SLC15A2 | |
| KIAA1191 | SLC20A1 | |
| KIAA1545 | SLC2A8 | |
| KIT | SLC35C2 | |
| KLF6 | SLC44A2 | |
| KRT18P13 | SMARCD3 | |
| L2HGDH | SOX4 | |
| LAMP1 | SP140 | |
| LGALS3 | SPOCK2 | |
| LGALS8 | SSR1 | |
| LILRA2 | STARD7 | |
| LILRA4 | STARD8 | |
| LILRB2 | STMN2 | |
| LILRB4 | TBC1D19 | |
| LIME1 | TCF4 | |
| LIMS2 | TCL1A | |
| LMNA | TMEM14C | |
| LOC100130171 | TMEM2 | |
| LOC100130367 | TP53I11 | |
| LOC100130856 | TREM1 | |
| LOC100131727 | TRIB2 | |
| LOC100132444 | TSPAN13 | |
| LOC144383 | TXNIP | |
| LOC286076 | USP24 | |
| LOC387841 | VASN | |
| LOC387882 | VCAN | |
| LOC392382 | VEGFB | |
| LOC399988 | VENTX | |
| LOC401720 | VSIG4 | |
| LOC642113 | ZAK | |
| LOC642755 | ZBP1 | |
| LOC645381 | ZFP36L1 | |
| LOC647506 | ZNF469 | |
| LOC648366 | ZNF503 | |
| LOC649210 | | |
| LOC649923 | | |
| LOC652493 | | |
| LOC652694 | | |
| LOC653468 | | |
| LOC653566 | | |
| LOC654191 | | |
| LOC728014 | | |
| LOC728093 | | |
| LOC728557 | | |
| LOC729086 | | |
| LPXN | | |
| LST1 | | |
| LTK | | |
| LYN | | |
| MARCKS | | |
| MBOAT2 | | |
| MBOAT7 | | |
| MCM4 | | |
| MED12L | | |
| MED27 | | |
| MEI1 | | |
| MGC13057 | | |
| MGC29506 | | |
| MGC33556 | | |
| MIF | | |
| MIR939 | | |
| MIST | | |
| MLKL | | |
| MS4A6A | | |
| MUPCDH | | |
| MYBPHL | | |
| MYO1D | | |
| MYO5C | | |
| NADK | | |
| NAV1 | | |
| NCF4 | | |
| NCLN | | |
| NDRG1 | | |
| NDRG2 | | |
| NFATC2IP | | |
| NGFRAP1 | | |
| NLRC3 | | |
| NRM | | |
| NRSN2 | | |
| NT5DC2 | | |
| NUBP1 | | |
| NUCB2 | | |
| OSBPL10 | | |
| OSBPL3 | | |
| PARM1 | | |
| PARP3 | | |
| PCNA | | |
| PDE9A | | |
| PDIA4 | | |
| PEPD | | |
| PIK3CD | | |
| PLAC8 | | |

TABLE 5-continued

Lists of genes identified from the microarray DEG analysis comparisons along the lineage progression from early pre-DC to mature eDC, for cDC1 and cDC2 respectively, and the list of the 62 common genes.

| Profile Genes cDC1 | Profile Genes cDC2 | 62 common elements |
|---|---|---|
| PLCD1 | STARD7 | |
| PLD3 | STMN2 | |
| PLEKHG2 | SULF2 | |
| PLP2 | SUSD3 | |
| PLXNB2 | TACSTD2 | |
| PMS2L4 | TBC1D19 | |
| POP5 | TCF4 | |
| POU2AF1 | TDRD1 | |
| PPM1H | TFPI | |
| PPP1R14A | TGM2 | |
| PRDM1 | TLR3 | |
| PRDX4 | TMEM109 | |
| PRKCZ | TMEM167B | |
| PRKD2 | TMEM216 | |
| PRR5 | TMEM97 | |
| PRSSL1 | TNFRSF13B | |
| PSEN2 | TNFRSF17 | |
| PSMB8 | TNFRSF21 | |
| PSORS1C1 | TNFSF12 | |
| PTGER2 | TNNI2 | |
| PTTG1 | TOP2A | |
| PTTG3P | TOX2 | |
| RAB30 | TP53I11 | |
| RAB32 | TP53INP1 | |
| RAB43 | TRIB1 | |
| RARRES3 | TRPM2 | |
| RASGRP2 | TSEN34 | |
| RASSF2 | TSEN54 | |
| RHBDF2 | TSPAN33 | |
| RHOC | TSPYL1 | |
| RNF130 | TUFT1 | |
| RNU6-15 | TXNDC5 | |
| RPP21 | TYMS | |
| RPS19BP1 | TYROBP | |
| RPS27L | UBE2C | |
| RTN1 | UBXN11 | |
| RUFY1 | UGCGL2 | |
| S100A4 | UNC119 | |
| S100A9 | UNG | |
| SAMD3 | VAC14 | |
| SCPEP1 | VISA | |
| SDF2L1 | VPS37B | |
| SEC11C | VPS37D | |
| SEMA4C | WDFY4 | |
| SEPT3 | WDR34 | |
| SERPINF2 | WFS1 | |
| SERPING1 | WWC3 | |
| SH2D3A | XBP1 | |
| SHD | ZBP1 | |
| SHE | ZBTB32 | |
| SHMT2 | ZFP36L1 | |
| SIAH1 | ZNF662 | |
| SIGLEC6 | ZNF821 | |
| SLC15A2 | | |
| SLC15A3 | | |
| SLC20A1 | | |
| SLC25A4 | | |
| SLC35A5 | | |
| SLC41A2 | | |
| SLC44A1 | | |
| SLC44A2 | | |
| SLC9A3R1 | | |
| SLCO3A1 | | |
| SMO | | |
| SNCA | | |
| SNN | | |
| SNX22 | | |
| SNX29 | | |
| SNX3 | | |
| SPATS2 | | |
| SSR4 | | |
| ST6GALNAC2 | | |
| STARD5 | | |

TABLE 6

List of anti-human antibodies used for flow cytometry.

| Name | Clone | Fluorophore | Source |
|---|---|---|---|
| CADM1 | 3E1 | Purified | MBL |
| CD116 | 4H1 | Biotion | Biolegend |
| CD117 | 104D2 | BV421 | Biolegend |
| CD11c | B-ly6 | V450 | BD Biosciences |
| CD11c | 3.9 | BV605 | Biolegend |
| CD123 | 7G3 | BUV395 | BD Biosciences |
| CD123 | 6H6 | PercP/Cy5.5 | BD Biosciences |
| CD135 | 4G8 | PE | BD Pharmigen |
| CD135 | 4G8 | BV711 | BD Biosciences |
| CD14 | RMO52 | ECD | Beckman Coulter |

TABLE 6-continued

List of anti-human antibodies used for flow cytometry.

| | | | |
|---|---|---|---|
| CD14 | M5E2 | BV711 | Biolegend |
| CD14 | M5E2 | BV650 | BD Biosciences |
| CD141 | AD5-14H12 | PE/Vio770 | Miltenyi Biotec |
| CD16 | 3G8 | APC/Cy7 | Biolegend |
| CD16 | 3G8 | BV650 | BD Biosciences |
| CD169 | 7-239 | PE | BD Biosciences |
| CD172α | SE5a5 | PECy7 | Biolegend |
| CD183 | 1C6/CXCR3 | APC | BD Biosciences |
| CD19 | SJ25C1 | BV650 | BD Biosciences |
| CD1c | L161 | PercP/Cy5.5 | Biolegend |
| CD1c | L161 | PE/Cy7 | Biolegend |
| CD1c | L161 | APC/Cy7 | Biolegend |
| CD2 | RPA-2.10 | BV421 | BD Biosciences |
| CD20 | 2H7 | BV650 | BD Biosciences |
| CD22 | HIB22 | BV421 | BD Biosciences |
| CD26 | BA5b | PE/Cy7 | Biolegend |
| CD272 | MIH26 | PE | Biolegend |
| CD283 | 40C1285.6 | PE | Abeam |
| CD289 | J15A7 | PE | BD Biosciences |
| CD3 | SP34-2 | BV650 | BD Biosciences |
| CD303 | AC144 | Biotin | Miltenyi Biotec |
| CD319 | 162.1 | PE | Biolegend |
| CD327 | 767329 | APC | R&D Systems |
| CD33 | WM53 | PE-CF594 | BD Biosciences |
| CD33 | AC104.3E3 | VioBlue | Miltenyi Biotec |
| CD33 | P67.6 | PercP/Cy5.5 | BD Biosciences |
| CD335 | 9E2 | PerCP5.5 | Biolegend |
| CD34 | 581 | Alexa Fluor 700 | BD Biosciences |
| CD40 | 5C3 | PercP/Cy5.5 | Biolegend |
| CD45 | HI30 | V500 | BD Biosciences |
| CD45RA | 5H9 | FITC | BD Biosciences |
| CD45RA | L48 | PE/Cy7 | BD Biosciences |
| CD5 | UCHT2 | BB515 | BD Biosciences |
| CD66b | G10F5 | PerCP5.5 | Biolegend |
| CD7 | 124-1D1 | PE | eBioscience |
| CD80 | ASL24 | PE | Biolegend |
| CD80 | 2D10 | BV421 | Biolegend |
| CD83 | HB15e | PE | Biolegend |
| CD86 | 2331 (FUN-1) | Biotin | BD Biosciences |
| CD88 | S5/1 | PE/Cy7 | Biolegend |
| Clec9a | 8F9 | APC | Biolegend |
| Clec9A | 3A4/Clec9A | PE | BD Biosciences |
| CX3CR1 | 2A9-1 | PE | Biolegend |
| CX3CR1 | K0124E1 | PE | Biolegend |
| CXCR3 | G025H7 | PE | Biolegend |
| FcεRIα | AER-37 | PerCP | Biolegend |
| FcεRIα | AER-37 | PE | Biolegend |
| HLA-DR | L243 | BV605 | Biolegend |
| HLA-DR | L243 | BV785 | Biolegend |
| IFNα | LT27:295 | FITC | Miltenyi Biotec |
| IL-12p40 | C8.6 | BV421 | BD Biosciences |
| ILT1 | REA219 | Biotin | Miltenyi Biotec |
| ILT3 | ZM4.1 | PE | Biolegend |
| IRF4 | 3E4 | PE | eBioscience |
| IRF8 | V3GYWCH | PercP/eFluor710 | eBioscience |
| TLR7 | A94B10 | PE | BD Biosciences |
| TNFα | Mab11 | Alexa Flour 700 | BD Biosciences |
| secondary | reagents: | | |
| Live/Dead blue | | equ DAPI | Life Technologies |
| Streptavidin | | BUV737 | BD Biosciences |
| Chicken IgY | | Alexa Fluor 647 | Jackson Immunoresearch |

EXAMPLES

Non-limiting examples of the disclosure, including the best mode, and a comparative example will be further described in greater detail by reference to specific Examples, which should not be construed as in any way limiting the scope of the disclosure.

Example 1—Methods

Blood, Bone Marrow and Spleen Samples

Human samples were obtained in accordance with a favorable ethical opinion from Singapore SingHealth and National Health Care Group Research Ethics Committees. Written informed consent was obtained from all donors according to the procedures approved by the National University of Singapore Institutional Review Board and SingHealth Centralised Institutional Review Board. Peripheral blood mononuclear cells (PBMC) were isolated by Ficoll-Paque (GE Healthcare) density gradient centrifugation of apheresis residue samples obtained from volunteer donors through the Health Sciences Authorities (HSA, Singapore). Blood samples were obtained from 4 patients with molecularly confirmed Pitt-Hopkins syndrome (PHS), who all showed the classical phenotype (44). Spleen tissue was obtained from patients with tumors in the pancreas who underwent distal pancreatomy (Singapore General Hospital, Singapore). Spleen tissue was processed as previously described (20). Bone marrow mononuclear cells were purchased from Lonza.

Generation of Single Cell Transcriptomes Using MARS-Seq

MARS-Seq using the Biomek FxP system (Beckman Coulter) as previously described (15) was performed for scmRNAseq of the DC compartment of the human peripheral blood. In brief, Lineage marker (Lin)(CD3/14/16/19/20/34)$^-$CD45$^+$CD135$^+$HLA-DR$^+$CD123$^+$CD33$^+$ single cells were sorted into individual wells of 384-well plates filled with 2 µl lysis buffer (Triton 0.2% (Sigma Aldrich) in molecular biology grade $H_2O$ (Sigma Aldrich), supplemented with 0.4 U/µl protein-based RNase inhibitor (Takara Bio Inc.), and barcoded using 400 nM IDT. Details regarding the barcoding procedure with poly-T primers were previously described (15). Samples were pre-incubated for 3 min at 80° C. and reverse transcriptase mix consisting of 10 mM DTT (Invitrogen), 4 mM dNTPs (NEB), 2.5 U/µl SuperScript III Reverse Transcriptase (Invitrogen) in 50 mM Tris-HCl (pH 8.3; Sigma), 75 mM KCl (Sigma), 3 mM MgCl2 (Sigma), ERCC RNA Spike-In mix (Life Technologies), at a dilution of 1:80*10$^7$ per cell was added to each well. The mRNA was reverse-transcribed to cDNA with one cycle of 2 min at 42° C., 50 min at 50° C., and 5 min at 85° C. Excess primers were digested with ExoI (NEB) at 37° C. for 30 min then 10 min at 80° C., followed by cleanup using SPRIselect beads at a 1.2× ratio (Beckman Coulter). Samples were pooled and second strands were synthesized using a Second Strand Synthesis kit (NEB) for 2.5 h at 16° C., followed by a cleanup using SPRIselect beads at a 1.4× ratio (Beckman Coulter). Samples were linearly amplified by T7-promoter guided in vitro transcription using the T7 High Yield RNA polymerase IVT kit (NEB) at 37° C. for 12 h. DNA templates were digested with Turbo DNase I (Ambion) for 15 min at 37° C., followed by a cleanup with SPRIselect beads at a 1.2× ratio (Beckman Coulter). The RNA was then fragmented in $Zn^{2+}$ RNA Fragmentation Solution (Ambion) for 1.5 min at 70° C., followed by cleanup with SPRIselect beads at a 2.0 ratio (Beckman Coulter). Barcoded ssDNA adapters (IDT; details of barcode see (15)) were then ligated to the fragmented RNAs in 9.5% DMSO (Sigma Aldrich), 1 mM ATP, 20% PEG8000 and 1 U/µl T4 RNA ligase I (NEB) solution in 50 mM Tris HCl pH7.5 (Sigma Aldrich), 10 mM MgCl2 and 1 mM DTT for 2 h at 22° C. A second reverse transcription reaction was then performed using Affinity Script Reverse Transcription buffer, 10 mM DTT, 4 mM dNTP, 2.5 U/µl Affinity Script Reverse Transcriptase (Agilent) for one cycle of 2 min at 42° C., 45 min at 50° C., and 5 min at 85° C., followed by a cleanup on SPRIselect beads at a 1.5× ratio (Beckman Coulter). The final libraries were generated by subsequent nested PCR reactions using 0.5 µM of each Illumina primer (IDT; details of primers see (15)) and KAPA HiFi HotStart Ready Mix (Kapa Biosystems) for 15 cycles according to manufacturer's protocol, followed by a final cleanup with SPRIselect beads at a 0.7× ratio (Beckman Coulter). The quality and quantity of the resulting libraries was assessed using an Agilent 2200 TapeStation instrument (Agilent), and libraries were subjected to next generation sequencing using an Illumina HiSeq1500 instrument (PE no index; read1: 61 reads (3 reads random nucleotides, 4 reads pool barcode, 53 reads sequence), read2: 13 reads (6 reads cell barcode, 6 reads unique molecular identifier)).

Pre-Processing, Quality Assessment and Control of MARS-Seq Single Cell Transcriptome Data Cell specific tags and Unique Molecular Identifiers (UMIs) were extracted (2,496 cells sequenced) from sequenced data-pool barcodes. Sequencing reads with ambiguous plate and/or cell-specific tags, UMI sequences of low quality (Phred<27), or reads that mapped to E. coli were eliminated using Bowtiel sequence analysis software (48), with parameters "-M -t --best --chunkmbs 64-strata". Fastq files were demultiplexed using the fastx_barcode_splitter from fastx_toolkit, and R1 reads (with trimming of pooled barcode sequences) were mapped to the human hg38+ERCC pseudo genome assembly using Bowtie "-m 1-t --best --chunkmbs 64-strata". Valid reads were then counted using UMIs if they mapped to the exon-based gene model derived from the BiomaRt HG38 data mining tool provided by Ensembl (46). A gene expression matrix was then generated containing the number of UMIs for every cell and gene. Additionally, UMIs and cell barcode errors were corrected and filtered as previously described (15).

Normalization and Filtering of MARS-Seq Single Cell Transcriptome Data

In order to account for differences in total molecule counts per cell, a down-sampling normalization was performed as suggested by several studies (15, 47). Here, every cell was randomly down-sampled to a molecule count of 1,050 unique molecules per cell (threshold details discussed below). Cells with molecule counts<1,050 were excluded from the analysis (Table 1: number of detected genes per cell). Additionally, cells with a ratio of mitochondrial versus endogenous genes exceeding 0.2, and cells with <90 unique genes, were removed from the analysis. Prior to Seurat analysis (48), expression tables were filtered to exclude mitochondrial and ribosomal genes to remove noise.

Analysis of MARS-Seq Single Cell Transcriptome Data

Analysis of the normalized and filtered single-cell gene expression data (8,657 genes across 710 single cell transcriptomes used in the final expression table) was achieved using Mpath (22), PCA, tSNE, connectivity MAP (cMAP) (21) and several functions of the Seurat single cell analysis package. cMAP analysis was performed using DEGs between pDC and cDC derived from the gene expression omnibu data series GSE35457 (20). For individual cells, cMAP generated enrichment scores that quantified the degree of enrichment (or "closeness") to the given gene signatures. The enrichment scores were scaled and assigned positive or negative values to indicate enrichment for pDC or cDC signature genes, respectively. A permutation test (n=1,000) between gene signatures was performed on each enrichment score to determine statistical significance. For the tSNE/Seurat analysis, a Seurat filter was used to include genes that were detected in at least one cell (molecule count=1), and excluded cells with <90 unique genes. To infer the structure of the single-cell gene expression data, a PCA was performed on the highly variable genes determined as genes exceeding the dispersion threshold of 0.75. The first two principle components were used to perform a tSNE that was combined with a DBSCAN clustering algorithm (19) to identify cells with similar expression profiles. DBSCAN was performed by setting 10 as the minimum number of reachable points and 4.1 as the reachable epsilon neighbourhood parameter; the latter was determined using a KNN plot integrated in the DBSCAN R package (49) (https://cran.r-project.org/web/packages/dbscan/). The clustering did not change when using the default minimal number of reachable points.

To annotate the clusters, the gene signatures of blood pDC, cDC1 and cDC2 were derived from the Gene Expression Omnibus data series GSE35457 (20) (Table 2: lists of signature genes, data processing described below) to calculate the signature gene expression scores of cell type-specific gene signatures, and then these signature scores were overlaid onto the tSNE plots. Raw expression data of $CD141^+$ (cDC1), $CD1c^+$ (cDC2) DCs and pDC samples from blood of up to four donors (I, II, V and VI) was imported into Partek® Genomics Suite® software, version 6.6 Copyright©; 2017 (PGS), where they were further processed. Data were quantile-normalized and log 2-transformed, and a batch-correction was performed for the donor using PGS. Differential probe expression was calculated from the normalized data (ANOVA, Fold-Change≥2 and FDR-adj. p-value<0.05) for the three comparisons of every cell type against the remaining cell types. The three lists of differentially-expressed (DE) probes were intersected and only exclusively-expressed probes were used for the cell-type specific gene signatures. The probes were then reduced to single genes, by keeping the probe for a corresponding gene with the highest mean expression across the dataset. Resulting gene signatures for blood pDCs, $CD1c^+$ and $CD141^+$ DCs contained 725, 457 and 368 genes, respectively. The signature gene expression score was calculated as the mean expression of all signature genes in a cluster. In order to avoid bias due to outliers, we calculated the trimmed mean (trim=0.08).

Monocle analysis was performed using the latest pre-published version of Monocle v.2.1.0 (23). The data were loaded into a monocle object and then log-transformed. Ordering of the genes was determined by dispersion analysis if they had an average expression of ≥0.5 and at least a dispersion of two times the dispersion fit. The dimensionality reduction was performed using the reduceDimension command with parameters max components=2, reduction method="DDRTree" and norm method="log". The trajectory was then built using the plot_cell_trajectory command with standard parameters.

Wishbone analysis (24) was performed using the Python toolkit downloaded from https://gothub.com/ManuSetty/wishbone. MARS-seq data were loaded using the wishbone.wb.SCData.from csv function with the parameters data_type='sc-seq' and normalize=True. Wishbone was then performed using wb.run_wishbone function with parameter start_cell="run1_CATG_AAGACA", components_list=[1, 2, 3, 4], num_waypoints=150, branch=True. Start_cell was randomly selected from the central cluster #4. Diffusion map analysis was performed using the scdata.run_diffusion_map function with default parameters (25). Wishbone revealed three trajectories giving rise to pDC, cDC1 and cDC2 respectively. Along each trajectory, the respective signature gene shows increasing expression (FIG. 7C). Although Wishbone results might be interpreted to suggest that cDC2 are early cells and differentiate into pDC and cDC1 on two separate branches, this is simply because Wishbone allows a maximum of two branches and assumes all cells fall on continuous trajectories. Nevertheless, it is able to delineate the three trajectories that are in concordance with Mpath, monocle, and diffusion map analysis.

C1 Single Cell mRNA Sequencing

Lin(CD3/14/16/19/20)⁻HLA-DR⁺CD33⁺CD123⁺ cells at 300 cells/µl were loaded onto two 5-10 µm C1 Single-Cell Auto Prep integrated fluidic circuits (Fluidigm) and cell capture was performed according to the manufacturer's instructions. Individual capture sites were inspected under a light microscope to confirm the presence of single, live cells. Empty capture wells and wells containing multiple cells or cell debris were discarded for quality control. A SMARTer Ultra Low RNA kit (Clontech) and Advantage 2 PCR Kit (Clontech) was used for cDNA generation. An ArrayControl™ RNA Spots and Spikes kit (with spike numbers 1, 4 and 7) (Ambion) was used to monitor technical variability, and the dilutions used were as recommended by the manufacturer. The concentration of cDNA for each single cell was determined by Quant-iT™ PicoGreen® dsDNA Reagent, and the correct size and profile was confirmed using DNA High Sensitivity Reagent Kit and DNA Extended Range LabChip (Perkin Elmer). Multiplex sequencing libraries were generated using the Nextera XT DNA Library Preparation Kit and the Nextera XT Index Kit (Illumina). Libraries were pooled and subjected to an indexed PE sequencing run of 2×51 cycles on an Illumina HiSeq 2000 (Illumina) at an average depth of 2.5-million row reads/cell.

C1 Single Cell Analysis

Raw reads were aligned to the human reference genome GRCh38 from GENCODE (53) using RSEM program version 1.2.19 with default parameters (51). Gene expression values in transcripts per million were calculated using the RSEM program and the human GENCODE annotation version 22. Quality control and outlier cell detection was performed using the SINGuLAR (Fluidigm) analysis toolset. cMAP analysis was performed using cDC1 versus cDC2 DEGs identified from Gene Expression Omnibus data series GSE35457 (20), and the enrichment scores were obtained. Similar to the gene set enrichment analyses, cMAP was used to identify associations of transcriptomic profiles with cell-type characteristic gene signatures.

Mpath Analysis of MARS- or C1 Single Cell mRNA Sequencing Data

Developmental trajectories were defined using the Mpath algorithm (22), which constructs multi-branching cell lineages and re-orders individual cells along the branches. In the analysis of the MARS-seq single cell transcriptomic data, we first used the Seurat R package to identify five clusters: for each cluster, Mpath calculated the centroid and used it as a landmark to represent a canonical cellular state; subsequently, for each single cell, Mpath calculated its Euclidean distance to all the landmarks, and identified the two nearest landmarks. Each individual cell was thus assigned to the neighborhood of its two nearest landmarks. For every pair of landmarks, Mpath then counted the number of cells that were assigned to the neighborhood, and used the determined cell counts to estimate the possibility of the transition between landmarks to be true. A high cell count implied a high possibility that the transition was valid. Mpath then constructed a weighted neighborhood network whereby nodes represented landmarks, edges represented a putative transition between landmarks, and numbers allocated to the edges represented the cell-count support for the transition. Given that single cell transcriptomic data tend to be noisy, edges with low cell-count support were considered likely artifacts. Mpath therefore removed the edges with a low cell support by using (0–n) (n–n represents cell count) to quantify the distance between nodes followed by applying a minimum spanning tree algorithm to find the shortest path that could connect all nodes with the minimum sum of distance. Consequently, the resulting trimmed network is the one that connects all landmarks with the minimum number of edges and the maximum total number of cells on the edges. Mpath was then used to project the individual cells onto the edge connecting its two nearest landmarks, and assigned a pseudo-time ordering to the cells according to the location of their projection points on the edge. In the analysis of the C1 single cell transcriptome data, we first used the cMAP analysis to identify cDC1-primed, un-primed, and cDC2-primed clusters, and then used Mpath to construct the lineage between these three clusters. The Mpath analysis was carried out in an un-supervised manner without prior knowledge of the starting cells or number of branches. This method can be used for situations of non-branching networks, bifurcations, and multi-branching networks with three or more branches.

Mass Cytometry Staining, Barcoding, Acquisition and Data Analysis

For mass cytometry, pre-conjugated or purified antibodies were obtained from Invitrogen, Fluidigm (pre-conjugated antibodies), Biolegend, eBioscience, Becton Dickinson or R&D Systems as listed in Table 3. For some markers, fluorophore- or biotin-conjugated antibodies were used as primary antibodies, followed by secondary labeling with anti-fluorophore metal-conjugated antibodies (such as the anti-FITC clone FIT-22) or metal-conjugated streptavidin, produced as previously described (16). Briefly, $3 \times 10^6$ cells/well in a U-bottom 96 well plate (BD Falcon, Cat #3077) were washed once with 200 µL FACS buffer (4% FBS, 2 mM EDTA, 0.05% Azide in 1×PBS), then stained with 100 µL 200 µM cisplatin (Sigma-Aldrich, Cat #479306-1G) for 5 min on ice to exclude dead cells. Cells were then incubated with anti-CADM1-biotin and anti-CD19-FITC primary antibodies in a 50 µL reaction for 30 min on ice. Cells were washed twice with FACS buffer and incubated with 50 µL heavy-metal isotope-conjugated secondary mAb cocktail for 30 min on ice. Cells were then washed twice with FACS buffer and once with PBS before fixation with 200 µL 2% paraformaldehyde (PFA; Electron Microscopy Sciences, Cat #15710) in PBS overnight or longer. Following fixation, the cells were pelleted and resuspended in 200 uL 1× permeabilization buffer (Biolegend, Cat #421002) for 5 mins at room temperature to enable intracellular labeling. Cells were then incubated with metal-conjugated anti-CD68 in a 50 µL reaction for 30 min on ice. Finally, the cells were washed once with permeabilization buffer and then with PBS before barcoding.

Bromoacetamidobenzyl-EDTA (BABE)-linked metal barcodes were prepared by dissolving BABE (Dojindo, Cat #B437) in 100 mM HEPES buffer (Gibco, Cat #15630) to a final concentration of 2 mM. Isotopically-purified $PdCl_2$ (Trace Sciences Inc.) was then added to the 2 mM BABE solution to a final concentration of 0.5 mM. Similarly, DOTA-maleimide (DM)-linked metal barcodes were prepared by dissolving DM (Macrocyclics, Cat #B-272) in L buffer (MAXPAR, Cat #PN00008) to a final concentration of 1 mM. $RhCl_3$ (Sigma) and isotopically-purified $LnCl_3$ was then added to the DM solution at 0.5 mM final concentration. Six metal barcodes were used: BABE-Pd-102, BABE-Pd-104, BABE-Pd-106, BABE-Pd-108, BABE-Pd-110 and DM-Ln-113.

All BABE and DM-metal solution mixtures were immediately snap-frozen in liquid nitrogen and stored at −80° C. A unique dual combination of barcodes was chosen to stain each tissue sample. Barcode Pd-102 was used at 1:4000 dilution, Pd-104 at 1:2000, Pd-106 and Pd-108 at 1:1000, Pd-110 and Ln-113 at 1:500. Cells were incubated with 100 µL barcode in PBS for 30 min on ice, washed in permeabilization buffer and then incubated in FACS buffer for 10 min on ice. Cells were then pelleted and resuspended in 100 µL nucleic acid Ir-Intercalator (MAXPAR, Cat #201192B) in 2% PFA/PBS (1:2000), at room temperature. After 20 min, cells were washed twice with FACS buffer and twice with water before a final resuspension in water. In each set, the cells were pooled from all tissue types, counted, and diluted to $0.5 \times 10^6$ cells/mL. EQ Four Element Calibration Beads (DVS Science, Fluidigm) were added at a 1% concentration prior to acquisition. Cell data were acquired and analyzed using a CyTOF Mass cytometer (Fluidigm).

The CyTOF data were exported in a conventional flow-cytometry file (.fcs) format and normalized using previously-described software (52). Events with zero values were randomly assigned a value between 0 and −1 using a custom R script employed in a previous version of mass cytometry software (53). Cells for each barcode were deconvolved using the Boolean gating algorithm within FlowJo. The $CD45^+Lin$ $(CD7/CD14/CD15/CD16/CD19/CD34)^-HLA$-$DR^+$ population of PBMC were gated using FlowJo and exported as a .fcs file. Marker expression values were transformed using the logicle transformation function (54). Random sub-sampling without replacement was performed to select 20,000 cell events. The transformed values of sub-sampled cell events were then subjected to t-distributed Stochastic Neighbor Embedding (tSNE) dimension reduction (18) using the markers listed in Table 3, and the Rtsne function in the Rtsne R package with default parameters. Similarly, isometric feature mapping (isoMAP) (34) dimension reduction was performed using vegdist, spantree and isomap functions in the vegan R package (55).

The vegdist function was run with method="euclidean". The spantree function was run with default parameters. The isoMAP function was run with ndim equal to the number of original dimensions of input data, and k=5. Phenograph clustering (26) was performed using the markers listed in Table 3 before dimension reduction, and with the number of nearest neighbors equal to 30. The results obtained from the tSNE, isoMAP and Phenograph analyses were incorporated as additional parameters in the .fcs files, which were then loaded into FlowJo to generate heat plots of marker expression on the reduced dimensions. The above analyses were performed using the cytofkit R package which provides a wrapper of existing state-of-the-art methods for cytometry data analysis (56).

Human Cell Flow Cytometry: Labeling, Staining, Analysis and Cell Sorting

All antibodies used for fluorescence-activated cell sorting (FACS) and flow cytometry were mouse anti-human monoclonal antibodies (mAbs), except for chicken anti-human CADM1 IgY primary mAb. The mAbs and secondary reagents used for flow cytometry are listed in Table 6. Briefly, $5 \times 10^6$ cells/tube were washed and incubated with Live/Dead blue dye (Invitrogen) for 30 min at 4° C. in phosphate buffered saline (PBS) and then incubated in 5% heat-inactivated fetal calf serum (FCS) for 15 min at 4° C. (Sigma Aldrich). The appropriate antibodies diluted in PBS with 2% fetal calf serum (FCS) and 2 mM EDTA were added to the cells and incubated for 30 min at 4° C., and then washed and detected with the secondary reagents. For intra-cytoplasmic or intra-nuclear labeling or staining, cells were fixed and permeabilized with BD Cytofix/Cytoperm (BD Biosciences) or with eBioscience FoxP3/Transcription Factor Staining Buffer Set (eBioscience/Affimetrix), respectively according to the manufacturer's instructions. Flow cytometry was performed using a BD LSRII or a BD FACSFortessa (BD Biosciences) and the data analyzed using BD FACSDiva 6.0 (BD Biosciences) or FlowJo v.10 (Tree Star Inc.). For isolation of precursor dendritic cells (pre-DC), PBMC were first depleted of T cells, monocytes and B cells with anti-CD3, anti-CD14 and anti-CD20 microbeads (Miltenyi Biotec) using an AutoMACS Pro Separator (Miltenyi Biotec) according to the manufacturer's instructions. FACS was performed using a BD FACSAriaII or BD FACSAriaIII (BD Biosciences). Wanderlust analysis (33) of flow cytometry data was performed using the CYT tool downloaded from https://www.c2 b2.columbia.edu/danapeerlab/html/cyt-dowload.html. As Wanderlust requires users to specify a starting cell, we selected one cell at random from the $CD45RA^+CD123^+$ population.

Cytospin and Scanning Electron Microscopy

Cytospins were prepared from purified cells and stained with the Hema 3 system according to the manufacturer's protocol (Fisher Diagnostics). Images were analyzed at 100× magnification with an Olympus BX43 upright microscope (Olympus). Scanning electron microscopy was performed as previously described (20).

Dendritic Cell (DC) Differentiation Co-Culture Assay on MS-5 Stromal Cells

MS-5 stromal cells were maintained and passaged as previously described (8). MS-5 cells were seeded in 96-well round-bottom plates (Corning) at 3,000 cells per well in complete alpha-Minimum Essential Media (α-MEM) (Life Technologies) supplemented with 10% fetal bovine serum (FBS) (Serana) and 1% penicillin/streptomycin (Nacalai Tesque). A total of 5,000 sorted purified cells were added 18-24 h later, in medium containing 200 ng/mL Flt3L (Miltenyi Biotec), 20 ng/mL SCF (Miltenyi Biotec), and 20 ng/mL GM-CSF (Miltenyi Biotec), and cultured for up to 5 days. The cells were then resuspended in their wells by physical dissociation and filtered through a cell strainer into a polystyrene FACS tube.

Mixed Lymphocyte Reaction

Naïve T cells were isolated from PBMC using Naïve Pan T-Cell Isolation Kit (Miltenyi Biotec) according to the manufacturer's instructions, and labeled with 0.2 µM carboxyfluorescein succinimidyl ester (CFSE) (Life Technologies) for 5 min at 37° C. A total of 5,000 cells from sorted DC subsets were co-cultured with 100,000 CFSE-labeled naïve T cells for 7 days in Iscove's Modified Dulbecco's Medium (IMDM; Life Technologies) supplemented with 10% KnockOut™ Serum Replacement (Life Technologies). On day 7, the T cells were stimulated with 10 µg/ml phorbol myristate acetate (InvivoGen) and 500 µg/ml ionomycin (Sigma Aldrich) for 1 h at 37° C. 10 µg/ml Brefeldin A solution was added for 4 h, after which the cells were labeled with cytokine-specific antibodies and analyzed by flow cytometry, as described above.

Electron Microscopy

Sorted cells were seeded on poly-lysine-coated coverslips for 1 h at 37° C. The cells were then fixed in 2% glutaraldehyde in 0.1 M cacoldylate buffer, pH 7.4 for 1 h, post fixed for 1 h with 2% buffered osmium tetroxide, then dehydrated in a graded series of ethanol solutions, before embedding in epoxy resin. Images were acquired with a Quemesa (SIS) digital camera mounted on a Tecnai 12 transmission electron microscope (FEI Company) operated at 80 kV.

Microarray Analysis

Total RNA was isolated from FACS-sorted blood pre-DC and DC subsets using a RNeasy® Micro kit (Qiagen). Total RNA integrity was assessed using an Agilent Bioanalyzer (Agilent) and the RNA Integrity Number (RIN) was calculated. All RNA samples had a RIN≥7.1. Biotinylated cRNA was prepared using an Epicentre TargetAmp™ 2-Round Biotin-aRNA Amplification Kit 3.0 according to the manufacturer's instructions, using 500 pg of total RNA starting material. Hybridization of the cRNA was performed on an Illumina Human-HT12 Version 4 chip set (Illumina). Microrarray data were exported from GenomeStudio (Illumina) without background subtraction. Probes with detection P-values>0.05 were considered as not being detected in the sample, and were filtered out. Expression values for the remaining probes were log 2 transformed and quantile normalized. For differentially-expressed gene (DEG) analysis, comparison of one cell subset with another was carried out using the limma R software package (57) with samples paired by donor identifiers. DEGs were selected with Benjamini-Hochberg multiple testing (58) corrected P-value<0.05. In this way, limma was used to select up and down-regulated signature genes for each of the cell subsets in the pre-DC data by comparing one subset with all other subsets pooled as a group. Expression profiles shown in FIG. 4E were from 62 common genes identified from the union of DEGs from comparing pre-cDC1 versus early pre-DC and cDC1 versus pre-cDC1, and the union of DEGs from comparing pre-cDC2 versus early pre-DC and cDC2 versus pre-cDC2 (Table 5 for the lists of DEGs for cDC1 lineage and cDC2 lineage, and the lists of the 62 common genes; FIG. 21 for Venn diagram comparison of the two lists of DEGs and identification of the 62 common genes).

Statistical Analyses

The Mann-Whitney test was used to compare data derived from patients with Pitt-Hopkins Syndrome and controls. The Kruskal-Wallis test, followed by the Dunn's multiple comparison test, was used to compare the expression level of individual genes in single cells in the MARS-seq single cell RNAseq dataset. Differences were defined as statistically significant when adjusted P<0.05. All statistical tests were performed using GraphPad Prism 6.00 for Windows (GraphPad Software). Correlation coefficients were calculated as Pearson's correlation coefficient.

HIV Infection of DCs and Stimulations

Sorted cells were pelleted and resuspended in complete X-vivo media at 0.4×10$^6$ cells/mL in 50 μlwere seeded in round bottom 96-well plates. In some experiments anti-Siglec-1 mAb (clone 7-239) or mIgG1 isotype control (Miltenyi) were added at 20 μg/mL and cells incubated for 30 minutes at 37° C. before adding the virus. For infections, 150 μlof media or dilutions (150μl or 50μl) of viral supernatants were added. AZT was added at 5 μM. CpG-A (ODN2216, Invivogen) was used at 5 μg/mL, CL264 (Invivogen) at 10 μg/mL and cells incubated 24 hours before infection. Infections were spinoculated for 2 hours at 800 g 25° C. unless stated otherwise. 48 hours after infection, cell culture supernatants were harvested and cells were fixed in 4% paraformaldehyde (PFA; Electron Microscopy Sciences) in PBS prior to analysis on a FACSVerse flow cytometer (BD). Alternatively, cells were stained with PE-Vio770 anti-Siglec-1 (Miltenyi) and analyzed on a FACS Fortessa (BD). Data were analyzed using FlowJo v10 and Prism v7 for Mac (GraphPad).

HIV Capture and Trans-Infection of Activated CD4$^+$ T Cells

Sorted cells were pelleted and resuspended in complete X-vivo media at 0.4 106 cells/mL and 50 μl were seeded in round bottom 96-well plates. In some experiments anti-Siglec-1 mAb or mIgG1 isotype control were added at 20 μg/mL and cells incubated for 30 minutes at 37° C. before adding the virus. HIV-1 X4GFP was added onto the cells (150 μl/well of HEK293FT culture supernatant) and incubated for 2 hours at 37° C. Cells were washed extensively and fixed in 4% PFA in PBS. p24 staining was performed using KC-57 RD1 mAb (Beckman Coulter, 6604667). For trans-infection experiment, sorted DC were washed extensively after the 2 hour-culture with HIV-1 X4GFP and activated CD4+ T cells were added at a ratio 1:1. Alternatively, CpG-A was added at 5 μg/mL, CL264 was added at 10 μg/mL onto DCs and cells incubated overnight before the addition of HIV-1 X4GFP. Cells were then washed and activated CD4+ T cells added. After 48 hours, cells were fixed in 2% PFA in PBS. Cells were then stained with PE-Cy7 anti-CD3 (BD) and analyzed on a FACS Verse (BD). Data were analyzed using FlowJo v10 and Prism v7 for Mac (GraphPad).

Human Cell Flow Cytometry: Labeling, Staining, Analysis and Cell Sorting

Peripheral blood mononuclear cells (PBMC) were isolated by Ficoll-Paque (GE Healthcare) density gradient centrifugation of apheresis residue samples obtained from volunteer donors and analysed by flow cytometry. Briefly, 5×10$^6$ cells/tube were washed and incubated with Live/Dead blue dye (Invitrogen) for 30 minutes at 4° C. in phosphate buffered saline (PBS) and then incubated in 5% heat-inactivated fetal calf serum (FCS) for 15 minutes at 4° C. (Sigma Aldrich). The appropriate antibodies diluted in PBS with 2% fetal calf serum (FCS) and 2 mM EDTA were added to the cells and incubated for 30 minutes at 4° C., and then washed and detected with the secondary reagents. Flow cytometry was performed using a BD LSRII or a BD FACSFortessa (BD Biosciences) and the data analyzed using BD FACSDiva 6.0 (BD Biosciences) or FlowJo v.10 (Tree Star Inc.).

Example 2—Results

Figure 1:
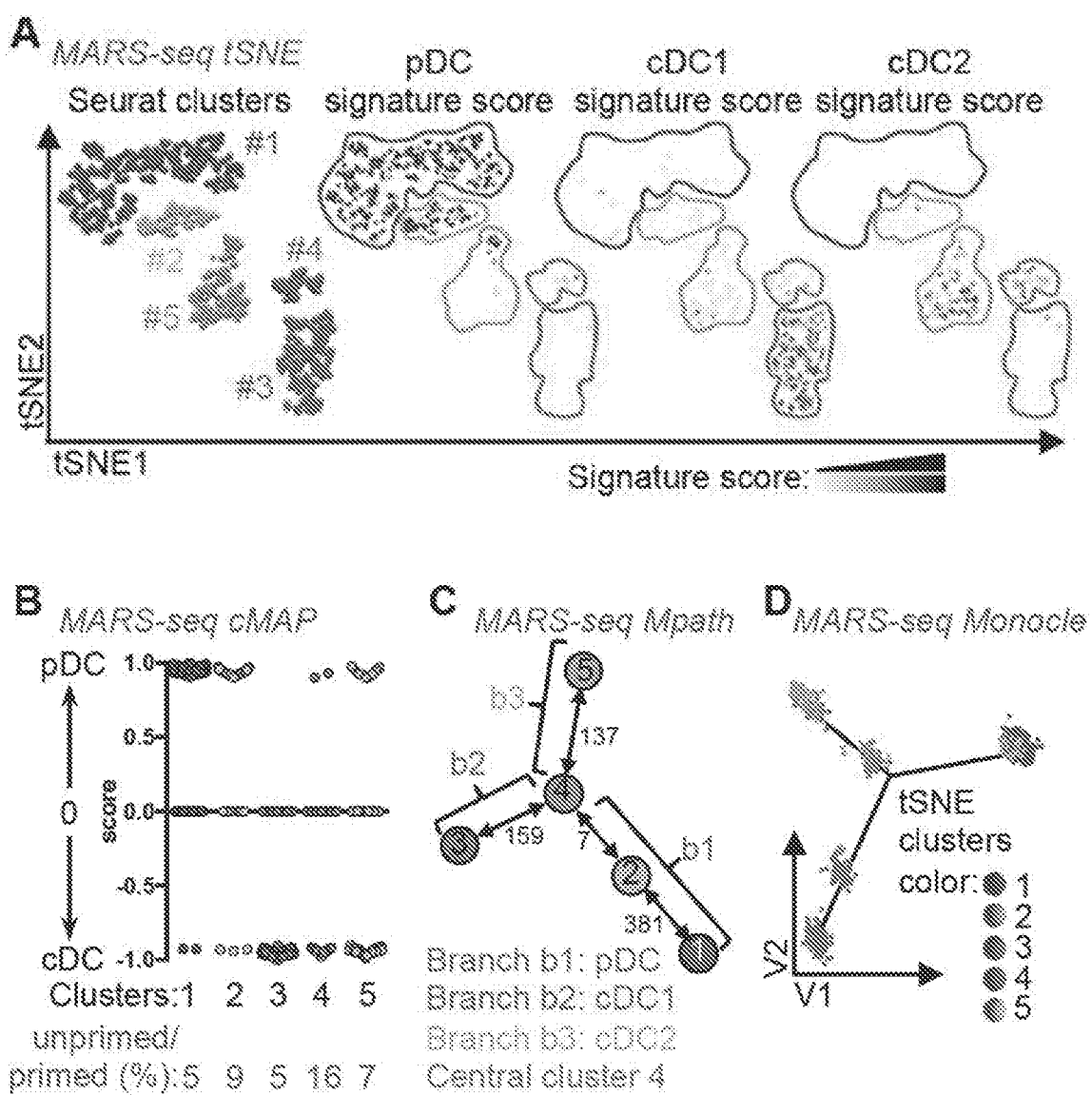
FIG. 1. MARS-seq and CyTOF identify rare $CD123^+$ $CD33^+$ putative DC precursors (pre-DC). (A-E) Lin(CD3/CD14/CD16/CD20/CD34)$^-$HLA-DR$^+$CD135$^+$ sorted PBMC were subjected to MARS-seq. (A) t-stochastic neighbor embedding (tSNE) plot of 710 cells fulfilling all quality criteria, colored by clusters identified by tSNE plus Seurat clustering, or by the relative signature score for pDC, cDC1 and cDC2. (B) Connectivity MAP (cMAP) analysis showing the degree of enrichment for pDC or cDC signature genes in the tSNE/Seurat clusters. (C) Mpath analysis applied to the tSNE/Seurat clusters defining their developmental relationship. Representations of the 710 cells by (D) Monocle, (E) Principal component analysis (PCA) and (F) Diffusion Map, highlighting the tSNE/Seurat clusters identified in (A). (G) Violin plots of tSNE/Seurat pDC clusters, cluster #4 and cDC clusters showing the expression of pDC and cDC signature genes with differential expression between cluster #4 and pDC clusters. Adjusted P-values calculated by Kruskal-Wallis test followed by Dunn's multiple comparisons procedure. (H, I) tSNE plots of CyTOF data from CD45$^+$Lin(CD7/CD14/CD15/CD16/CD19/CD34)$^-$HLA-DR$^+$ PBMC, showing (H) gates defining the $CD123^+CD33^+$ cells and DC subsets, and (I) relative expression of selected markers. (J) Subsets defined in (H) were overlaid onto 2D-contour plots for phenotypic comparison. The gating strategy prior to MARS-seq is shown in FIG. 6A.
Figure 1:
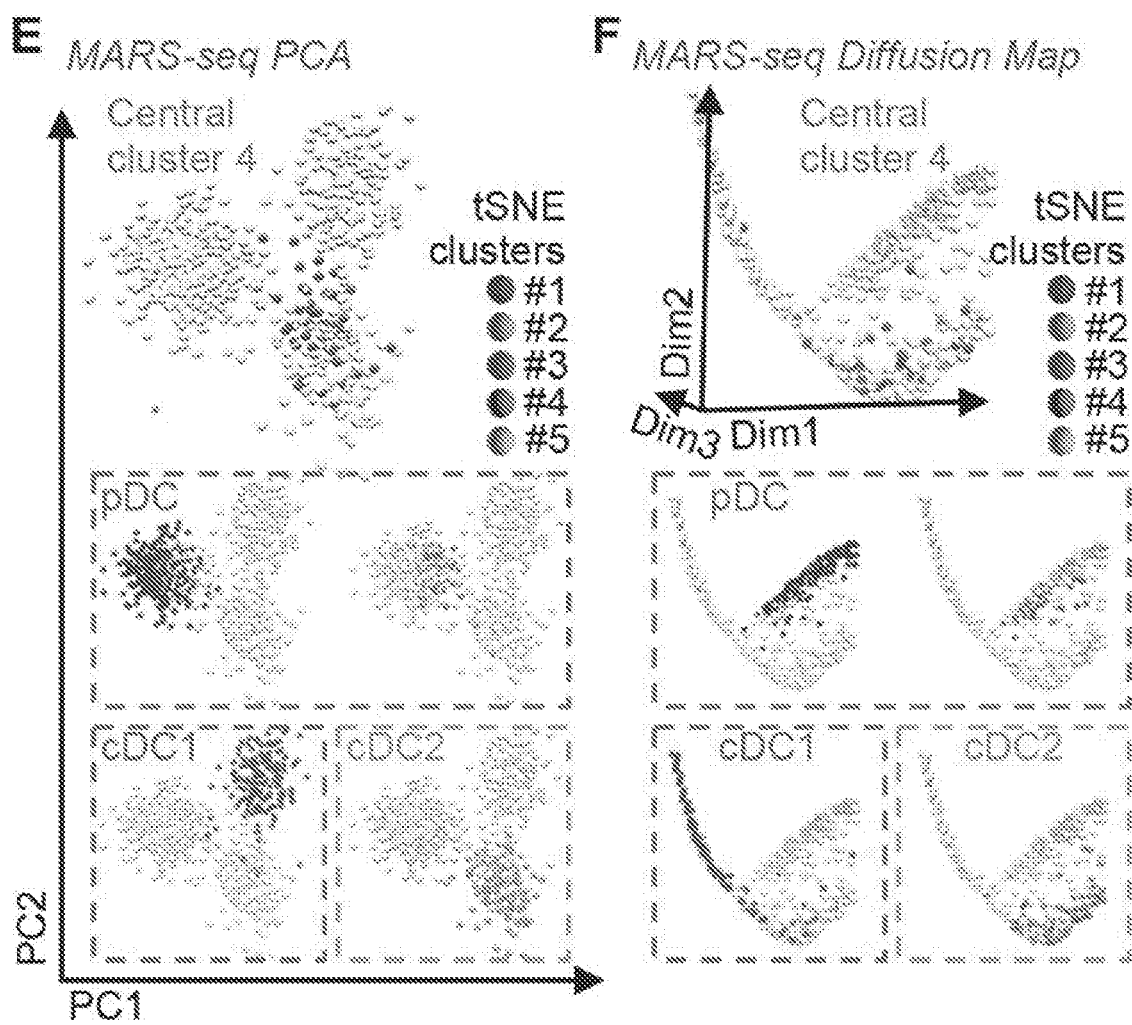
Figure 1:
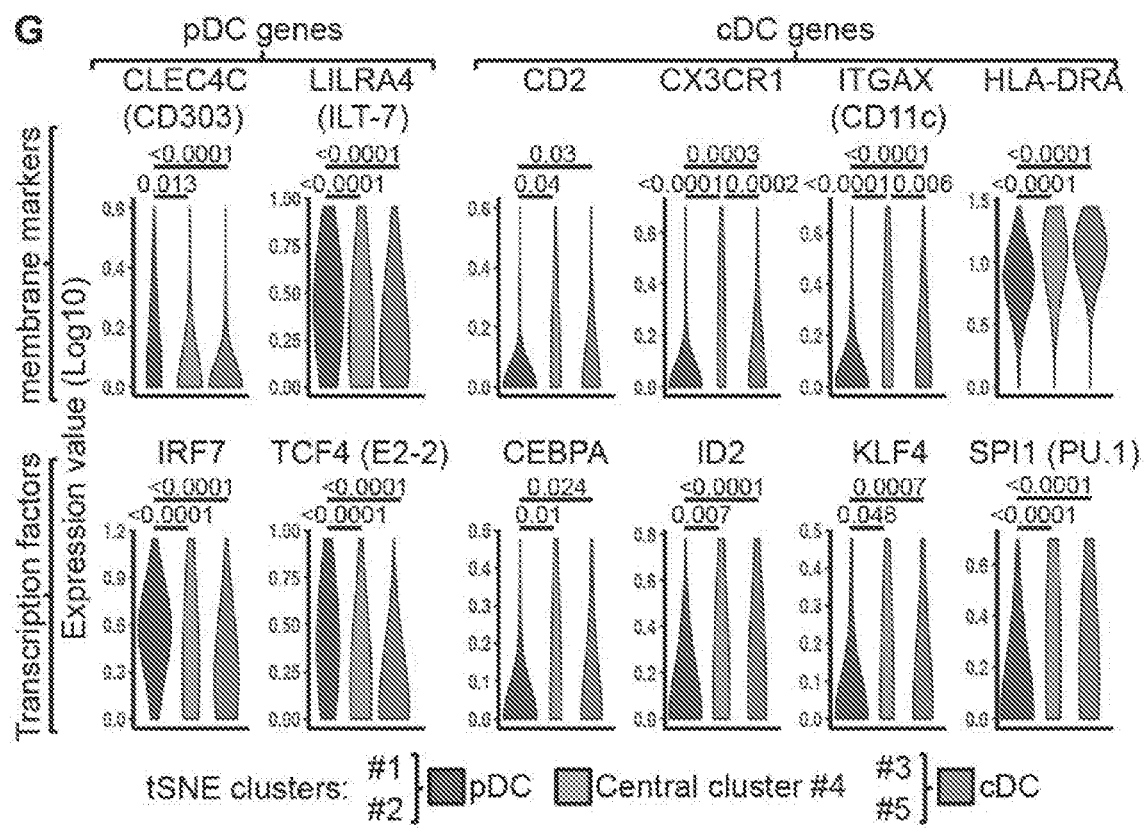
Figure 1:
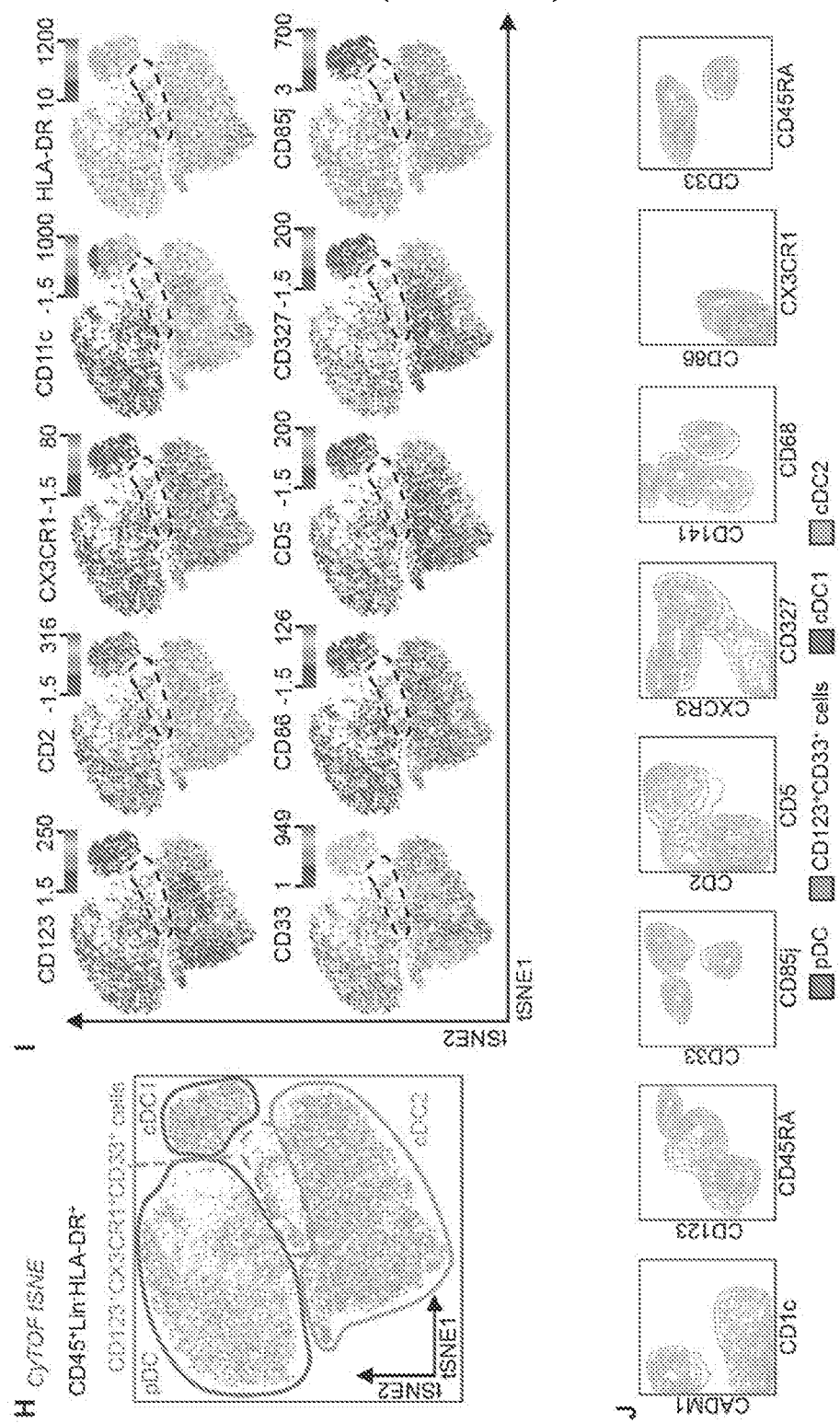
Figure 6:
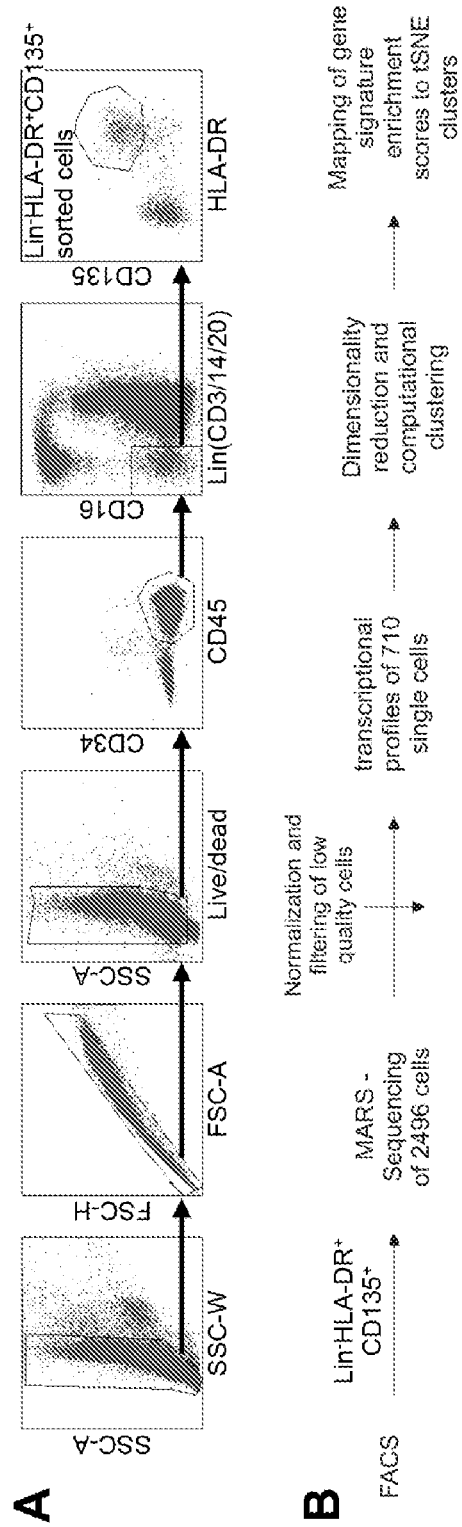
FIG. 6. (A) Gating strategy for FACS of single cells from total Lin⁻HLA-DR⁺CD135⁺ cells. (B) Workflow of the MARS-seq single cell data analysis. (C) Association between molecule counts and cells. Cell IDs were sorted from highest to lowest number of unique molecular identifier (UMI) or molecule counts. The data are presented on a log 10 axis. The three lines correspond to molecule counts of 650 (B), 1,050 (R) and 1,700 (G) per cell. The grey area indicates the range of molecule counts from 400 to 1,200 UMIs per cell. Cells with <1,050 molecules were removed from the analysis (n=1,786 cells). A total of 710 high-quality cells were used for further downstream analyses. (D) Density plot (top panel) representing the distribution of cells with a certain number of molecules, and the first (middle panel) and second derivative (bottom panel) of the density function. The three lines correspond to molecule counts of 650 (B), 1,050 (R) and 1,700 (G) per cell. (E) Principal component analysis (PCA) after simulation at different normalization thresholds. Points were colored according to the different runs. (F) Correlation plot of average expression of genes in run2 (y-axis) versus average expression of genes in run1 (x-axis). The data are presented on a log 10 axis. The Pearson correlation coefficient was 0.99. (G) t-distributed stochastic neighbor embedding (tSNE) analysis of the 710 single cells, colored by run association, showed an even distribution of the cells within the tSNE plot. Lines represent a linear fit of the points. The distributions of the points along the tSNE component 1 and component 2 were represented as density plots on the top or right panel, respectively. (H) Frequency of cells in the five determined clusters for run1 and run2. (I) Mean-variability plot showed average expression and dispersion for each gene. This analysis was used to determine highly variable gene expression (labeled by gene symbol). The 36 highly variable genes were used to perform a dimensionality reduction of the single-cell data by PCA. (J) The highest gene loadings in the first and second principal component (PC1 and PC2) from the PCA of 710 high quality cells are shown.
Figure 6:
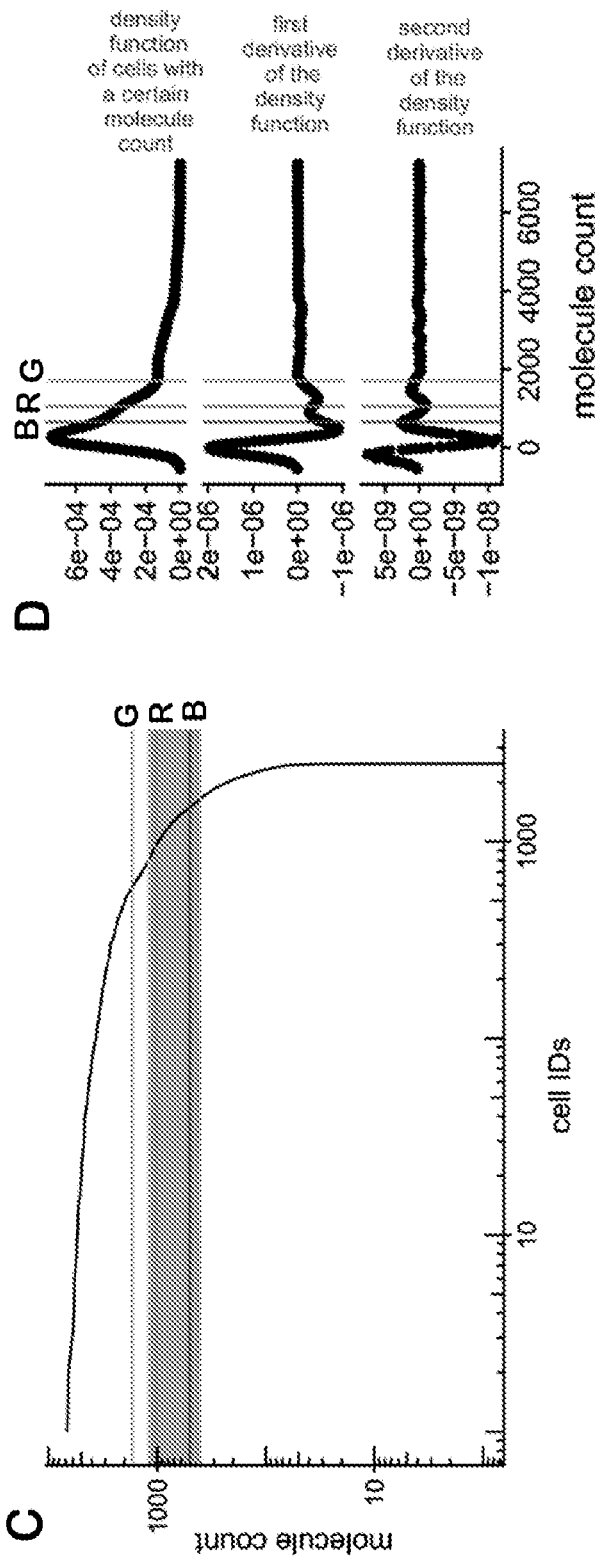
Figure 6:
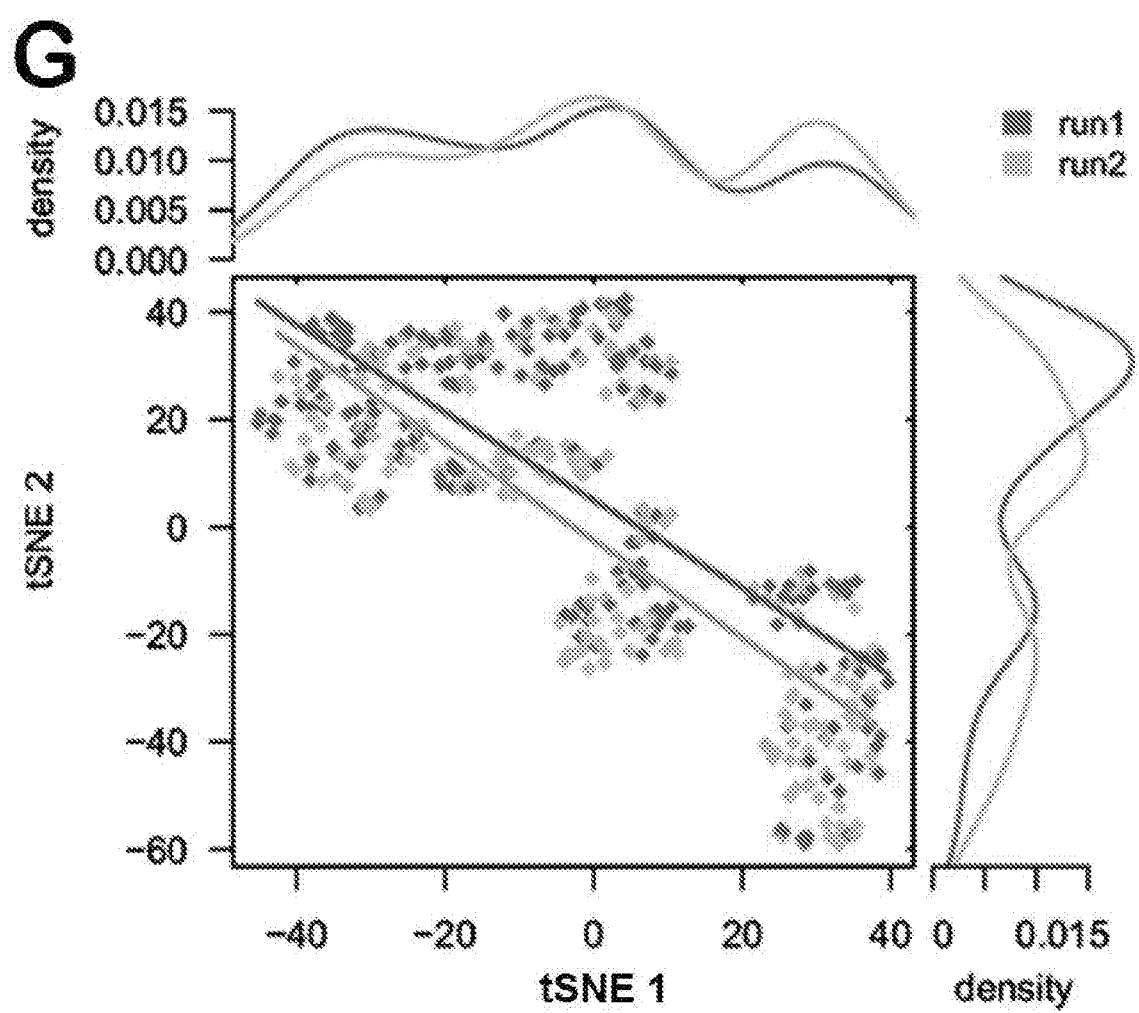
Figure 6:
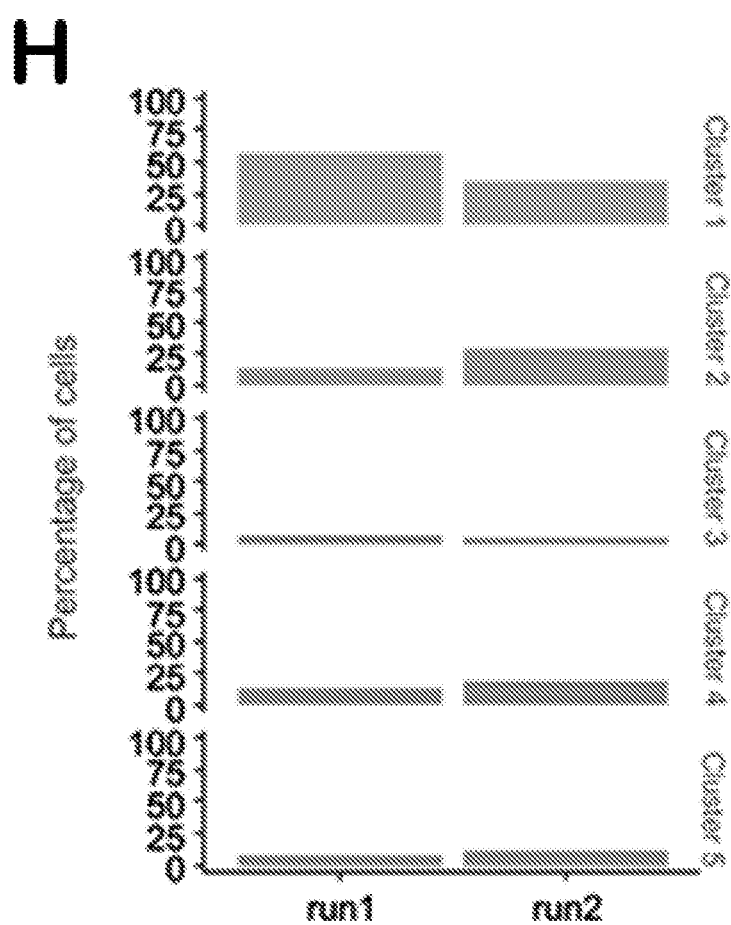
Figure 6:
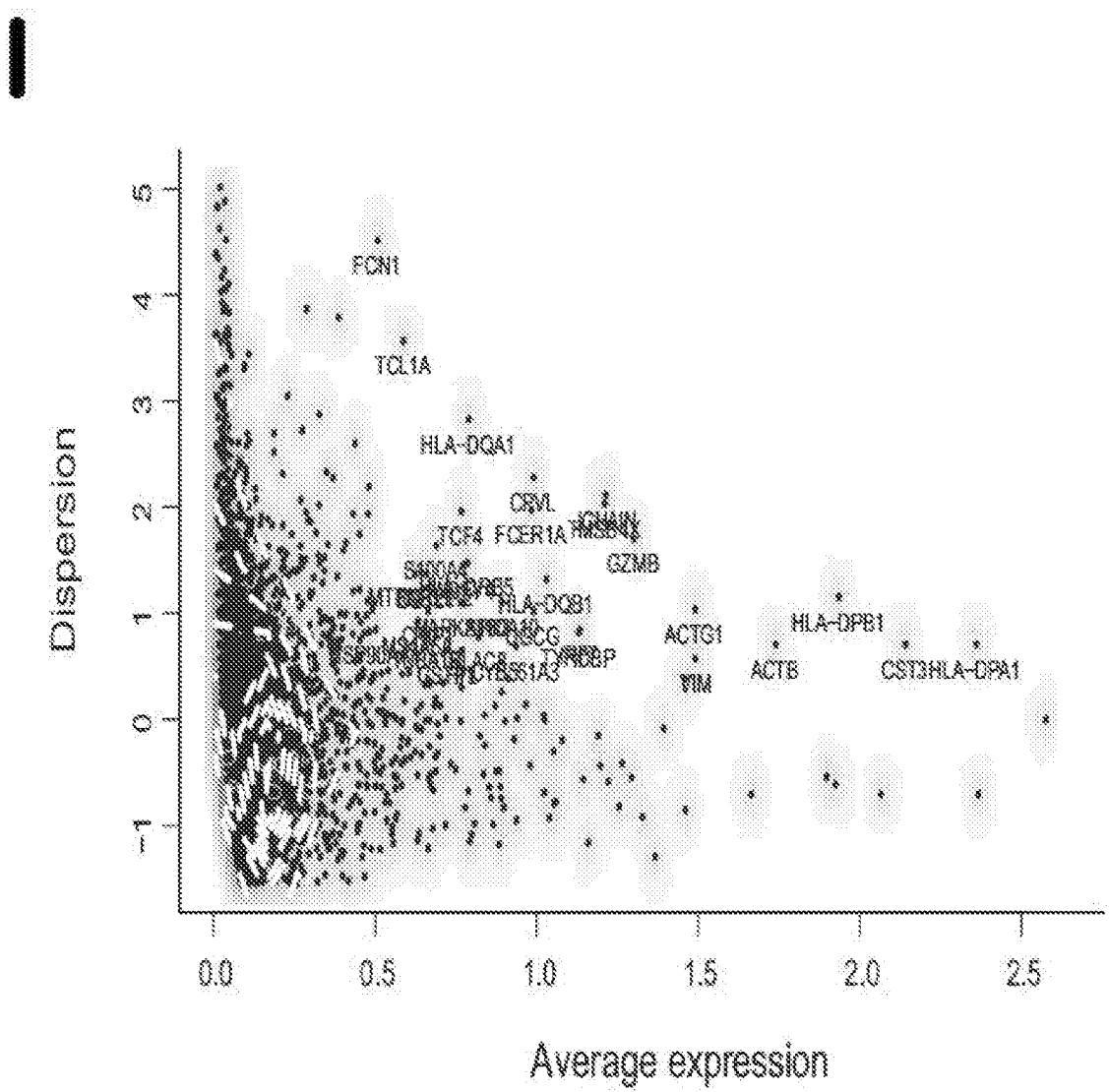
Figure 6:
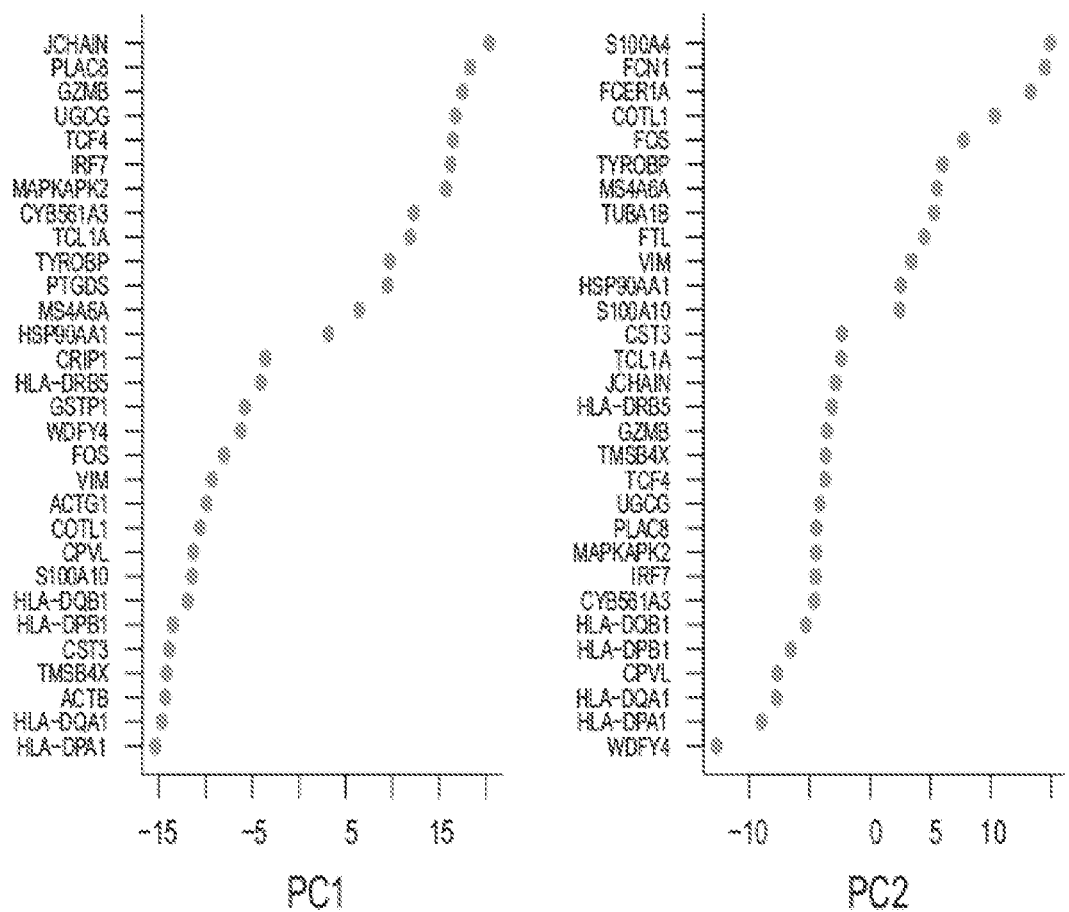

Unbiased Identification of DC Precursors by Unsupervised Single-Cell RNAseq and CyTOF Using PBMC isolated from human blood, massively-parallel single-cell mRNA sequencing (MARS-seq) (15) was performed to assess the transcriptional profile of 710 individual cells within the lineage marker (Lin)(CD3/CD14/CD16/CD20/CD34)$^-$, HLA-DR$^+$CD135$^+$ population (12, 13) (FIG. 1, A to G, and FIG. 6A: sorting strategy, FIG. 6, B to J: workflow and quality control, Table 1: number of detected genes). The MARS-seq data were processed using non-linear dimensionality reduction via t-stochastic neighbor embedding (tSNE), which enables unbiased visualization of high-dimensional similarities between cells in the form of a two-dimensional map (16-18).

Density-based spatial clustering of applications with noise (DBSCAN) (19) on the tSNE dimensions identified five distinct clusters of transcriptionally-related cells within the selected PBMC population (FIG. 1A, and FIG. 6G). To define the nature of these clusters, gene signature scores were calculated for pDC, cDC1 and cDC2 (as described in (20), Table 2: lists of signature genes), and the expression of the signatures attributed to each cell were overlaid onto the tSNE visualization. Clusters #1 and #2 (containing 308 and 72 cells, respectively) were identified as pDC, cluster #3 (containing 160 cells) as cDC1, and cluster #5 (containing 120 cells) as cDC2. Cluster #4 (containing 50 cells) lay in between the cDC1 (#3) and cDC2 (#5) clusters and possessed a weak, mixed pDC/cDC signature (FIG. 1A). A connectivity MAP (cMAP) analysis (21) was employed to calculate the degree of enrichment of pDC or cDC signature gene transcripts in each individual cell. This approach confirmed the signatures of pDC (#1 and #2) and cDC (#3 and #5) clusters, and showed that most cells in cluster #4 expressed a cDC signature (FIG. 1B).

Figure 7:
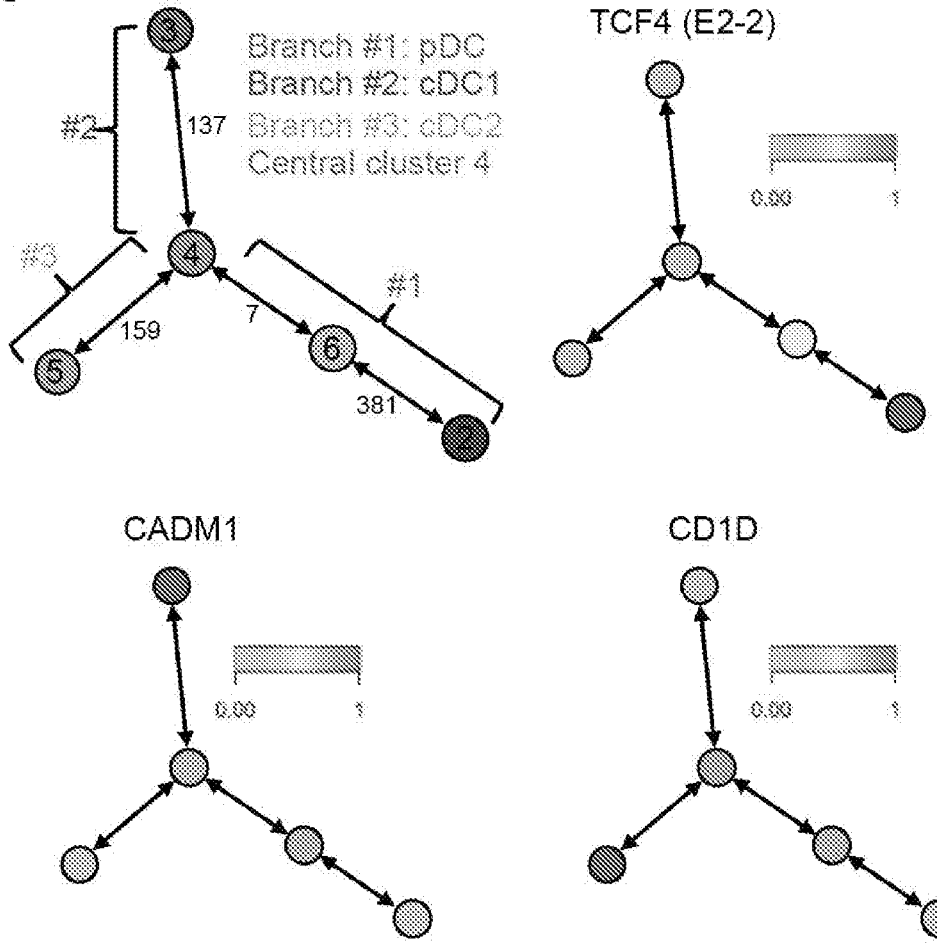
FIG. 7. (A) Relative expression of signature genes of pDC (TCF4), cDC1 (CADM1) and cDC2 (CD1D) in Mpath clusters defined in FIG. 1C. (B) Weighted neighborhood network of the Mpath analysis shown in FIG. 1C. (C) Analysis of MARS-seq data using the Wishbone algorithm. In the 2D-t-distributed stochastic neighbor embedding (tSNE) plot (upper panels) and in the 3D-Diffusion Map (lower panels) (See FIGS. 1, A and F, respectively), cells were colored according to the values of the Wishbone trajectory (left panels) or the values of the Wishbone branches (right panels). Line chart (top right panel) of expression of signature genes along Wishbone trajectory. X-axis represents pseudo-time of Wishbone trajectory. Solid line represents backbone trajectory, dotted lines represent separate trajectories along the two branches. Heat maps (bottom right panels) of expression of signature genes along Wishbone trajectory on the two branches.
Figure 7:
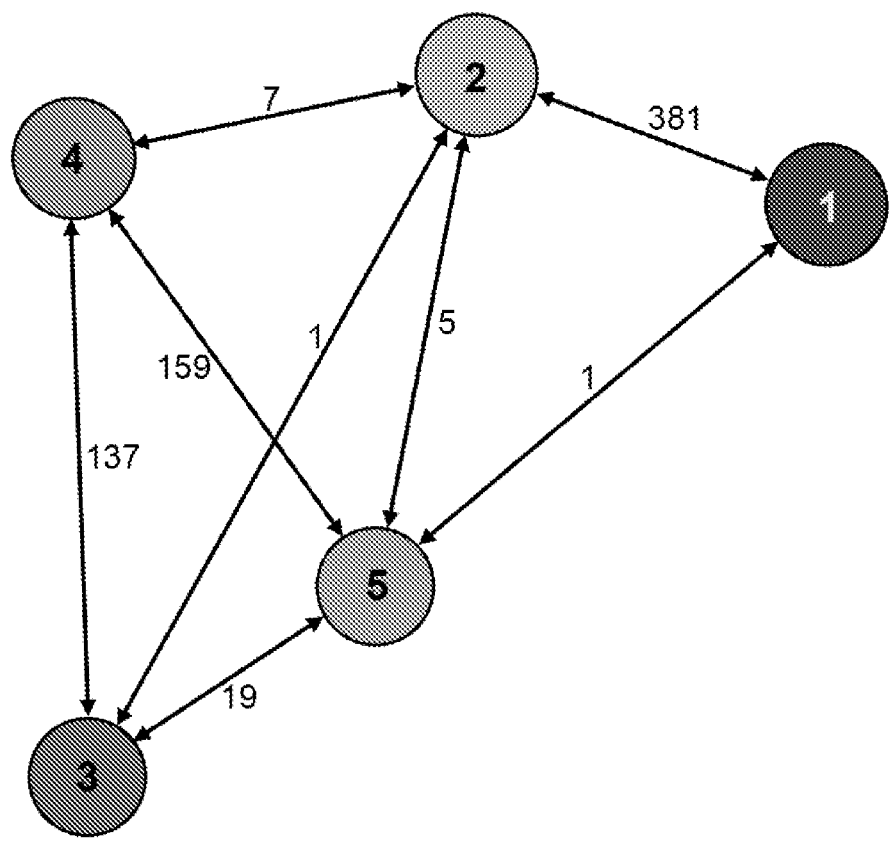
Figure 7:
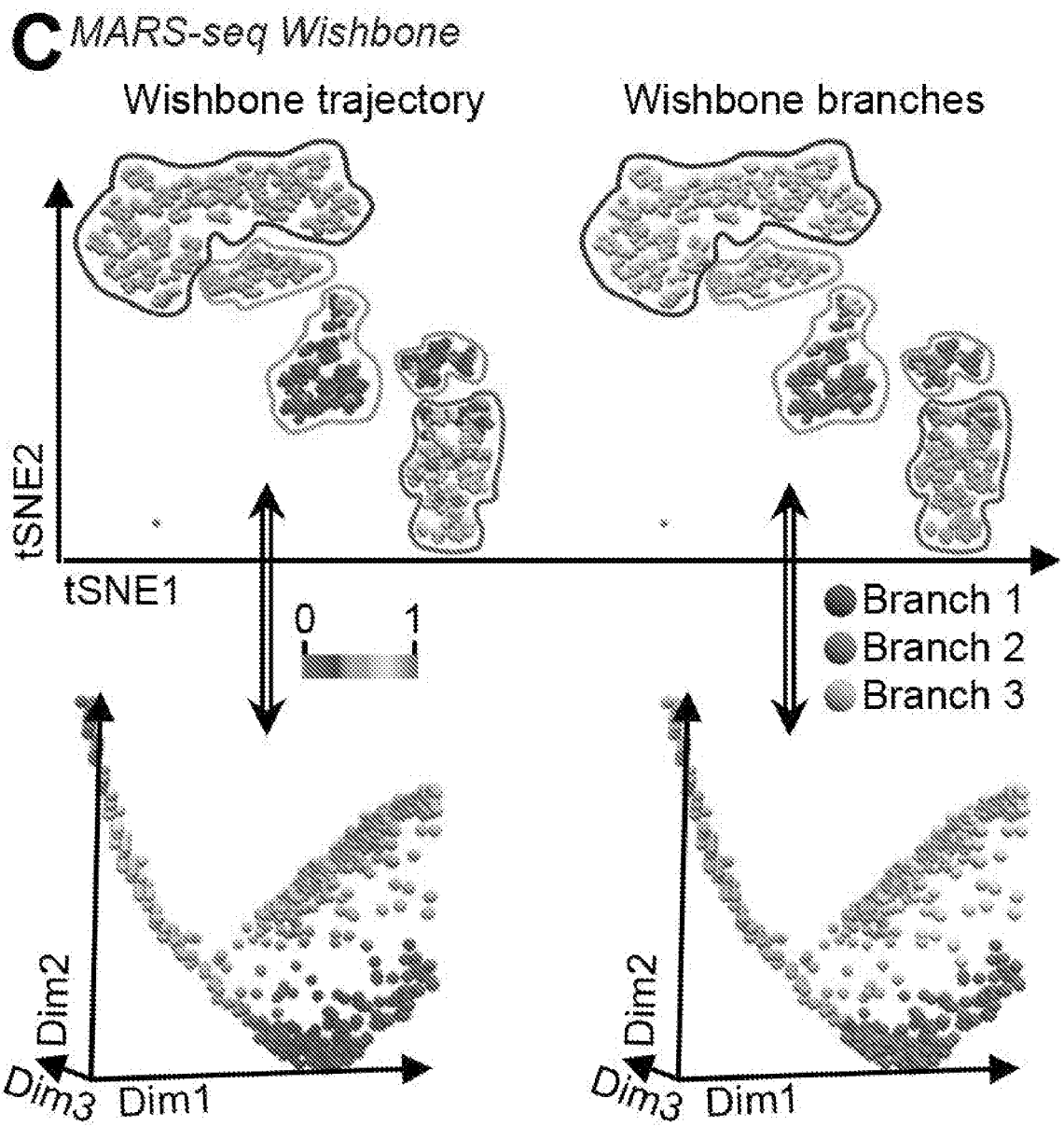

The Mpath algorithm (22) was then applied to the five clusters to identify hypothetical developmental relationships based on these transcriptional similarities between cells (FIG. 1C, and FIGS. 7, A and B). Mpath revealed that the five clusters were grouped into three distinct branches with one central cluster (cluster #4) at the intersection of the three branches (FIG. 1C, and FIG. 7A). The Mpath edges connecting cluster #4 to cDC1 cluster #3 and cDC2 cluster #5 have a high cell count (159 and 137 cells, respectively), suggesting that the transition from cluster #4 to clusters #3 and #5 is likely valid, and indicates that cluster #4 could contain putative cDC precursors (FIG. 1C). In contrast, the edge connecting cluster #4 and pDC cluster #2 has a cell count of only 7 (FIG. 1C, and FIG. 7B), which suggests that this connection is very weak. The edge connecting cluster #4 and #2 was retained when Mpath trimmed the weighted neighborhood network (FIG. 7B), simply due to the feature of the Mpath algorithm that requires all clusters to be connected (22).

Monocle (23), principal component analyses (PCA), Wishbone (24) and Diffusion Map algorithms (25) were used to confirm these findings. Monocle and PCA resolved the cells into the same three branches as the original Mpath analysis, with the cells from the tSNE cluster #4 again falling at the intersection (FIGS. 1, D and E). Diffusion Map and Wishbone analyses indicated that there was a continuum between clusters #3 (cDC1), #4 and #5 (cDC2): cells from cluster #4 were predominantly found in the DiffMap_dim2$^{low}$ region, and cells from clusters #3 and #5 were progressively drifting away from the DiffMap_dim2$^{low}$ region towards the left and right, respectively. The pDC clusters (#1 and #2) were clearly separated from all other clusters (FIG. 1F, and FIG. 7C). In support of this observation, cells from these pDC clusters had a higher expression of pDC-specific markers and transcription factors (TF) than the cDC clusters (#3 and #5) and central cluster #4. Conversely, cells in cluster #4 expressed higher levels of markers and TF associated with all cDC lineage than the pDC clusters (FIG. 1G). This points to the possibility that cluster #4 represented a population of putative uncommitted cDC precursors.

Figure 8:
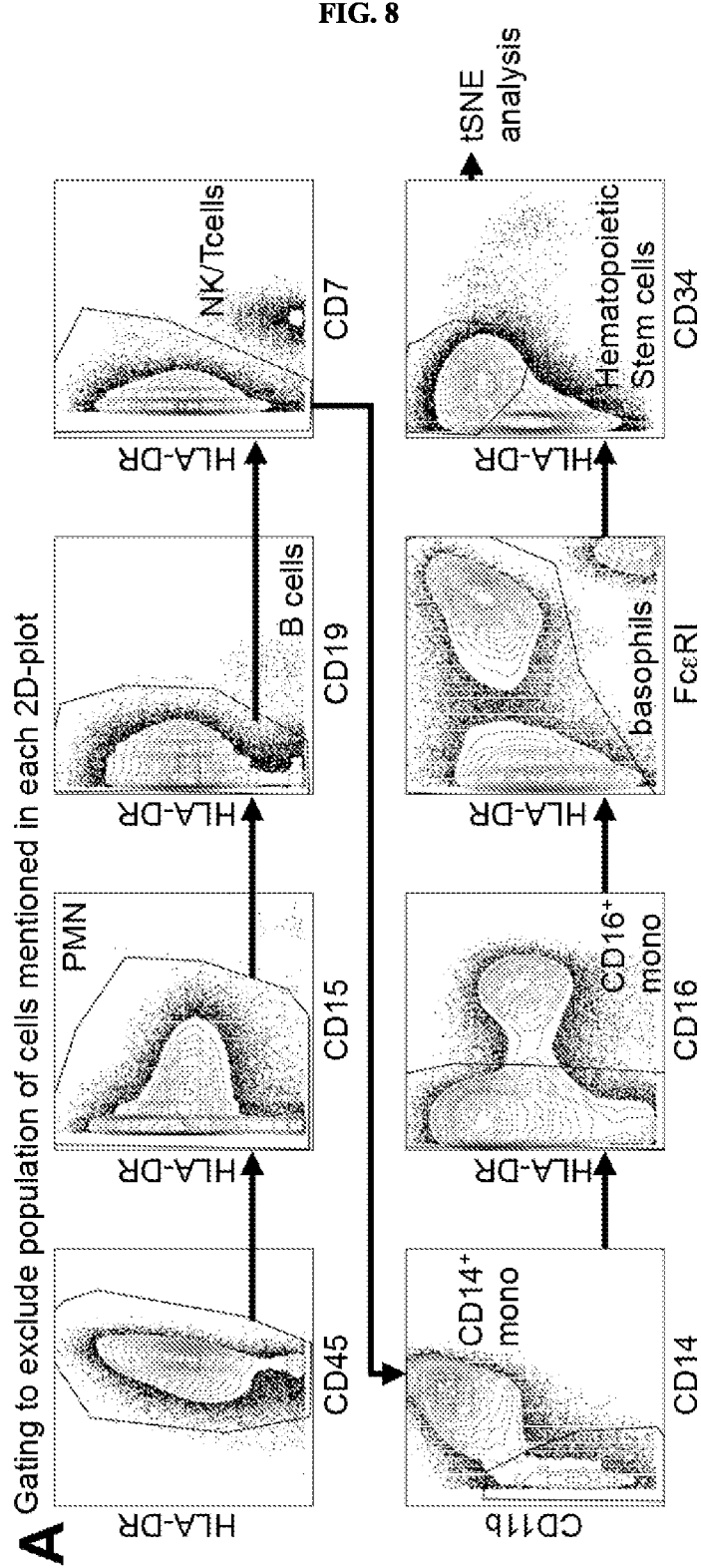
FIG. 8. (A) Gating strategy of CD45⁺Lin(CD7/CD14/CD15/CD16/CD19/CD34)⁻HLA-DR⁺ blood mononuclear cells from CyTOF analysis for downstream t-distributed stochastic neighbor embedding (tSNE) as shown in FIG. 1, E to G. The name of the excluded population(s) is indicated in each corresponding 2D-plot. (B) tSNE plots of the CyTOF data from FIG. 1, H to J showing the expression level of cDC2-, cDC1- and pDC-specific markers. (C) Unsupervised phenograph clustering identified 10 clusters that were overlaid onto the tSNE1/2 plot of the CyTOF data from FIGS. 1, H and I.
Figure 8:
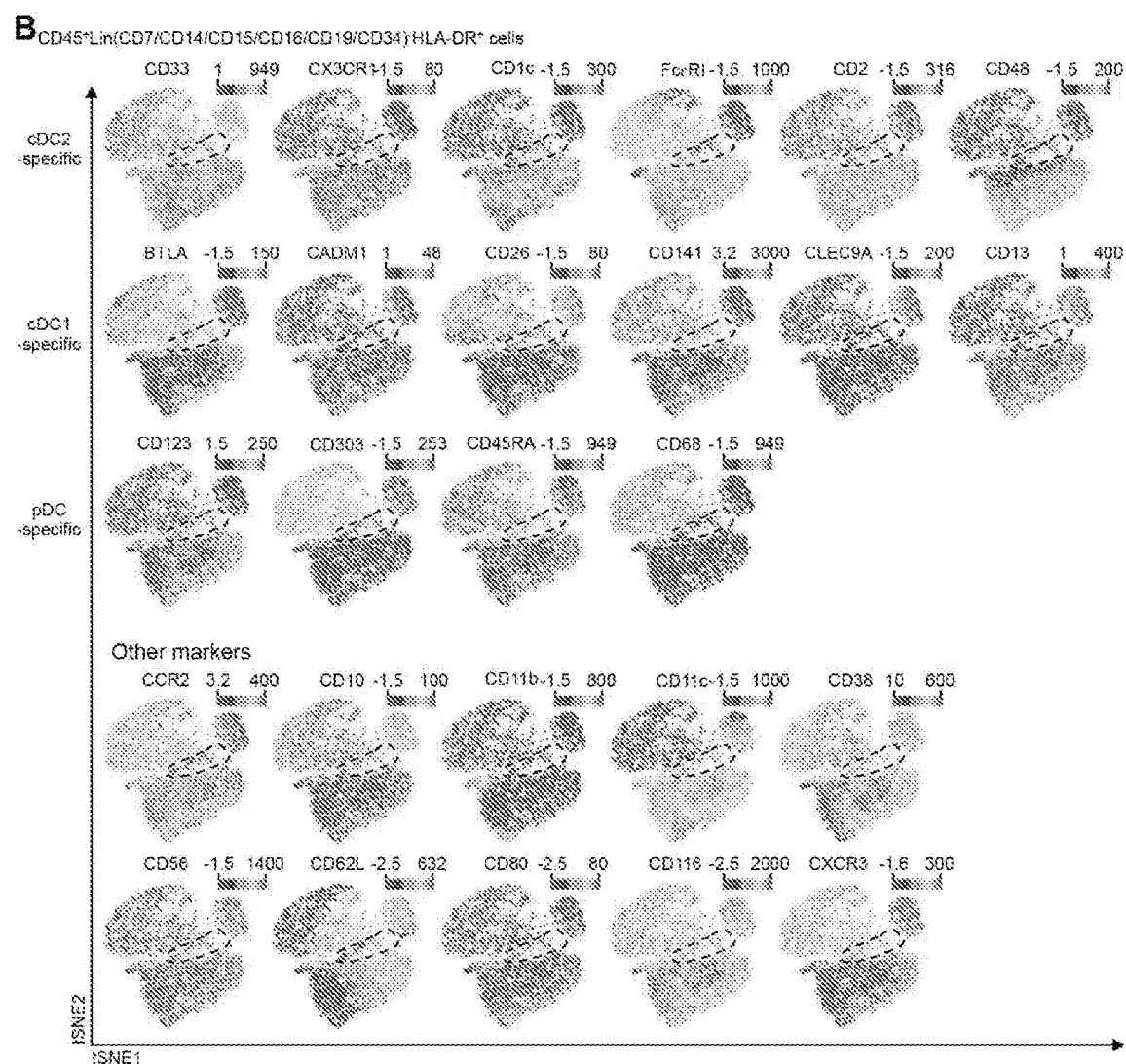
Figure 8:
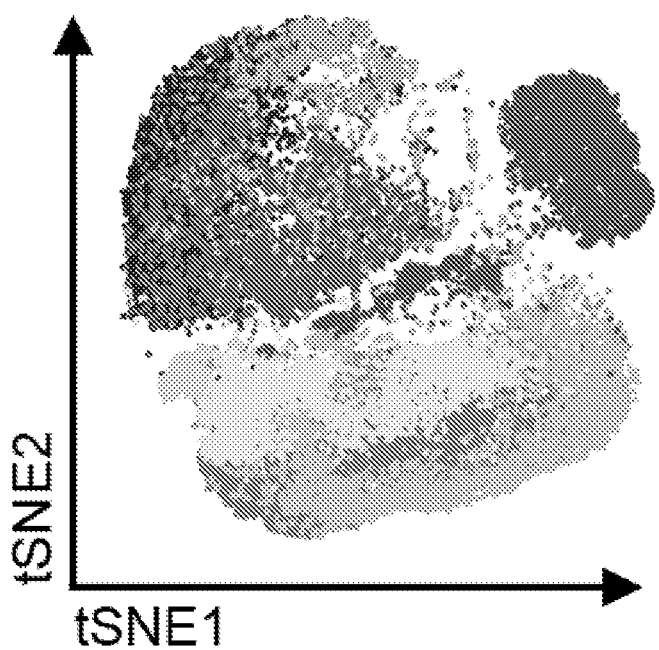

Next, CyTOF—which simultaneously measures the intensity of expression of up to 38 different molecules at the single cell level—was employed to further understand the composition of the delineated sub-populations. A panel of 38 labeled antibodies were designed to recognize DC lineage and/or progenitor-associated surface molecules (Table 3, FIG. 1, H to J, and FIG. 8), and the molecules identified in cluster #4 by MARS-seq, such as CD2, CX3CR1, CD11c and HLA-DR (FIG. 1I). Using the tSNE algorithm, the CD45$^+$Lin(CD7/CD14/CD15/CD16/CD19/CD34)$^-$HLA-DR$^+$ PBMC fraction (FIG. 8A) resolved into three distinct clusters representing cDC1, cDC2 and pDC (FIG. 1H). An intermediate cluster at the intersection of the cDC and pDC clusters that expressed both cDC-associated markers (CD11c/CX3CR1/CD2/CD33/CD141/BTLA) and pDC-associated markers (CD45RA/CD123/CD303) (FIG. 1, I to J, and FIG. 8B) corresponded to the MARS-seq cluster #4. The delineation of these clusters was confirmed when applying the phenograph unsupervised clustering algorithm (26) (FIG. 8C). The position of the intermediate CD123$^+$CD33$^+$ cell cluster was distinct, and the cells exhibited high expression of CD5, CD327, CD85j, together with high levels of HLA-DR and the cDC-associated molecule CD86 (FIG. 1, I to J). Taken together, these characteristics raise the question of whether CD123$^+$CD33$^+$ cells might represent circulating human pre-DC.

Pre-DC Exist within the pDC Fraction and Give Rise to cDC

Figure 2:
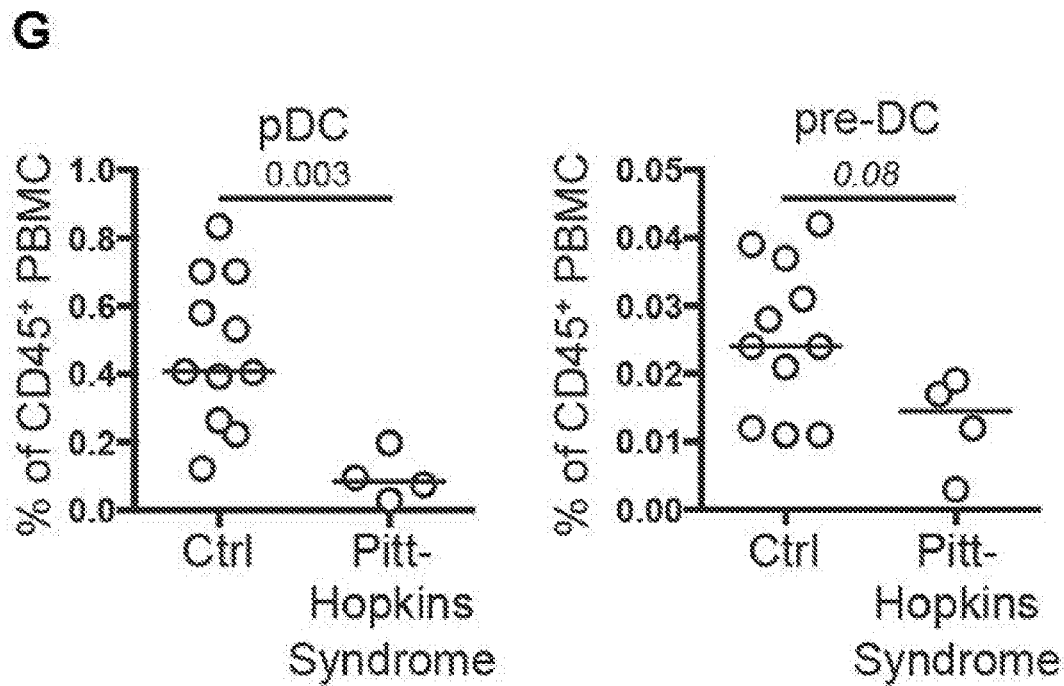
FIG. 2. Characterization of human pre-DC. (A) Flow cytometric identification of pre-DC and pDC within PBMC and spleen cell suspensions. (B) Expression of CD303/CD304/CD123/CD11c by blood pre-DC and DC subsets. (C) % pre-DC within spleen (n=3) and PBMC (n=6) CD45$^+$ populations. (D) Wright-Giemsa staining of sorted blood pre-DC and DC subsets. (E) Electron micrographs of pre-DC and pDC [(RER (arrowheads), centriole (C) and microtubules (small arrows), near RER cisterna are indicated). (F) DC subsets or pre-DC were co-cultured for 5 days with MS-5 feeder-cells, FLT3L, GM-CSF and SCF. Their capacity to differentiate into cDC1 or cDC2 was measured by flow cytometry. (n=3) (G) Frequency of pDC and pre-DC from control subjects (Ctrl, n=11) and Pitt-Hopkins Syndrome (PHS) patients (n=4). P-values calculated by Mann-Whitney test. Error bars represent mean+/− SEM.
Figure 9:
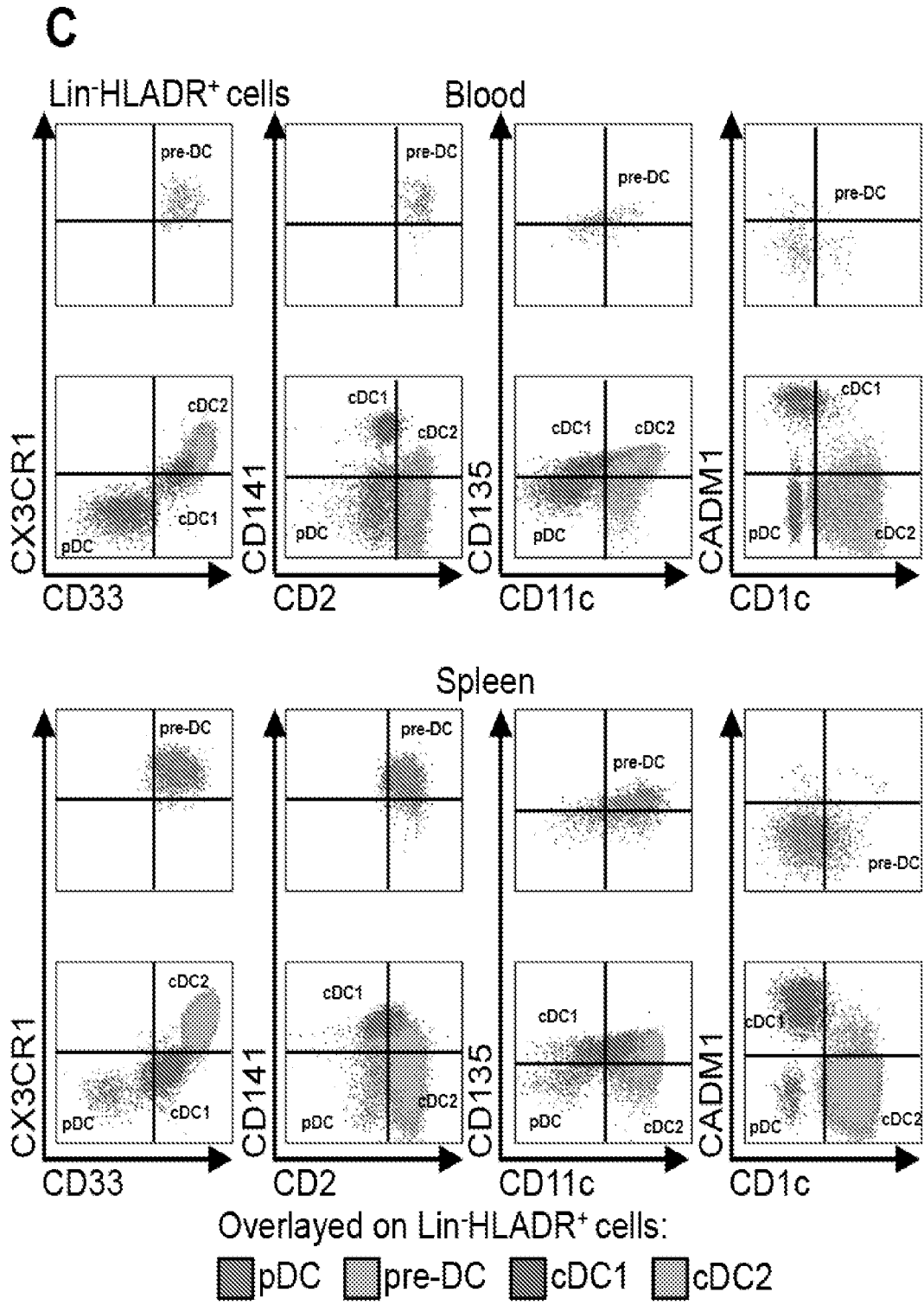
FIG. 9. (A) Gating of flow cytometry data to identify the Lin⁻HLA-DR⁺ cell population displayed in FIG. 2A (blood data displayed). (B) Classical contour plots of CyTOF data from FIG. 1 showing the same gating strategy as applied in the flow cytometry analyses shown in FIG. 2A. (C) Flow cytometry data showing the relative expression of CD33, CX3CR1, CD2, CD141, CD11c, CD135, CD1c and CADM1 by pre-DC, pDC, cDC1 and cDC2 defined in FIG.
Figure 9:
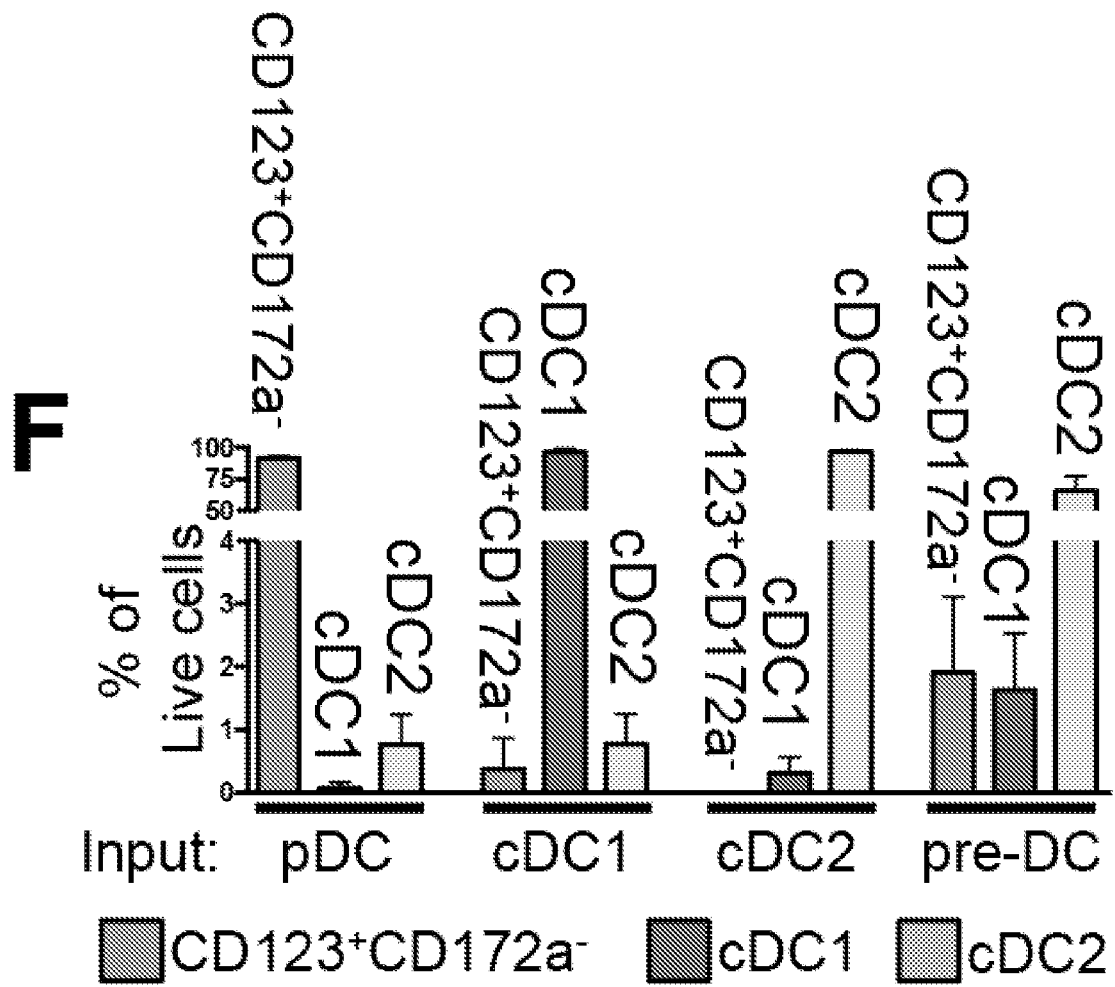

The CD123$^+$CD33$^+$ cell cluster within the Lin$^-$HLA-DR$^+$ fraction of the PBMC was analyzed by flow cytometry. Here, CD123$^+$CD33$^-$ pDC, CD45RA$^{+/-}$CD123$^-$cDC1 and cDC2, and CD33$^+$CD45RA$^+$CD123$^+$ putative pre-DC were identified (FIG. 2A, and FIG. 9A). The putative pre-DC expressed CX3CR1, CD2, CD303 and CD304, with low CD11c expression, whereas CD123$^+$CD33$^-$ pDC exhibited variable CD2 expression (FIGS. 2, A and B, and FIGS. 9, B and C).

The analysis was extended to immune cells from the spleen and identified a similar putative pre-DC population, which was more abundant than in blood and expressed higher levels of CD11c (FIGS. 2, A and C, and FIG. 9D).

Both putative pre-DC populations in the blood and spleen expressed CD135 and intermediate levels of CD141 (FIG. 9C). Wright-Giemsa staining of putative pre-DC sorted from the blood revealed an indented nuclear pattern reminiscent of classical cDC, a region of perinuclear clearing, and a basophilic cytoplasm reminiscent of pDC (FIG. 2D).

At the ultra-structural level, putative pre-DC and pDC exhibited distinct features, despite their morphological similarities (FIG. 2E, and FIG. 9E): putative pre-DC possessed a thinner cytoplasm, homogeneously-distributed mitochondria (m), less rough endoplasmic reticulum (RER), an indented nuclear pattern, a large nucleus and limited cytosol, compared to pDC; pDC contained a smaller nucleus, abundant cytosol, packed mitochondria, well-developed and polarized cortical RER organized in parallel cisterna alongside numerous stacks of rough ER membranes, suggesting a developed secretory apparatus, in agreement with previously-published data (27).

The differentiation capacity of pre-DC to that of cDC and pDC, through stromal culture in the presence of FLT3L, GMCSF and SCF were compared, as previously described (8). After 5 days, the pDC, cDC1 and cDC2 populations remained predominantly in their initial states, whereas the putative pre-DC population had differentiated into cDC1 and cDC2 in the known proportions found in vivo (14, 20, 28, 29) (FIG. 2F, FIG. 9F, and FIG. 10). Altogether, these data suggest that CD123$^+$CD33$^+$CD45RA$^+$CX3CR1$^+$CD2$^+$ cells are circulating pre-DC with cDC differentiation potential.

Breton and colleagues (9) recently reported a minor population of human pre-DC (highlighted in FIG. 11A), which shares a similar phenotype with the Lin$^-$ CD123$^+$CD33$^+$CD45RA$^+$ pre-DC defined here (FIGS. 11, A and B). The present results reveal that the pre-DC population in blood and spleen is markedly larger than the one identified within the minor CD303$^-$CD141$^-$CD117$^+$ fraction considered previously (FIGS. 11, C and D).

Pre-DC are Functionally Distinct from pDC

IFNα-secreting pDC can differentiate into cells resembling cDC when cultured with IL-3 and CD40L (10, 11), and have been considered DC precursors (11). However, when traditional ILT3$^+$ ILT1$^-$ (10) or CD4$^+$CD11c$^-$ (11) pDC gating strategies were used, a "contaminating" CD123+ CD33+CD45RA+ pre-DC sub-population in both groups (FIGS. 11, E and F) was detected. This "contaminating" sub-population result raises the question on whether other properties of traditionally-classified "pDC populations" might be attributed to pre-DC.

Pitt-Hopkins Syndrome (PHS) is characterized by abnormal craniofacial and neural development, severe mental retardation, and motor dysfunction, and is caused by haploinsufficiency of TCF4, which encodes the E2-2 transcription factor—a central regulator of pDC development (31). Patients with PHS had a marked reduction in their blood pDC numbers compared to healthy individuals, but retained a population of pre-DC (FIG. 2G, and FIG. 13), which likely accounts for the unexpected CD45RA+CD123+CD303$^{lo}$ cell population reported in these patients (32). Taken together, the present data indicate that, while pre-DC and pDC share some phenotypic features, they can be separated by their differential expression of several markers, including CD33, CX3CR1, CD2, CD5 and CD327. pDC are bona fide IFNα-producing cells, but the reported IL-12 production and CD4+ T-cell allostimulatory capacity of pDC can likely be attributed to "contaminating" pre-DC, which can give rise to both cDC1 and cDC2.

Identification and Characterization of Committed Pre-DC Subsets

The murine pre-DC population contains both uncommitted and committed pre-cDC1 and pre-cDC2 precursors (7). Thus, microfluidic scmRNAseq was used to determine whether the same was true for human blood pre-DC, (FIG. 14A: sorting strategy, FIGS. 14, B and C: workflow and quality control, Table 4: number of expressed genes).

The additional single cell gene expression data relative to the MARS-seq strategy used for FIG. 1, A to G (2.5 million reads/cell and an average of 4,742 genes detected per cell vs 60,000 reads/cell and an average of 749 genes detected per cell, respectively) was subjected to cMAP analysis, which calculated the degree of enrichment for cDC1 or cDC2 signature gene transcripts (20) for each single cell (FIG. 3A). Among the 92 analyzed pre-DC, 25 cells exhibited enrichment for cDC1 gene expression signatures, 12 cells for cDC2 gene expression signatures, and 55 cells showed no transcriptional similarity to either cDC subset.

Further Mpath analysis showed that these 55 "unprimed" pre-DC were developmentally related to cDC1-primed and cDC2-primed pre-DC, and thus their patterns of gene expression fell between the cDC1 and cDC2 signature scores by cMAP (FIG. 3B, and FIG. 15). These data suggest that the human pre-DC population contains cells exhibiting transcriptomic priming towards cDC1 and cDC2 lineages, as observed in mice (7).

This heterogeneity within the pre-DC population by flow cytometry were further subjected to identification using either pre-DC-specific markers (CD45RA, CD327, CD5) or markers expressed more intensely by pre-DC compared to cDC2 (BTLA, CD141). 3D-PCA analysis of the Lin−HLA-DR+CD33+ population (containing both differentiated cDC and pre-DC) identified three major cell clusters: CADM1+ cDC1, CD1c+cDC2 and CD123+ pre-DC (FIG. 3C, and FIG. 16A).

Interestingly, while cells located at the intersection of these three clusters (FIG. 3D) expressed lower levels of CD123 than pre-DC, but higher levels than differentiated cDC (FIG. 3C), they also expressed high levels of pre-DC markers (FIG. 3D, and FIG. 16A). It is possible that these CD45RA+CD123$^{lo}$ cells might be committed pre-DC that are differentiating into either cDC1 or cDC2 (FIG. 3E). The Wanderlust algorithm (34), which orders cells into a constructed trajectory according to their maturity, confirmed the developmental relationship between pre-DC (early events), CD45RA+CD123$^{lo}$ cells (intermediate events) and mature cDC (late events) (FIG. 3F). Flow cytometry of PBMC identified CD123+CADM1−CD1c− putative uncommitted pre–DC, alongside putative CADM1+CD1c− pre-cDC1 and CADM1−CD1c+ pre-cDC2 within the remaining CD45RA+ cells (FIG. 3G, and FIG. 16B). These three populations were also present, and more abundant, in the spleen (FIG. 16C).

Importantly, in vitro culture of pre-DC subsets sorted from PBMC did not give rise to any CD303+ cells (which would be either undifferentiated pre-DC or differentiated pDC), whereas early pre-DC gave rise to both cDC subsets, and pre-cDC1 and pre-cDC2 differentiated exclusively into cDC1 and cDC2 subsets, respectively (FIG. 3H, FIG. 16D, and FIG. 17).

Scanning electron microscopy confirmed that early pre-DC are larger and rougher in appearance than pDC, and that committed pre-DC subsets closely resemble their mature cDC counterparts (FIG. 3I, and FIG. 18A).

Phenotyping of blood pre-DC by flow cytometry (FIG. 18B) identified patterns of transitional marker expression throughout the development of early pre-DC towards pre-cDC1/2 and differentiated cDC1/2. Specifically, CD45RO and CD33 were acquired in parallel with the loss of CD45RA; CD5, CD123, CD304 and CD327 were expressed abundantly by early pre-DC, intermediately by pre-cDC1 and pre-cDC2, and rarely if at all by mature cDC and pDC; FcεRI and CD1c were acquired as early pre-DC commit towards the cDC2 lineage, concurrent with the loss of BTLA and CD319 expression; early pre-DC had an intermediate expression of CD141 that dropped along cDC2 differentiation but was increasingly expressed during commitment towards cDC1, with a few pre-cDC1 already starting to express Clec9A; and IRF8 and IRF4-transcription factors regulating cDC lineage development (2, 3)—were expressed by early pre-DC and pre-cDC1, while pre-cDC2 maintained only IRF4 expression (FIG. 18C).

Pre-DC and DC subsets were next sorted from blood and microarray analyses were performed to define their entire transcriptome. 3D-PCA analysis of the microarray data showed that pDC were clearly separated from other pre-DC and DC subsets along the horizontal PC1 axis (FIG. 4A, and FIG. 19). The combination of the PC2 and PC3 axes indicated that pre-cDC1 occupied a position between early pre-DC and cDC1 and, although cDC2 and pre-cDC2 exhibited similar transcriptomes, pre-cDC2 were positioned between cDC2 and early pre-DC along the PC3 axis (FIG. 4A).

Hierarchical clustering of differentially-expressed genes (DEG) confirmed the similarities between committed pre-DC and their corresponding mature subset (FIG. 20). The greatest number of DEG was between early pre-DC and pDC (1249 genes) among which CD86, CD2, CD22, CD5, ITGAX (CD11c), CD33, CLEC10A, SIGLEC6 (CD327), THBD, CLEC12A, KLF4 and ZBTB46 were more highly expressed by early pre-DC, while pDC showed higher expression of CD68, CLEC4C, TCF4, PACSIN1, IRF7 and TLR7 (FIG. 4B). An evolution in the gene expression pattern was evident from early pre-DC, to pre-cDC1 and then cDC1 (FIG. 4C), whereas pre-cDC2 were similar to cDC2 (FIG. 4D, and FIG. 20). The union of DEGs comparing pre-cDC1versus early pre-DC and cDC1 versus pre-cDC1 has 62 genes in common with the union of DEGs from comparing pre-cDC2 versus early pre-DC and cDC2 versus pre-cDC2. These 62 common genes include the transcription factors BATF3, ID2 and TCF4 (E2-2), and the pre-DC markers CLEC4C (CD303), SIGLEC6 (CD327), and IL3RA (CD123) (FIG. 4E, FIG. 21 and Table 5).

The progressive reduction in transcript abundance of SIGLEC6 (CD327), CD22 and AXL during early pre-DC to cDC differentiation was also mirrored at the protein level (FIG. 4F). Key transcription factors involved in the differentiation and/or maturation of DC subsets showed a progressive change in their expression along the differentiation path from pre-DC to mature cDC (FIG. 4G). Finally, pathway analyses revealed that pre-DC exhibited an enrichment of cDC functions relative to pDC, and were maintained in a relatively immature state compared to mature cDC (FIG. 22).

Unsupervised Mapping of DC Ontogeny

To understand the relatedness of the cell subsets, an unsupervised isoMAP analysis (34) was performed of human BM cells, obtained from CyTOF analysis, for non-linear dimensionality reduction (FIG. 5A, and FIG. 23A). This analysis focused on the Lin$^-$CD123$^{hi}$ fraction and identified CD123$^{h1}$CD34$^+$CDP (phenograph cluster #5), from which branched CD34$^-$CD123$^+$CD327$^+$CD33$^+$ pre-DC (clusters #1 and #2) and CD34$^-$CD123$^+$CD303$^+$CD68$^+$ pDC (clusters #3 and #4) which both progressively acquired their respective phenotypes. Cells in the pre-DC branch increasingly expressed CD2, CD11c, CD116 and, at a later stage, CD1c.

IsoMAP analysis of Lin$^-$CD123$^+$ cells in the peripheral blood identified two parallel lineages, corresponding to pre-DC and pDC, in which a CDP population was not detected (FIG. 5B). IsoMAP and phenograph analysis of pre-DC extracted from the isoMAP analysis of FIG. 5A (BM, clusters #1 and #2) and FIG. 5B (blood, cluster #6) revealed the three distinct pre-DC subsets (FIG. 5C) as defined by their unique marker expression patterns (FIGS. 23, B and C).

Figure 5:
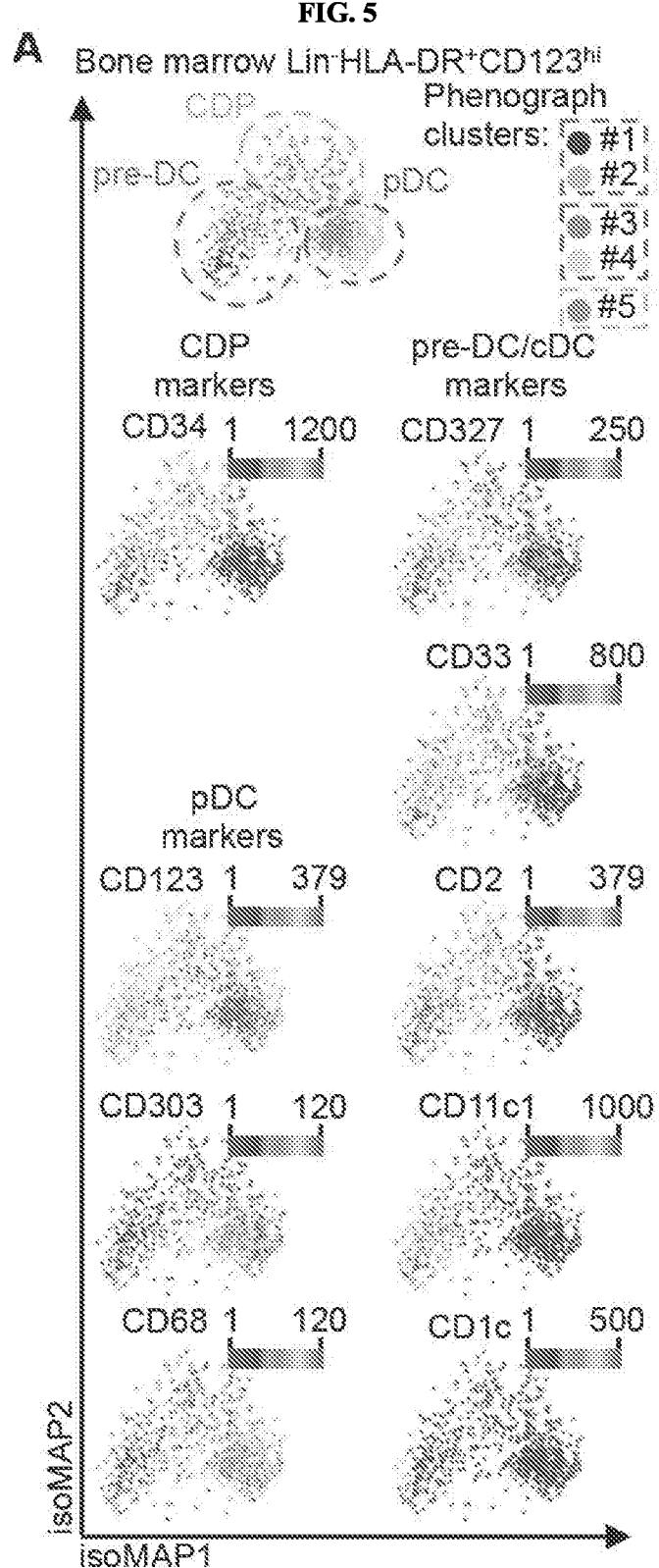
FIG. 5. Unsupervised mapping of DC ontogeny using CyTOF. CyTOF data from bone marrow (BM) and PBMC were analyzed using isoMAP dimensionality reduction to compare overall phenotypic relatedness of cell populations, and were automatically subdivided into clusters using the phenograph algorithm. (A, B) IsoMAP1-2 plots showing the expression level of common DC progenitor (CDP), pDC, pre-DC and cDC-specific markers within (A) BM and (B) blood Lin(CD3/CD7/CD14/CD15/CD19/CD34)⁻HLA-DR⁺CD123⁺ cells. (C) Phenotypic association between Lin⁻HLA-DR⁺CD123^hi BM and CD123⁺ PBMC, showing progression from CDP towards pDC or pre-DC in the BM, and the clear separation of pDC and pre-DC in the blood. Cells within the pre-DC phenograph clusters (clusters #1 and #2 in the BM, and #6 in the blood) and cells within the pDC phenograph clusters (clusters #3 and #4 in the BM, and #7 in the blood) were further analyzed by isoMAP to define pre-DC subsets (left panels, and FIGS. 23, C and D) and heterogeneity among pDC (right panels, and FIGS. 23, D and E).
Figure 5:
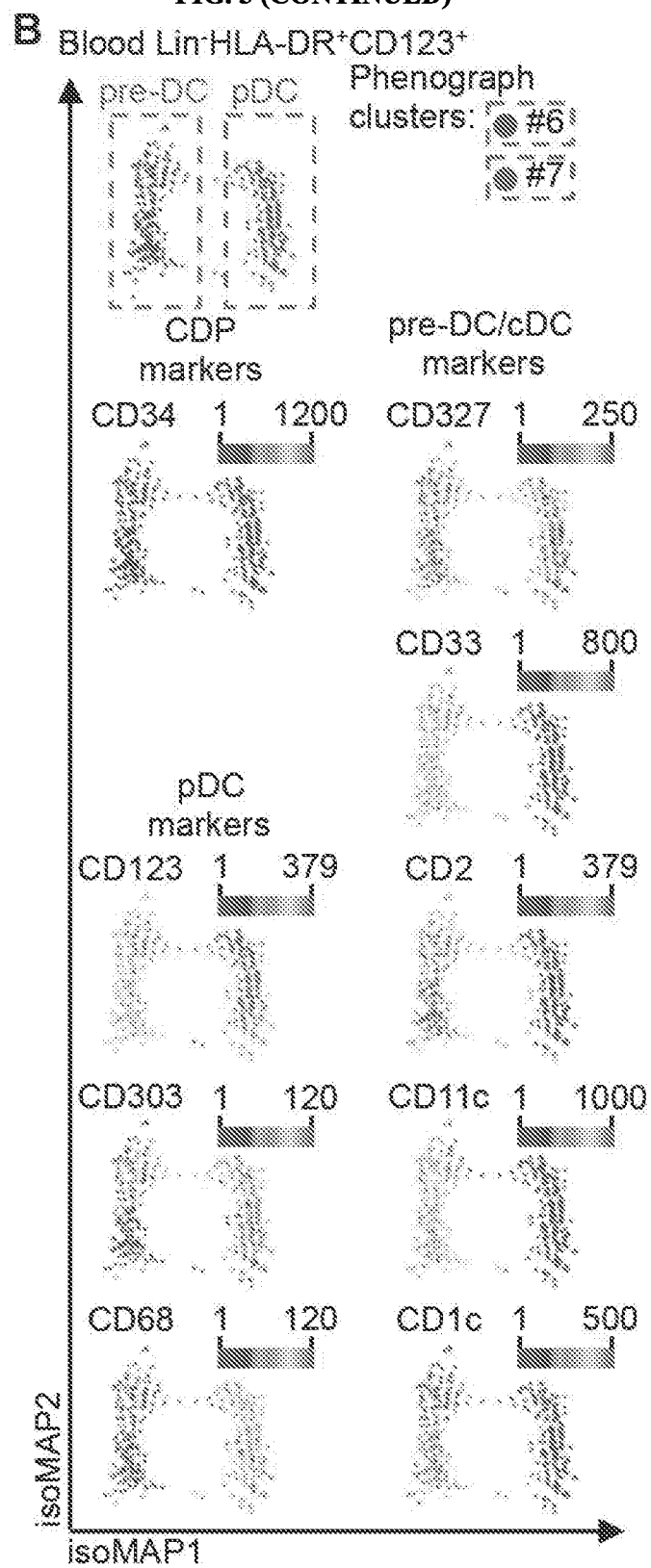
Figure 5:
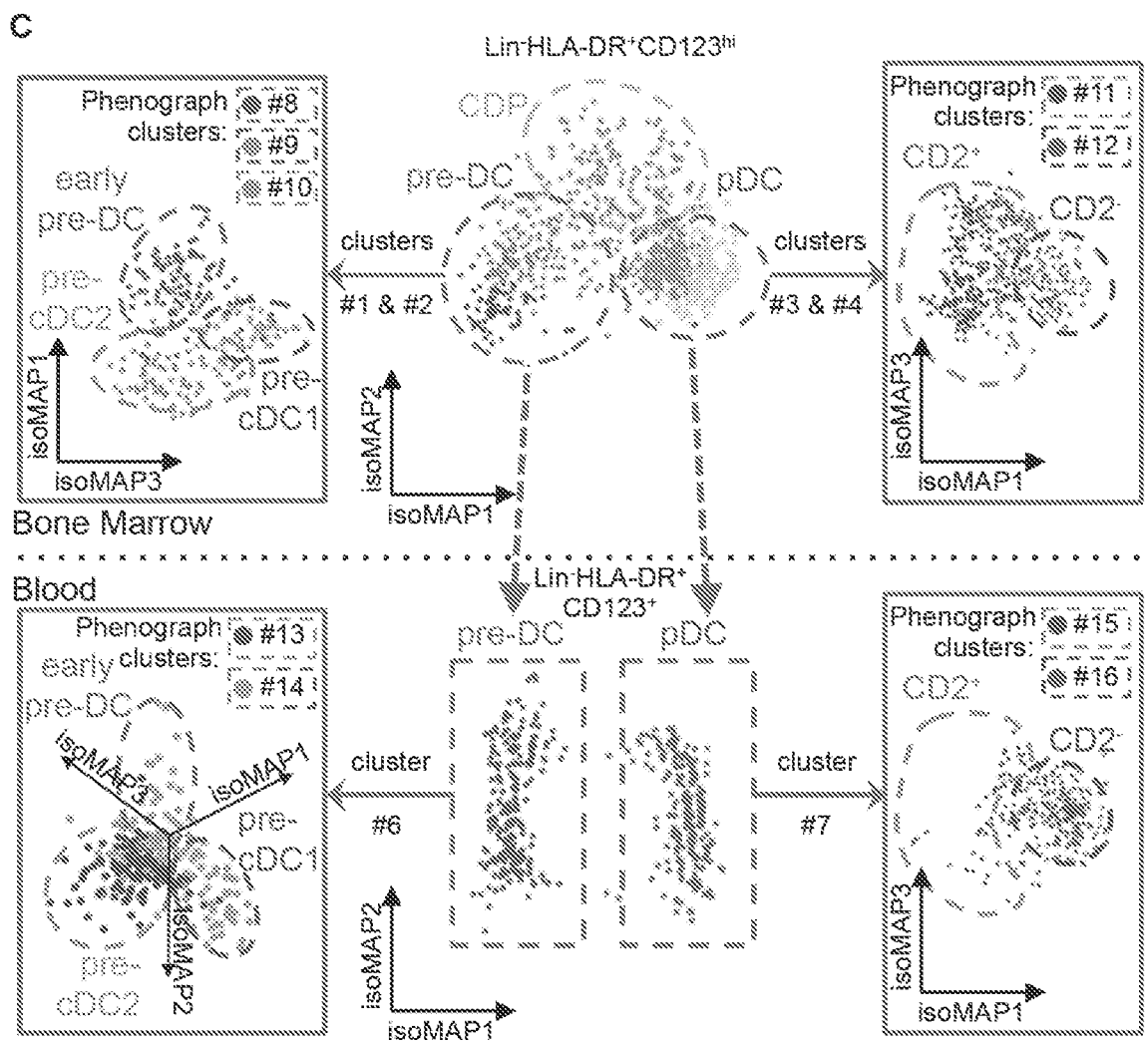

In summary, the developmental stages of DC from the BM to the peripheral blood through CyTOF were traced which shows that the CDP population in the BM bifurcates into two pathways, developing into either pre-DC or pDC in the blood (FIG. 5, A to C). This pre-DC population is heterogeneous and exists as distinct subsets detectable in both the blood and BM (FIG. 5C, and FIGS. 23, B and C). Furthermore, an intriguing heterogeneity in blood and BM pDC was uncovered, which warrants further investigation (FIG. 6C, and FIGS. 23, D and E).

Validation of Down Sampling Threshold for Normalization of MARS-Seq Single Cell Transcriptome Data High variance in terms of quality of single-cell transcriptomes is expected in a single-cell RNA sequencing experiment due to the low quantity of RNA input material. This caveat necessitates stringent quality control in order to avoid a bias introduced by low quality single-cell transcriptomes. In single-cell transcriptomics it is, therefore, common practice to remove low quality transcriptomes to ensure an unbiased and biologically meaningful analysis (59, 60). Different strategies have been used to filter out low quality cells, including an empirically determined cutoff for cell filtering (59), a down sampling strategy to normalize and filter low quality cells (15), and various filtering cutoffs from 600 UMIs/cell or 400 UMIs/cells (15), <500 molecule counts per cell (61) and <200 UMIs/cell (62). To the best of our knowledge, a mathematically determined cut-off was not reported in any of these studies. As these previous studies were performed on murine cells, and quality filters in single-cell data have to be established within the respective dataset, the present approach had adapted the filtering strategy to human cells. To determine the quality threshold for the present dataset, several diagnostics were used to estimate the optimal cutoff for down sampling of molecule counts. Firstly, the cumulative distribution of molecule counts were visualized, where cells on the x-axis were ordered by decreasing UMI count (FIG. 6C). Here, in a certain region there was a period of strong decline in the number of molecule counts per cell. This region corresponded to a range of molecule counts between 400 and 1200 UMIs per cell. The next metric used to judge an objective threshold (FIG. 6D) was the molecule count distribution of all cells. Many of the cell barcodes had <650 molecule counts—these cell barcodes most likely represented the background signal of the present MARS-seq data set. The number of cell barcodes with a certain number of molecules decreases with increasing molecule count per cell; through this visualization, natural breakpoints in the distribution that could be used as an objective threshold for filtering and normalization were identified, as these breakpoints mark a change in the data structure and quality, and indicate the transition from background to signal, or from low-quality transcriptomes to high-quality transcriptomes. Here, three notable points were identified (FIG. 6D), which corresponded to molecule counts of 650 (B), 1,050 (R) and 1,700 (G) per cell. To objectively determine which of these points represented a shift in data quality from low to high quality transcriptomes, a turning point needed to be identified (FIG. 6D). In the density plot (FIG. 6D, top panel), the three lines (G, R, B) are the breakpoints where the slope of the density function ($1^{st}$ derivative of density, FIG. 6D, middle panel) has a sudden change. On the B line, the downward slope (1st derivative) changes from being very steep to less steep, so that the $2^{nd}$ derivative is the highest at this point. Similarly, on the R line, the downward slope changes from less steep to more steep, so the $2^{nd}$ derivative is the lowest. Based on these observations, the three turning points were identified by the $2^{nd}$ derivative (FIG. 6D, bottom panel). When a cutoff of 650 was applied, the number of molecule counts per cell was too low and the three DC populations—plasmacytoid DC (pDC) and conventional DC (cDC) subsets cDC1 and cDC2, could not be distinguished by principal component analysis (PCA; FIG. 6E). When a cutoff of 1,700 was applied, the number of cells retained was too low. Therefore, the 1,050 cutoff was an optimal tradeoff between the number of cells analyzed (cells retained after filtering by down sampling normalization) and the number of molecule counts in a cell (gene expression information that remains after discarding molecule counts by down sampling).

To ensure data reproducibility, stability and independence of the chosen molecule cutoff, the initial analyses were stimulated using cutoffs of 650, 1,050, 1,700 and 2,350 molecule counts (FIG. 6E). All four chosen simulation values exhibited the same general data topology if the data were dimensionally-reduced using PCA, thus proving that the biological data structure was robust and independent of filtering thresholds. In addition, the influence of the filtering threshold on the gene loadings within the first two principal components were correlated. Principal component 1 (PC1) of the dataset down-sampled to 1,050 molecule counts was highly correlated with PC1 of the datasets down-sampled to either 650 or 1,700 molecule counts (Pearson=0.996 and 0.999, respectively). The same was true for PC2 (Pearson=0.960 and 0.925, respectively). These results indicated that the chosen filtering cutoff of 1,050 was representative and objectively-derived.

The MARS-seq data obtained in this disclosure were generated by two independent experiments (run1 and run2), which were combined for further data analysis. After normalization, the correlation between the average molecule count of all genes in run1 vs run2 was assessed (FIG. 6F, which shows the high correlation between the average molecular counts in both runs (r=0.994)). When assessing for a batch effect, it is important to ensure that runs do not determine the clustering itself. The t-distributed stochastic neighbor embedding (tSNE) values were plotted (FIG. 6G) (cells of run1 and run2 in equal proportions) together with their density estimates. This analysis showed that the general distribution and, therefore, the clustering was not governed by the run, which is in line with the observation that the present clustering identified biologically reasonable groups that clearly corresponded to the three DC populations (pDC, cDC1 and cDC2) (FIG. 1A). Consequently, the observed clusters were not explained by the variance between the runs, but by biology.

The frequencies of cell types were comapred, as determined by the clustering, within the two runs (FIG. 6H). This showed that the ratio between the cells in different clusters was comparable between the two runs. Of note, the ratio does not need to be identical in both runs (61). In addition, this analysis showed that no cluster dominated a single run. Due to the fact that we are taking relatively small samples from a large total population, the frequencies of cell types are expected to show natural variation between runs, which could explain slight shifts in cellular frequencies.

DISCUSSION

Using unsupervised scmRNAseq and CyTOF analyses, the complexity of the human DC lineage at the single cell level was unraveled, revealing a continuous process of differentiation that starts in the BM with CDP, and diverges at the point of emergence of pre-DC and pDC potentials, culminating in maturation of both lineages in the blood.

A previous study using traditional surface marker-based approaches had suggested the presence of a minor pre-DC population in PBMC (9), but the combination of high-dimensional techniques and unbiased analyses employed here shows that this minor population had been markedly underestimated: as the present results reveal a population of pre-DC that overlaps with that observed by Breton and colleagues (9) within the CD117$^+$CD303$^-$CD141$^-$ fraction of PBMC, but accounts for >10 fold the number of cells in peripheral blood than was originally estimated, and is considerably more diverse (FIG. 11C).

Recent work in mice found uncommitted and subset-committed pre-DC subsets in the BM (7, 35). Here, similarly, three functionally- and phenotypically-distinct pre-DC populations in human PBMC, spleen and BM were identified which are: uncommitted pre-DC and two populations of subset-committed pre-DC (FIG. 24 and FIG. 25). In line with the concept of continuous differentiation from the BM to the periphery, the proportion of uncommitted cells was higher in the pre-DC population in the BM than in the blood. Altogether, these findings support a two-step model of DC development whereby a central transcriptomic subset-specific program is imprinted on DC precursors from the CDP stage onwards, conferring a core subset identity irrespective of the final tissue destination; in the second step of the process, peripheral tissue-dependent programming occurs to ensure site-specific functionality and adaptation (7, 35).

An important aspect of unbiased analyses is that cells are not excluded from consideration on the basis of preconceptions concerning their surface phenotype. Pre-DC was found to express most of the markers that classically defined pDC, such as CD123, CD303 and CD304. Thus, any strategy relying on these markers to identify and isolate pDC will have inadvertently included CD123$^+$CD33$^+$ pre-DC as well. While this calls for reconsideration of some aspects of pDC population biology, it may also explain earlier findings including that: pDC cultures possess cDC potential and acquire cDC-like morphology (10, 11), as recently observed in murine BM pDC (36); pDC mediate Th1 immunity through production of IFNα and IL-12 (10, 37-41); pDC exhibit naïve T-cell allostimulatory capacity (30, 39); and pDC express co-stimulatory molecules and exhibit antigen-presentation/cross-presentation capabilities at the expense of IFNα secretion (37, 42).

These observations could be attributed to the undetected pre-DC in the pDC populations described by these studies, and indeed it has been speculated that the IL-12 production observed in these early studies might be due to the presence of contaminating CD11c$^+$cDC (43). The present disclosure addressed this possibility by separating CX3CR1$^+$CD33$^+$CD123$^+$CD303$^+$CD304$^+$ pre-DC from CX3CR1$^-$CD33$^-$CD123$^+$CD303$^+$CD304$^+$"pure" pDC and showing that pDC could not polarize or induce proliferation of naïve CD4 T cells, whereas pre-DC had this capacity. Thus, it is of paramount importance that pre-DC be excluded from pDC populations in future studies, particularly when using commercial pDC isolation kits. Finally, if pDC are stripped of all their cDC properties, it raises the question as to whether they truly belong to the DC lineage, or rather are a distinct type of innate IFN-I-producing lymphoid cell. It also remains to be shown whether the BM CD34$^+$CD123$^{hi}$ CDP population is also a mixture of independent bona fide cDC progenitors and pDC progenitors.

Beyond the identification of pre-DC, the present data revealed previously-unappreciated transcriptional and phenotypic heterogeneity within the circulating mature DC populations. This was particularly clear in the case of cDC2 and pDC, which were grouped into multiple Mpath clusters in the single-cell RNAseq analysis, and showed marked dispersion in the tSNE analysis of the CyTOF data with phenotypic heterogeneity. IsoMAP analysis of the CyTOF data also revealed another level of pDC heterogeneity by illustrating the progressive phenotypic transition from CDP into CD2$^+$ pDC in the BM, involving intermediate cells that could be pre-pDC. Whether a circulating pre-pDC population exists remains to be concluded. Finally, defining the mechanisms that direct the differentiation of uncommitted pre-DC into cDC1 or cDC2, or that maintain these cells in their initial uncommitted state in health and disease could lead to the development of new therapeutic strategies to modulate this differentiation process.

The present disclosure provides that pre-DC cells are susceptible to HIV-1 infection with both R5 and X4 tropic viruses (FIG. 34) and that the infection is enhanced in the presence of Vpx (viral protein X) (FIG. 35). It is further disclosed that pre-treatment with an antibody of CD169 induces a decrease in HIV-1 infection of pre-DC, with the antibody showing higher potency towards X4 virus (FIG. 36).

FIG. 37 provides that in addition to being the most susceptible to HIV-1 infection, in the presence of Vpx, the infected pre-DC cells are also able to transmit the virus to activated CD4 T cells, which are the major target of HIV-1 infection. Therefore, it is possible that pre-DC is a new target for HIV-1 therapy.

FIG. 38 shows the increased proportion of the circulating pre-DC subset in various inflammatory conditions such as lichen planus, atopic dermatitis, psoriasis and obesity. Additionally, increased pre-DC was also shown for cancer and infectious diseases (FIG. 38). Moreover, in Systemic lupus erythematosus (SLE), the proportion of circulating pre-DC is correlated with the SLEDAI score, a measure of disease activity as shown in FIG. 38. Therefore, it is also provided methods to diagnose or predict progression of local or systemic inflammatory, autoimmune, infectious, metabolic diseases/conditions based on the detection of changes in pre-DC populations.

In summary, human blood and tissue DC, and their precursors in the BM were identified by expression of the CD135 and HLA-DR. The CD135$^+$HLA-DR$^-$ fraction of human blood using several integrated high-dimensional analysis techniques (single-cell mRNA sequencing and mass cytometry using Cytometry by Time of Flight mass spectrometry or CyTOF). These approaches supersede traditional surface marker-based approaches, and identified a population of pre-DC within the conventionally-defined pDC population. The current combination of markers for DC progenitors has never been described before and allows to distinguish pre-DC subsets from circulating pDC; indeed, so far, all experimental observations on pDC have been made in the presence of contaminating pre-DC. These pre-DC possess a unique phenotype and distinct functional properties that were previously attributed to pDC. Extending the analysis of the present disclosure to all DC populations in the blood and BM, the entire DC lineage arising from the BM was identified, and revealed the transcriptional priming of pre-DC towards distinct DC subsets. These data offer new insights into DC heterogeneity and ontogeny, and highlight unexplored avenues for investigation of the therapeutic potential of DC subset-specific targeting.

REFERENCES

1. A. Schlitzer, N. McGovern, F. Ginhoux, Dendritic cells and monocyte-derived cells: Two complementary and integrated functional systems. *Semin. Cell Dev. Biol.* 41, 9-22 (2015).
2. M. Merad, P. Sathe, J. Helft, J. Miller, A. Mortha, The dendritic cell lineage: ontogeny and function of dendritic cells and their subsets in the steady state and the inflamed setting. *Annu. Rev. Immunol.* 31, 563-604 (2013).
3. M. Guilliams et al., Dendritic cells, monocytes and macrophages: a unified nomenclature based on ontogeny. *Nat. Rev. Immunol.* 14, 571-578 (2014).
4. K. Liu et al., In vivo analysis of dendritic cell development and homeostasis. *Science.* 324, 392-397 (2009).
5. F. Ginhoux et al., The origin and development of nonlymphoid tissue CD103+ DCs. *J. Exp. Med.* 206, 3115-3130 (2009).
6. N. Onai et al., A clonogenic progenitor with prominent plasmacytoid dendritic cell developmental potential. *Immunity.* 38, 943-957 (2013).
7. A. Schlitzer et al., Identification of cDC1- and cDC2-committed DC progenitors reveals early lineage priming at the common DC progenitor stage in the bone marrow. *Nat. Immunol.* 16, 718-728 (2015).
8. J. Lee et al., Restricted dendritic cell and monocyte progenitors in human cord blood and bone marrow. *J. Exp. Med.* 212, 385-399 (2015).
9. G. Breton et al., Circulating precursors of human CD1c+ and CD141+ dendritic cells. *J. Exp. Med.* 212, 401-413 (2015).
10. M. Cella et al., Plasmacytoid monocytes migrate to inflamed lymph nodes and produce large amounts of type I interferon. *Nat. Med.* 5, 919-923 (1999).
11. G. Grouard et al., The enigmatic plasmacytoid T cells develop into dendritic cells with interleukin (IL)-3 and CD40-ligand. *J. Exp. Med.* 185, 1101-1111 (1997).
12. S. Doulatov et al., Revised map of the human progenitor hierarchy shows the origin of macrophages and dendritic cells in early lymphoid development. *Nat. Immunol.* 11, 585-593 (2010).
13. J. D. Griffin et al., Differential expression of HLA-DR antigens in subsets of human CFU-GM. *Blood.* 66, 788-795 (1985).
14. A. Dzionek et al., BDCA-2, BDCA-3, and BDCA-4: Three Markers for Distinct Subsets of Dendritic Cells in Human Peripheral Blood. *The Journal of Immunology.* 165, 6037-6046 (2000).
15. D. A. Jaitin et al., Massively parallel single-cell RNA-seq for marker-free decomposition of tissues into cell types. *Science.* 343, 776-779 (2014).
16. 16. B. Becher et al., High-dimensional analysis of the murine myeloid cell system. *Nat. Immunol.* 15, 1181-1189 (2014).
17. E.-A. D. Amir et al., viSNE enables visualization of high dimensional single-cell data and reveals phenotypic heterogeneity of leukemia. *Nat. Biotechnol.* 31, 545-552 (2013).
18. L. Van der Maaten, Visualizing data using t-SNE. *Journal of Machine Learning Research.* 9, 2579-2625 (2008).
19. M. Ester, H. P. Kriegel, J. Sander, X. Xu, A density-based algorithm for discovering clusters in large spatial databases with noise. *Kdd* (1996).
20. M. Haniffa et al., Human tissues contain CD141hi cross-presenting dendritic cells with functional homology to mouse CD103+ nonlymphoid dendritic cells. *Immunity.* 37, 60-73 (2012).
21. J. Lamb, The Connectivity Map: Using Gene-Expression Signatures to Connect Small Molecules, Genes, and Disease. *Science.* 313, 1929-1935 (2006).
22. J. Chen, A. Schlitzer, S. Chakarov, F. Ginhoux, M. Poidinger, Mpath maps multi-branching single-cell trajectories revealing progenitor cell progression during development. *Nat Commun.* 7, 11988 (2016).
23. C. Trapnell et al., The dynamics and regulators of cell fate decisions are revealed by pseudotemporal ordering of single cells. *Nat. Biotechnol.* 32, 381-386 (2014).
24. M. Setty et al., Wishbone identifies bifurcating developmental trajectories from single-cell data. *Nat. Biotechnol.* 34, 637-645 (2016).
25. R. R. Coffman et al., Geometric diffusions as a tool for harmonic analysis and structure definition of data: multiscale methods. *Proceedings of the National Academy of Sciences.* 102, 7432-7437 (2005).
26. J. H. Levine et al., Data-Driven Phenotypic Dissection of AML Reveals Progenitor-like Cells that Correlate with Prognosis. *Cell.* 162, 184-197 (2015).
27. C. Sadaka, M.-A. Marloie-Provost, V. Soumelis, P. Benaroch, Developmental regulation of MHC II expression and transport in human plasmacytoid-derived dendritic cells. *Blood.* 113, 2127-2135 (2009).
28. S. L. Jongbloed et al., Human CD141+(BDCA-3)+ dendritic cells (DCs) represent a unique myeloid DC subset that cross-presents necrotic cell antigens. *J. Exp. Med.* 207, 1247-1260 (2010).
29. K. P. A. MacDonald et al., Characterization of human blood dendritic cell subsets. *Blood.* 100, 4512-4520 (2002).

30. T. Matsui et al., CD2 distinguishes two subsets of human plasmacytoid dendritic cells with distinct phenotype and functions. *J. Immunol.* 182, 6815-6823 (2009).
31. B. Reizis, A. Bunin, H. S. Ghosh, K. L. Lewis, V. Sisirak, Plasmacytoid dendritic cells: recent progress and open questions. *Annu. Rev. Immunol.* 29, 163-183 (2011).
32. B. Cisse et al., Transcription factor E2-2 is an essential and specific regulator of plasmacytoid dendritic cell development. *Cell.* 135, 37-48 (2008).
33. S. C. Bendall et al., Single-cell trajectory detection uncovers progression and regulatory coordination in human B cell development. *Cell.* 157, 714-725 (2014).
34. 36. J. B. Tenenbaum, V. de Silva, J. C. Langford, A global geometric framework for nonlinear dimensionality reduction. *Science.* 290, 2319-2323 (2000).
35. G. E. Grajales-Reyes et al., Batf3 maintains autoactivation of Irf8 for commitment of a CD8α(+) conventional DC clonogenic progenitor. *Nat. Immunol.* 16, 708-717 (2015).
36. A. Schlitzer et al., Identification of CCR9-murine plasmacytoid DC precursors with plasticity to differentiate into conventional DCs. *Blood.* 117, 6562-6570 (2011).
37. A. Krug et al., Toll-like receptor expression reveals CpG DNA as a unique microbial stimulus for plasmacytoid dendritic cells which synergizes with CD40 ligand to induce high amounts of IL-12. *Eur. J. Immunol.* 31, 3026-3037 (2001).
38. A. Dzionek et al., Plasmacytoid dendritic cells: from specific surface markers to specific cellular functions. *Hum. Immunol.* 63, 1133-1148 (2002).
39. M. Cella, F. Facchetti, A. Lanzavecchia, M. Colonna, Plasmacytoid dendritic cells activated by influenza virus and CD40L drive a potent TH1 polarization. *Nat. Immunol.* 1, 305-310 (2000).
40. T. Ito et al., Plasmacytoid dendritic cells prime IL-10-producing T regulatory cells by inducible costimulator ligand. *J. Exp. Med.* 204, 105-115 (2007).
41. J.-F. Fonteneau et al., Activation of influenza virus-specific CD4+ and CD8+ T cells: a new role for plasmacytoid dendritic cells in adaptive immunity. *Blood.* 101, 3520-3526 (2003).
42. G. Hoeffel et al., Antigen crosspresentation by human plasmacytoid dendritic cells. *Immunity.* 27, 481-492 (2007).
43. Y.-J. Liu, IPC: professional type 1 interferon-producing cells and plasmacytoid dendritic cell precursors. *Annu. Rev. Immunol.* 23, 275-306 (2005).
44. C. F. de Winter et al., Phenotype and natural history in 101 individuals with Pitt-Hopkins syndrome through an internet questionnaire system. *Orphanet J. Rare Dis.* 11, 37 (2016).
45. B. Langmead, C. Trapnell, M. Pop, S. L. Salzberg, Ultrafast and memory-efficient alignment of short DNA sequences to the human genome. *Genome Biol.* 10, R25 (2009).
46. A. Yates et al., Ensembl 2016. *Nucleic Acids Res.* 44, D710-6 (2016).
47. D. Grun et al., Single-cell messenger RNA sequencing reveals rare intestinal cell types. *Nature.* 525, 251-255 (2015).
48. R. Satija, J. A. Farrell, D. Gennert, A. F. Schier, A. Regev, Spatial reconstruction of single-cell gene expression data. *Nat. Biotechnol.* 33, 495-502 (2015).
49. M. Hahsler, M. Piekenbrock, dbscan: Density Based Clustering of Applications with Noise (DBSCAN) and Related Algorithms. R package version 1.0-0. https://CRAN.R-project.org/package=dbscan (2017).
50. J. Harrow et al., GENCODE: the reference human genome annotation for The ENCODE Project. *Genome Res.* 22, 1760-1774 (2012).
51. B. Li, C. N. Dewey, RSEM: accurate transcript quantification from RNA-Seq data with or without a reference genome. *BMC Bioinformatics.* 12, 323 (2011).
52. R. Finck et al., Normalization of mass cytometry data with bead standards. *Cytometry A.* 83, 483-494 (2013).
53. E. W. Newell, N. Sigal, S. C. Bendall, G. P. Nolan, M. M. Davis, Cytometry by time-of-flight shows combinatorial cytokine expression and virus-specific cell niches within a continuum of CD8+ T cell phenotypes. *Immunity.* 36, 142-152 (2012).
54. D. R. Parks, M. Roederer, W. A. Moore, A new "Logicle" display method avoids deceptive effects of logarithmic scaling for low signals and compensated data. *Cytometry A.* 69, 541-551 (2006).
55. J. Oksanen et al., vegan: Community Ecology Package. R package version 2.4-2. https://CRAN.R-project.org/package=vegan (2017).
56. H. Chen et al., Cytofkit: A Bioconductor Package for an Integrated Mass Cytometry Data Analysis Pipeline. *PLoS Comput Biol.* 12, e1005112 (2016).
57. G. K. Smyth, Linear models and empirical bayes methods for assessing differential expression in microarray experiments. *Stat Appl Genet Mol Biol.* 3, Article3 (2004).
58. Y. Benjamini, Y. Hochberg, Controlling the false discovery rate: a practical and powerful approach to multiple testing. *Journal of the royal statistical society Series B (Methodological)* 57, 289-300 (1995).
59. B. Morandi et al., Distinctive Lack of CD48 Expression in Subsets of Human Dendritic Cells Tunes NK Cell Activation. *The Journal of Immunology.* 175, 3690-3697 (2005).
60. H. Strobl et al., Identification of CD68+lin– peripheral blood cells with dendritic precursor characteristics. *The Journal of Immunology.* 161, 740-748 (1998).
61. L. Galibert et al., Nectin-like protein 2 defines a subset of T-cell zone dendritic cells and is a ligand for class-I-restricted T-cell-associated molecule. *J. Biol. Chem.* 280, 21955-21964 (2005).
62. M. Cheng et al., Characterization of species-specific genes regulated by E2-2 in human plasmacytoid dendritic cells. *Sci Rep.* 5, 10752 (2015).

The invention claimed is:
1. A method of detecting a precursor of conventional dendritic cell (cDC) (pre-DC) in a sample, comprising (i) detecting the presence of biomarkers selected from a group consisting of: (a) a combination of CD169 and CD327 and at least one of CD271 and CD324, or both; and (b) a combination of CD169, CD327 and AXL and at least one of CD271 and CD324, or both,
and wherein the detecting comprises: (A) contacting the sample with one or more of an antibody or an antigen-binding fragment of an antibody specific for the biomarkers and detecting binding between the biomarkers and the antibody or the antigen-binding fragment of an antibody; or (B) mass cytometry or flow cytometry.
2. The method of claim 1, wherein the biomarker(s) is selected from a group consisting of:
(a) a combination of CD169, CD327, and CD271;
(b) a combination of CD169, CD327, and CD324;
(c) a combination of CD169, CD327, AXL, and CD271;
(d) a combination of CD169, CD327, AXL, and CD324;

(e) a combination of CD169, CD327, CD271, and CD324; and (f) a combination of CD169, CD327, AXL, CD271, and CD324.

3. The method of claim 1, wherein the detecting comprises contacting a sample suspected of containing pre-DC, comprising early pre-DC, pre-cDC1 and/or pre-cDC2 cells, with the antibody or the antigen-binding fragment of an antibody.

4. The method of claim 3, wherein the antibody or the antigen-binding fragment of an antibody is coupled to a detectable label selected from a group consisting of: a fluorescent label, a radioactive label, a chemical label, an enzymatic label, a protein label, a magnetic label and a heavy metal.

5. The method of claim 1, wherein the sample is selected from a group consisting of: a blood sample; a tissue sample selected from a group consisting of bone marrow, lung, spleen, liver, heart, bone, skin, adipose tissue, dermis, intestine, urinary bladder, tendon, ligament, muscle, fascia, neurologic tissue, vessel, kidney, cartilage, sections of tissues such as biopsy and autopsy samples, frozen sections of tissues taken for histologic purposes, archival samples, explants and primary and/or transformed cell cultures derived from patient tissues and/or any other suitable tissue; a cell sample selected from a group consisting of peripheral blood mononuclear cells; and a bodily fluid sample selected from a group consisting of lymph fluids, cystic fluids, sputum, stool, tears, mucus, ascitic fluid, cystic fluid, urine, nipple exudates and nipple aspirates.

* * * * *